United States Patent
Kubo et al.

(10) Patent No.: US 8,846,164 B2
(45) Date of Patent: Sep. 30, 2014

(54) COMPOUND HAVING PROPYL ETHER AS BONDING GROUP, LIQUID CRYSTAL COMPOSITION THEREOF AND LIQUID CRYSTAL DISPLAY DEVICE THEREOF

(75) Inventors: Takahiro Kubo, Chiba (JP); Hiroyuki Tanaka, Chiba (JP)

(73) Assignees: JNC Corporation, Tokyo (JP); JNC Petrochemical Corporation, Tokyo (JP)

(*) Notice: Subject to any disclaimer, the term of this patent is extended or adjusted under 35 U.S.C. 154(b) by 70 days.

(21) Appl. No.: 13/813,655

(22) PCT Filed: Jul. 27, 2011

(86) PCT No.: PCT/JP2011/067062
§ 371 (c)(1),
(2), (4) Date: Feb. 1, 2013

(87) PCT Pub. No.: WO2012/020643
PCT Pub. Date: Feb. 16, 2012

(65) Prior Publication Data
US 2013/0126783 A1  May 23, 2013

(30) Foreign Application Priority Data
Aug. 11, 2010  (JP) ................. 2010-180228

(51) Int. Cl.
| | | |
|---|---|---|
| C09K 19/30 | (2006.01) | |
| C09K 19/20 | (2006.01) | |
| C07C 25/13 | (2006.01) | |
| C07C 43/225 | (2006.01) | |
| C09K 19/34 | (2006.01) | |
| C07D 309/06 | (2006.01) | |
| C09K 19/04 | (2006.01) | |

(52) U.S. Cl.
CPC .......... *C09K 19/3066* (2013.01); *C09K 19/3402* (2013.01); *C07D 309/06* (2013.01); *C09K 2019/3425* (2013.01); *C09K 2019/0444* (2013.01); *C09K 19/20* (2013.01)
USPC .................. 428/1.1; 252/299.63; 252/299.66; 568/645; 568/647; 570/129

(58) Field of Classification Search
USPC .............. 568/645, 647; 570/129; 252/299.63, 252/299.66; 428/1.1
See application file for complete search history.

(56) References Cited

U.S. PATENT DOCUMENTS

| | | | | |
|---|---|---|---|---|
| 5,238,600 A | * | 8/1993 | Kelly ........................ | 252/299.63 |
| 6,544,604 B2 | * | 4/2003 | Matsui et al. .................. | 428/1.1 |

FOREIGN PATENT DOCUMENTS

| | | |
|---|---|---|
| EP | 1179522 | 2/2002 |
| JP | 02-025440 | 1/1990 |
| JP | 10-237024 | 9/1998 |
| JP | 2004-075667 | 3/2004 |
| JP | 2007-261954 | 10/2007 |

\* cited by examiner

*Primary Examiner* — Shean C Wu
(74) *Attorney, Agent, or Firm* — Jianq Chyun IP Office

(57) ABSTRACT

A liquid crystal compound is described, which has stability to heat, light and so forth, keeps a nematic phase in a wide temperature range, has a small viscosity, a suitable optical anisotropy and a suitable elastic constant $K_{33}$, and further has a large negative dielectric anisotropy and an excellent compatibility with other liquid crystal compounds. The liquid crystal compound is represented by formula (1):

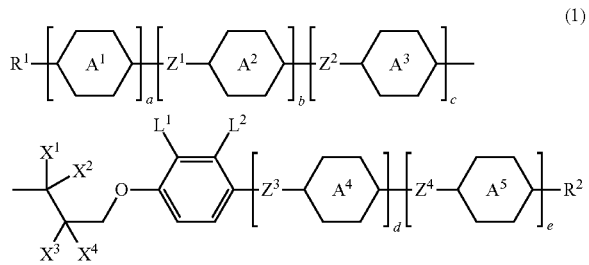

wherein, for example, $R^1$ is alkyl having 1 to 10 carbons, $R^2$ is alkoxy having 1 to 10 carbons; ring $A^1$, ring $A^2$ and ring $A^5$ are 1,4-cyclohexylene, 1,4-phenylene, or 1,4-phenylene in which arbitrary hydrogen is replaced by fluorine; $Z^1$ and $Z^4$ are a single bond, —$CH_2CH_2$— or —$CH=CH$—; a, b and e are 0 or 1, and c and d is 0; $X^1$, $X^2$ and $X^4$ are hydrogen, and $X^3$ is fluorine; and $L^1$ and $L^2$ are fluorine.

14 Claims, No Drawings

COMPOUND HAVING PROPYL ETHER AS BONDING GROUP, LIQUID CRYSTAL COMPOSITION THEREOF AND LIQUID CRYSTAL DISPLAY DEVICE THEREOF

CROSS-REFERENCE TO RELATED APPLICATION

This application is a 371 of international application of PCT application serial no. PCT/JP2011/067062, filed on Jul. 27, 2011, which claims the priority benefit of Japan application no. 2010-180228, filed on Aug. 11, 2010. The entirety of each of the above-mentioned patent applications is hereby incorporated by reference herein and made a part of this specification.

TECHNICAL FIELD

The present invention relates to a new liquid crystal compound and a new liquid crystal composition. More specifically, the invention relates to a liquid crystal compound that has a negative dielectric anisotropy ($\Delta\varepsilon$), and has a bonding group in which hydrogen in 1-position or 2-position of propyl ether is replaced by fluorine, a liquid crystal composition containing the liquid crystal compound and a liquid crystal display device including the liquid crystal composition.

BACKGROUND ART

A liquid crystal display device typified by a liquid crystal display panel, a liquid crystal display module and so forth utilizes optical anisotropy, dielectric anisotropy and so forth of a liquid crystal compound (generically meaning a compound having a liquid crystal phase such as a nematic phase or a smectic phase, and a compound having no liquid crystal phase but being useful as a component of a liquid crystal composition, according to the invention). As an operating mode of the liquid crystal display device, such a variety of modes are known as a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode and a polymer sustained alignment (PSA) mode.

In the operating modes, the ECB mode, the IPS mode, the VA mode and so forth utilize homeotropic orientation of liquid crystal molecules. In particular, the IPS mode and the VA mode are known to allow improvement in a limited viewing angle as a disadvantage of a conventionally applied display mode such as the TN mode and the STN mode.

Then, as a component of a liquid crystal composition that has a negative dielectric anisotropy and can be used in the liquid crystal display devices according to the operating modes, a research has been so far conducted for many liquid crystal compounds having propyl ether as a bonding group and many liquid crystal compounds in which hydrogen on propyl ether is replaced by fluorine, oxygen or a methyl group. However, such compounds do not have a large negative dielectric anisotropy really.

For example, an examination has been made for compound (A) having propyl ether as a bonding group (see Patent literature No. 1). However, such a compound does not have a large negative dielectric anisotropy really.

Moreover, an examination has been made for compound (B) having a bonding group in which hydrogen on propyl ether is replaced by fluorine (see Patent literature No. 2). However, compound (B) does not have a large negative dielectric anisotropy really.

Moreover, an examination has been made for compound (C) having a bonding group in which hydrogen on propyl ether is replaced by oxygen (see Patent literature No. 3). However, compound (C) does not have a large negative dielectric anisotropy really.

Furthermore, an examination has been made for compound (D) having a bonding group in which hydrogen on propyl ether is replaced by fluorine and oxygen (see Patent literature No. 4). However, compound (D) does not have a large negative dielectric anisotropy really.

Furthermore, an examination has been made for compound (E) having a bonding group in which hydrogen on propyl ether is replaced by a methyl group (see Patent literature No. 5). However, compound (E) does not have a large negative dielectric anisotropy really.

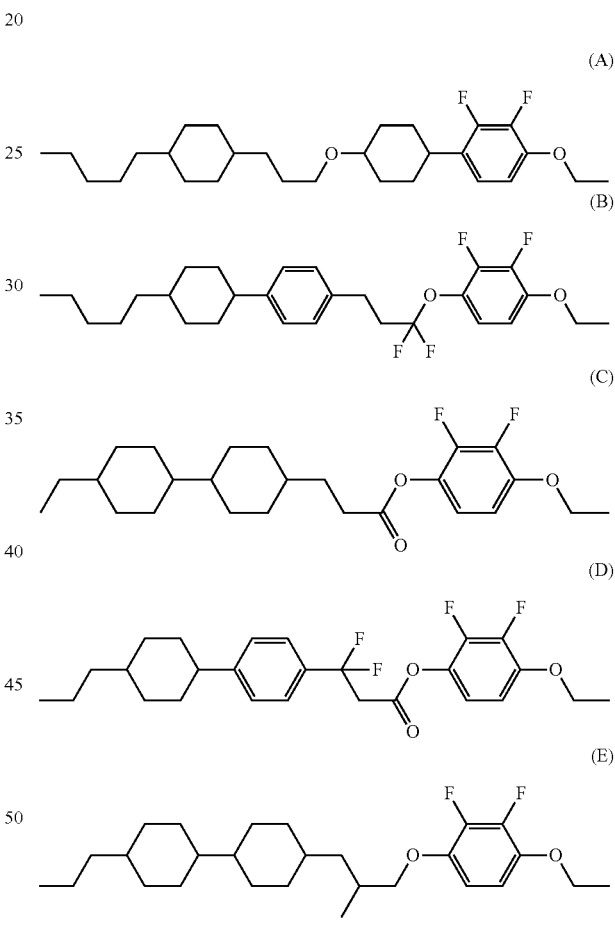

PRIOR-ART DOCUMENTS

Patent Documents

Patent literature No. 1: JP H02-025440 A.
Patent literature No. 2: EP 1179522 B.
Patent literature No. 3: JP 2004-075667 A.
Patent literature No. 4: JP H10-237024 A.
Patent literature No. 5: JP 2007-261954 A.

SUMMARY OF INVENTION

Technical Problem

Thus, even a liquid crystal display device according to an operating mode such as an IPS mode and a VA mode still has a problem, as compared with CRT. For example, an improvement in response speed, an improvement in a contrast and a decrease in a driving voltage are desired.

A display device operated according to the IPS mode or the VA mode described above is mainly constituted of a liquid crystal composition having a negative dielectric anisotropy. However, in order to further improve the characteristics, a liquid crystal compound contained in the liquid crystal composition is required to have characteristics as described in (1) to (8) below. More specifically, the liquid crystal compound is required to have the characteristics of:

(1) being chemically stable and physically stable;
(2) having a high clearing point (clearing point: phase transition temperature between a liquid crystal phase and an isotropic phase);
(3) having a low minimum temperature of the liquid crystal phase (a nematic phase, a smectic phase or the like), in particular, a low minimum temperature of the nematic phase;
(4) having a small viscosity;
(5) having a suitable optical anisotropy;
(6) having a large negative dielectric anisotropy;
(7) having a suitable elastic constant $K_{33}$ ($K_{33}$: bend elastic constant); and
(8) having an excellent compatibility with other liquid crystal compounds.

When the composition containing the chemically and physically stable liquid crystal compound as described in (1) is used for the display device, a voltage holding ratio can be increased.

In the composition containing the liquid crystal compound having the high clearing point, or the low minimum temperature of the liquid crystal phase as described in (2) and (3), a temperature range of the nematic phase can be extended, and thus the composition can be used in the form of the display device in a wide temperature range.

Furthermore, when the composition containing the compound having the small viscosity as described in (4), and the compound having the large elastic constant $K_{33}$ as described in (7) is used in the form of the display device, the response speed can be improved. In a case of the display device using the composition containing the compound having the suitable optical anisotropy as described in (5), an improvement in the contrast in the display device can be achieved. A device requires a composition having a small optical anisotropy to a composition having a large optical anisotropy depending on a design of the device. A research has been recently conducted for a technique for improving the response speed by decreasing a cell thickness. Accordingly, a liquid crystal composition having a large optical anisotropy is also required.

In addition thereto, when the liquid crystal compound has a large negative dielectric anisotropy, a threshold voltage of the liquid crystal composition containing the compound can be decreased. Therefore, in a case of the display device using the composition containing the compound having the large negative dielectric anisotropy as described in (6), the driving voltage of the display device can be decreased and electric power consumption thereof can also be decreased. Furthermore, the driving voltage of the display device can be decreased and the electric power consumption thereof can also be decreased by using the composition containing the compound having the small elastic constant $K_{33}$ as described in (7) in the form of the display device.

In order to develop characteristics that are difficult to be output by a single compound, the liquid crystal compound is generally used in the form of a liquid crystal composition prepared by mixing the compound with a number of other liquid crystal compounds. Accordingly, as described in (8), the liquid crystal compound used for the display device has preferably the excellent compatibility with other liquid crystal compounds and so forth. The display device is also used sometimes in the wide temperature range including a temperature below a freezing point. Therefore, the display device preferably includes a compound having a good compatibility even from a low temperature region in some cases.

A first aim of the invention is to provide a liquid crystal compound that has stability to heat, light and so forth, keeps a nematic phase in a wide temperature range, has a small viscosity, a suitable optical anisotropy and a suitable elastic constant $K_{33}$, and further has a large negative dielectric anisotropy and an excellent compatibility with other liquid crystal compounds.

A second aim of the invention is to provide a liquid crystal compound that has stability to heat and light, a small viscosity, a suitable optical anisotropy and a large negative dielectric anisotropy, a suitable elastic constant $K_{33}$ and a low threshold voltage, and further a liquid crystal composition that contains the compound, and satisfies at least one of characteristics such as a high maximum temperature of a nematic phase (maximum temperature: phase transition temperature between the nematic phase and an isotropic phase), and a low minimum temperature of the nematic phase. The second aim is also to provide a liquid crystal composition having a suitable balance regarding at least two of the characteristics.

A third aim of the invention is to provide a liquid crystal display device that contains the composition and has a short response time, a low electric power consumption, a low driving voltage, a large contrast and can be used in a wide temperature range.

Solution to Problem

In view of the aims, the present inventors have diligently continued to conduct research, as a result, have found that a liquid crystal compound having a bonding group in which hydrogen in 1-position or 2-position of propyl ether is replaced by fluorine in a specified structure having propyl ether in the bonding group has stability to heat, light and so forth, keeps a nematic phase in a wide temperature range, has a small viscosity, a suitable optical anisotropy and a suitable elastic constant $K_{33}$, and further has a large negative dielectric anisotropy and an excellent compatibility with other liquid crystal compounds. The present inventors have also found that a liquid crystal composition containing the compound has stability to heat and light, a small viscosity, a suitable optical anisotropy, a suitable elastic constant $K_{33}$, a large negative dielectric anisotropy and a small threshold voltage, and further satisfies at least one of characteristics such as a high maximum temperature of the nematic phase and a low minimum temperature of the nematic phase, and has a suitable balance regarding at least two of characteristics. The present inventors have further found that a liquid crystal display device including the composition has a short response time, a small electric power consumption and a small driving voltage and a large contrast ratio, and thus can be used in a wide temperature range. Thus, the present inventors have completed the invention.

More specifically, the invention includes matters as described in items 1 to 14 below.

Item 1. A compound represented by formula (1):

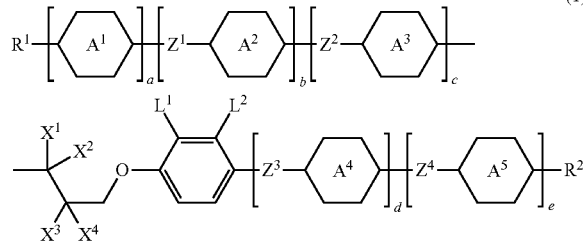

wherein, in formula (1), $R^1$ and $R^2$ are independently hydrogen, halogen or alkyl having 1 to 20 carbons, and in the alkyl, arbitrary —$CH_2$— may be replaced by —O— or —S— and arbitrary —$(CH_2)_2$— may be replaced by —CH=CH—, and in the groups, arbitrary hydrogen may be replaced by halogen; ring $A^1$, ring $A^2$, ring $A^3$, ring $A^4$ and ring $A^5$ are independently 1,4-cyclohexylene, tetrahydropyran-2,5-diyl, tetrahydropyran-3,6-diyl, 1,4-phenylene, or 1,4-phenylene in which arbitrary hydrogen is replaced by fluorine; $Z^1$, $Z^2$, $Z^3$ and $Z^4$ are independently a single bond, —$CH_2CH_2$—, —CH=CH—, —C≡C—, —COO—, —COO—, —$CF_2O$—, —$OCF_2$—, —$CH_2O$—, —$OCH_2$—, —$C(FX^{11})C(X^{12}X^{13})CH_2O$—, —$OCH_2C(X^{12}X^{13})C(FX^{11})$—$CH_2C(X^{13}F)CH_2O$— and —$OCH_2C(X^{13}F)CH_2$—; a, b, c, d and e are independently 0 or 1, a sum of a, b and c is 1, 2 or 3, a sum of d and e is 0, 1 or 2, and a sum of a, b, c, d and e is 1, 2 or 3; $X^1$, $X^2$, $X^3$ and $X^4$ are independently hydrogen or fluorine, one or two of $X^1$, $X^2$, $X^3$ and $X^4$ is fluorine; $X^{11}$, $X^{12}$ and $X^{13}$ are independently hydrogen or fluorine, zero (0) or one of $X^{11}$, $X^{12}$ and $X^{13}$ is fluorine; and $L^1$ and $L^2$ are independently hydrogen or fluorine, and at least one of $L^1$ and $L^2$ is fluorine.

Item 2. The compound according to item 1, wherein, in formula (1), all of $Z^1$, $Z^2$, $Z^3$ and $Z^4$ is a single bond.

Item 3. The compound according to item 1, represented by any one of formulas (1-1) to (1-4):

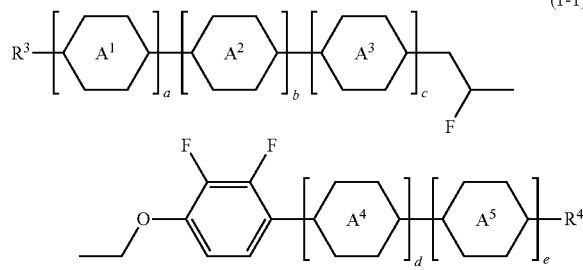

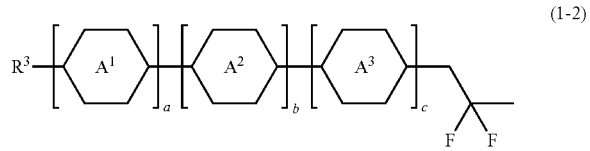

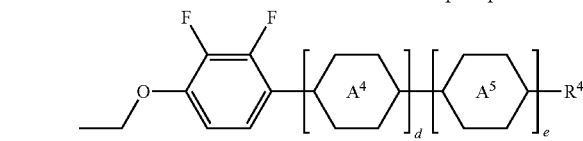

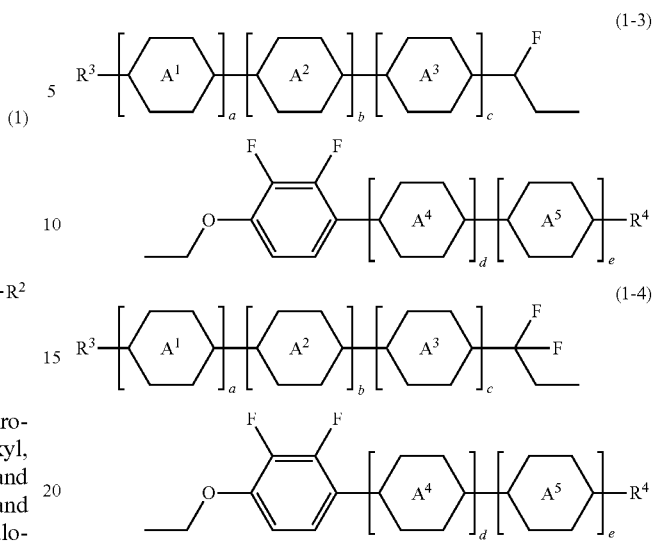

wherein, in formulas (1-1) to (1-4), $R^3$ and $R^4$ are independently hydrogen, halogen or alkyl having 1 to 15 carbons, and in the alkyl, arbitrary —$CH_2$— may be replaced by —O— or —S— and arbitrary —$(CH_2)_2$— may be replaced by —CH=CH—, and in the groups, arbitrary hydrogen may be replaced by halogen; ring $A^1$, ring $A^2$, ring $A^3$, ring $A^4$ and ring $A^5$ are independently 1,4-cyclohexylene, tetrahydropyran-2,5-diyl, tetrahydropyran-3,6-diyl, 1,4-phenylene, or 1,4-phenylene in which arbitrary hydrogen is replaced by fluorine; a, b, c, d and e are independently 0 or 1, a sum of a, b and c is 1, 2 or 3, a sum of d and e is 0, 1 or 2, and a sum of a, b, c, d and e is 1, 2 or 3.

Item 4. The compound according to item 1, represented by any one of formulas (1-1-1) to (1-1-5), formulas (1-2-1) to (1-2-5), formulas (1-3-1) to (1-3-5) and formulas (1-4-1) to (1-4-5):

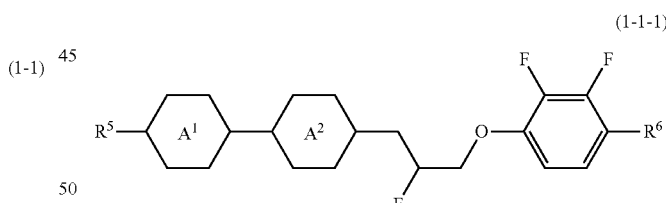

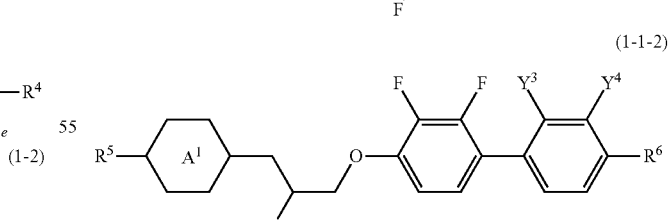

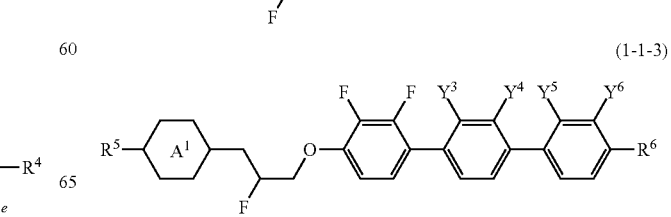

(1-1-4)
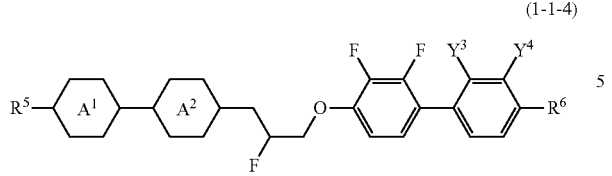

(1-1-5)
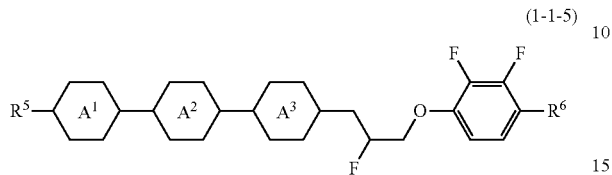

(1-2-1)
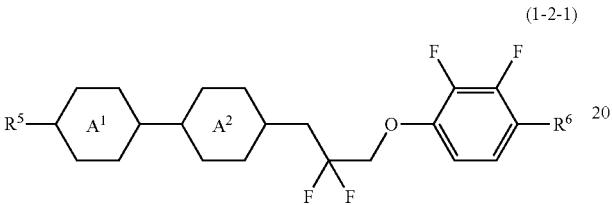

(1-2-2)
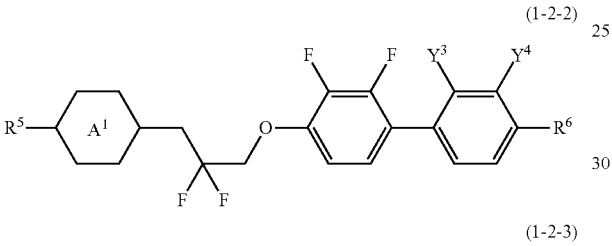

(1-2-3)
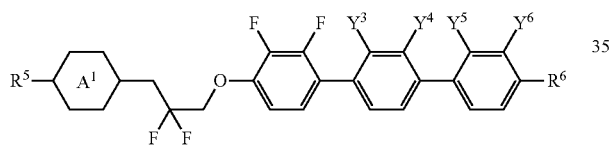

(1-2-4)
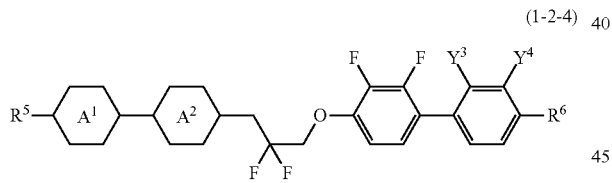

(1-2-5)
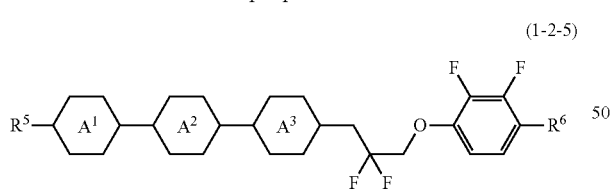

(1-3-1)
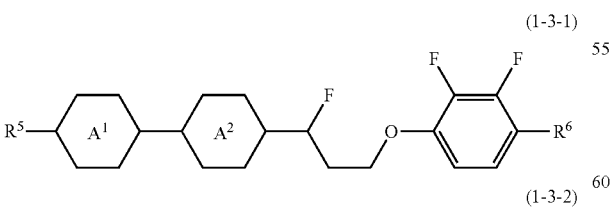

(1-3-2)
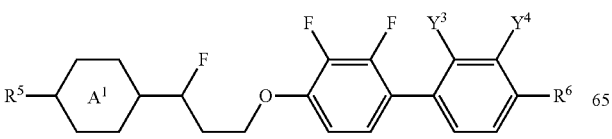

(1-3-3)
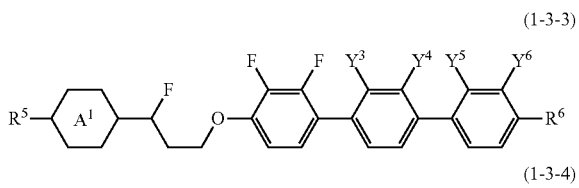

(1-3-4)
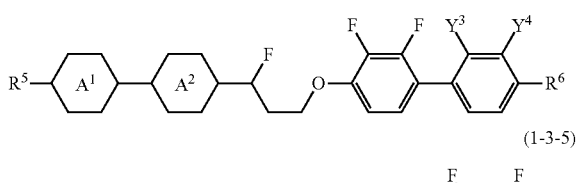

(1-3-5)
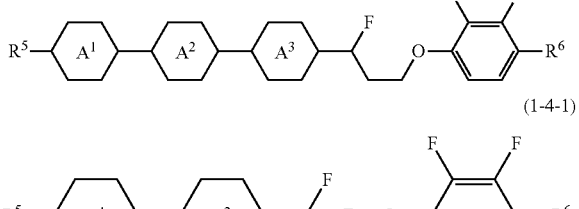

(1-4-1)
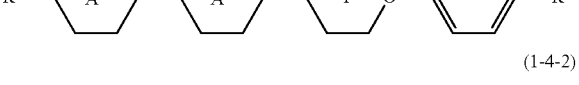

(1-4-2)
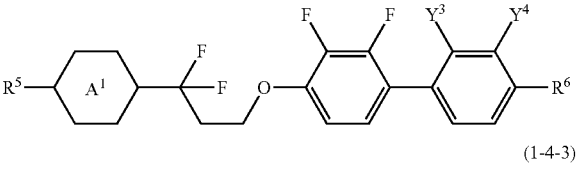

(1-4-3)
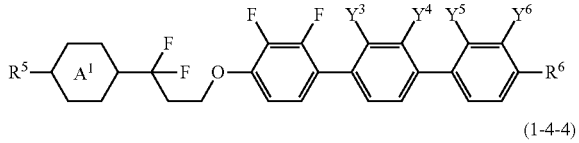

(1-4-4)
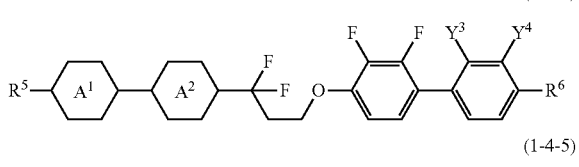

(1-4-5)
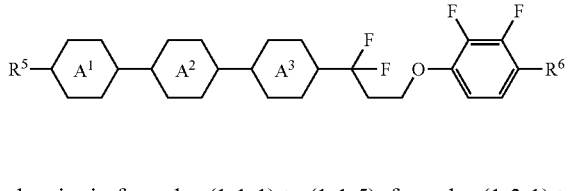

wherein, in formulas (1-1-1) to (1-1-5), formulas (1-2-1) to (1-2-5), formulas (1-3-1) to (1-3-5) and formulas (1-4-1) to (1-4-5), $R^5$ and $R^6$ are independently hydrogen, halogen or alkyl having 1 to 10 carbons, and in the alkyl, arbitrary —$CH_2$— may be replaced by —O— or —S— and arbitrary —$(CH_2)_2$— may be replaced by —CH=CH—, and in the groups, arbitrary hydrogen may be replaced by halogen; ring $A^1$, ring $A^2$ and ring $A^3$ are independently 1,4-cyclohexylene, tetrahydropyran-2,5-diyl, tetrahydropyran-3,6-diyl, 1,4-phenylene, or 1,4-phenylene in which arbitrary hydrogen is replaced by fluorine; and $Y^3$, $Y^4$, $Y^5$ and $Y^6$ are independently hydrogen or fluorine.

Item 5. The compound according to item 1, represented by any one of formulas (1-1-1-1) and (1-1-2-1):

(1-1-1-1)

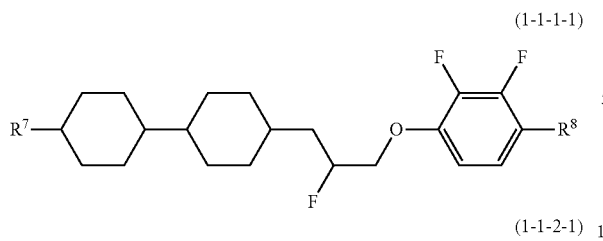

(1-1-2-1)

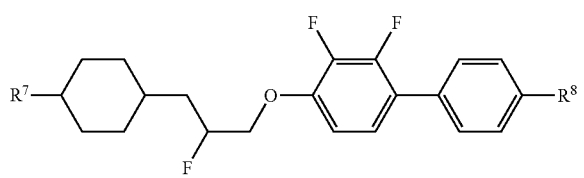

wherein, in formulas (1-1-1-1) and (1-1-2-1), $R^7$ is alkyl having 1 to 10 carbons and $R^8$ is alkoxy having 1 to 10 carbons.

Item 6. A liquid crystal composition comprising two or more components, containing at least one compound according to items 1 to 5, as one component.

Item 7. The liquid crystal composition according to item 6, containing at least one compound selected from the group of compounds represented by each of formulas (2), (3) and (4), as one component:

(2)

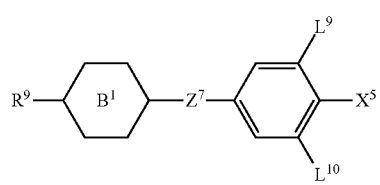

(3)

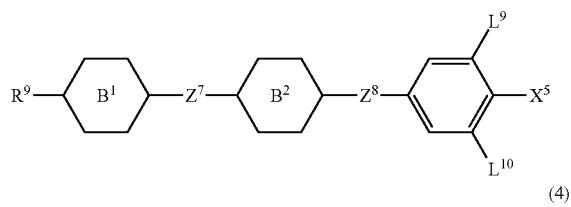

(4)

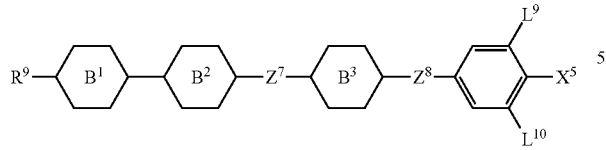

wherein, in formulas (2) to (4), $R^9$ is independently alkyl having 1 to 10 carbons or alkenyl having 2 to 10 carbons, and in the alkyl and the alkenyl, arbitrary hydrogen may be replaced by fluorine and arbitrary —$CH_2$— may be replaced by —O—;

$X^5$ is fluorine, chlorine, —$OCF_3$, —$OCHF_2$, —$CF_3$, —$CHF_2$, —$CH_2F$, —$CF=F_2$, —$OCF_2CHF_2$ or —$OCF_2CHFCF_3$;

ring $B^1$, ring $B^2$ and ring $B^3$ are independently 1,4-cyclohexylene, 1,3-dioxane-2,5-diyl, pyrimidine-2,5-diyl, 1-pyran-2,5-diyl, 1,4-phenylene, 2-fluoro-1,4-phenylene, 3-fluoro-1,4-phenylene or 3,5-difluoro-1,4-phenylene;

$Z^7$ and $Z^8$ are independently —$(CH_2)_2$—, —$(CH_2)_4$—, —COO—, —$CF_2O$—, —$OCF_2$—, —CH=CH—, —C≡C—, —$CH_2O$— or a single bond; and $L^9$ and $L^{10}$ are independently hydrogen or fluorine.

Item 8. The liquid crystal composition according to item 6, containing at least one compound selected from the group of compounds represented by formula (5), as one component:

(5)

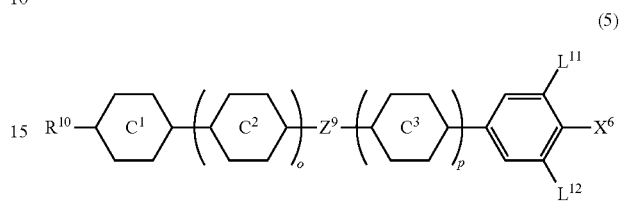

wherein, in formula (5), $R^{10}$ is alkyl having 1 to 10 carbons or alkenyl having 2 to 10 carbons, and in the alkyl and the alkenyl, arbitrary hydrogen may be replaced by fluorine and arbitrary —$CH_2$— may be replaced by —O—;

$X^6$ is —C≡N or —C≡C—C≡N;

ring $C^1$, ring $C^2$ and ring $C^3$ are independently 1,4-cyclohexylene, 1,4-phenylene in which arbitrary hydrogen may be replaced by fluorine, 1,3-dioxane-2,5-diyl, 1-pyran-2,5-diyl or pyrimidine-2,5-diyl;

$Z^9$ is —$(CH_2)_2$—, —COO—, —$CF_2O$—, —$OCF_2$—, —C≡C—, —$CH_2O$— or a single bond;

$L^{11}$ and $L^{12}$ are independently hydrogen or fluorine; and o is 0, 1 or 2, p is 0 or 1, and a sum of o and p is 0, 1, 2 or 3.

Item 9. The liquid crystal composition according to item 6, containing at least one compound selected from the group of compounds represented by each of formulas (6), (7), (8), (9), (10) and (11), as one component:

(6)

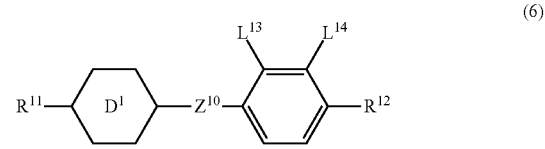

(7)

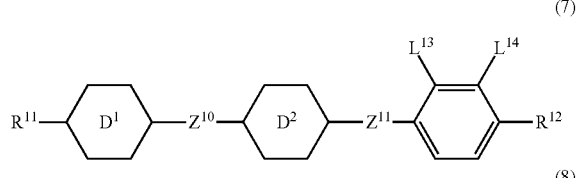

(8)

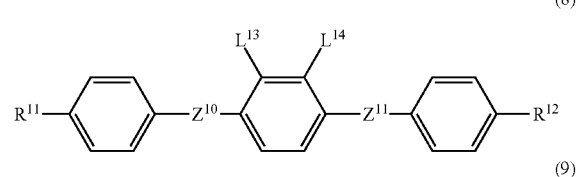

(9)

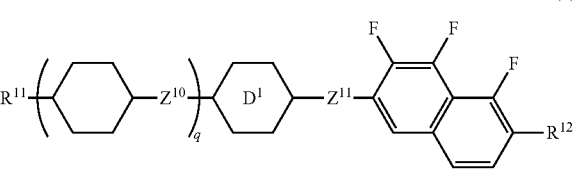

-continued

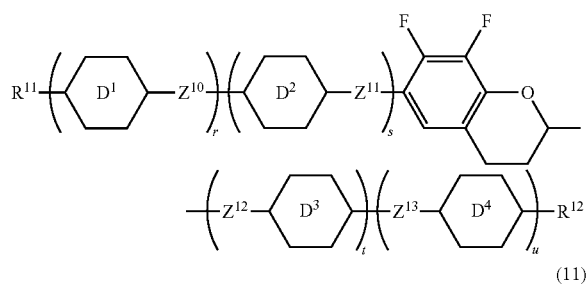

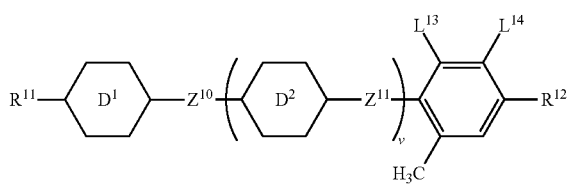

wherein, in formulas (6) to (11), $R^{11}$ and $R^{12}$ are independently alkyl having 1 to 10 carbons or alkenyl having 2 to 10 carbons, and in the alkyl and the alkenyl, arbitrary hydrogen may be replaced by fluorine and arbitrary —$CH_2$— may be replaced by —O—; ring $D^1$, ring $D^2$, ring $D^3$ and ring $D^4$ are independently 1,4-cyclohexylene, 1,4-cyclohexenylene, 1,4-phenylene in which arbitrary hydrogen may be replaced by fluorine, 6-pyran-2,5-diyl or decahydro-2,6-naphthalene; $Z^{10}$, $Z^{11}$, $Z^{12}$ and $Z^{13}$ are independently —$(CH_2)_2$—, —COO—, —$CH_2O$—, —$OCF_2$—, —$OCF_2(CH_2)_2$— or a single bond; $L^{13}$ and $L^{14}$ are independently fluorine or chlorine; and q, r, s, t, u and v are independently 0 or 1, and a sum of r, s, t and u is 1 or 2.

Item 10. The liquid crystal composition according to item 6, further containing at least one compound selected from the group of compounds represented by each of formulas (12), (13) and (14):

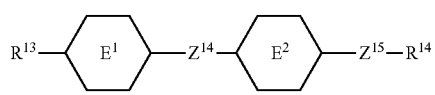

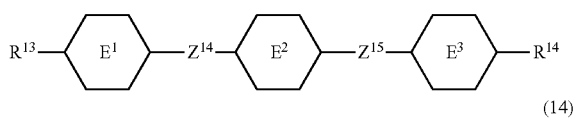

wherein, in formulas (12) to (14), $R^{13}$ and $R^{14}$ are independently alkyl having 1 to 10 carbons or alkenyl having 2 to 10 carbons, and in the alkyl and the alkenyl, arbitrary —$CH_2$— may be replaced by —O—; ring $E^1$, ring $E^2$ and ring $E^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{14}$ and $Z^{15}$ are independently —C≡C—, —COO—, —$(CH_2)_2$—, —CH=CH— or a single bond.

Item 11. The liquid crystal composition according to item 9, further containing at least one compound selected from the group of compounds represented by formulas (12), (13) and (14) according to item 10.

Item 12. The liquid crystal composition according to item 6, further containing at least one optically active compound.

Item 13. The liquid crystal composition according to item 6, further containing at least one antioxidant and/or an ultraviolet absorber.

Item 14. A liquid crystal display device, including the liquid crystal composition according to any one of items 6 to 13.

Usage of terms herein is as described below. The liquid crystal compound is a generic term for a compound having a liquid crystal phase such as the nematic phase or a smectic phase and a compound having no liquid crystal phase but being useful as a component of the liquid crystal composition. The liquid crystal compound, the liquid crystal composition and the liquid crystal display device may be abbreviated as "compound," "composition" and "device," respectively. The liquid crystal display device is a generic term for a liquid crystal display panel and a liquid crystal display module. A maximum temperature of the nematic phase is a phase transition temperature between the nematic phase and an isotropic phase, and may simply be abbreviated as "clearing point" or "maximum temperature." A minimum temperature of the nematic phase may simply be abbreviated as "minimum temperature." "Compound represented by formula (1)" may be abbreviated as "compound (1)." The abbreviation may apply also to the compound represented by formula (2) and so forth. In formula (1) to formula (13), symbols B, D, E or the like surrounded by a hexagonal shape correspond to ring B, ring D, ring E or the like, respectively. The amount of the compound expressed in terms of "percentage" is expressed in terms of "weight percent (% by weight)" based on the total amount of the composition. A plurality of same symbols such as ring $A^1$, $Y^1$ and B are described in an identical or different formula, and the symbols may have identical or different definitions, respectively.

"Arbitrary" represents any of not only positions but also numbers without including a case where the number is zero (0). An expression "arbitrary A may be replaced by B, C or D" includes a case where arbitrary A is replaced by B, a case where arbitrary A is replaced by C, and a case where arbitrary A is replaced by D, and also a case where a plurality of A are replaced by at least two of B to D. For example, an expression "alkyl in which arbitrary —$CH_2$— may be replaced by —O— or —CH=CH—" includes alkyl, alkenyl, alkoxy, alkoxyalkyl, alkoxyalkenyl and alkenyloxyalkyl. In addition, according to the invention, a case in which two successive —$CH_2$— are replaced by —O— to form —O—O— or the like is not preferred. A case in which a terminal —$CH_2$— in alkyl is replaced by —O— is not preferred, either. Hereinafter, the invention will be further explained.

Advantageous Effects of Invention

A compound of the invention has general physical properties necessary for the compound, namely, stability to heat, light and so forth, a wide temperature range of a liquid crystal phase, a good compatibility with other compounds, a large negative dielectric anisotropy and a suitable optical anisotropy. A liquid crystal composition of the invention contains at least one of the compounds, and has a high maximum temperature of a nematic phase, a low minimum temperature of the nematic phase, a small viscosity and a low threshold voltage. A liquid crystal display device of the invention includes the composition, and has a wide temperature range in which the device can be used, a short response time, a low electric power consumption, a large contrast ratio and a low driving voltage.

DESCRIPTION OF EMBODIMENTS

1-1 Compound of the Invention

A first embodiment of the invention concerns a compound represented by formula (1):

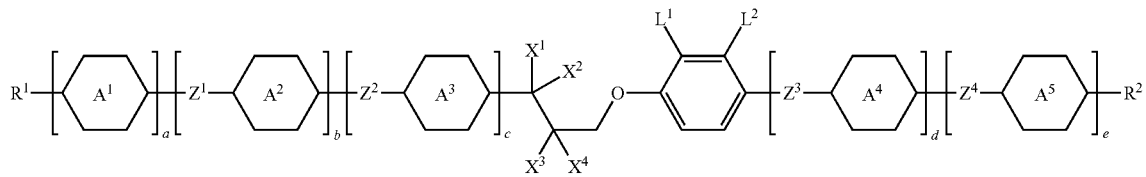

(1)

$R^1$ and $R^2$ are independently hydrogen, halogen or alkyl having 1 to 20 carbons, and in the alkyl, arbitrary —$CH_2$— may be replaced by —O— or —S— and arbitrary —$(CH_2)_2$— may be replaced by —CH=CH—, and in the groups, arbitrary hydrogen may be replaced by halogen. More specifically, $R^1$ and $R^2$ are hydrogen, halogen, alkyl, alkoxy, alkoxyalkyl, alkoxyalkoxy, thioalkyl, thioalkylalkoxy, alkenyl, alkenyloxy, alkenyloxyalkyl, alkoxyalkenyl and so forth, and arbitrary hydrogen in the groups may be replaced by halogen. A straight chain is preferred to a branched chain. Even if $R^1$ or $R^2$ is a branched-chain group, when $R^1$ or $R^2$ is optically active, $R^1$ or $R^2$ is preferred. A preferred configuration of —CH=CH— in alkenyl depends on a position of a double bond. A trans configuration is preferred in alkenyl having the double bond in an odd-numbered position, such as —CH=$CHCH_3$, —CH=$CHC_2H_5$, —CH=$CHC_3H_7$, —CH=$CHC_4H_9$, —$C_2H_4$—CH=$CHCH_3$ and —$C_2H_4$—CH=$CHC_2H_5$. A cis configuration is preferred in alkenyl having the double bond in an even-numbered position, such as —$CH_2$CH=$CHCH_3$, —$CH_2$CH=$CHC_2H_5$ and —$CH_2$CH=$CHC_3H_7$. Alkenyl having a preferred configuration has a high maximum temperature or a wide temperature range of a liquid crystal phase. A detailed description is found in Mol. Cryst. Liq. Cryst., 1985, 131, 109 and Mol. Cryst. Liq. Cryst., 1985, 131, 327.

Alkyl may have a straight chain or a branched chain. Specific examples of alkyl include —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$ and —$C_{15}H_{31}$.

Alkoxy may have a straight chain or a branched chain. Specific examples of alkoxy include —$OCH_3$, —$OC_2H_5$, —$OC_3H_7$, —$OC_4H_9$, —$OC_6H_{13}$, —$OC_7H_{15}$, —$OC_8H_{17}$, —$OC_9H_{19}$, —$OC_{10}H_{21}$, —$OC_{12}H_{25}$, —$OC_{13}H_{27}$ and —$OC_{14}H_{29}$.

Alkoxyalkyl may have a straight chain or a branched chain. Specific examples of alkoxyalkyl include —$CH_2OCH_3$, —$CH_2OC_2H_5$, —$CH_2OC_3H_7$, —$(CH_2)_2$—$OCH_3$, —$(CH_2)_2$—$OC_2H_5$—$(CH_2)_2$—$OC_3H_7$, —$(CH_2)_3$—$OCH_3$—$(CH_2)_4$—$OCH_3$ and —$(CH_2)_5$—$OCH_3$.

Alkenyl may have a straight chain or a branched chain. Specific examples of alkenyl include —CH=$CH_2$, —CH=$CHCH_3$, —$CH_2$CH=$CH_2$, —CH=$CHC_2H_5$, —$CH_2$CH=$CHCH_3$, —$(CH_2)_2$—CH=$CH_2$, —CH=$CHC_3H_7$, —$CH_2$CH=$CHC_2H_5$, —$(CH_2)_2$—CH=$CHCH_3$ and —$(CH_2)_3$—CH=$CH_2$.

Alkenyloxy may have a straight chain or a branched chain. Specific examples of alkenyloxy include —$OCH_2$CH=$CH_2$, —$OCH_2$CH=$CHCH_3$ and —$OCH_2$CH=$CHC_2H_5$.

Specific examples of alkyl in which arbitrary hydrogen is replaced by halogen include —$CH_2F$, —$CHF_2$, —$CF_3$, —$(CH_2)_2$—F, —$CF_2CH_2F$, —$CF_2CHF_2$, —$CH_2CF_3$, —$CF_2CF_3$, —$(CH_2)_3$—F, —$(CF_2)_3$—F, —$CF_2CHFCF_3$, —$CHFCF_2CF_3$, —$(CH_2)_4$—F, —$(CF_2)_4$—F, —$(CH_2)_5$—F and —$(CF_2)_5$—F.

Specific examples of alkoxy in which arbitrary hydrogen is replaced by halogen include —$OCH_2F$, —$OCHF_2$, —$OCF_3$, —O—$(CH_2)_2$—F, —$OCF_2CH_2F$, —$OCF_2CHF_2$, —$OCH_2CF_3$, —O—$(CH_2)_3$—F, —O—$(CF_2)_3$—F, —$OCF_2CHFCF_3$, —$OCHFCF_2CF_3$, —O$(CH_2)_4$—F, —O—$(CF_2)_4$—F, —O—$(CH_2)_5$—F and —O—$(CF_2)_5$—F.

Specific examples of alkenyl in which arbitrary hydrogen is replaced by halogen include —CH=CHF, —CH=$CF_2$, —CF=CHF, —CH=$CHCH_2F$, —CH=$CHCF_3$, —$(CH_2)_2$—CH=$CF_2$, —$CH_2$CH=$CHCF_3$ and —CH=$CHCF_2CF_3$.

$R^1$ or $R^2$ is preferably halogen, alkyl having 1 to 15 carbons, alkenyl having 2 to 15 carbons, alkyl having 1 to 15 carbons in which arbitrary hydrogen is replaced by halogen, or alkoxy having 2 to 15 carbons in which arbitrary hydrogen is replaced by halogen. Moreover, most preferred examples of $R^1$ and $R^2$ include fluorine, chlorine, —$CH_3$, —$C_2H_5$, —$C_3H_7$, —$C_4H_9$, —$C_5H_{11}$, —$C_6H_{13}$, —$C_7H_{15}$, —$C_8H_{17}$, —CH=$CH_2$, —CH=$CHCH_3$, —$CH_2$CH=$CH_2$, —CH=$CHC_2H_5$, —$CH_2$CH=$CHCH_3$, —$(CH_2)_2$—CH=$CH_2$, —CH=$CHC_3H_7$, —$CH_2$CH=$CHC_2H_5$, —$(CH_2)_2$—CH=$CHCH_3$, —$(CH_2)_3$, CH=$CH_2$, —$CH_3$, —$OC_2H_5$, —$OC_3H_7$, —$OC_4H_9$, —$OC_5H_{11}$, —$CF_3$, —$CHF_2$, —$CH_2F$, —$OCF_3$, —$OCHF_2$ or —$OCH_2F$.

In formula (1), ring $A^1$, ring $A^2$, ring $A^3$, ring $A^4$ and ring $A^5$ are independently 1,4-cyclohexylene, tetrahydropyran-2,5-diyl, tetrahydropyran-3,6-diyl, 1,4-phenylene, or 1,4-phenylene in which arbitrary hydrogen is replaced by fluorine.

When the rings are 1,4-cyclohexylene, optical anisotropy ($\Delta n$) can be decreased and viscosity can be decreased, and when the liquid crystal compound is added to a liquid crystal composition, a maximum temperature of a nematic phase can be increased.

When the rings are 1,4-phenylene in which arbitrary hydrogen may be replaced by fluorine, the optical anisotropy ($\Delta n$) can be comparatively increased, and simultaneously an orientational order parameter can be increased.

In formula (1), $Z^1$, $Z^2$, $Z^3$ and $Z^4$ are independently a single bond, —$CH_2CH_2$—, —CH=CH—, —C≡C—, —COO—, —OCO—, —$CF_2$O—, —$OCF_2$—, —$CH_2$O—, —$OCH_2$—, —C($FX^{11}$)C($X^{12}X^{13}$)$CH_2$O—, —$OCH_2O(X^{12}X^{13})$C($FX^{11}$)—, —$CH_2$C($X^{13}$F)$CH_2$O— and —$OCH_2$C($X^{13}$F)$CH_2$—. Herein, $X^{11}$, $X^{12}$ and $X^{13}$ are independently hydrogen or fluorine, and zero or one of $X^{11}$, $X^{12}$ and $X^{13}$ is fluorine.

Preferred examples of $Z^1$, $Z^2$, $Z^3$ and $Z^4$ include a single bond, —$CH_2CH_2$—, —CH=CH—, —C≡C—, —COO—, —$CF_2$O—, —$CH_2$O— and —$OCH_2$—. In the bonds, trans is preferred to cis in a configuration with regard to the double bond of a bonding group such as —CH=CH—. Most preferred $Z^1$, $Z^2$, $Z^3$ and $Z^4$ are a single bond.

In formula (1), $X^1$, $X^2$, $X^3$ and $X^4$ are independently hydrogen or fluorine, and one or two of $X^1$, $X^2$, $X^3$ and $X^4$ is fluorine.

In formula (1), $L^1$ and $L^2$ are independently hydrogen or fluorine, and at least one of $L^1$ or $L^2$ is fluorine. $L^1$ and $L^2$ are preferably fluorine.

In formula (1), a, b, c, d and e are independently 0 or 1, a sum of a, b and c is 1, 2 or 3, a sum of d and e is 0, 1 or 2, and a sum of a, b, c, d and e is 1, 2 or 3.

1-2 Properties of Compound of the Invention and Method for Adjusting the Properties Compound (1) of the invention will be explained in more detail. Under conditions in which a device is ordinarily used, the compound has a very high physical and chemical stability and a good compatibility with other compounds. A composition containing the compound is stable under conditions in which the device is ordinarily used. Even if the composition is kept at a low temperature, the compound will not deposit in the form of crystals (or a smectic phase). The compound has general physical properties required for the compound, namely, a suitable optical anisotropy and a suitable dielectric anisotropy. Moreover, compound (1) has a large negative dielectric anisotropy. A compound having a large dielectric anisotropy is useful as a component for decreasing a threshold voltage of the composition.

In compound (1), physical properties such as a clearing point, optical anisotropy and dielectric anisotropy can be arbitrarily adjusted by suitably selecting a combination of $R^1$, $R^2$, ring $A^1$, ring $A^2$, ring $A^3$, ring $A^4$, ring $A^5$, $Z^1$, $Z^2$, $Z^3$, $Z^4$, $X^1$, $X^2$, $X^3$, $X^4$, $L^1$, $L^2$, a b, c, d and e. An effect of the constituents on the physical properties of compound (1) will be explained below.

When either $L^1$ or $L^2$ is hydrogen, a temperature range of the liquid crystal phase is wide, and the clearing point is high. When both of $L^1$ and $L^2$ are fluorine, the dielectric anisotropy is negatively larger.

In a case of a combination in which a sum of a, b, c, d and e is 1, compatibility with other compounds is high, and in a case of a combination in which a sum thereof is 3, the temperature range of the liquid crystal phase is wide, and the clearing point is high.

When all of ring $A^1$, ring $A^2$, ring $A^3$, ring $A^4$ and ring $A^5$ is 1,4-cyclohexylene, the clearing point is high and the viscosity is small. When at least one of ring $A^1$, ring $A^2$, ring $A^3$, ring $A^4$ and ring $A^5$ is 1,4-phenylene, the optical anisotropy is comparatively large and the orientational order parameter is comparatively large. Moreover, when all of ring $A^1$, ring $A^2$, ring $A^3$, ring $A^4$ and ring $A^5$ is 1,4-phenylene, the optical anisotropy is particularly large.

When $R^1$ and $R^2$ have a straight chain, the temperature range of the liquid crystal phase is wide and the viscosity is small. When $R^1$ and $R^2$ have a branched chain, the compatibility with other liquid crystal compounds is good. A compound in which $R^1$ or $R^2$ is an optically active group is useful as a chiral dopant. A reverse twisted domain to be generated in the device can be prevented by adding the compound to the composition. A compound in which $R^1$ and $R^2$ are not an optically active group is useful as the component of the composition. When $R^1$ and $R^2$ are alkenyl, a preferred configuration depends on the position of the double bond. Alkenyl having the preferred configuration has the high maximum temperature or the wide temperature range of the liquid crystal phase.

When $Z^1$, $Z^2$, $Z^3$ and $Z^4$ are a single bond, —CH$_2$CH$_2$—, —CH=CH—, —CF$_2$O—, —OCF$_2$—, —CH$_2$O— or —OCH$_2$—, the viscosity is small. When $Z^1$, $Z^2$, $Z^3$ and $Z^4$ are a single bond, —(CH$_2$)$_2$—, CF$_2$O—, —OCF$_2$— or —CH—CH—, the viscosity is smaller. When $Z^1$, $Z^2$, $Z^3$ and $Z^4$ are —CH=CH—, the temperature range of the liquid crystal phase is wide, and an elastic constant ratio $K_{33}/K_{11}$ ($K_{33}$: bend elastic constant, $K_{11}$: spray elastic constant) is large. When $Z^1$, $Z^2$, $Z^3$ and $Z^4$ are —X≡C—, the optical anisotropy is large. When $Z^1$, $Z^2$, $Z^3$ and $Z^4$ are a single bond, —(CH$_2$)$_2$, —CH$_2$O—, —CF$_2$O— or —OCF$_2$—, compound (1) is comparatively chemically stable, and comparatively hard to cause deterioration. When $Z^1$, $Z^2$, $Z^3$ and $Z^4$ are —C(FX$^{11}$)C(X$^{12}$X$^{13}$)CH$_2$O—, —OCH$_2$O(X$^{12}$X$^{13}$)C(FX$^{11}$)—, —CH$_2$C(X$^{13}$F)CH$_2$O— or —OCH$_2$C(X$^{13}$F) CH$_2$—, the dielectric anisotropy is negatively large.

As described above, a compound having objective physical properties can be obtained by suitably selecting kinds of ring A, terminal group R, bonding group Z and so forth. Accordingly, compound (1) is useful as the component of the composition to be used for a device according to a PC, TN, STN, ECB, OCB, IPS, VA mode or the like.

1-3 Specific Examples of Compound (1)

Preferred examples of compound (1) are represented by formulas (1-1) to (1-4) described in item 3. Further preferred examples are represented by formulas (1-1-1) to (1-1-5), formulas (1-2-1) to (1-2-5), formulas (1-3-1) to (1-3-5) and formulas (1-4-1) to (1-4-5) described in item 4. Most preferred examples are represented by formulas (1-1-1-1) and (1-1-2-1) described in item 5.

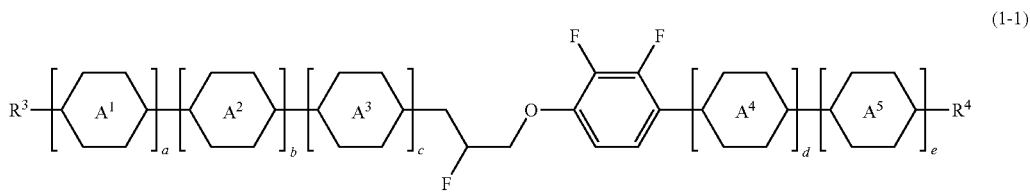

(1-1)

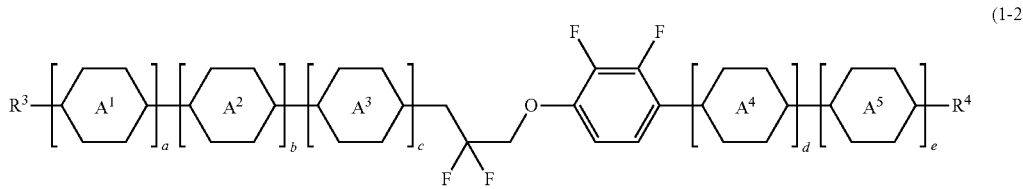

(1-2)

(1-3)
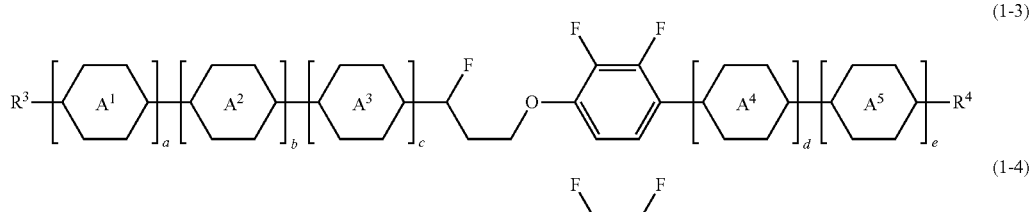

(1-4)
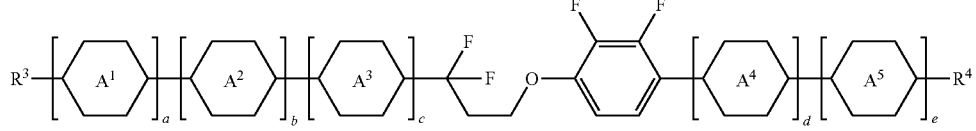

In formulas (1-1) to (1-4), $R^3$ and $R^4$ are independently hydrogen, halogen or alkyl having 1 to 15 carbons, and in the alkyl, arbitrary —CH$_2$— may be replaced by —O— or —S— and arbitrary —(CH$_2$)$_2$— may be replaced by —CH=CH—, and in the groups, arbitrary hydrogen may be replaced by halogen; ring A$^1$, ring A$^2$, ring A$^3$, ring A$^4$ and ring A$^5$ are independently 1,4-cyclohexylene, tetrahydropyran-2,5-diyl, tetrahydropyran-3,6-diyl, 1,4-phenylene, or 1,4-phenylene in which arbitrary hydrogen is replaced by fluorine; and a, b, c, d and e are independently 0 or 1, a sum of a, b and c is 1, 2 or 3, a sum of d and e is 0, 1 or 2, and a sum of a, b, c, d and e is 1, 2, or 3.

(1-1-1)
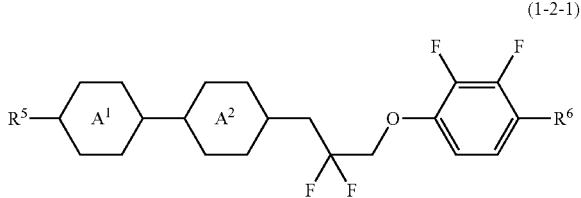

(1-1-2)
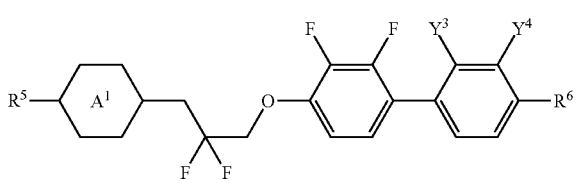

(1-1-3)
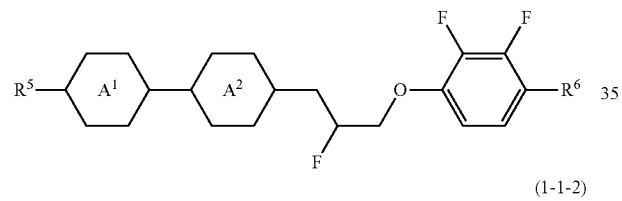

(1-1-4)
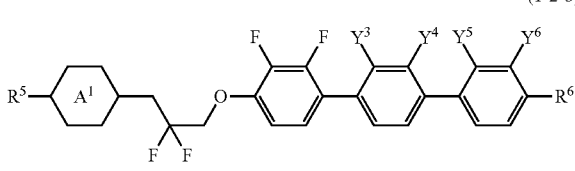

(1-1-5)
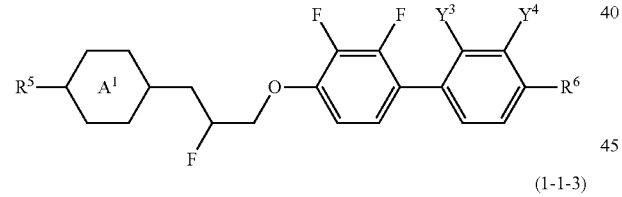

(1-2-1)
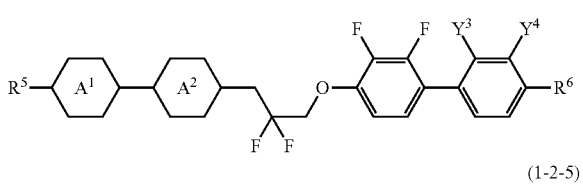

(1-2-2)
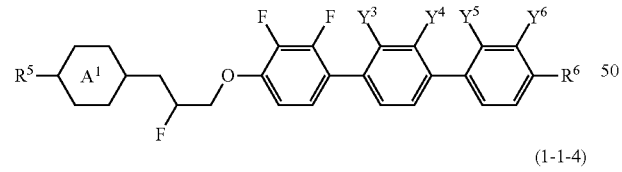

(1-2-3)
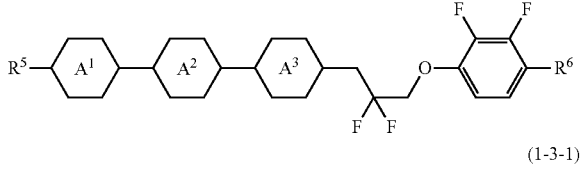

(1-2-4)
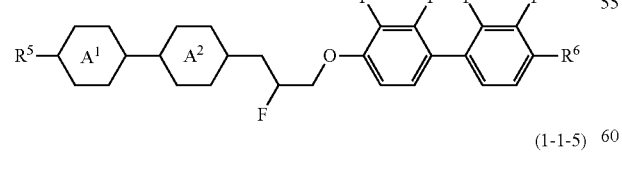

(1-2-5)
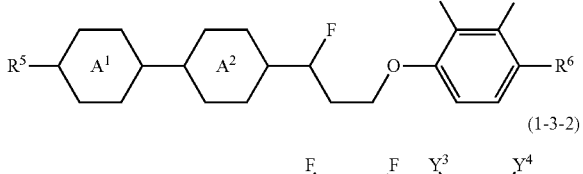

(1-3-1)
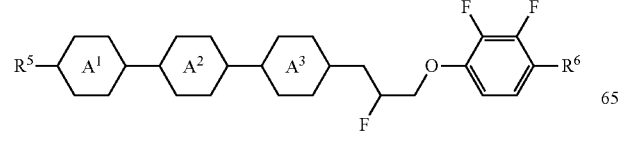

(1-3-2)
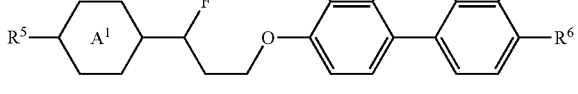

-continued

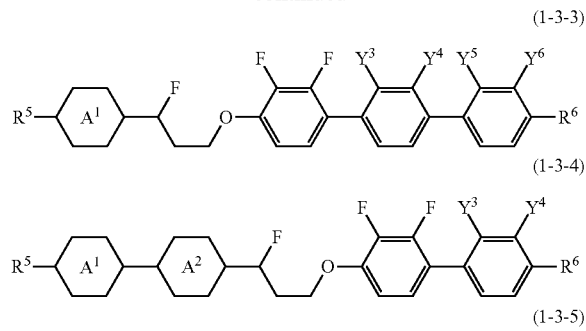

(1-3-3)

(1-3-4)

(1-3-5)

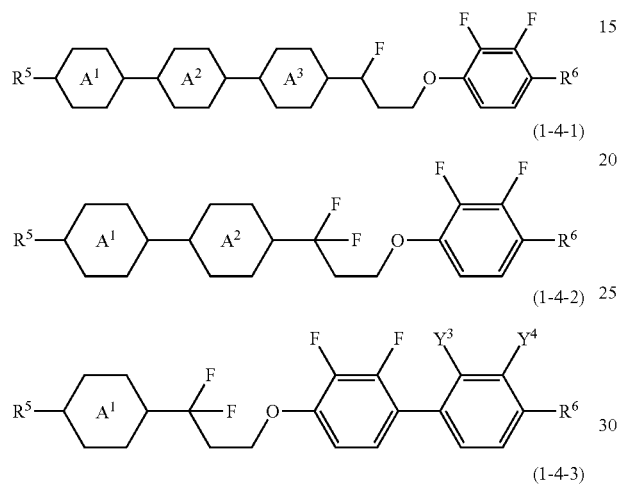

(1-4-1)

(1-4-2)

(1-4-3)

(1-4-4)

(1-4-5)

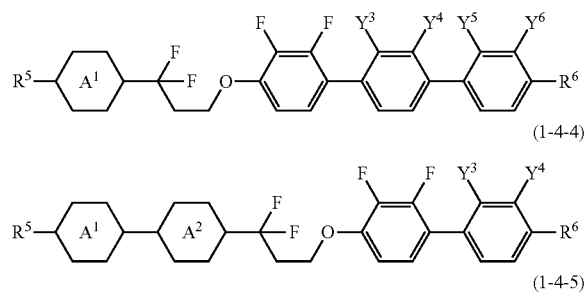

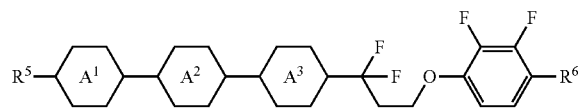

In formulas (1-1-1) to (1-1-5), formulas (1-2-1) to (1-2-5), formulas (1-3-1) to (1-3-5) and formulas (1-4-1) to (1-4-5), $R^5$ and $R^6$ are independently hydrogen, halogen, or alkyl having 1 to 10 carbons, and in the alkyl, arbitrary —$CH_2$— may be replaced by —O— or —S— and arbitrary —$(CH_2)_2$— may be replaced by —CH=CH—, and in the groups, arbitrary hydrogen may be replaced by halogen; ring $A^1$, ring $A^2$ and ring $A^3$ are independently 1,4-cyclohexylene, tetrahydropyran-2,5-diyl, tetrahydropyran-3,6-diyl, 1,4-phenylene, or 1,4-phenylene in which arbitrary hydrogen is replaced by fluorine; and $Y^3$, $Y^4$, $Y^5$ and $Y^6$ are independently hydrogen or fluorine.

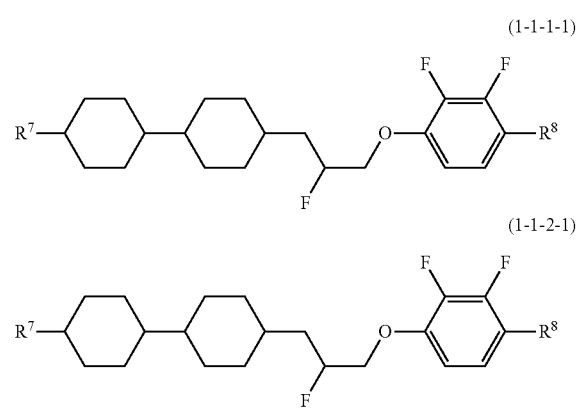

(1-1-1-1)

(1-1-2-1)

In formulas (1-1-1-1) and (1-1-2-1), $R^7$ is alkyl having 1 to 10 carbons, and $R^8$ is alkoxy having 1 to 10 carbons.

1-4 Synthesis of Compound (1)

Next, synthesis of compound (1) will be explained. Compound (1) can be prepared by suitably combining techniques in synthetic organic chemistry. Methods for introducing objective terminal groups, rings and bonding groups into starting materials are described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza, in Japanese) (Maruzen Co., Ltd.).

1-4-1 Method for Forming Bonding Group Z

One example of methods for forming bonding group Z in compound (1) is as described in a scheme below. In the scheme, $MSG^1$ or $MSG^2$ is a monovalent organic group having at least one ring. A plurality of $MSG^1$ (or $MSG^2$) used in the scheme may be identical or different. Compounds (1A) to (1G) correspond to compound (1).

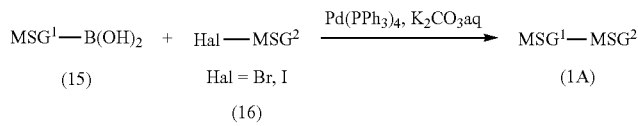

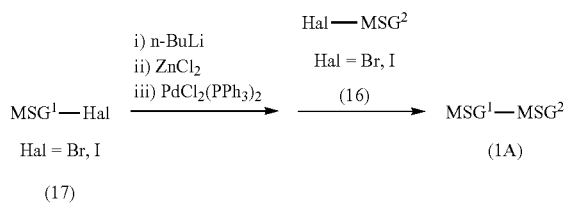

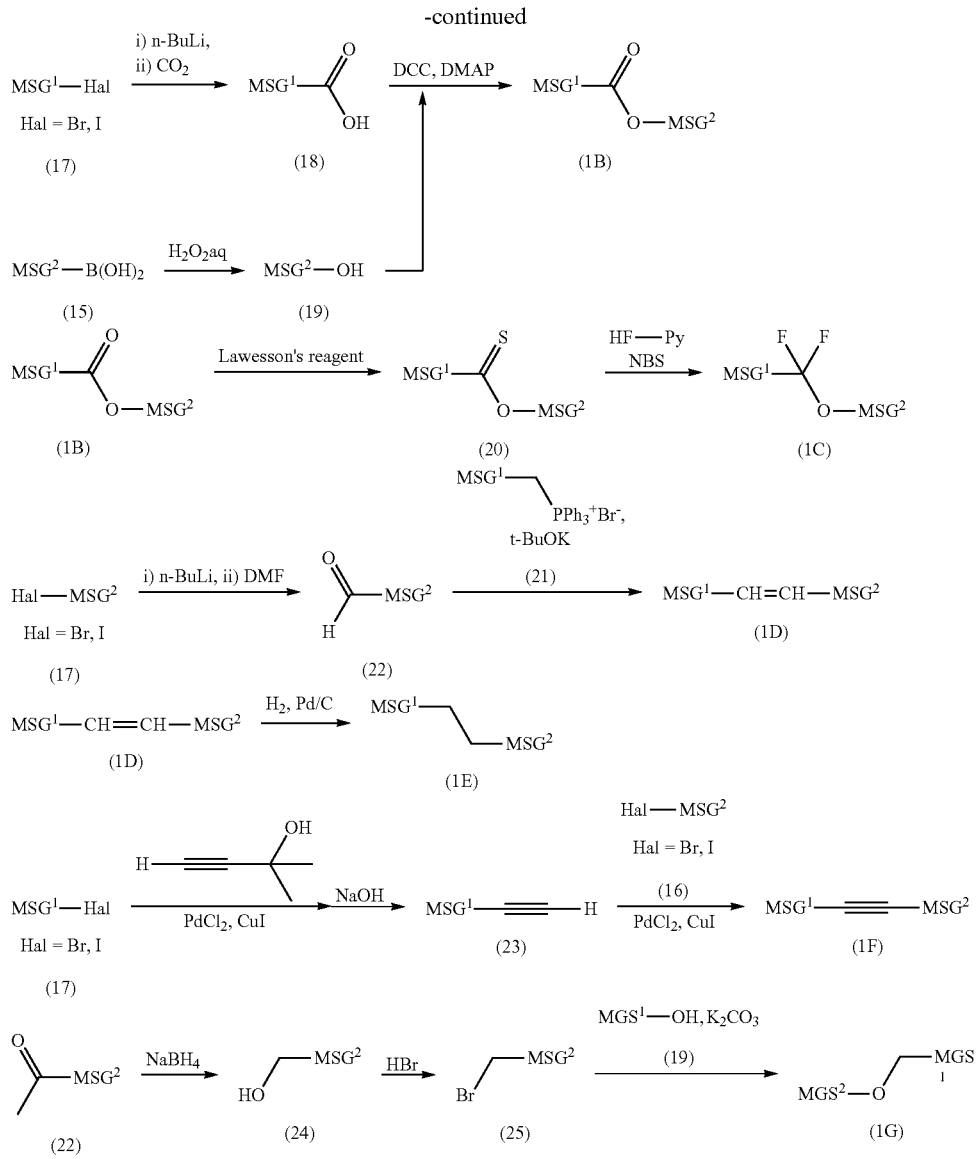

Next, methods for forming various kinds of bonds of bonding group Z in compound (1) will be explained in section (I) to section (XI) below.

(I) Formation of a Single Bond

Compound (1A) is prepared by allowing arylboronic acid (15) to react, in the presence of an aqueous solution of carbonate and a catalyst such as tetrakis(triphenylphosphine)palladium, with compound (16) prepared according to a known method. Compound (1A) is also prepared by allowing compound (17) prepared according to a known method to react with n-butyllithium and subsequently with zinc chloride, and further with compound (16) in the presence of a catalyst such as dichlorobis(triphenylphosphine)palladium.

(II) Formation of —COO— and —COO—

Carboxylic acid (18) is obtained by allowing compound (17) to react with n-butyllithium and subsequently with carbon dioxide. Compound (1B) having —COO— is prepared by performing, in the presence of 1,3-dicyclohexylcarbodiimide (DCC) and 4-dimethylaminopyridine (DMAP), dehydration of compound (18) and phenol (19) prepared according to a known method. A compound having —COO— is also prepared according to the method.

(III) Formation of —CF$_2$O— and —OCF$_2$—

Compound (20) is obtained by treating compound (1B) with a thiation reagent such as Lawesson's reagent. Compound (1C) having —CF$_2$O— is prepared by fluorinating compound (20) with a hydrogen fluoride pyridine complex and N-bromosuccinimide (NBS). See M. Kuroboshi et al., Chem. Lett., 1992, 827. Compound (1C) is also prepared by fluorinating compound (20) with (diethylamino)sulfur trifluoride (DAST). See W. H. Bunnelle et al., J. Org. Chem. 1990, 55, 768. A compound having —OCF$_2$— is also prepared according to the method. The bonding groups can also be formed according to the method described in Peer. Kirsch et al., Angew. Chem. Int. Ed. 2001, 40, 1480.

(IV) Formation of —CH═CH—

Aldehyde (22) is obtained by treating compound (17) with n-butyllithium and then allowing the treated compound (17) to react with formamide such as N,N-dimethylformamide (DMF). Compound (1D) is prepared by allowing phosphorus ylide generated by treating phosphonium salt (21) prepared according to a known method with a base such as potassium tert-butoxide to react with aldehyde (22). Because a cis isomer is generated depending on reaction conditions, the cis isomer is isomerized to a trans isomer according to a known method, when necessary.

(V) Formation of —$(CH_2)_2$—

Compound (1E) is prepared by hydrogenating compound (1D) in the presence of a catalyst such as palladium on carbon.

(VI) Formation of —C≡C—

Compound (23) is obtained by allowing compound (17) to react with 2-methyl-3-butyn-2-ol in the presence of a catalyst including dichloropalladium and copper halide, and then performing deprotection under basic conditions. Compound (1F) is prepared by allowing compound (23) to react with compound (16) in the presence of a catalyst including dichlorobistriphenylphosphine palladium and copper halide.

(VII) Formation of —$CH_2O$— or —$OCH_2$—

Compound (24) is obtained by reducing compound (22) with a reducing agent such as sodium borohydride. Compound (25) is obtained by halogenating compound (24) with hydrobromic acid or the like. Compound (1G) is prepared by allowing compound (25) to react with compound (19) in the presence of potassium carbonate or the like.

1-4-2 Method for Preparing Ring A

Starting materials are commercially available or synthetic processes are well known for rings such as 1,4-cyclohexylene, tetrahydropyran-2,5-diyl, tetrahydropyran-3,6-diyl, 1,4-phenylene, 2-fluoro-1,4-phenylene, 2,3-difluoro-1,4-phenylene, 2,5-difluoro-1,4-phenylene, 2,6-difluoro-1,4-phenylene and 2,3,5,6-tetrafluoro-1,4-phenylene.

1-4-3 Method for Preparing Compound (1)

A plurality of methods for preparing a compound represented by formula (1) are known. An example thereof is described herein. Aldehyde derivative (31) is allowed to react with ethyl bromofluoroacetate (32) in the presence of zinc or the like, and thus ester derivative (33) is derived therefrom. Then, ester derivative (33) is allowed to react with 1,8-diazobicyclo[5,4,6]undec-7-en (DBU), carbon disulfide and methyl iodide, and further to react with di-tert-butylperoxide and diphenyl phosphine oxide, and thus ester derivative (34) is derived therefrom. Ester derivative (34) is reduced with lithium aluminum hydride, and thus alcohol derivative (35) is derived therefrom. Then, alcohol derivative (35) is allowed to couple with alcohol or phenol derivative (36) in the presence of diethyl azodicarboxylate (DEAD), triphenylphosphine or the like, and thus compound (1) in which $X^1$, $X^2$ and $X^4$ are hydrogen and $X^3$ is fluorine can be derived therefrom.

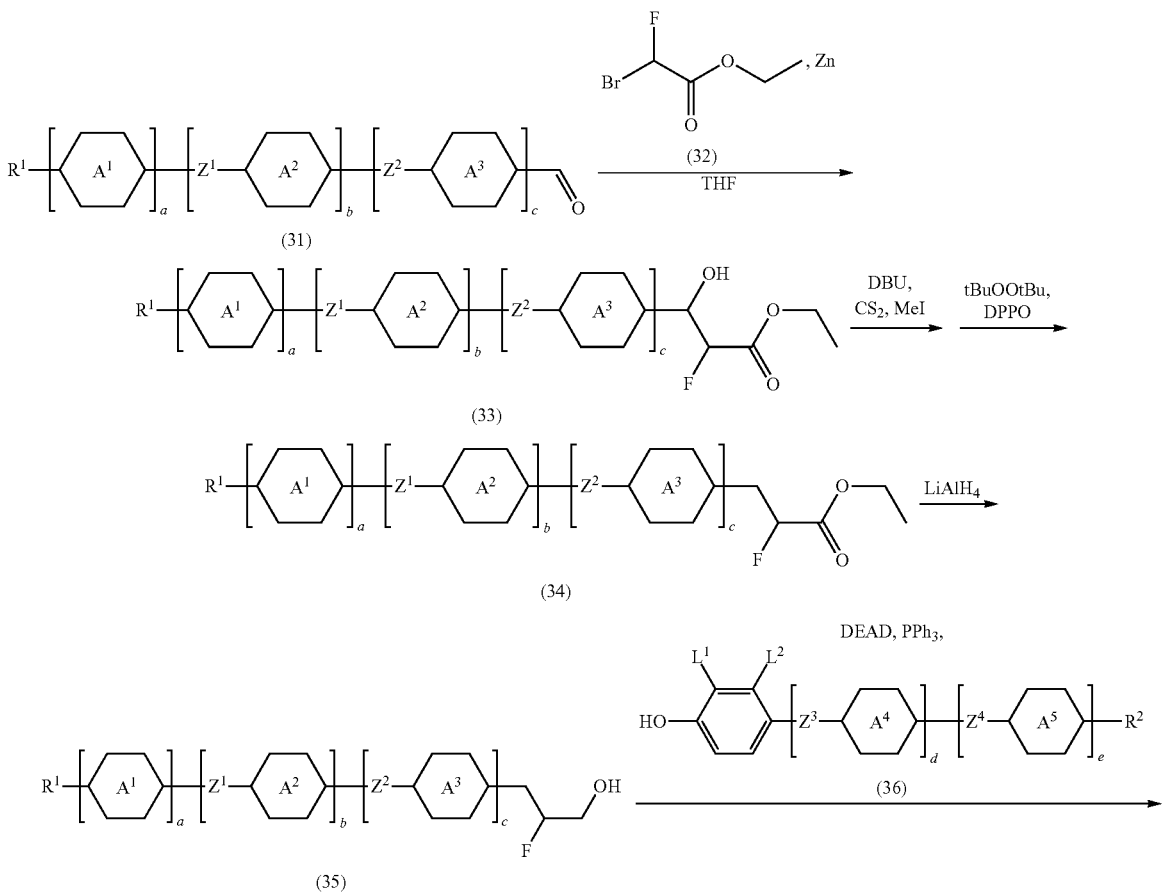

-continued

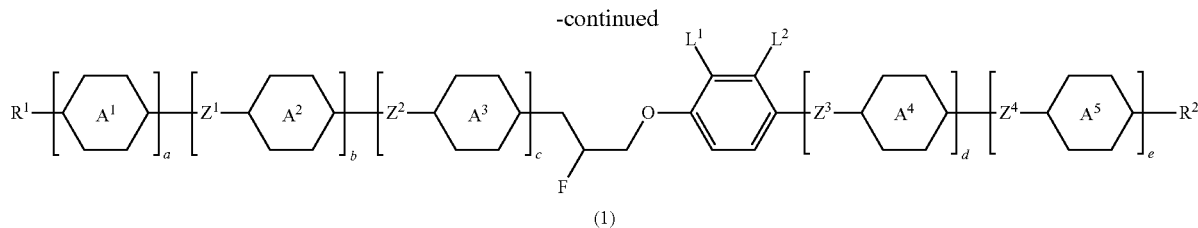

(1)

In the formulas, $R^1$, $R^2$, ring $A^1$, ring $A^2$, ring $A^3$, ring $A^4$, ring $A^5$, $Z^1$, $Z^2$, $Z^3$, $Z^4$, $L^1$, $L^2$, a, b, c, d and e are defined in a manner identical with the definitions in item 1.

Among the compounds represented by formula (1), when $X^1$ and $X^3$ are fluorine and $X^2$ and $X^4$ are hydrogen, compound (1) can also be prepared by a method as described below.

Ester derivative (33) prepared by the method described above is reduced with lithium aluminum hydride, and thus alcohol derivative (37) is derived therefrom. Then, alcohol derivative (37) is allowed to couple with alcohol or phenol derivative (36) in the presence of diethyl azodicarboxylate (DEAD), triphenyl phosphine or the like, and thus alcohol derivative (38) is derived therefrom. Alcohol derivative (37) is fluorinated using a fluorinating agent such as bis-(2-methoxyethyl)aminosulfate trifluoride (Deoxo-Fluor), and thus compound (1) can be derived therefrom.

Among the compounds represented by formula (1), when $X^3$ and $X^4$ are fluorine and $X^1$ and $X^2$ are hydrogen, compound (1) can also be prepared by using ethyl bromodifluoroacetate (39) in place of ethyl bromofluoroacetate (32) in the method described above.

(39)

Among the compounds represented by formula (1), when $X^1$ is fluorine and $X^2$, $X^3$ and $X^4$ are hydrogen, compound (1)

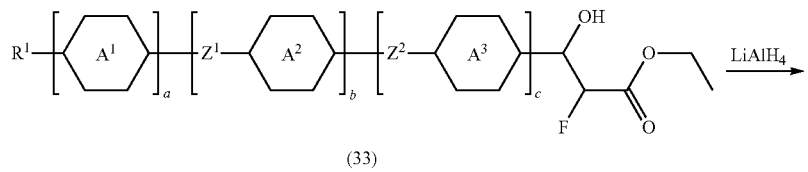

(33)

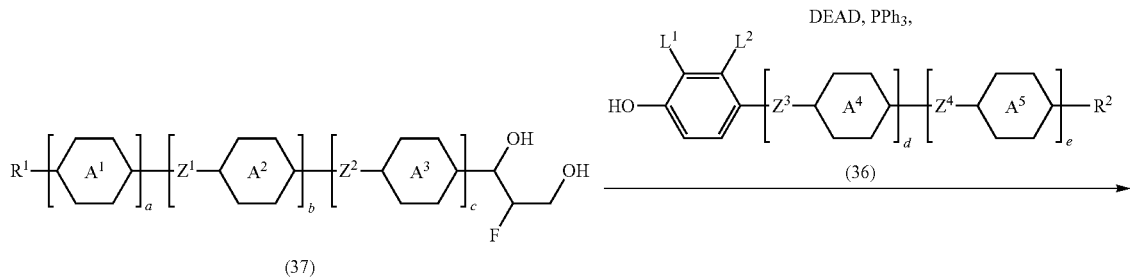

(37)

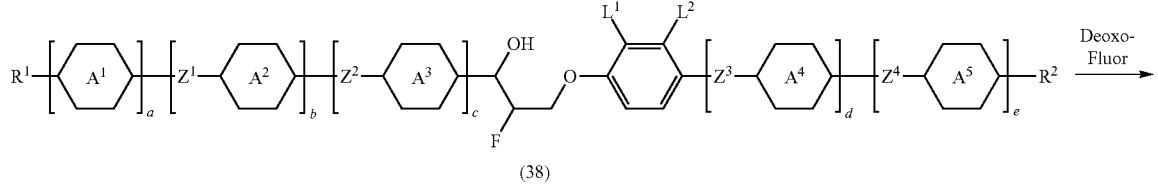

(38)

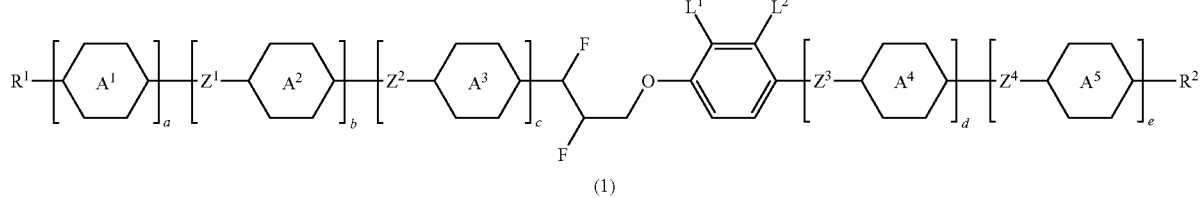

(1)

In the formulas, $R^1$, $R^2$, ring $A^1$, ring $A^2$, ring $A^3$, ring $A^4$, ring $A^5$, $Z^1$, $Z^2$, $Z^3$, $Z^4$, $L^1$, $L^2$, a, b, c, d and e are defined in a manner identical with the definitions in item 1.

can also be prepared by using ethyl bromoacetate (40) in place of ethyl bromofluoroacetate (32) in the method described above.

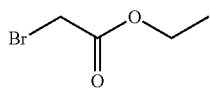

(40)

Among the compounds represented by formula (1), when $X^1$ and $X^2$ are fluorine and $X^3$ and $X^4$ are hydrogen, according to the method described above, alcohol derivative (42) is prepared by using ethyl bromoacetate (40), then alcohol derivative (42) is oxidized with an oxidizing agent such as potassium permanganate, and thus ketone derivative (43) is derived therefrom. Then, ketone derivative (43) is fluorinated by using a fluorinating agent such as DAST, and thus compound (1) can be derived therefrom.

adding to component A a component selected from the group of components B, C, D and E as described below.

The component to be added to component A is preferably a mixture prepared by mixing component B including at least one kind compound selected from the group of compounds represented by formulas (2), (3) and (4), and/or component C including at least one kind compound selected from the group of compounds represented by formula (5), and/or component D including at least one kind compound selected from the group of compounds represented by formulas (6), (7), (8), (9), (10) and (11). Furthermore, the threshold voltage, the temperature range of the liquid crystal phase, a value of optical anisotropy, a value of dielectric anisotropy, the viscosity and so forth can be adjusted by addition of component E including at least one kind compound selected from the group of compounds represented by formulas (12), (13) and (14).

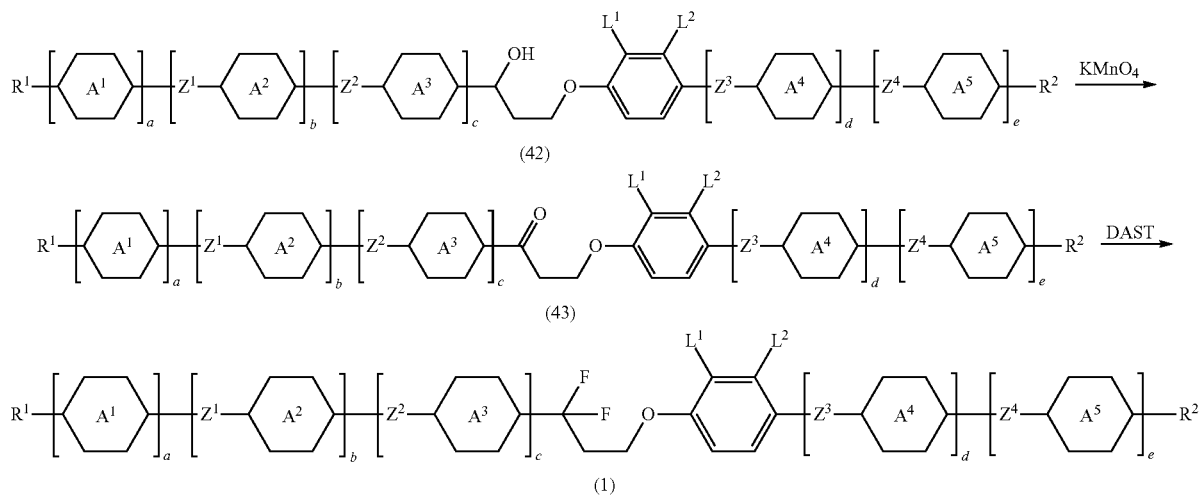

In the formulas, $R^1$, $R^2$, ring $A^1$, ring $A^2$, ring $A^3$, ring $A^4$, ring $A^5$, $Z^1$, $Z^2$, $Z^3$, $Z^4$, $L^1$, $L^2$, a, b, c, d and e are defined in a manner identical with the definitions in item 1.

2 Composition of the Invention

Hereinafter, the liquid crystal composition of the invention will be explained. The component of the liquid crystal composition is characterized by containing at least one kind of compound (1), but may contain two or more kinds of compound (1), or may be consisted of compound (1). When the liquid crystal composition of the invention is prepared, the component thereof can also be selected by taking the dielectric anisotropy of compound (1) into consideration, for example. The liquid crystal composition in which the component is selected has a small viscosity, a large negative dielectric anisotropy, a suitable elastic constant $K_{33}$ and a low threshold voltage, and also has a high maximum temperature of the nematic phase (maximum temperature: phase transition temperature between the nematic phase and an isotropic phase) and a low minimum temperature of the nematic phase.

Liquid Crystal Composition (1)

The liquid crystal composition of the invention is needed to contain the compound represented by formula (1) according to the invention as component A. The liquid crystal composition may be a composition containing only component A, or a composition containing component A and any other component whose name is not particularly described herein. However, the liquid crystal composition having various characteristics according to the invention can be provided by Moreover, each component of the liquid crystal composition used in the invention has no significant difference in physical characteristics even if each component is an analog including an isotopic element of each element.

Among types of component B described above, suitable examples of compounds represented by formula (2) may be represented by formulas (2-1) to (2-16), suitable examples of compounds represented by formula (3) may be represented by formulas (3-1) to (3-112), and suitable examples of compounds represented by formula (4) may be represented by formulas (4-1) to (4-54).

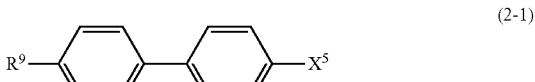

(2-1)

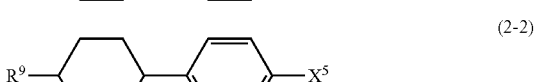

(2-2)

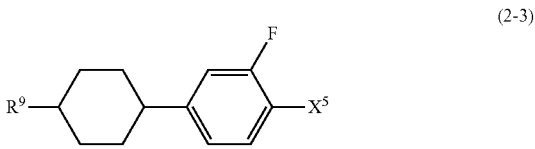

(2-3)

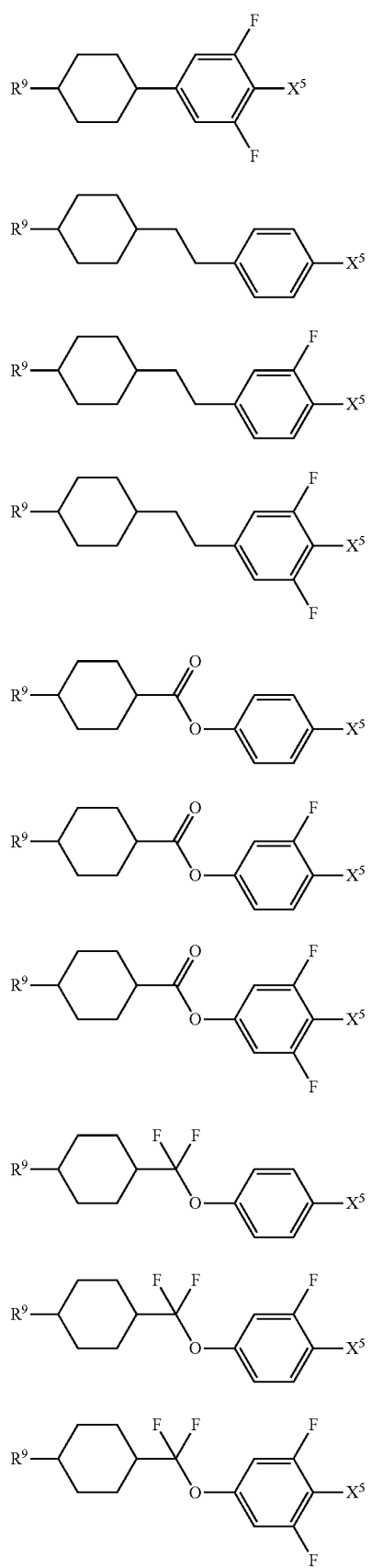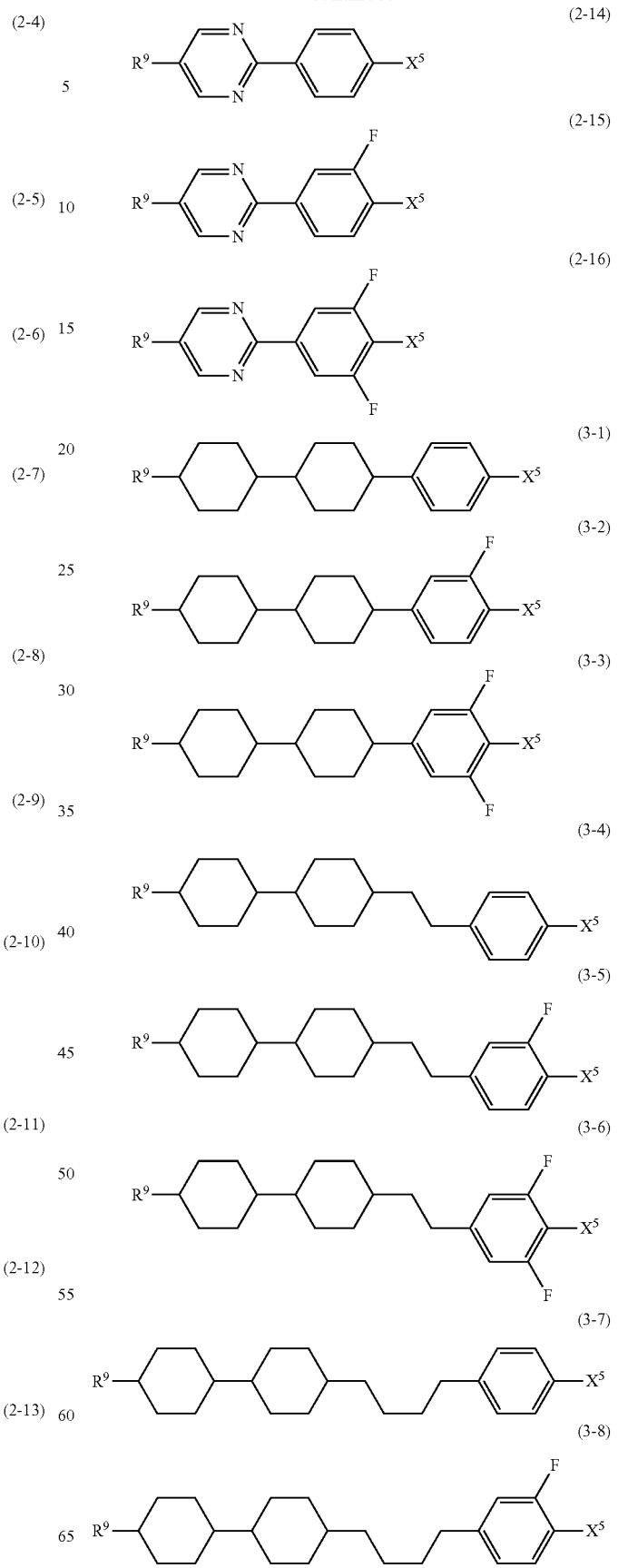

(3-9)
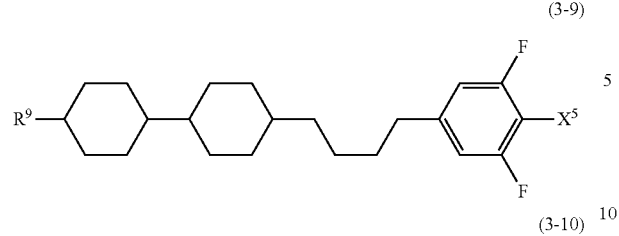
(3-10)
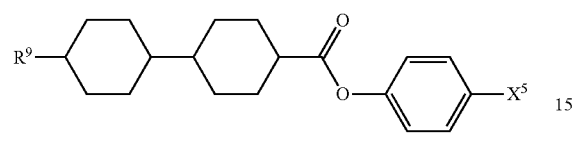
(3-11)
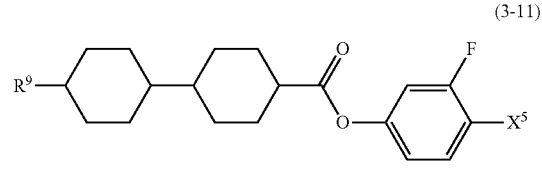
(3-12)
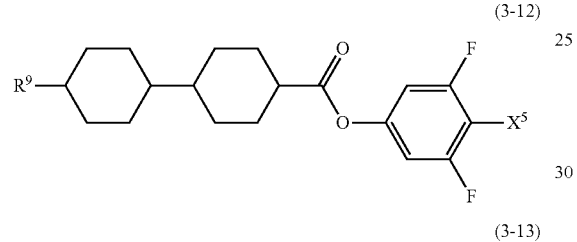
(3-13)
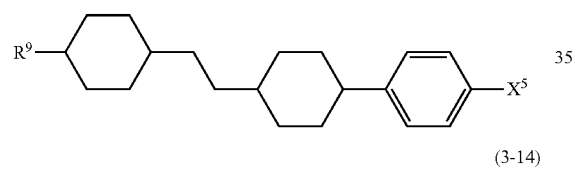
(3-14)
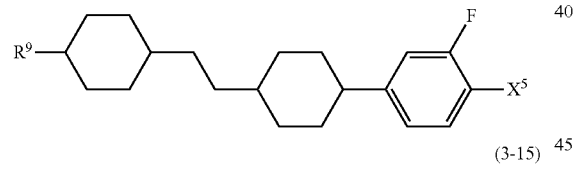
(3-15)
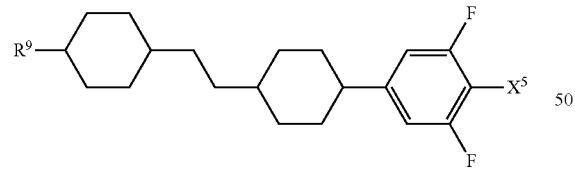
(3-16)
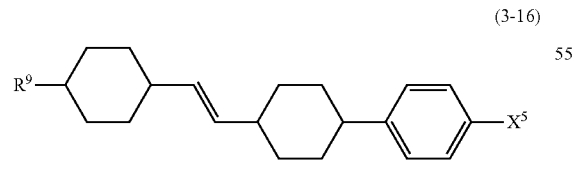
(3-17)
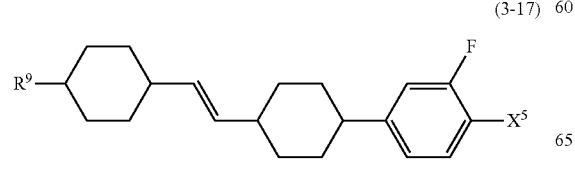
(3-18)
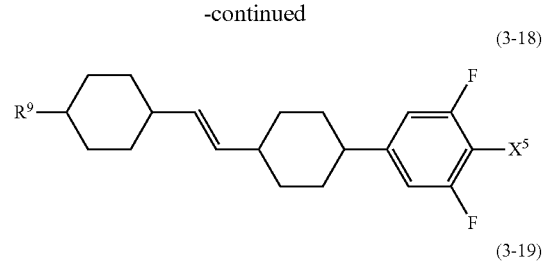
(3-19)
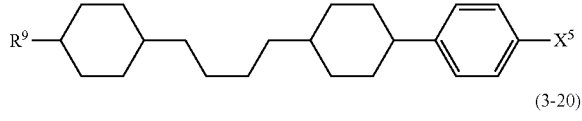
(3-20)
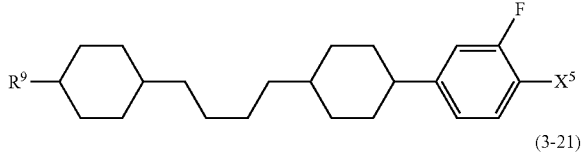
(3-21)
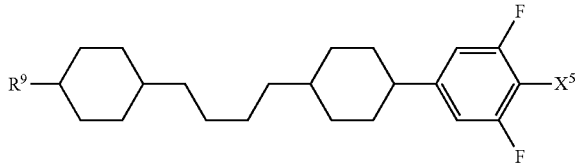
(3-22)
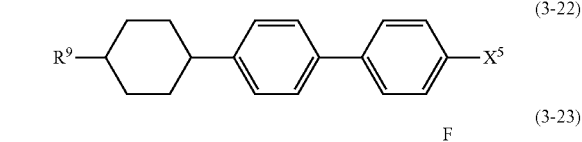
(3-23)
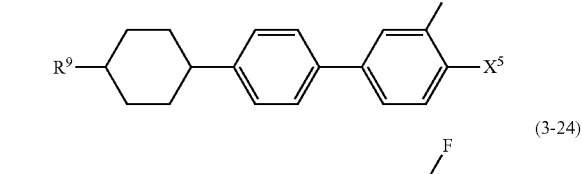
(3-24)
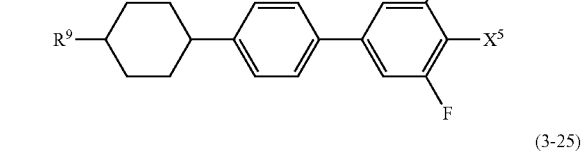
(3-25)
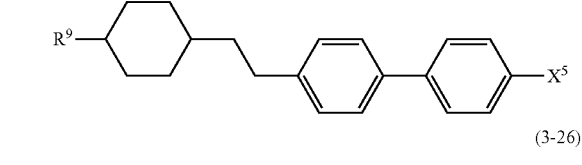
(3-26)
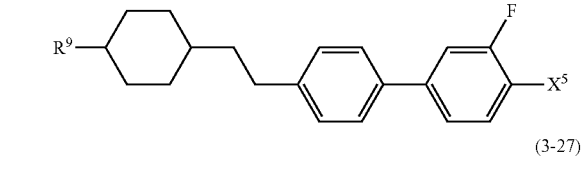
(3-27)
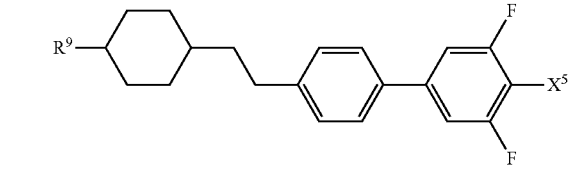

(3-28)
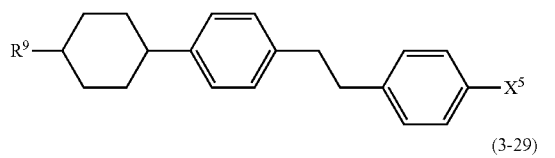
(3-29)
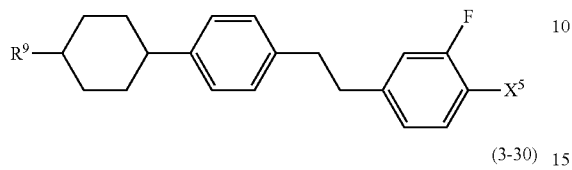
(3-30)
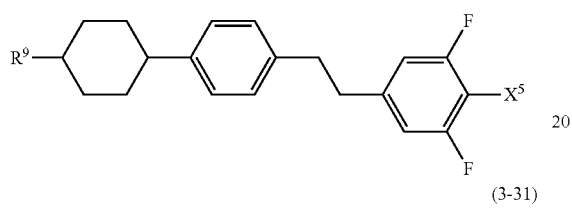
(3-31)
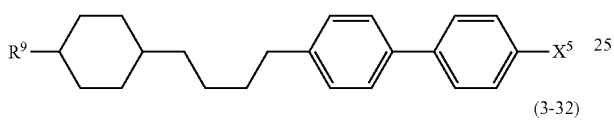
(3-32)
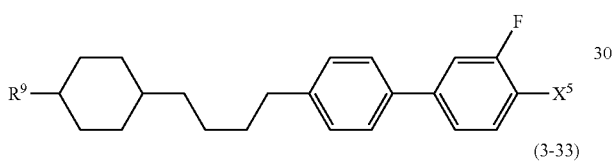
(3-33)
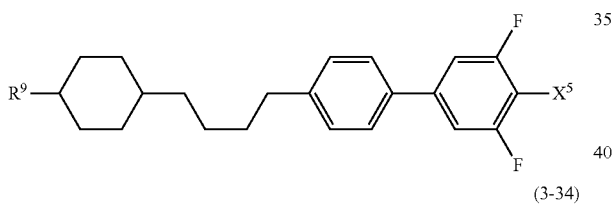
(3-34)
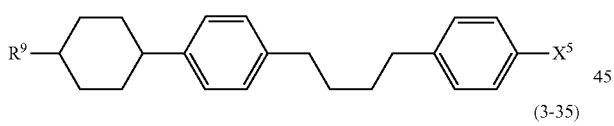
(3-35)
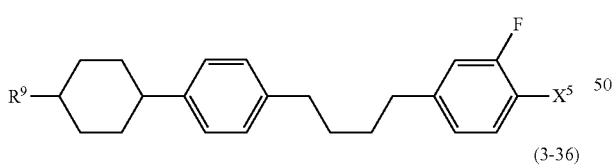
(3-36)
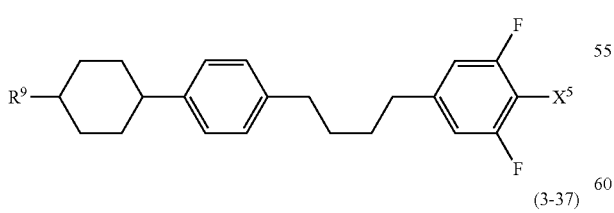
(3-37)
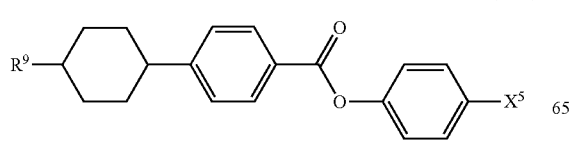
(3-38)
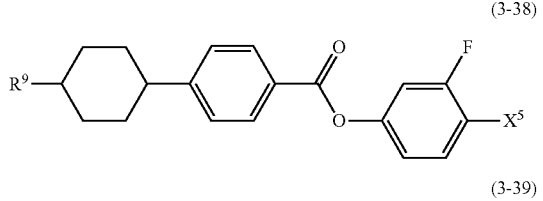
(3-39)
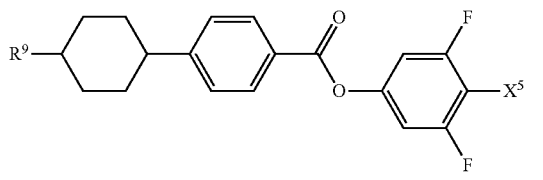
(3-40)
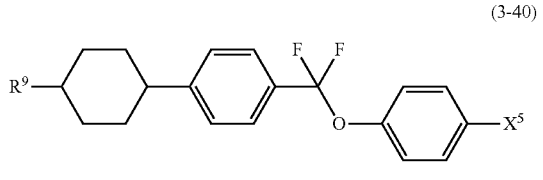
(3-41)
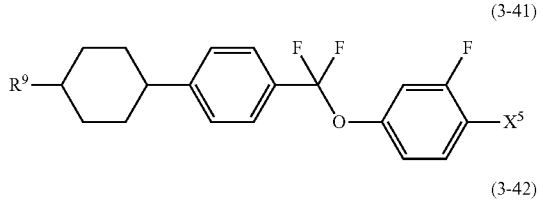
(3-42)
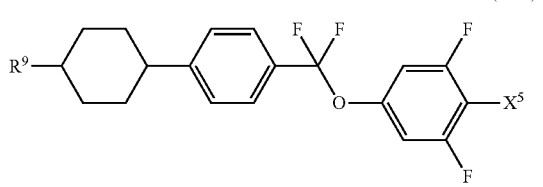
(3-43)
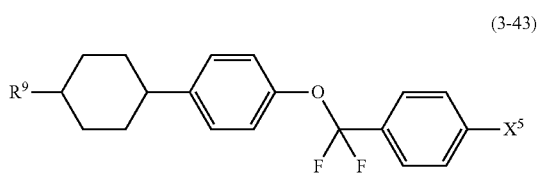
(3-44)
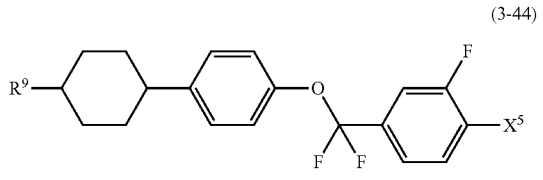
(3-45)
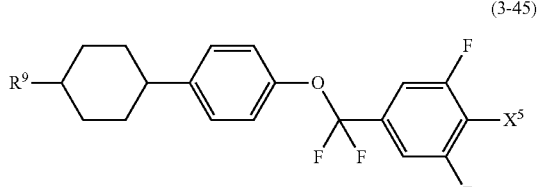
(3-46)

-continued
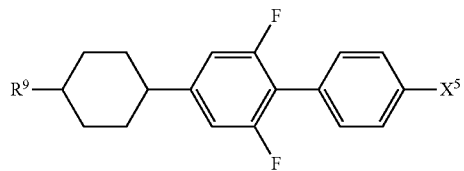
(3-47)
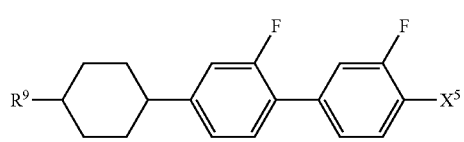
(3-48)
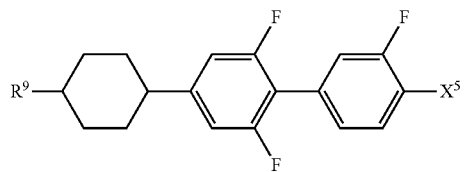
(3-49)
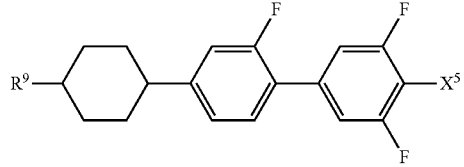
(3-50)
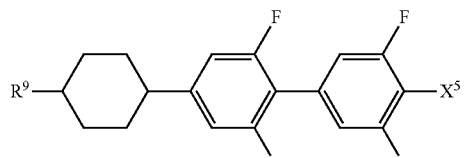
(3-51)
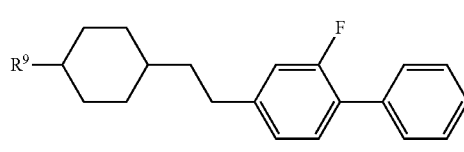
(3-52)
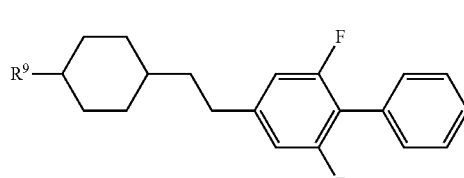
(3-53)
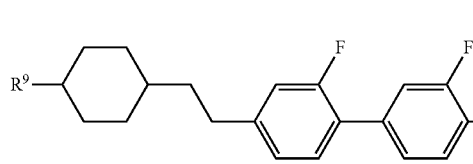
(3-54)
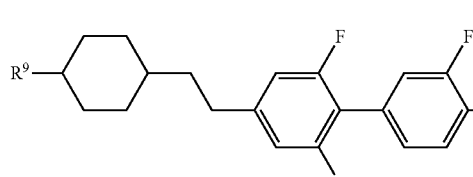
(3-55)
-continued
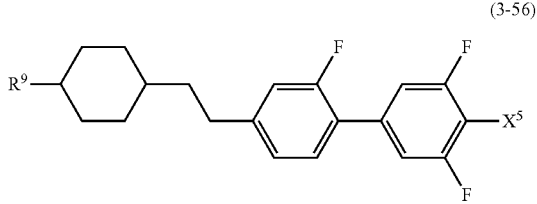
(3-56)
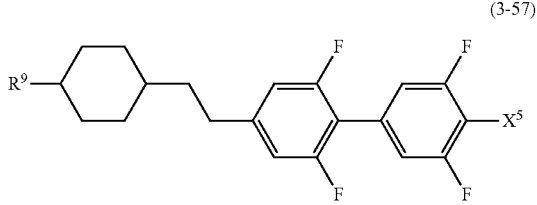
(3-57)
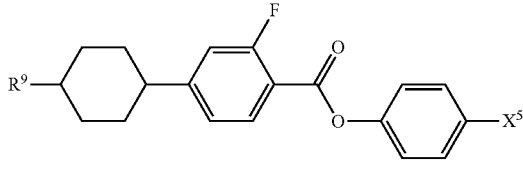
(3-58)
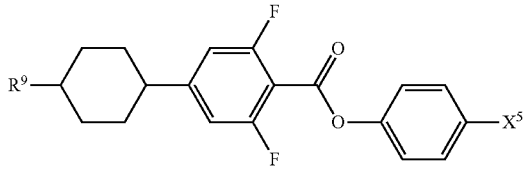
(3-59)
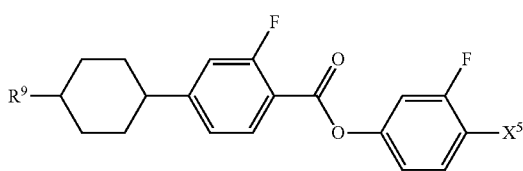
(3-60)
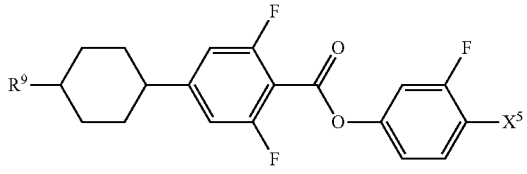
(3-61)
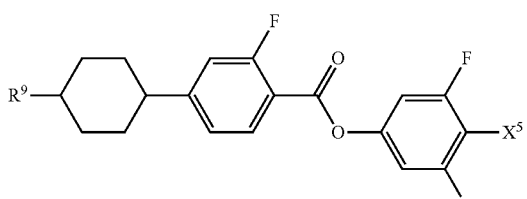
(3-62)

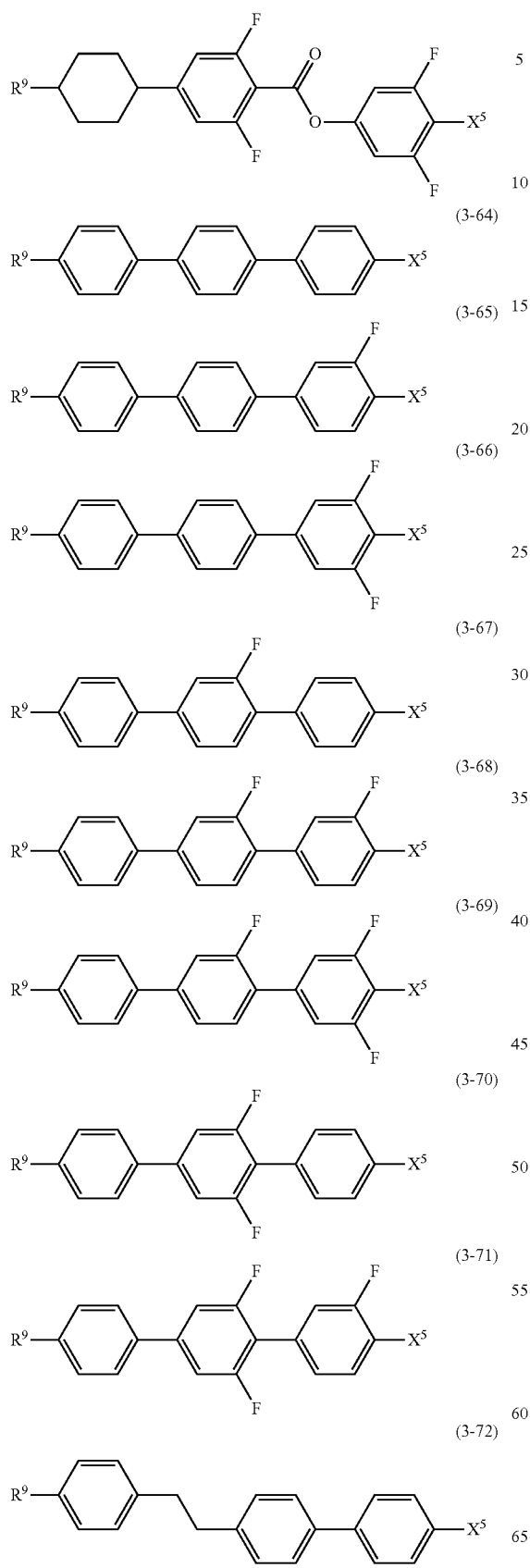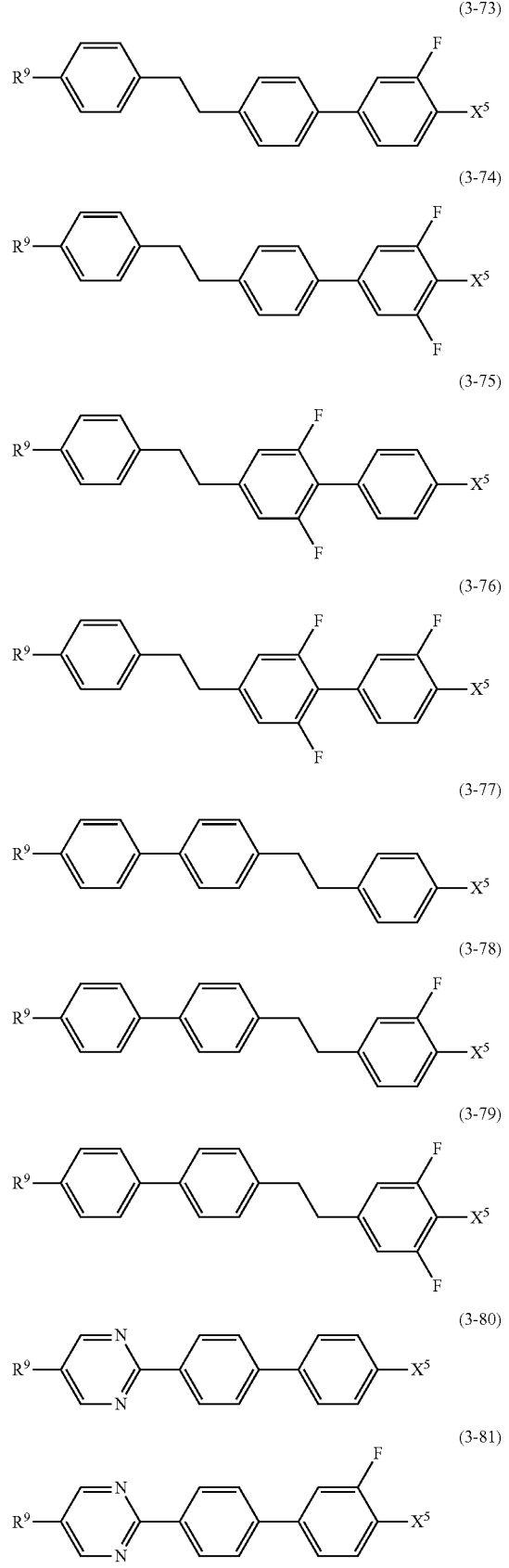

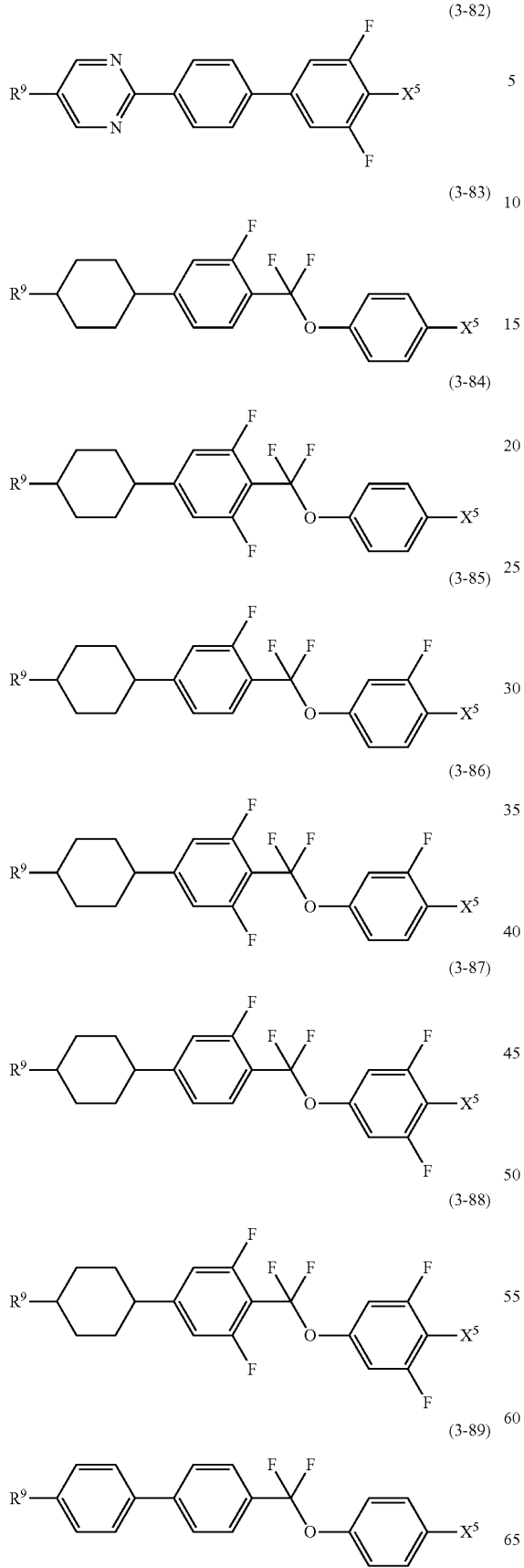
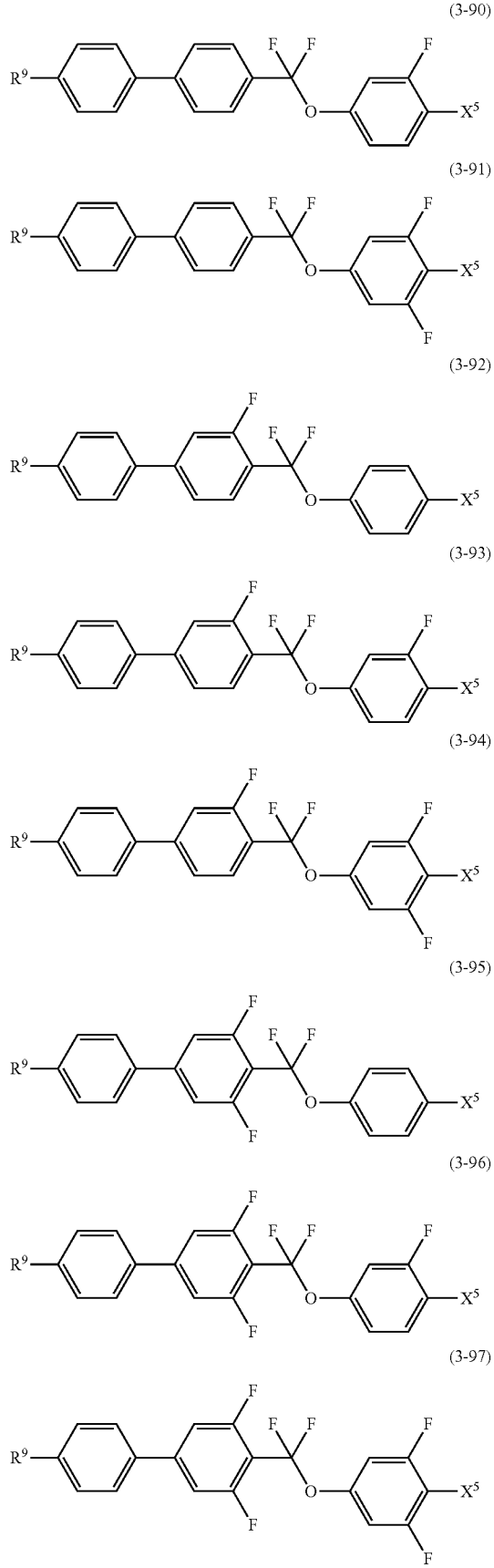

(3-98) 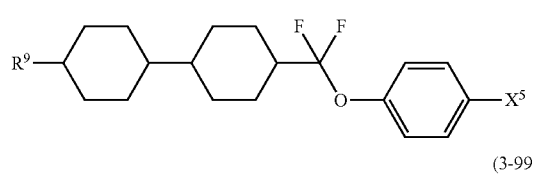
(3-99) 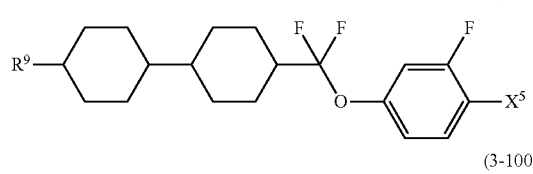
(3-100) 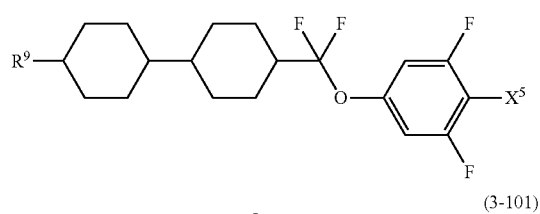
(3-101) 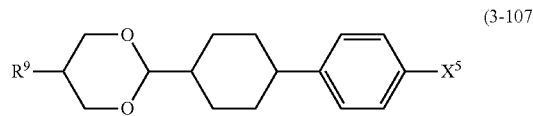
(3-102) 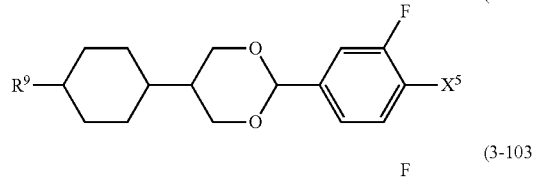
(3-103) 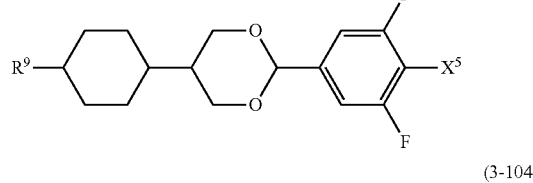
(3-104) 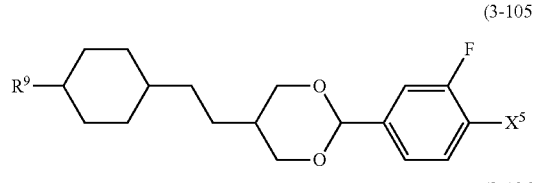
(3-105)
(3-106)
(3-107)
(3-108) 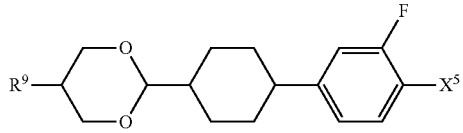
(3-109) 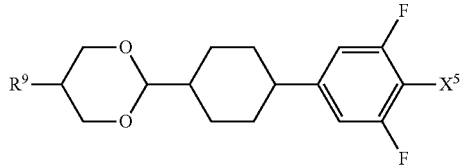
(3-110) 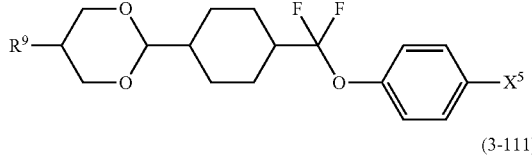
(3-111) 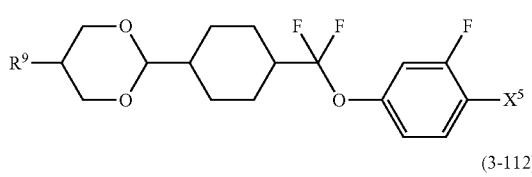
(3-112) 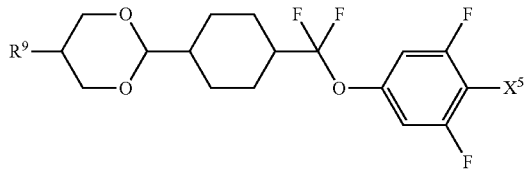
(4-1) 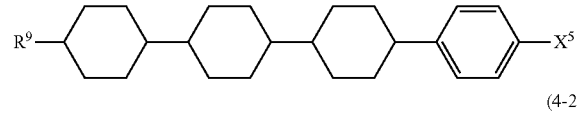
(4-2) 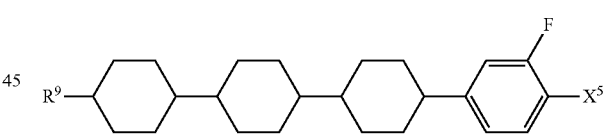
(4-3) 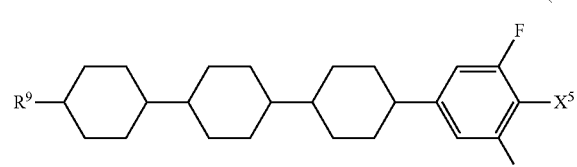
(4-4) 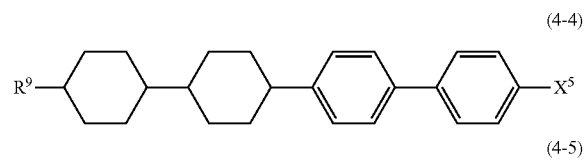
(4-5) 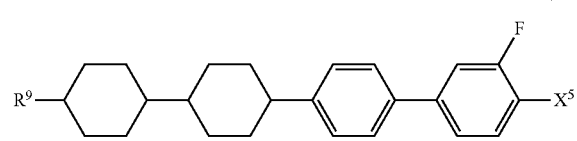

(4-6) 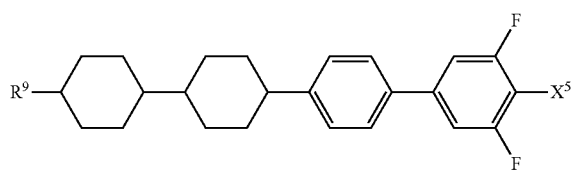
(4-7) 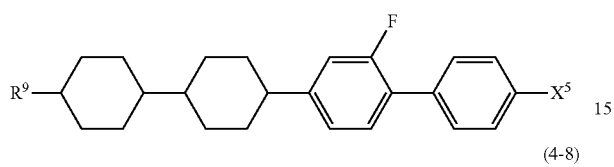
(4-8) 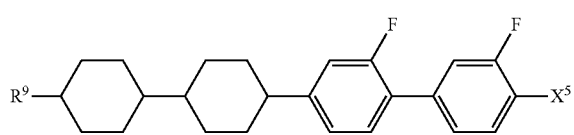
(4-9) 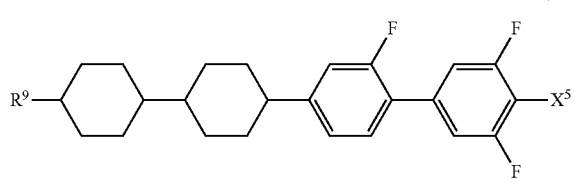
(4-10) 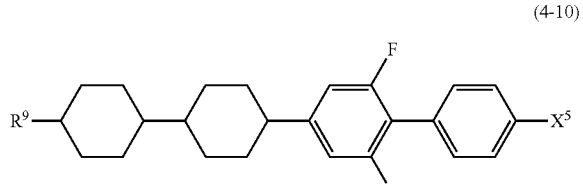
(4-11) 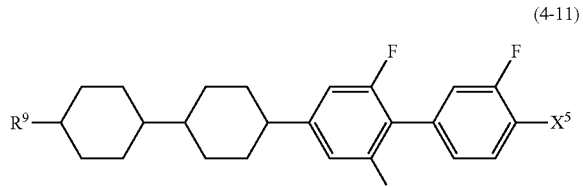
(4-12) 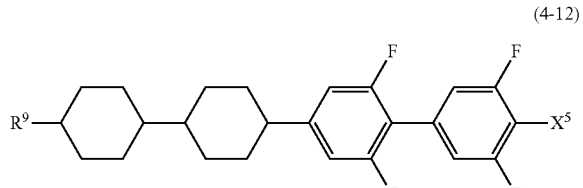
(4-13) 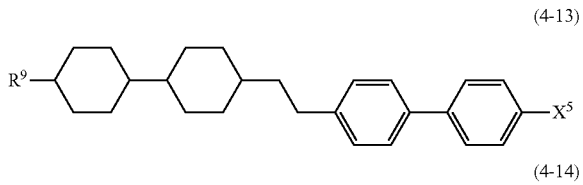
(4-14) 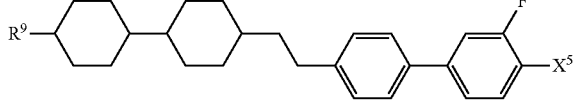
(4-15) 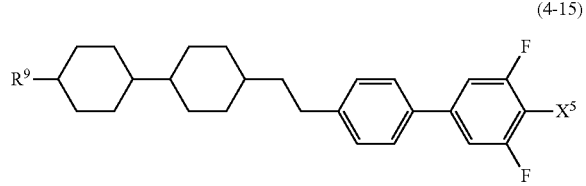
(4-16) 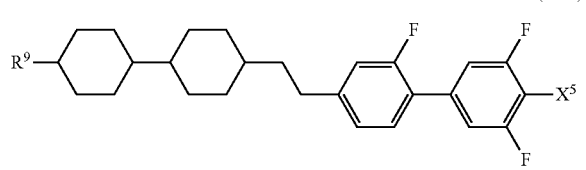
(4-17) 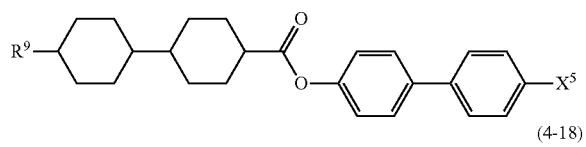
(4-18) 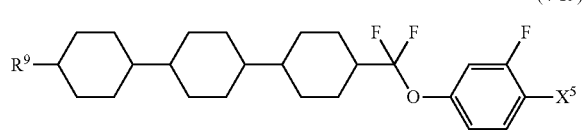
(4-19) 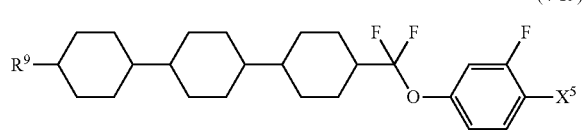
(4-20) 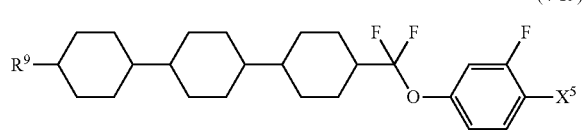
(4-21) 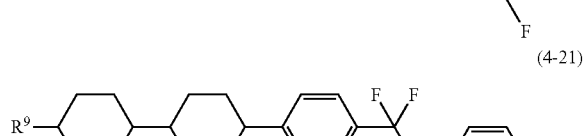
(4-22) 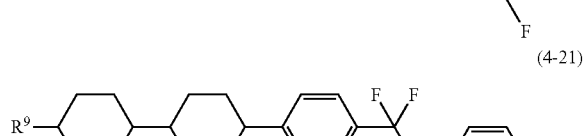
(4-23) 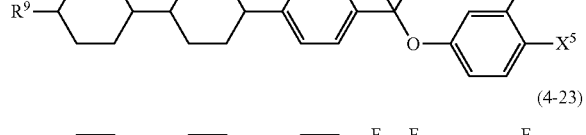
(4-24) 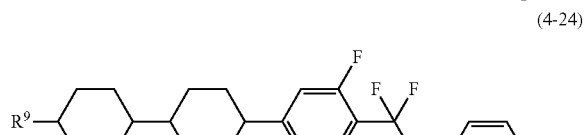

(4-25)
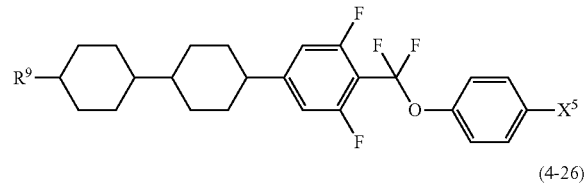
(4-26)
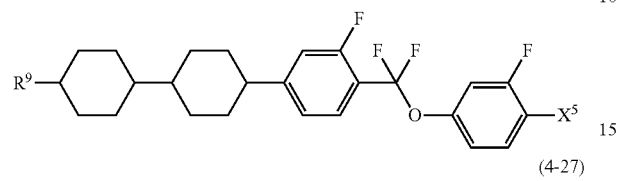
(4-27)
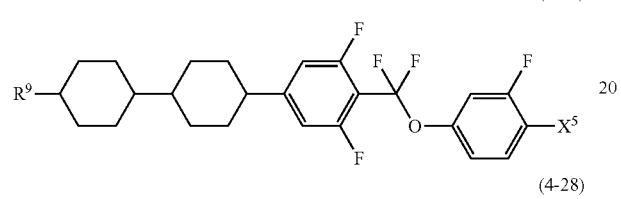
(4-28)
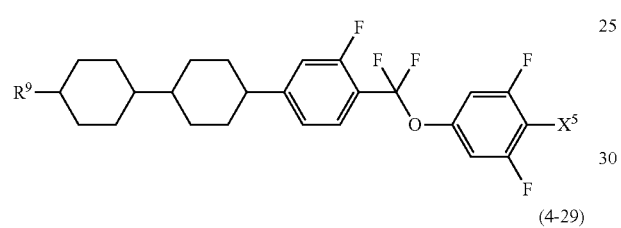
(4-29)
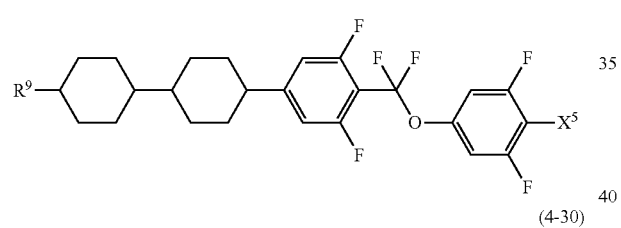
(4-30)
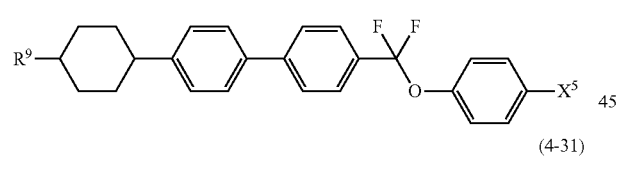
(4-31)
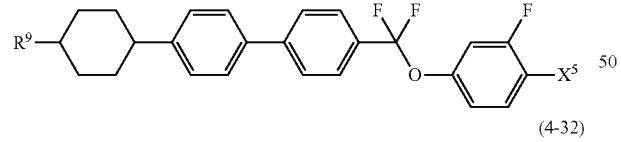
(4-32)
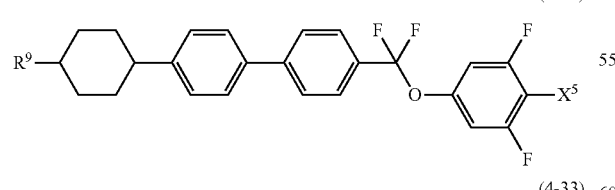
(4-33)
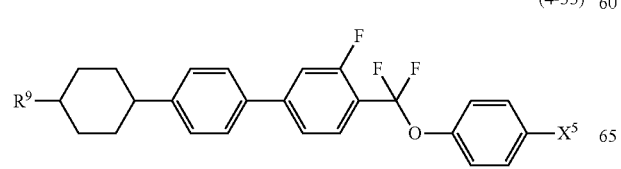
(4-34)
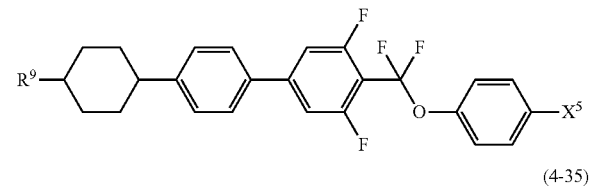
(4-35)
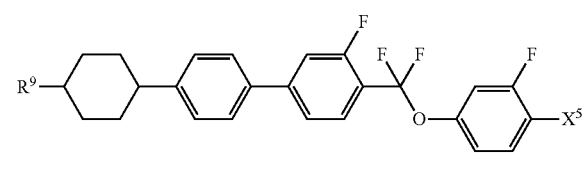
(4-36)
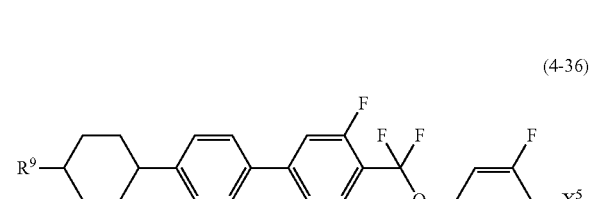
(4-37)
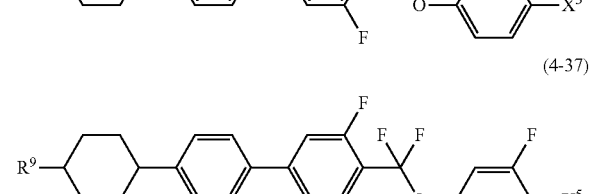
(4-38)
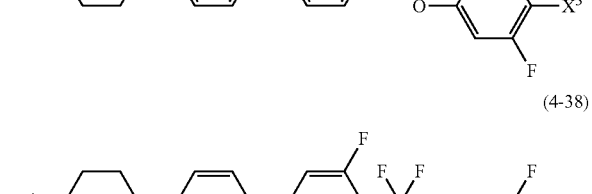
(4-39)
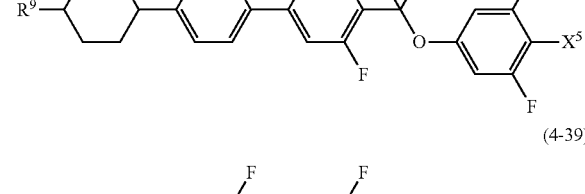
(4-40)
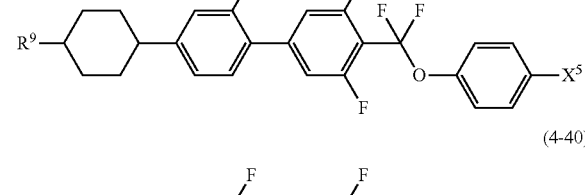
(4-41)
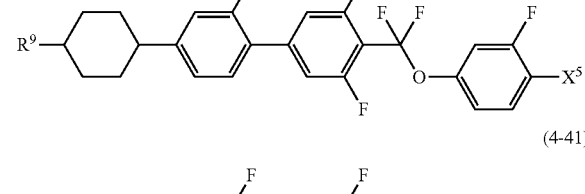

(4-42)
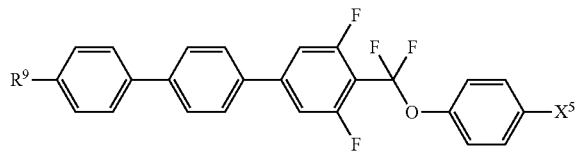

(4-43)
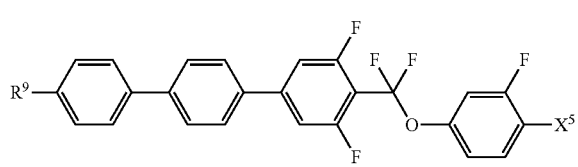

(4-44)
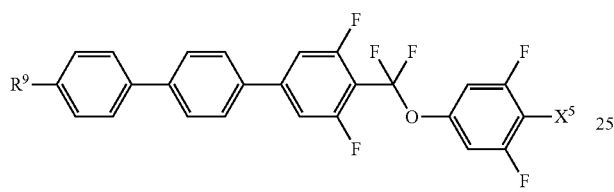

(4-45)
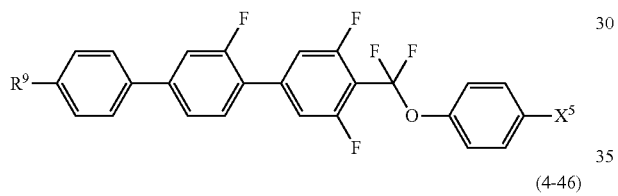

(4-46)
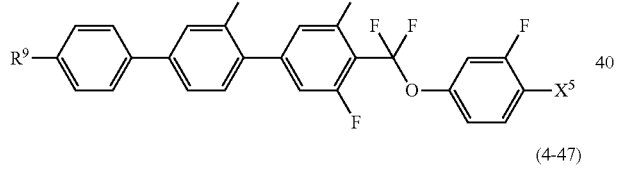

(4-47)
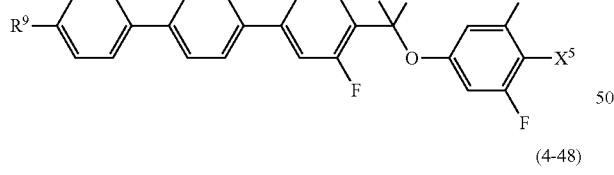

(4-48)
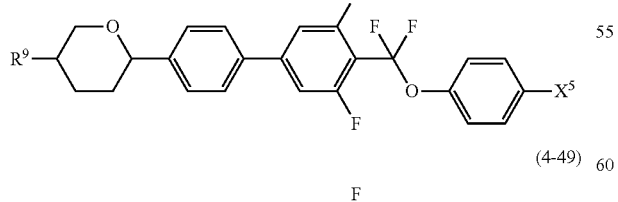

(4-49)
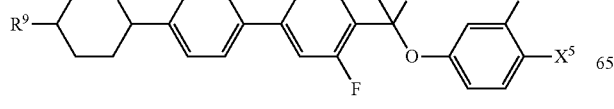

(4-50)
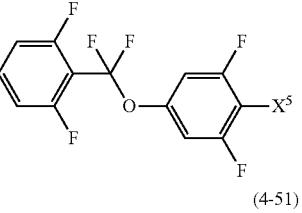

(4-51)
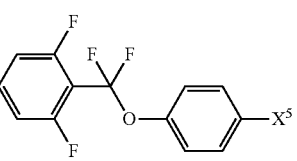

(4-52)
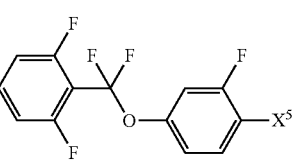

(4-53)
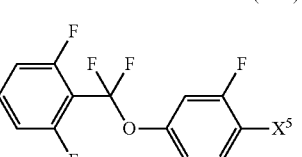

(4-54)
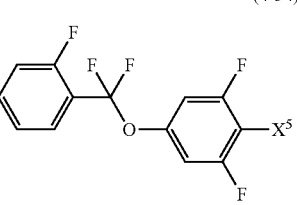

In the formulas, $R^9$ and $X^5$ are defined in a manner identical with the definitions in item 7.

The compounds represented by formulas (2), (3) and (4), namely component B, have a positive dielectric anisotropy and a superior thermal stability and chemical stability, and therefore are used for preparing the liquid crystal composition for TFT and PSA modes. The content of component B in the liquid crystal composition of the invention is suitably in the range of 1% to 99% by weight, preferably, 10% to 97% by weight, further preferably, 40% to 95% by weight, based on the total amount of the liquid crystal composition. Moreover, the viscosity can be adjusted by further adding the compounds (component E) represented by formulas (12), (13) and (14).

In formula (5) according to item 8, when o is 2, two of ring $C^2$ may be identical or different. Suitable examples of the compounds represented by formula (5), namely component C, may be represented by formulas (5-1) to (5-64).

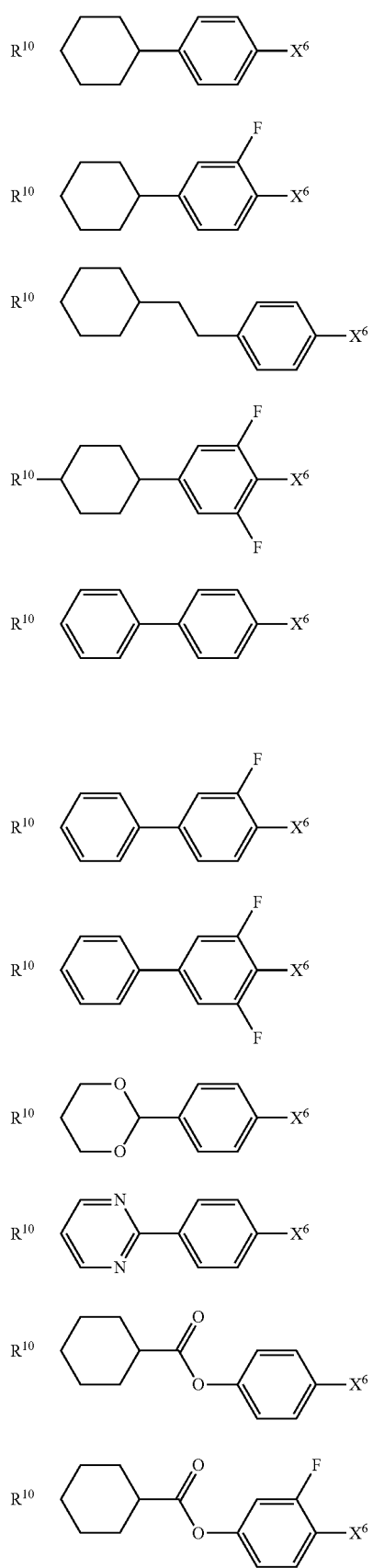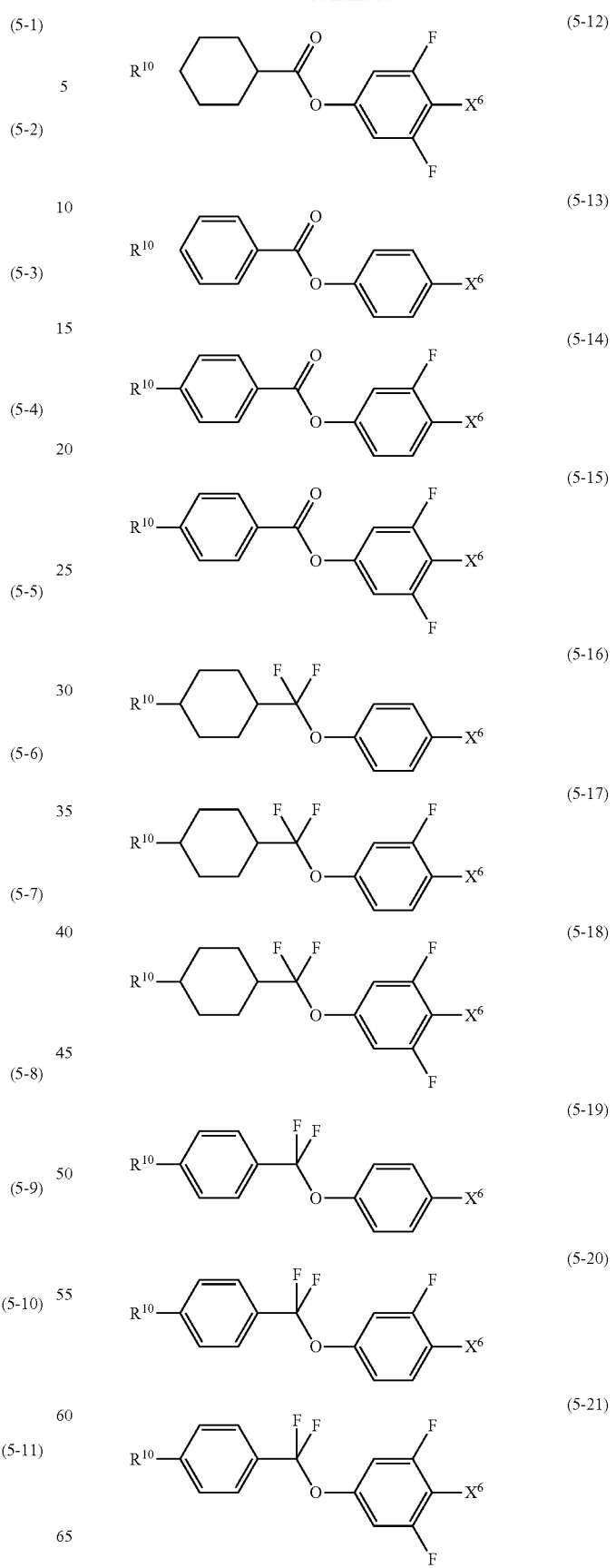

(5-22) 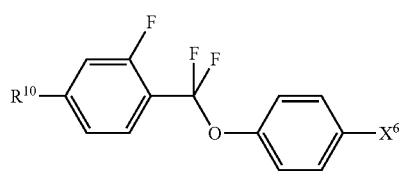
(5-23) 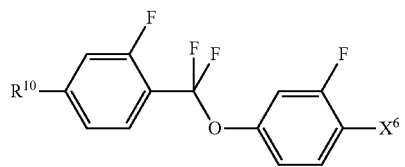
(5-24) 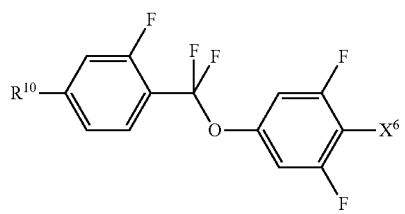
(5-25) 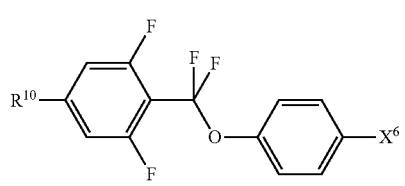
(5-26) 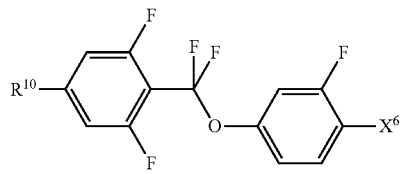
(5-27) 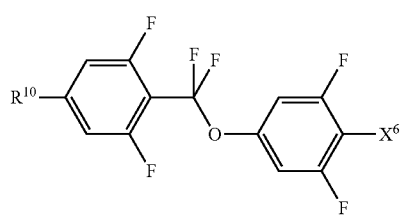
(5-28) 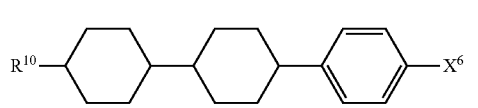
(5-29) 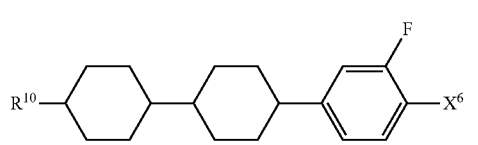
(5-30) 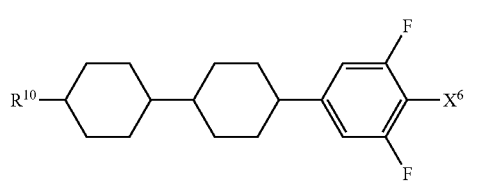
(5-31) 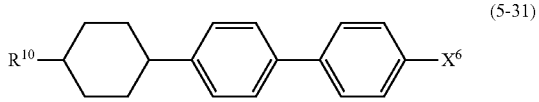
(5-32) 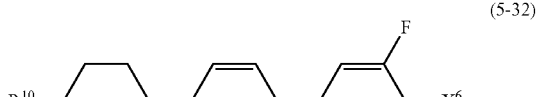
(5-33) 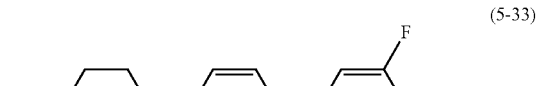
(5-34) 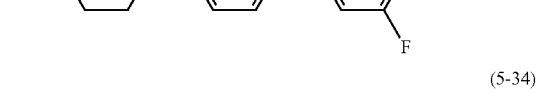
(5-35) 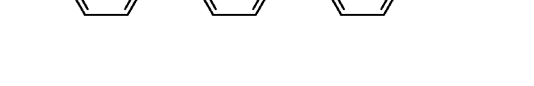
(5-36) 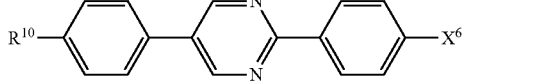
(5-37) 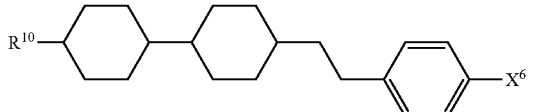
(5-38) 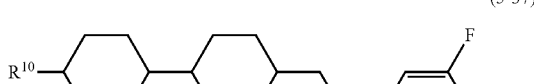
(5-39) 
(5-40) 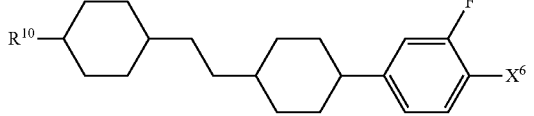

(5-41) 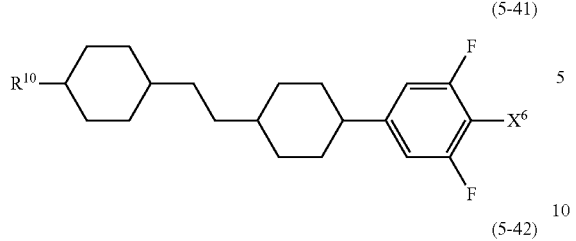
(5-42) 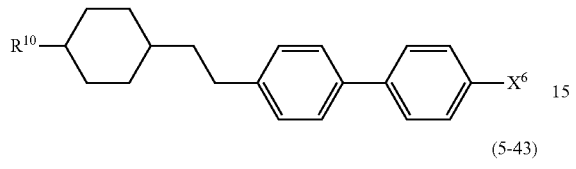
(5-43) 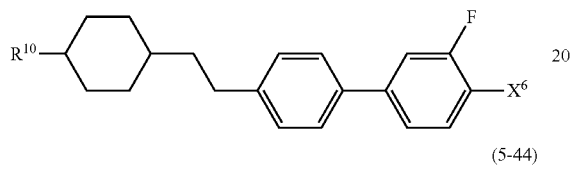
(5-44) 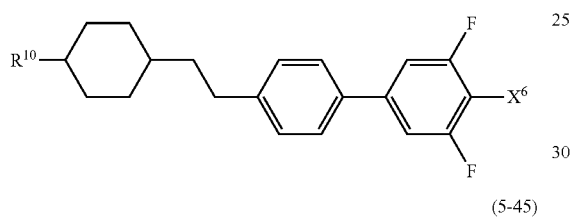
(5-45) 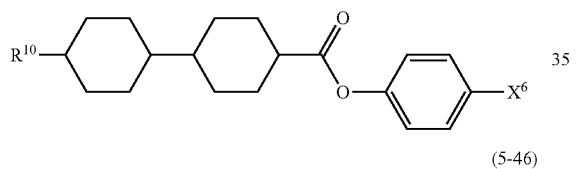
(5-46) 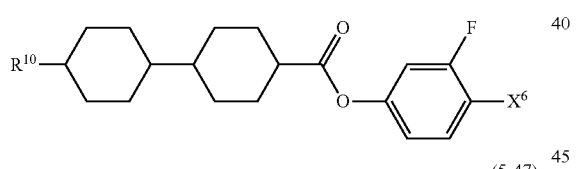
(5-47) 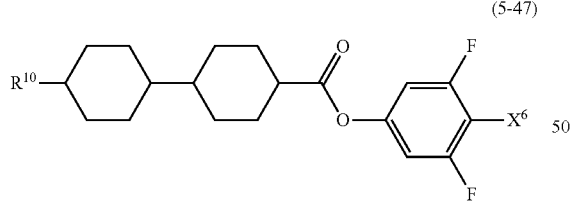
(5-48) 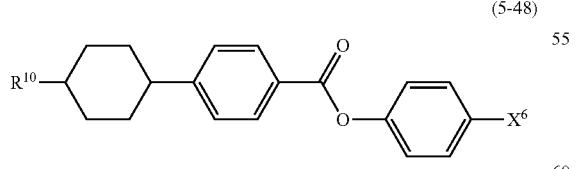
(5-49) 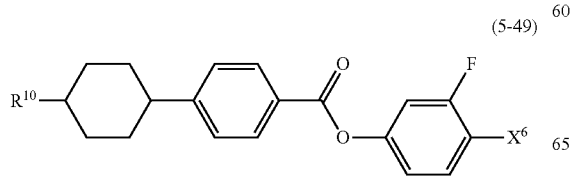
(5-50) 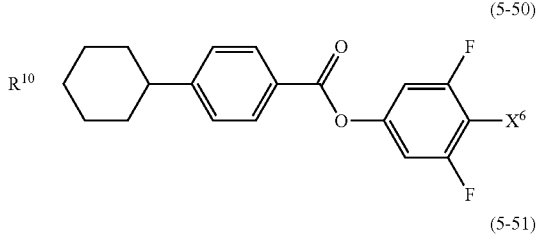
(5-51) 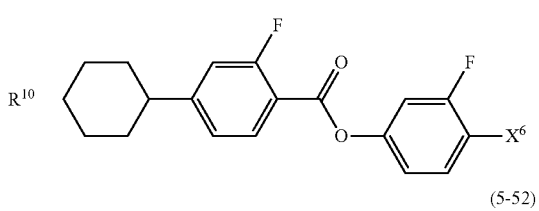
(5-52) 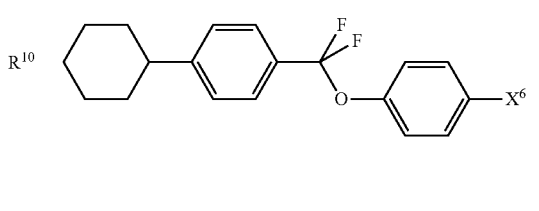
(5-53) 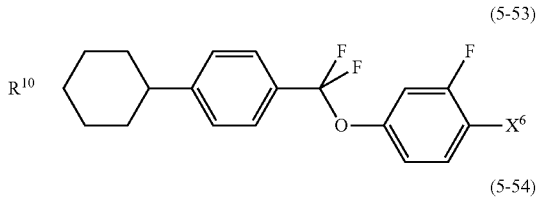
(5-54) 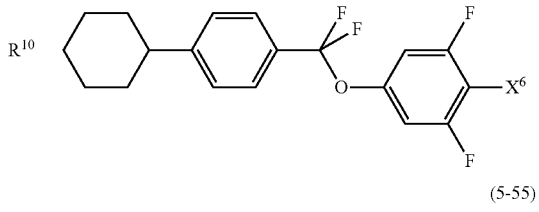
(5-55) 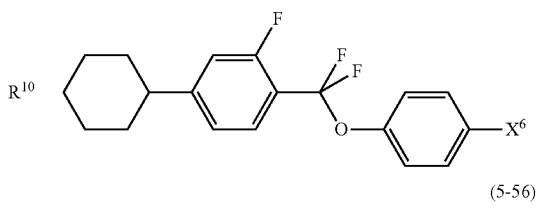
(5-56) 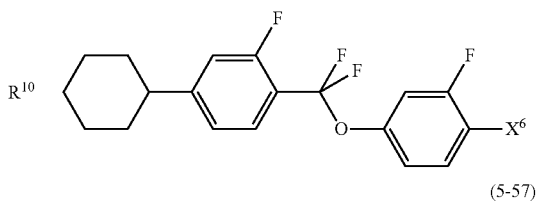
(5-57) 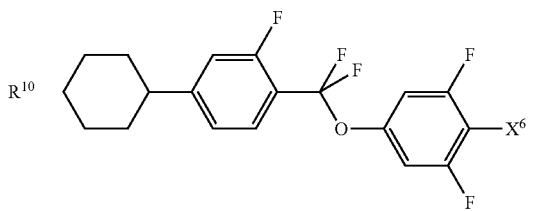

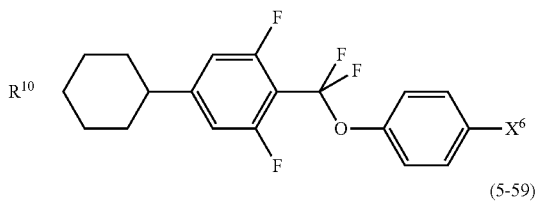
(5-58)

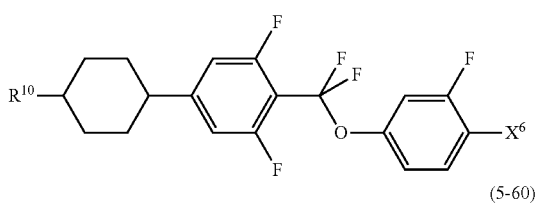
(5-59)

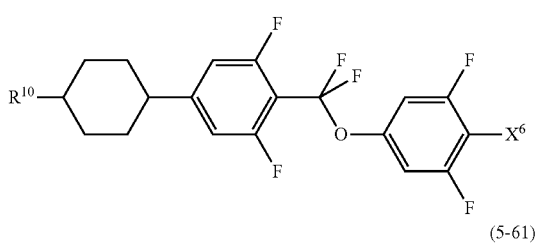
(5-60)

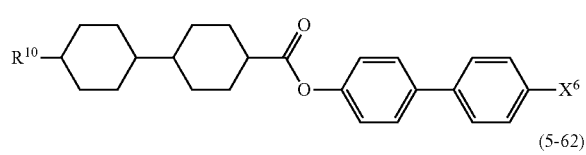
(5-61)

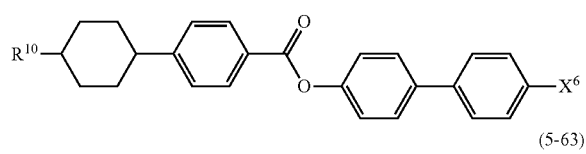
(5-62)

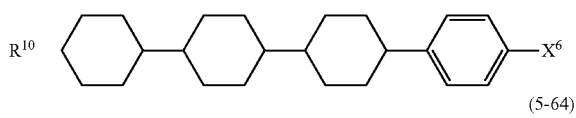
(5-63)

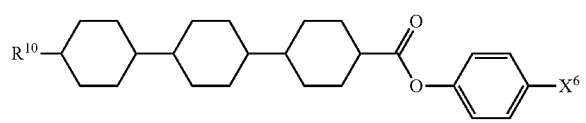
(5-64)

In the formulas, $R^{10}$ and $X^6$ are defined in a manner identical with the definitions in item 8.

The compounds represented by formula (5), namely component C, have a very large positive dielectric anisotropy, and therefore are mainly used for preparing the liquid crystal composition for the STN mode, TN mode or PSA mode. The threshold voltage of the composition can be decreased by adding component C. Moreover, the viscosity and the value of optical anisotropy can be adjusted, and the temperature range of the liquid crystal phase can be extended. Furthermore, component C can also be used for improving steepness.

When preparing the liquid crystal composition for the STN mode or the TN mode, the content of component C in the range of 0.1% to 99.9% by weight, preferably, 10% to 97% by weight, further preferably, 40% to 95% by weight can be applied. Moreover, the threshold voltage, the temperature range of the liquid crystal phase, the value of optical anisotropy, the value of dielectric anisotropy, the viscosity and so forth can be adjusted by mixing a component as described later.

The component to be added to component A is preferably a mixture prepared by mixing component D including at least one kind compound selected from the group of compounds represented by formulas (6), (7), (8), (9), (10) and (11). Furthermore, the threshold voltage, the temperature range of the liquid crystal phase, the value of optical anisotropy, the value of dielectric anisotropy, the viscosity and so forth can be adjusted by adding component E including at least one kind compound selected from the group of compounds represented by each of formulas (12), (13) and (14).

Component D including at least one kind compound selected from the group of compounds represented by formulas (6), (7), (8), (9), (10) and (11) is preferred when preparing the liquid crystal composition having the negative dielectric anisotropy for use in the device according to the vertical alignment mode (VA mode), the polymer sustained alignment mode (PSA mode) or the like.

Moreover, each component of the liquid crystal composition used in the invention has no significant difference in physical characteristics even if each component is the analog including the isotopic element of each element.

Suitable examples of the compounds (component D) represented by formulas (6), (7), (8), (9), (10) and (11) may be represented by formulas (6-1) to (6-6), formulas (7-1) to (7-15), formula (8-1), formulas (9-1) to (9-3), formulas (10-1) to (10-11) and formulas (11-1) to (11-10).

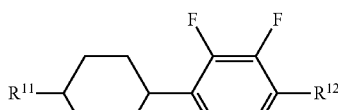
(6-1)

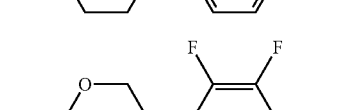
(6-2)

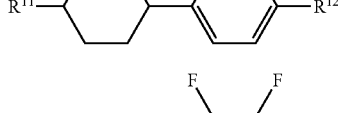
(6-3)

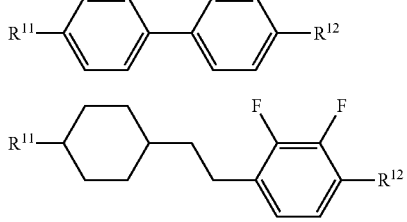
(6-4)

(6-5)
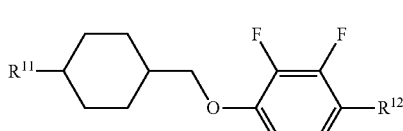

(6-6)
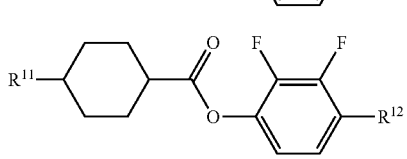

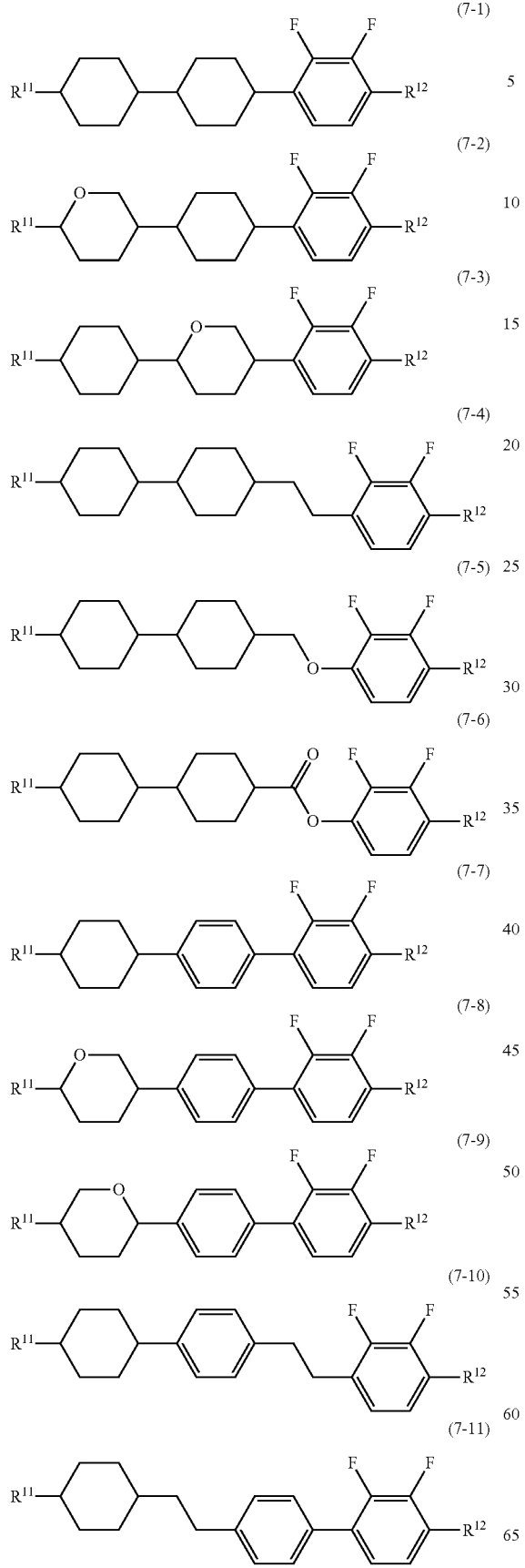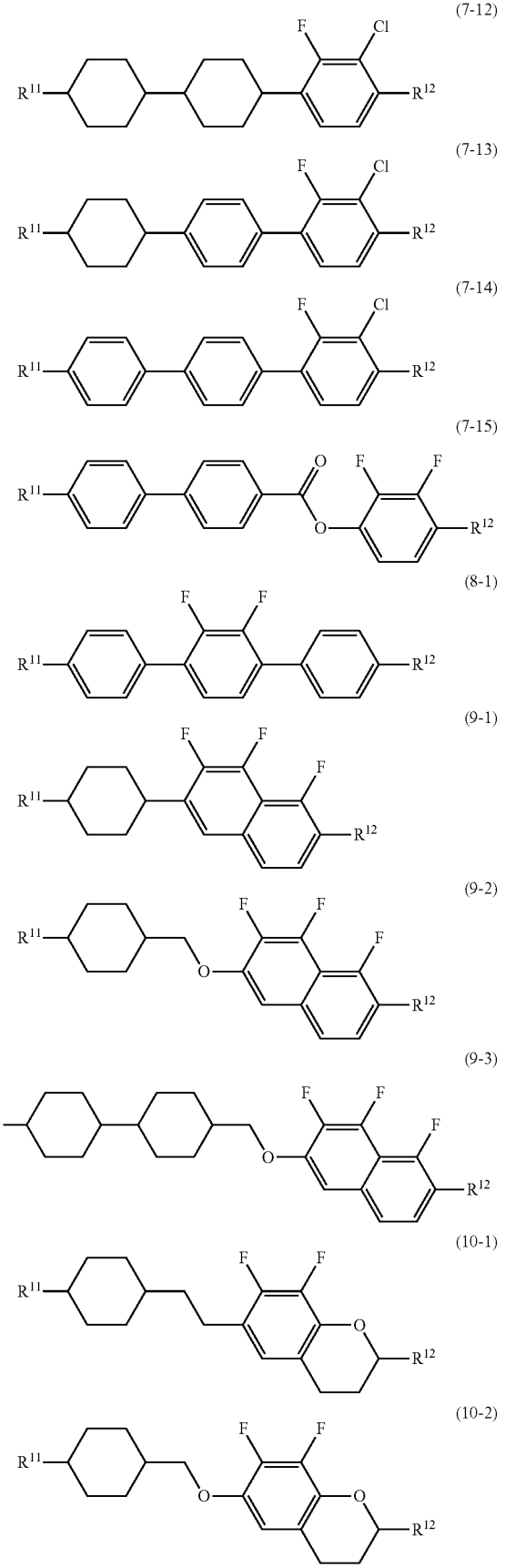

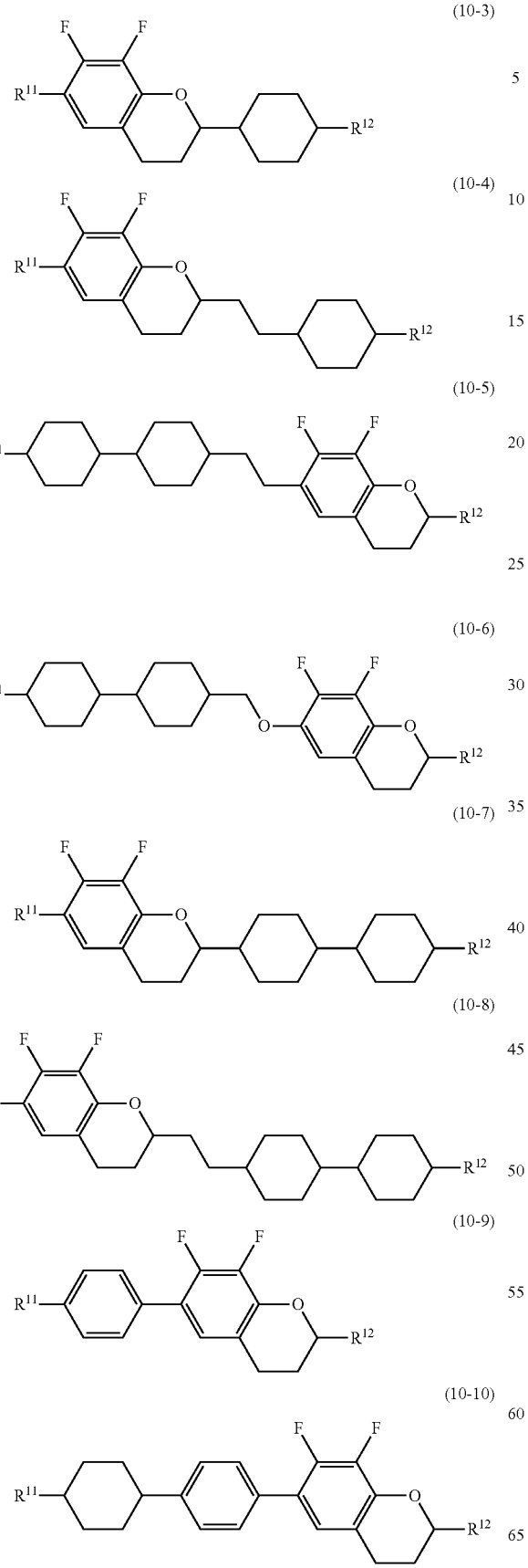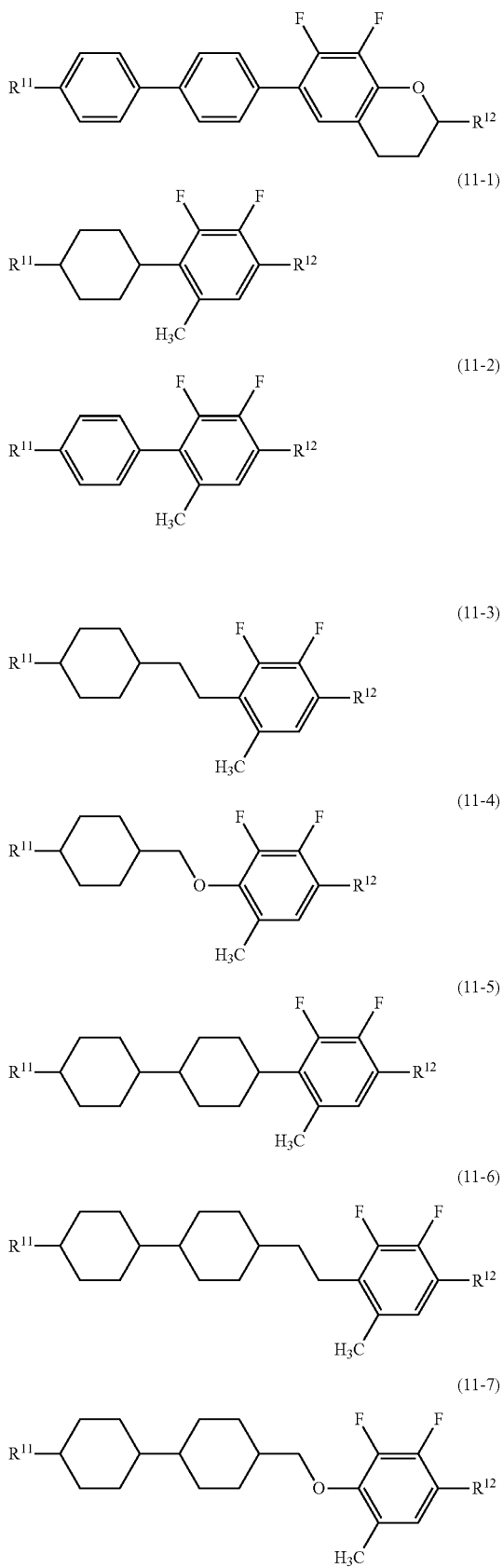

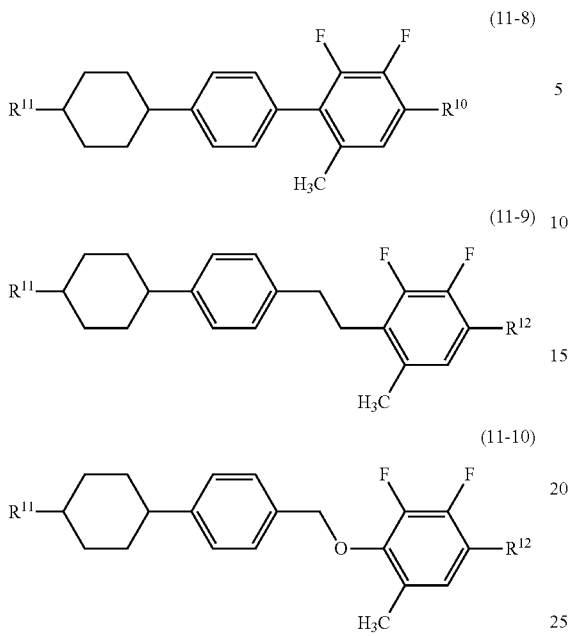

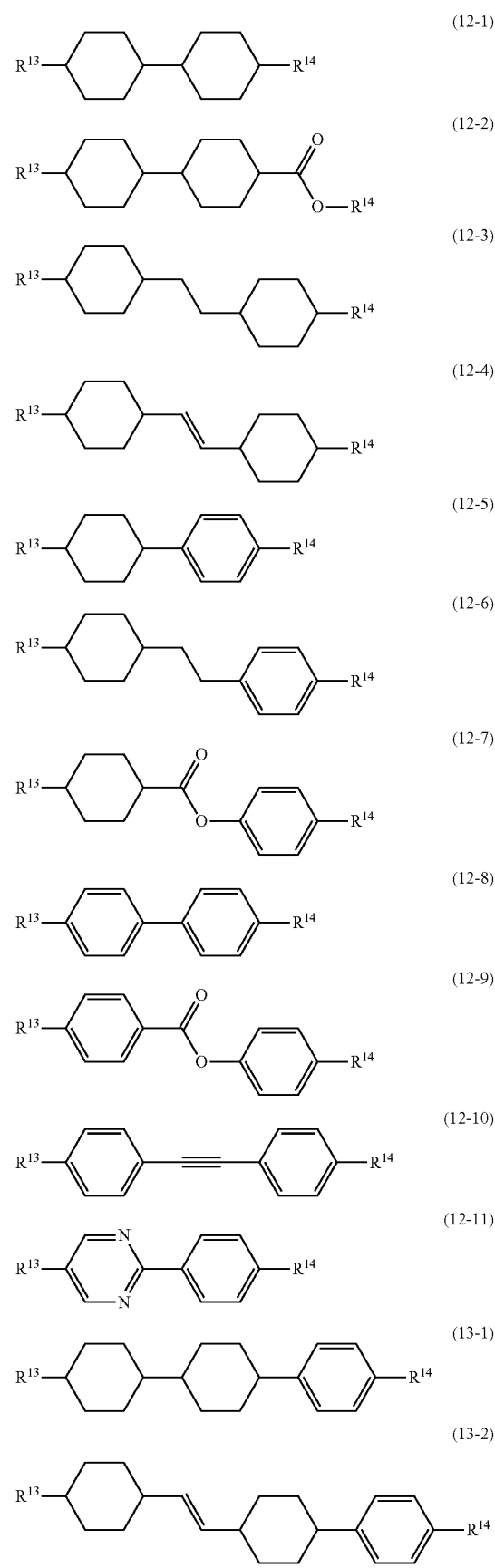

In the formulas, $R^{11}$ and $R^{12}$ are defined in a manner identical with the definitions in item 9.

The compounds of component D are mainly used for the liquid crystal composition having the negative dielectric anisotropy for use in the VA mode or the PSA mode. When the content thereof increases, the threshold voltage of the composition decreases but the viscosity increases. Accordingly, the content is preferably decreased as long as a desired value of threshold voltage is satisfied. However, the content less than 40% by weight does not allow voltage driving in some cases because an absolute value of dielectric anisotropy of component D is about 5.

Among types of component D, the compound represented by formula (6) is effective mainly in adjusting the threshold voltage, the viscosity, and the value of optical anisotropy because the compound is a two-ring compound. The compounds represented by formulas (7) and (8) are also effective in increasing the clearing point, extending a nematic range, decreasing the threshold voltage or increasing the value of optical anisotropy or the like because the compound is a three-ring compound. The compounds represented by formulas (9), (10) and (11) are also effective in decreasing the threshold voltage and so forth.

When preparing the composition for use in the VA mode or the PSA mode, the content of component D is preferably 40% by weight or more, further preferably, in the range of 50% to 95% by weight, based on the total amount of the composition. The elastic constant can be controlled and a voltage-transmission curve of the composition can be controlled by mixing component D. When component D is mixed with the composition having the positive dielectric anisotropy, the content of component D is preferably 30% by weight or less based on the total weight of the composition.

Suitable examples of the compounds (component E) represented by formulas (12), (13) and (14) may be represented by formulas (12-1) to (12-11), formulas (13-1) to (13-19) and formulas (14-1) to (14-6).

-continued
(13-3)
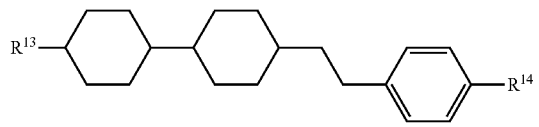
(13-4)
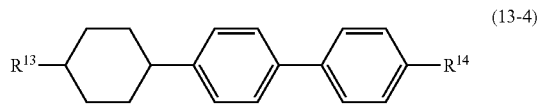
(13-5)
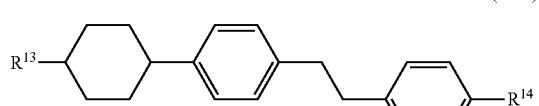
(13-6)
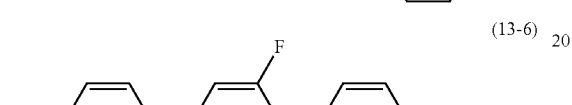
(13-7)
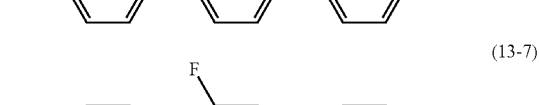
(13-8)
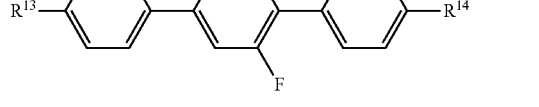
(13-9)
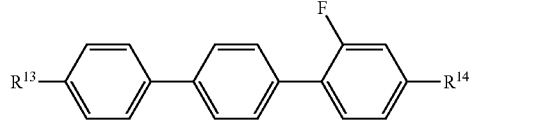
(13-10)
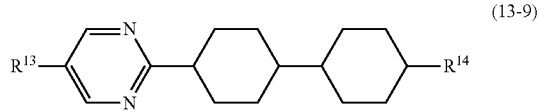
(13-11)
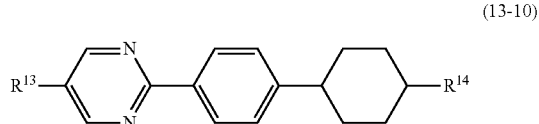
(13-12)
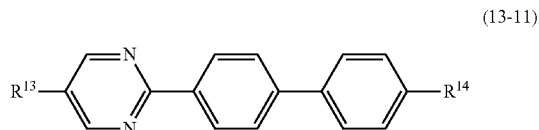
(13-13)
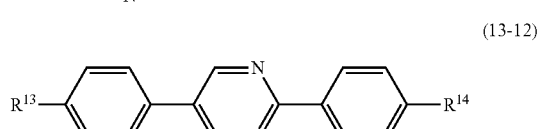
-continued
(13-14)
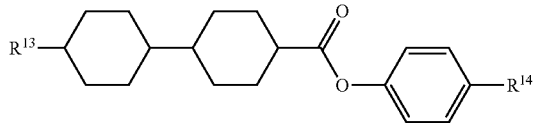
(13-15)
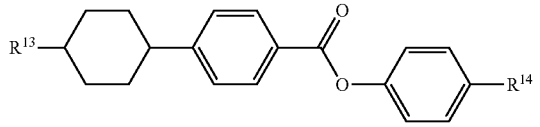
(13-16)
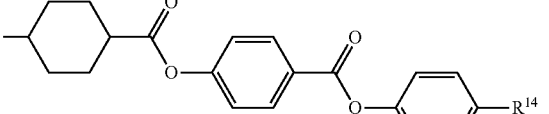
(13-17)
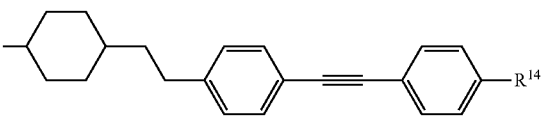
(13-18)
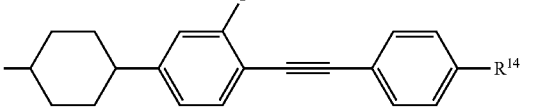
(13-19)
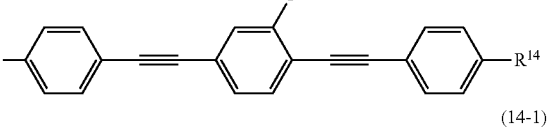
(14-1)
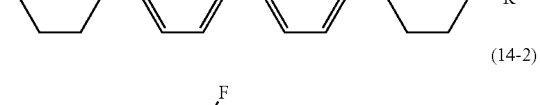
(14-2)
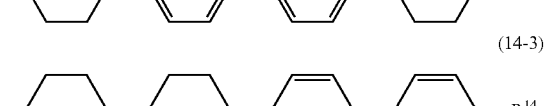
(14-3)
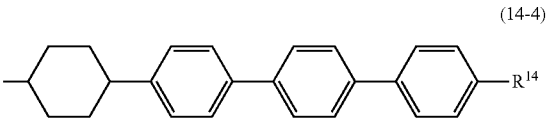
(14-4)
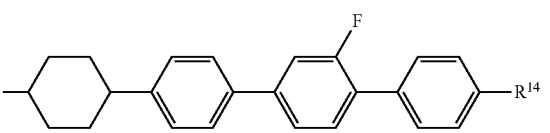
(14-5)

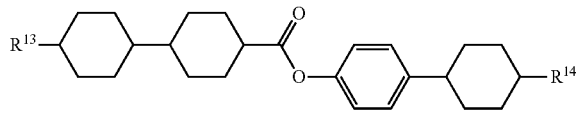

(14-6)

In the formulas, $R^{13}$ and $R^{14}$ are defined in a manner identical with the definitions in item 10.

The compounds (component E) represented by formulas (12), (13) and (14) have a small absolute value of dielectric anisotropy, and are close to neutrality. The compound represented by formula (12) is effective mainly in adjusting the viscosity or the value of optical anisotropy, and the compounds represented by formulas (13) and (14) are effective in extending the nematic range such as increasing the clearing point, or adjusting the value of optical anisotropy.

When the content of the compounds expressed as component E increases, the threshold voltage of the liquid crystal composition increases and the viscosity decreases. Therefore, the content is desirably as high as possible as long as the desired value of threshold voltage of the liquid crystal composition is satisfied. When preparing the liquid crystal composition for use in the VA mode or the PSA mode, the content of component E is preferably 30% by weight or more, further preferably, 40% by weight or more, based on the total weight of the composition.

The liquid crystal composition of the invention preferably contains at least one kind compound represented by formula (1) according to the invention in the range of 0.1% to 99% by weight for developing excellent characteristics.

The liquid crystal composition of the invention is generally prepared according to a known method, for example, dissolving necessary components under a high temperature. Moreover, an additive well known to those skilled in the art is added depending on an application. Thus, as described later, a liquid crystal composition of the invention in which an optically active compound or a polymerizable compound and a polymerization initiator are contained, and a liquid crystal composition for use in a GH mode to which a dye is added can be prepared, for example. The additive is ordinarily well known to those skilled in the art, and is described in detail in literatures and so forth.

The liquid crystal composition of the invention may further contain at least one optically active compound in the liquid crystal composition of the invention.

As the optically active compound, a known chiral dopant is added. The chiral dopant is effective in inducing a helical structure in liquid crystals to adjust a necessary twist angle and thus preventing a reverse twist. Specific examples of the chiral dopant include optically active compounds (Op-1) to (Op-13) as described below.

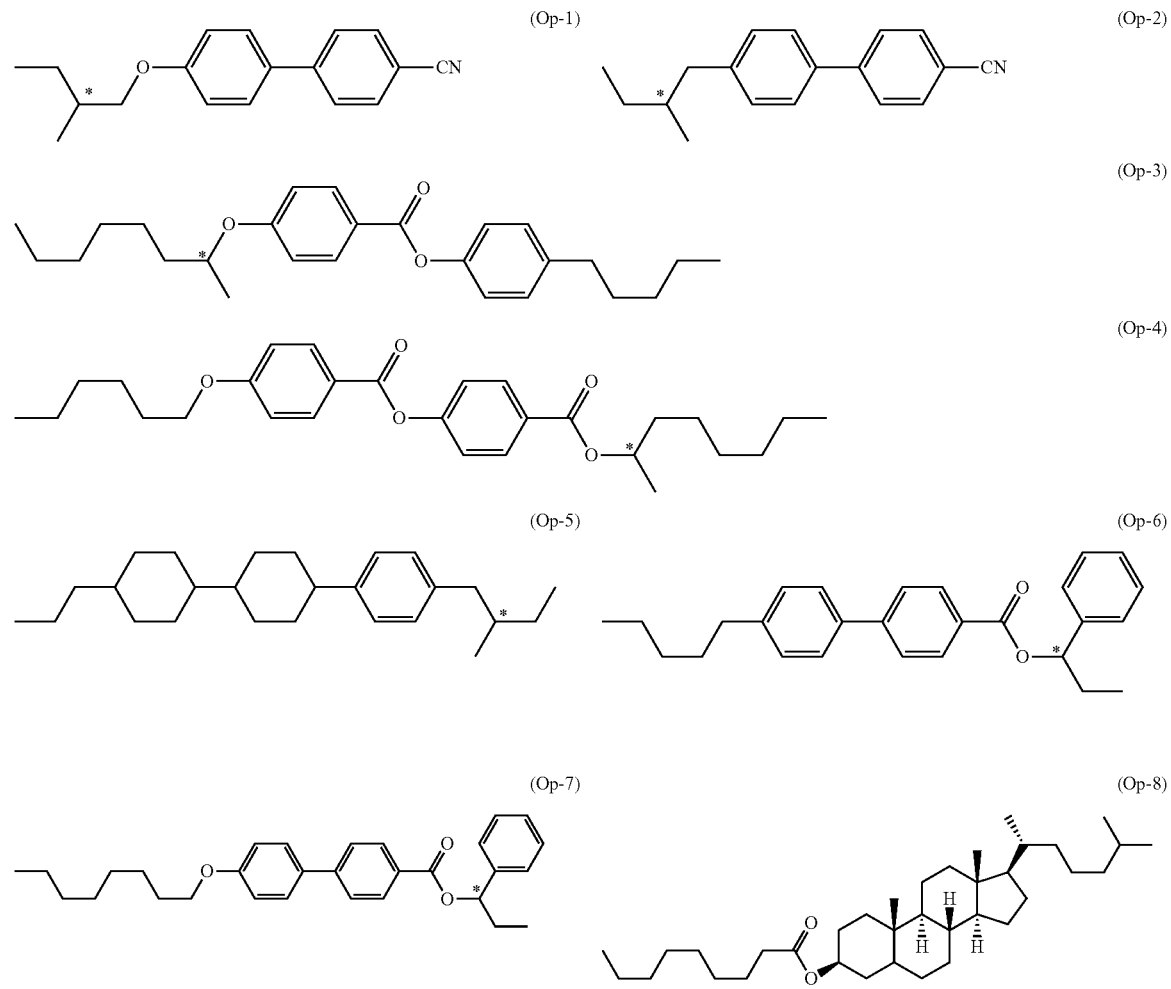

-continued

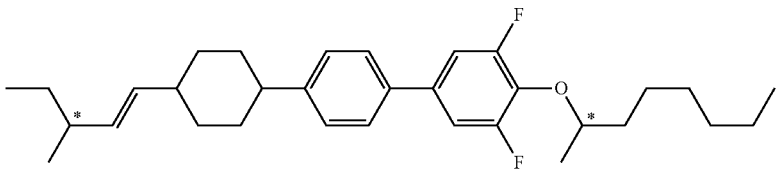
(Op-9)

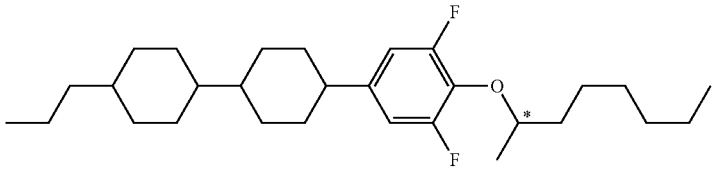
(Op-10)

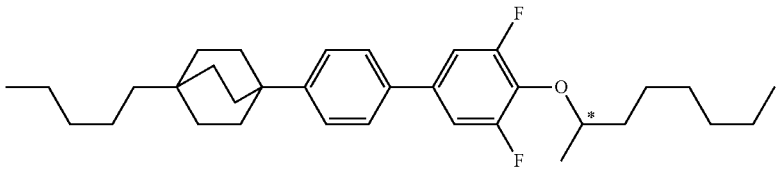
(Op-11)

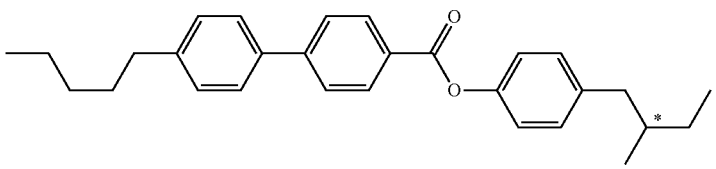
(Op-12)

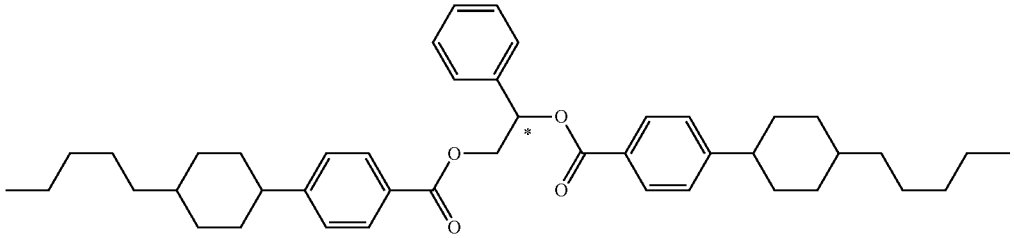
(Op-13)

A helical pitch of the liquid crystal composition of the invention is ordinarily adjusted by adding the optically active compounds. The helical pitch is preferably adjusted in the range of 40 to 200 micrometers for the liquid crystal composition for use in the TFT mode and the TN mode. The helical pitch is preferably adjusted in the range of 6 to 20 micrometers for the liquid crystal composition for use in the STN mode. The helical pitch is preferably adjusted in the range of 1.5 to 4 micrometers for a liquid crystal composition for use in a bistable TN mode. Two or more optically active compounds may be added for the purpose of adjusting temperature dependence of the helical pitch.

If a dichroic dye such as a merocyanine, stylyl, azo, azomethine, azoxy, quinophthalone, anthraquinone or tetrazine dye is added, the liquid crystal composition of the invention can also be used as the liquid crystal composition for use in the GH mode.

The liquid crystal composition of the invention can also be used as a liquid crystal composition for use in NCAP prepared by microencapsulating nematic liquid crystals, and a polymer dispersed liquid crystal display device (PDLCD) prepared by forming a three-dimensional network polymer in the liquid crystals, including a polymer network liquid crystal display device (PNLCD), and also as a liquid crystal composition for use in an electrically controlled birefringence (ECB) mode or a DS mode.

The liquid crystal composition of the invention can also be used as the liquid crystal composition for use in the polymer sustained alignment (PSA) mode by adding the polymerizable compound. Examples of the polymerizable compound include a compound having a polymerizable group, such as an acrylate, a methacrylate, a vinyl compound, a vinyloxy compound, propenyl ether, an epoxy compound (oxirane, oxetane) or vinyl ketone. The polymerizable compound is preferably polymerized by irradiation with ultraviolet light or the like in the presence of a suitable initiator such as a photopolymerization initiator. Suitable conditions for polymerization, suitable types of initiator and suitable amounts thereof are known to those skilled in the art and are described in literatures. For example, Irgacure 651 (registered trademark), Irgacure 184 (registered trademark) or Darocure 1173 (registered trademark) (Ciba Japan K. K), each being the photopolymerization initiator, is suitable for radical polymerization.

Method for Preparing the Liquid Crystal Composition

The liquid crystal composition of the invention can be prepared as described below. For example, when a compound constituting each component is liquid, the composition can be prepared by mixing and shaking respective compounds, or when the compound contains a solid, the composition can be prepared by mixing respective compounds, heating dissolving the compounds to convert the compounds into a liquid in each other, and then shaking the liquid. The liquid crystal composition of the invention can also be prepared according to other known methods.

Characteristics of Liquid Crystal Composition

In the liquid crystal composition of the invention, the maximum temperature of the nematic phase can be adjusted to 70° C. or higher and the minimum temperature of the nematic phase can be adjusted to −20° C. or lower, and therefore the temperature range of the nematic phase is wide. Accordingly, the liquid crystal display device including the liquid crystal composition can be used in a wide temperature range.

In the liquid crystal composition of the invention, the optical anisotropy can be adjusted in the range of 0.10 to 0.13, and also in the range of 0.05 to 0.18 by appropriately adjusting the composition and so forth.

In the liquid crystal composition of the invention, the liquid crystal composition having the dielectric anisotropy ordinarily in the range of −5.0 to −2.0, preferably, in the range of −4.5 to −2.5 can also be obtained. The liquid crystal composition having the dielectric anisotropy in the range of −4.5 to −2.5 can be suitably used as a liquid crystal display device to be operated according to the IPS, VA or PSA mode.

Liquid Crystal Display Device

The liquid crystal composition of the invention can be used not only in a liquid crystal display device that has an operating mode such as the PC, TN, STN, OCB or PSA mode, and is driven according to an AM mode, but also in a liquid crystal display device that has the operating mode such as the PC, TN, STN, OCB, VA or IPS mode, and is driven according to a passive matrix (PM) mode.

The liquid crystal display devices according to the AM and PM modes can be applied to any of reflective, transmissive and transflective liquid crystal displays and so forth.

The liquid crystal composition of the invention can also be used for a dynamic scattering (DS) mode device using a liquid crystal composition to which a conducting agent is added, a nematic curvilinear aligned phase (NCAP) device prepared by microencapsulating the liquid crystal composition and a polymer dispersed (PD) device having a three-dimensional network polymer formed in the liquid crystal composition, for example, a polymer network (PN) device.

Above all, because the liquid crystal composition of the invention has the characteristics described above, the composition can be suitably used in the liquid crystal display device driven by the operating mode such as the VA, IPS or PSA mode and according to the AM mode, in which the liquid crystal composition having the negative dielectric anisotropy is used, and particularly suitably used in the liquid crystal display device driven by the VA mode and according to the AM mode.

In addition, a direction of an electric field is perpendicular to a liquid crystal layer in the liquid crystal display device driven by the TN mode, the VA mode or the like. On the other hand, the direction of the electric field is parallel to the liquid crystal layer in the liquid crystal display device driven by the IPS mode or the like. In addition, a structure of the liquid crystal display device driven by the VA mode has been reported by K. Ohmuro, S. Kataoka, T. Sasaki and Y. Koike, SID '97 Digest of Technical Papers, 28, 845 (1997), and a structure of the liquid crystal display device driven by the IPS mode has been reported in WO 1991/10936 A (patent family: U.S. Pat. No. 5,576,867 B).

EXAMPLES

In the following, the invention will be explained in greater detail by way of Examples. However, the invention is not limited by the Examples. Unless otherwise noted, "%" is expressed in terms of "% by weight."

Because a compound obtained was identified using of a nuclear magnetic resonance spectrum obtained according to $^1$H-NMR analysis, a gas chromatogram obtained according to gas chromatography (GC) analysis and so forth, analytical methods will be first explained.

$^1$H-NMR Analysis:

As a measuring apparatus, DRX-500 (made by Bruker BioSpin Corporation) was used. A sample prepared in Examples and so forth was dissolved in a deuterated solvent such as $CDCl_3$ in which the sample was soluble, and measurement was carried out under the conditions of room temperature, 500 MHz and 24 times of accumulation. In explaining the nuclear magnetic resonance spectrum obtained, s, d, t, q and m stand for a singlet, a doublet, a triplet, a quartet and a multiplet, respectively. Tetramethylsilane (TMS) was used as a standard reference material for a zero point of chemical shifts, δ values.

GC Analysis:

As a measuring apparatus, GC-14B Gas Chromatograph made by Shimadzu Corporation was used. As a column, capillary column CBP1-M25-025 (length 25 m, bore 0.22 mm, film thickness 0.25 μm); dimethylpolysiloxane as a stationary liquid phase; non-polar) made by Shimadzu Corporation was used. Helium was used as a carrier gas, and a flow rate was adjusted at 1 milliliter per minute. Temperature in a sample injector was set at 300° C. and temperature of a detector (FID) part was set at 300° C.

A sample was dissolved in toluene and prepared to be a 1% solution, and 1 microliter of the resultant solution was injected into the sample injector.

As a recorder, C-R6A Chromatopac made by Shimadzu Corporation or the equivalent thereof was used. The resultant gas chromatogram showed a retention time of a peak and a value of a peak area corresponding to each of component compounds.

In addition, as a solvent for diluting the sample, for example, chloroform or hexane may also be used. Moreover, as the column, capillary column DB-1 (length 30 m, bore 0.32 mm, film thickness 0.25 μm) made by Agilent Technologies Inc., HP-1 (length 30 m, bore 0.32 mm, film thickness 0.25 μm) made by Agilent Technologies Inc., Rtx-1 (length 30 m, bore 0.32 mm, film thickness 0.25 μm) made by Restek Corporation, BP-1 (length 30 m, bore 0.32 mm, film thickness 0.25 μm) made by SGE International Pty. Ltd., and so forth may also be used.

A ratio of peak areas in the gas chromatogram corresponds to a ratio of component compounds. In general, weight percent of each of the component compounds in an analytical sample is not completely identical with a percentage of each of the peak areas in the analytical sample. However, when the column described above was used in the invention, the weight percent of each of the component compounds in the analytical sample substantially corresponds to the percentage of each of the peak areas in the analytical sample because a correction coefficient is essentially 1 (one). The reason is that no significant difference exists in the correction coefficients of the liquid crystal compounds. In order to more accurately determine a composition ratio of the liquid crystal compounds in the liquid crystal composition using the gas chromatogram, an internal standard method using the gas chromatogram is applied. Each liquid crystal compound component (test-component) weighed accurately in a fixed amount and a standard liquid crystal compound (standard reference material) are simultaneously measured according to gas chromatography, and relative intensity as a ratio of peak areas obtained between the test-component and the standard reference material is calculated in advance. Then, when correction is made using the relative intensity of the peak area of each component to the peak area of the standard reference material, the composition ratio of the liquid crystal compounds in the liquid crystal composition can be more accurately determined according to the gas chromatographic analysis.

Sample for Determining Values of Physical Properties of Liquid Crystal Compound and so Forth A sample for determining values of physical properties of the liquid crystal compound includes two types of cases: a case where the compound per se is used as the sample, and a case where the compound is mixed with mother liquid crystals to be used as the sample.

In the latter case where the sample prepared by mixing the compound with the mother liquid crystals is used, measurement is carried out according to the method described below. First, a sample is prepared by mixing 15% of the liquid crystal compound obtained and 85% of the mother liquid crystals. Then, according to an extrapolation method based on an equation as described below, extrapolated values are calculated from measured values of the sample obtained. The extrapolated values are described as the values of physical properties of the compound.

(Extrapolated value)={100×measured value of a sample)−(% of mother liquid crystals)×(measured value of the mother liquid crystals)}/(% of the compound).

When a smectic phase or crystals precipitated at 25° C. even at the above ratio of the compound to the mother liquid crystals, a ratio of the compound to the mother liquid crystals was changed in the order of (10%:900), (5%:95%) and (1%:99%). The physical properties of the sample were measured using a composition at a ratio in which the smectic phase or the crystals did not precipitate at 25° C. The extrapolated values were determined according to the above equation, and described as the values of physical properties of the compound.

As the mother liquid crystals used for measurement, various kinds exist. For example, a composition (%) of mother liquid crystals i is as described below.

Mother Liquid Crystals i:

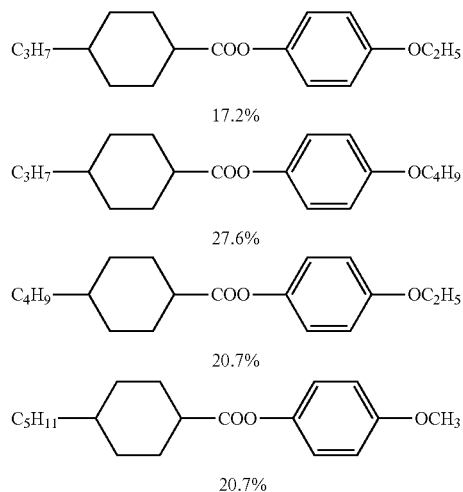

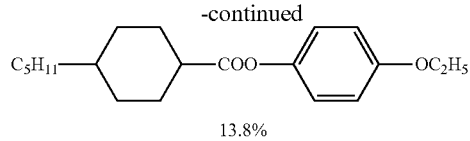

13.8%

Method for Determining Values of Physical Properties of Liquid Crystal Compound and so Forth Values of physical properties were determined according to the methods described later. Most of the measuring methods are described in EIAJ ED-2521A of the Standard of Electronic Industries Association of Japan, or modified thereon. Moreover, no TFT was attached to a TN device used for measurement.

Among measured values, in the case where the liquid crystal compound per se was used as the sample, values obtained were described as experimental data. In the case where a mixture of the liquid crystal compound with the mother liquid crystals was used as the sample, values obtained according to the extrapolation method were described as experimental data.

Phase Structure and Phase Transition Temperature (° C.):

Measurement was carried out according to method (1) and method (2) as described below.

(1) A compound was placed on a hot plate of a melting point apparatus (FP52 Hot Stage made by Mettler Toledo International Inc.) equipped with a polarizing microscope, and a state of phase and a change thereof were observed with the polarizing microscope while the compound was heated at a rate of 3° C. per minute, and a type of liquid crystal phase was specified.

(2) A sample was heated and then cooled at a rate of 3° C. per minute using a differential scanning calorimeter, DSC-7 System or Diamond DSC System, made by PerkinElmer, Inc. A starting point (on set) of an endothermic peak or an exothermic peak caused by a phase change of the sample was determined by extrapolation, and thus a phase transition temperature was determined.

Hereinafter, the crystals were expressed as C, and when the crystals were further distinguishable, each of the crystals was expressed as $C_1$ or $C_2$. The smectic phase was expressed as S and a nematic phase as N. A liquid (isotropic) was expressed as I. When smectic A phase, smectic B phase, smectic C phase or smectic F phase was distinguishable among the smectic phases, the phases were expressed as $S_A$, $S_B$, $S_c$ or $S_F$, respectively. As an expression of the phase transition temperature, for example, "C 50.0 N 100.0 I" means that a phase transition temperature from the crystals to the nematic phase (CN) is 50.0° C., and a phase transition temperature from the nematic phase to the liquid (NI) is 100.0° C. A same rule applied to any other expression.

Maximum Temperature of a Nematic Phase ($T_{NI}$; ° C.):

A sample (mixture of the liquid crystal compound and the mother liquid crystals) was placed on a hot plate of a melting point apparatus (FP52 Hot Stage made by Mettler Toledo International Inc.) equipped with a polarizing microscope, and was observed with the polarizing microscope while heating the sample at a rate of 1° C. per minute. Temperature when part of the sample began to change from the nematic phase to the isotropic liquid was described as a maximum temperature of the nematic phase. Hereinafter, a higher limit of the temperature range of the nematic phase may simply be abbreviated as "maximum temperature."

Compatibility at a Low Temperature:

Samples in which a compound and the mother liquid crystals were mixed for the compound to be 15%, 10%, 5%, 3% and 1% were prepared and put in glass vials. After the glass vials were kept in freezers at temperatures of −10° C. or −20° C. for a predetermined period of time, whether or not the crystals or the smectic phase precipitated was observed.

Viscosity (Bulk Viscosity; η; Measured at 20° C.; mPa·s):

A mixture of a liquid crystal compound and the mother liquid crystals was measured using a cone-plate (E type) rotational viscometer.

Optical Anisotropy (Refractive Index Anisotropy; Δn):

Measurement was carried out by means of Abbe refractometer with a polarizing plate mounted on an ocular, using light at a wavelength of 589 nanometers under a temperature of 25° C. A surface of a main prism was rubbed in one direction, and then a sample (mixture of a liquid crystal compound and the mother liquid crystals) was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of optical anisotropy (Δn) was calculated from an equation: Δn=n∥−n⊥.

Dielectric Anisotropy (Δε; Measured at 25° C.):

A sample (mixture of a liquid crystal compound and the mother liquid crystals) was put in a liquid crystal cell in which a distance (gap) between two glass substrates was about 9 micrometers and a twist angle was 80 degrees. A voltage of 20 V was applied to the cell, and a dielectric constant (∈∥) in the major axis direction of liquid crystal molecules was measured. A voltage of 0.5 V was applied to the cell, and a dielectric constant (∈⊥) in the minor axis direction of the liquid crystal molecules was measured. A value of dielectric anisotropy was calculated from an equation: Δ∈=∈∥−∈⊥.

Example 1

Synthesis of 4-(3-(4-ethoxy-2,3-difluorophenoxy)-2-fluoropropyl)-4'-propyl-1,1'-bi(cyclohexane) (No. 56)

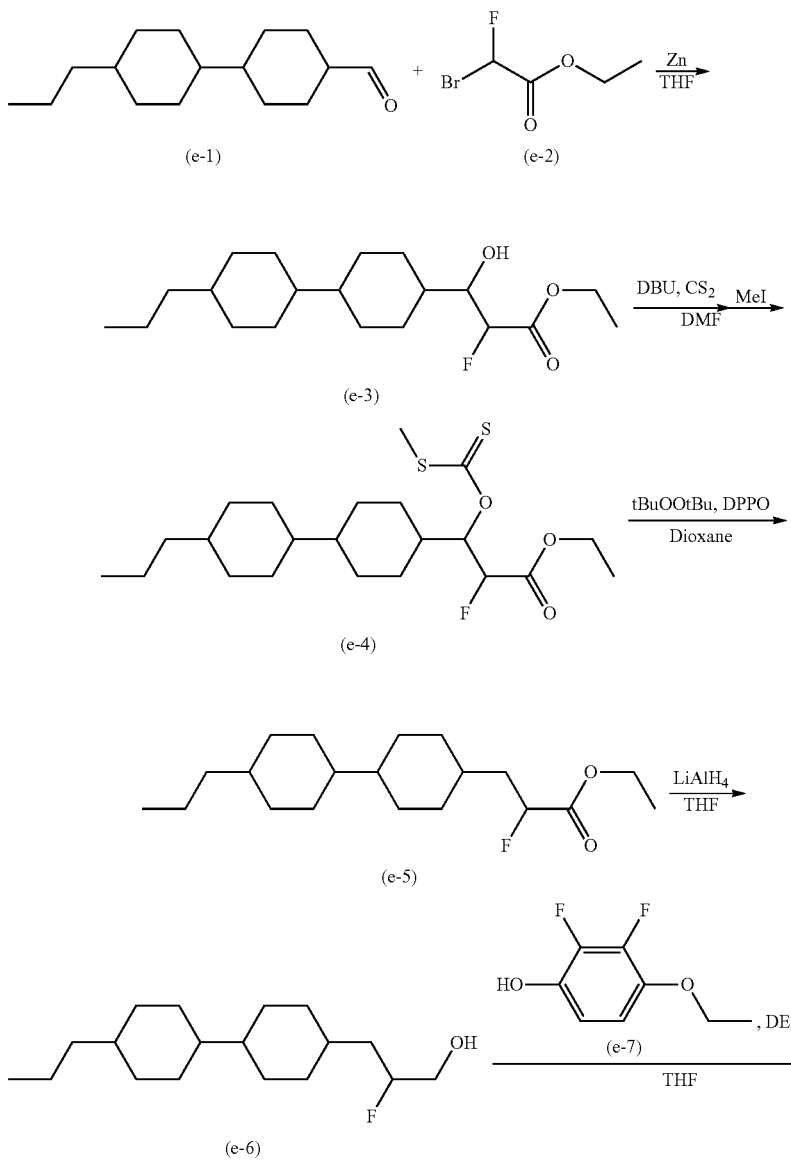

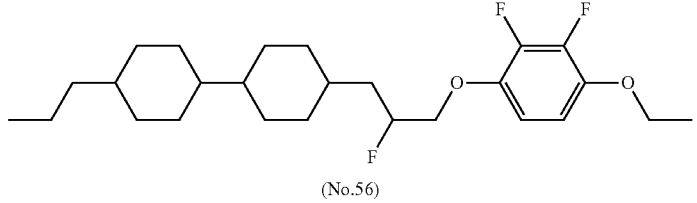

(No.56)

First Step

To a reaction vessel under a nitrogen atmosphere, 1.1 g of well-dried zinc, 2.6 g of ethyl bromofluoroacetate (e-2) and 10 ml of THF were added, and the resultant mixture was cooled to 0° C. and stirred for 1 hour. The solution was slowly added dropwise in a temperature range of 20° C. to 25° C. to another reaction vessel under a nitrogen atmosphere in which 2.0 g of 4'-propyl-[1,1'-bi(cyclohexane)]-4-carboaldehyde (e-1) and 10 ml of THF were put, and the resultant mixture was further subjected to heating reflux for 4 hours. After cooling the resultant reaction mixture to 25° C., 100 ml of 1 N HCl aqueous solution and 100 ml of ethyl acetate were added to separate the mixture into an organic layer and an aqueous layer, and an extraction operation was performed. The resultant organic layer was isolated, and washed with water, a saturated aqueous solution of sodium hydrogencarbonate and water, and then the resultant solution was dried over anhydrous magnesium sulfate. Then, the solvent was distilled off under reduced pressure, the resultant residue was purified by a preparative isolation operation by means of column chromatography using a mixed solvent of toluene and ethyl acetate (toluene:ethyl acetate=9:1 in a volume ratio) as an eluent and silica gel as a filler, the resultant product was dried, and thus 3.7 g of ethyl 2-fluoro-3-hydroxy-3-(4'-propyl-[1,1'-bi(cyclohexane)]-4-yl)propanoate (e-3) was obtained.

Second Step

To a reaction vessel under a nitrogen atmosphere, 3.7 g of ethyl 2-fluoro-3-hydroxy-3-(4'-propyl-[1,1'-bi(cyclohexane)]-4-yl)propanoate (e-3), 6.5 g of DBU, 6.5 ml of carbon disulfide and 40 ml of DMF were added, and the resultant mixture was stirred at 25° C. for 1.5 hours. Subsequently, 15.3 g of methyl iodide was added to a reaction mixture, and the resultant mixture was stirred at 25° C. for 1.5 hours. Then, 100 ml of water and 100 ml of ethyl acetate were added to separate the mixture into an organic layer and an aqueous layer, and an extraction operation was performed. The resultant organic layer was isolated, and washed with water, an aqueous solution of sodium thiosulfate, and water, and then the resultant solution was dried over anhydrous magnesium sulfate. The resultant solution was concentrated under reduced pressure, the resultant residue was purified by a preparative isolation operation by means of column chromatography using a mixed solvent of heptane and ethyl acetate (heptane:ethyl acetate=9:1 in a volume ratio) as an eluent and silica gel as a filler, the resultant product was dried, and thus 2.2 g of ethyl 2-fluoro-3-(((methylthio)carbonothioyl)oxy)-3-(4'-propyl-[1,1'-bi(cyclohexane)]-4-yl)propanoate (e-4) was obtained. A yield based on compound (e-1) was 60.2%.

Third Step

To a reaction vessel under a nitrogen atmosphere, 2.2 g of ethyl 2-fluoro-3-(((methylthio)carbonothioyl)oxy)-3-(4'-propyl-[1,1'-bi(cyclohexane)]-4-yl) propanoate (e-4), 0.5 ml of di-tert-butylperoxide, 1.0 g of DPPO and 40 ml of dioxane were added, and the resultant mixture was subjected to heating reflux for 48 hours. After cooling the resultant reaction mixture to 25° C., 100 ml of water and 100 ml of ethyl acetate were added to separate the mixture into an organic layer and an aqueous layer, and an extraction operation was performed. The resultant organic layer was isolated, and washed with water, and then the resultant solution was dried over anhydrous magnesium sulfate. The resultant solution was concentrated under reduced pressure, the resultant residue was purified by a preparative isolation operation by means of column chromatography using a mixed solvent of heptane and ethyl acetate (heptane:ethyl acetate=9:1 in a volume ratio) as an eluent and silica gel as a filler, the resultant product was dried, and thus 1.4 g of ethyl 2-fluoro-3-(4'-propyl-[1,1'-bi(cyclohexane)]-4-yl) propanoate (e-5) was obtained. A yield based on compound (e-4) was 86.7%.

Fourth Step

To a reaction vessel under a nitrogen atmosphere, 0.3 g of lithium aluminum hydride and 10 ml of THF were added and the resultant mixture was cooled to −10° C. Thereto, 1.4 g of ethyl 2-fluoro-3-(4'-propyl-[1,1'-bi(cyclohexane)]-4-yl)propanoate (e-5) dissolved in 10 ml of THF was added dropwise in a temperature range of −10° C. to 0° C. Then, the resultant mixture was heated to 25° C., and stirred for 1 hour. Subsequently, 100 ml of 1 N HCl aqueous solution and 100 ml of ethyl acetate were added to separate the mixture into an organic layer and an aqueous layer, and an extraction operation was performed. The resultant organic layer was isolated, and washed with water, and then the resultant solution was dried over anhydrous magnesium sulfate. The resultant solution was concentrated under reduced pressure, the resultant residue was purified by a preparative isolation operation by means of column chromatography using a mixed solvent of toluene and ethyl acetate (toluene:ethyl acetate=5:1 in a volume ratio) as an eluent and silica gel as a filler, the resultant product was dried, and thus 1.2 g of 2-fluoro-3-(4'-propyl-[1,1'-bi(cyclohexane)]-4-yl)propan-1-ol (e-6) was obtained. A yield based on compound (e-5) was 92.8%.

Fifth Step

To a reaction vessel under a nitrogen atmosphere, 1.2 g of 2-fluoro-3-(4'-propyl-[1',1'-bi(cyclohexane)]-4-yl)propan-1-ol (e-6), 0.8 g of 4-ethoxy-2,3-difluorophenol (e-6), 1.2 g of triphenyl phosphine and 10 ml of THF were added, and the resultant mixture was cooled to −10° C. Thereto, 2.0 ml of toluene solution of 2.2 M DEAD was added dropwise in a temperature range of −10° C. to 0° C. Then, the resultant mixture was heated to 25° C. and stirred for 1 hour. Subsequently, 100 ml of water and 100 ml of ethyl acetate were added to separate the mixture into an organic layer and an aqueous layer, and an extraction operation was performed. The resultant organic layer was isolated, and washed with water, and then the resultant solution was dried over anhydrous magnesium sulfate. The resultant solution was concentrated under reduced pressure, the resultant residue was purified by a preparative isolation operation by means of column chromatography using a mixed solvent of heptane and toluene (heptane:toluene=2:1 in a volume ratio) as an eluent and silica gel as a filler. Furthermore, the resultant mixture was purified by recrystallization from a mixed solvent of heptane and Solmix A-11 (registered trademark) (Japan Alcohol Trading company, Ltd.) (heptane:Solmix=1:1 in a volume ratio), and the resultant product was dried, and thus 1.1 g of 4-(3-(4-ethoxy-2,3-difluorophenoxy)-2-fluoropropyl)-4'-propyl-1,1'-bi(cyclohexane) (No. 56) was obtained.

A chemical shift δ (ppm) according to ¹H-NMR analysis was as described below, and the compound obtained could be identified to be 4-(3-(4-ethoxy-2,3-difluorophenoxy)-2-fluo- Maximum temperature ($T_{NI}$)=127.3° C.; dielectric anisotropy (Δ∈)=−9.46; optical anisotropy (Δn)=0.100.

Example 2

Synthesis of 4'-ethoxy-2,3-difluoro-4-(2-fluoro-3-(4-propylcyclohexyl)propoxy)-1,1'-biphenyl (No. 166)

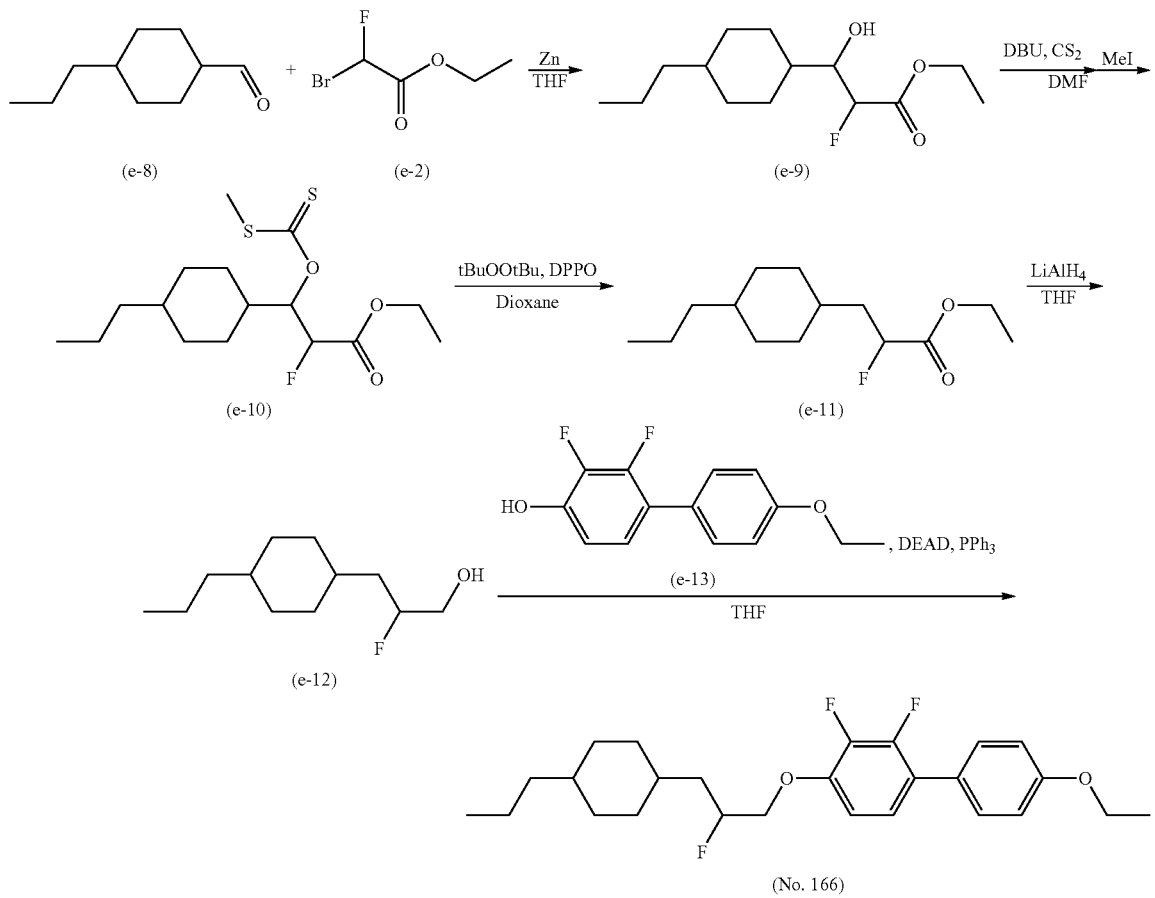

ropropyl)-4'-propyl-1,1'-bi (cyclohexane) (No. 56). In addition, a solvent for measurement was CDCl₃.

Chemical shift δ (ppm); 6.69-6.60 (m, 2H), 4.99-4.83 (m, 1H), 4.12-4.01 (m, 4H), 1.90-1.68 (m, 9H), 1.49-1.37 (m, 5H), 1.33-1.25 (m, 3H), 1.14-1.12 (m, 3H), 1.01-0.92 (m, 9H), 0.87 (t, 3H).

A transition temperature of compound (No. 56) obtained was as described below.

Transition temperature: C 66.9 $S_B$ 86.0 N 136.5 I.

Physical Properties of Compound (No. 56)

Liquid crystal composition B including 85% of mother liquid crystals i and 15% of 4-(3-(4-ethoxy-2,3-difluorophenoxy)-2-fluoropropyl)-4'-propyl-1,1'-bi(cyclohexane) (No. 56) obtained according to Example 1 was prepared. Physical properties of liquid crystal composition B obtained were measured and extrapolated values of physical properties of compound (No. 56) were determined based on the calculation by extrapolating the measured values. The values were as described below.

First Step

To a reaction vessel under a nitrogen atmosphere, 1.7 g of well-dried zinc, 3.6 g of ethyl bromofluoroacetate (e-2) and 10 ml of THF were added, and the resultant mixture was cooled to 0° C. and stirred for 1 hour. The solution was slowly added dropwise in a temperature range of 20° C. to 25° C. to another reaction vessel under a nitrogen atmosphere in which 2.0 g of 4-propylcyclohexane carboaldehyde (e-8) and 10 ml of THF were put, and the resultant mixture was further subjected to heating reflux for 4 hours. After cooling the resultant reaction mixture to 25° C., 100 ml of 1 N HCl aqueous solution and 100 ml of ethyl acetate were added to separate the mixture into an organic layer and an aqueous layer, and an extraction operation was performed. Then, the resultant organic layer was isolated, and washed with water, a saturated aqueous solution of sodium hydrogencarbonate and water, and then the resultant solution was dried over anhydrous magnesium sulfate. Then, the solvent was distilled off under reduced pressure, the resultant residue was purified by a preparative isolation operation by means of column chromatography using a mixed solvent of toluene and ethyl acetate (toluene:ethyl acetate=9:1 in a volume ratio) as an eluent and silica gel as a filler, the resultant product was dried, and thus 3.8 g of ethyl 2-fluoro-3-hydroxy-3-(4-propylcyclohexyl) propanoate (e-9) was obtained.

Second Step

To a reaction vessel under a nitrogen atmosphere, 3.8 g of ethyl 2-fluoro-3-hydroxy-3-(4-propylcyclohexyl)propanoate (e-9), 8.9 g of DBU, 8.7 ml of carbon disulfide and 40 ml of DMF were added, and the resultant mixture was stirred at 25° C. for 1.5 hours. Subsequently, 20.5 g of methyl iodide was added to a reaction mixture, and the resultant mixture was stirred at 25° C. for 1.5 hours. Then, 100 ml of water and 100 ml of ethyl acetate were added to separate the mixture into an organic layer and an aqueous layer, and an extraction operation was performed. The resultant organic layer was isolated, and washed with water, an aqueous solution of sodium thiosulfate, and water, and then the resultant solution was dried over anhydrous magnesium sulfate. The resultant solution was concentrated under reduced pressure, the resultant residue was purified by a preparative isolation operation by means of column chromatography using a mixed solvent of heptane and ethyl acetate (heptane:ethyl acetate=9:1 in a volume ratio) as an eluent and silica gel as a filler, the resultant product was dried, and thus 2.1 g of ethyl 2-fluoro-3-(((methylthio)carbonothioyl)oxy)-3-(4-propylcyclohexyl)propanoate (e-10) was obtained. A yield based on compound (e-8) was 46.3%.

Third Step

To a reaction vessel under a nitrogen atmosphere, 2.1 g of ethyl 2-fluoro-3-(((methylthio)carbonothioyl)oxy)-3-(4-propylcyclohexyl)propanoate (e-10), 0.5 ml of di-tert-butylperoxide, 1.2 g of DPPO and 40 ml of dioxane were added, and the resultant mixture was subjected to heating reflux for 48 hours. After cooling the resultant reaction mixture to 25° C., 100 ml of water and 100 ml of ethyl-acetate were added to separate the mixture into an organic layer and an aqueous layer, and an extraction operation was performed. The resultant organic layer was isolated, and washed with water, and then the resultant solution was dried over anhydrous magnesium sulfate. The resultant solution was concentrated under reduced pressure, the resultant residue was purified by a preparative isolation operation by means of column chromatography using a mixed solvent of heptane and ethyl acetate (heptane:ethyl acetate=9:1 in a volume ratio) as an eluent and silica gel as a filler, the resultant product was dried, and thus 1.1 g of ethyl 2-fluoro-3-(4-propylcyclohexyl)propanoate (e-11) was obtained. A yield based on compound (e-10) was 74.5%.

Fourth Step

To a reaction vessel under a nitrogen atmosphere, 0.3 g of lithium aluminum hydride and 10 ml of THF were added, and the resultant mixture was cooled to −10° C. Thereto, 1.1 g of ethyl 2-fluoro-3-(4-propylcyclohexyl)propanoate (e-11) dissolved in 10 ml of THF was added dropwise in a temperature range of −10° C. to 0° C. Then, the resultant mixture was heated to 25° C., and stirred for 1 hour. Subsequently, 100 ml of 1 N HCl aqueous solution and 100 ml of ethyl acetate were added to separate the mixture into an organic layer and an aqueous layer, and an extraction operation was performed. The resultant organic layer was isolated, and washed with water, and then the resultant solution was dried over anhydrous magnesium sulfate. The resultant solution was concentrated under reduced pressure, the resultant residue was purified by a preparative isolation operation by means of column chromatography using a mixed solvent of toluene and ethyl acetate (toluene:ethyl acetate=5:1 in a volume ratio) as an eluent and silica gel as a filler, the resultant product was dried, and thus 0.68 g of 2-fluoro-3-(4-propylcyclohexyl)propan-1-ol (e-12) was obtained. A yield based on compound (e-11) was 75.7%.

Fifth Step

To a reaction vessel under a nitrogen atmosphere, 0.68 g of 2-fluoro-3-(4-propylcyclohexyl)propan-1-ol (e-12), 0.9 g of 4'-ethoxy-2,3-difluoro-[1,1'-biphenyl]-4-ol (e-13), 1.0 g triphenyl phosphine and 10 ml of THF were added, and the resultant mixture was cooled to −10° C. Thereto, 1.7 ml of toluene solution of 2.2 M DEAD was added dropwise in a temperature range of −10° C. to 0° C. Then, the resultant mixture was heated to 25° C. and stirred for 1 hour. Subsequently, 100 ml of water and 100 ml of ethyl acetate were added to separate the mixture into an organic layer and an aqueous layer, and an extraction operation was performed. The resultant organic layer was isolated, and washed with water, and then the resultant solution was dried over anhydrous magnesium sulfate. The resultant solution was concentrated under reduced pressure, the resultant residue was purified by a preparative isolation operation by means of column chromatography using a mixed solvent of heptane and toluene (heptane:toluene:=2:1 in a volume ratio) as an eluent and silica gel as a filler. Furthermore, the resultant mixture was purified by recrystallization from a mixed solvent of heptane and Solmix A-11 (registered trademark) (Japan Alcohol Trading company, Ltd.) (heptane:Solmix=1:1 in a volume ratio), and the resultant product was dried, and thus 0.77 g of 4'-ethoxy-2,3-difluoro-4-(2-fluoro-3-(4-propylcyclohexyl) propoxy)-1,1'-biphenyl (No. 166) was obtained. A yield based on compound (e-12) was 52.3%.

A chemical shift δ (ppm) according to $^1$H-NMR analysis was as described below, and the compound obtained could be identified to be 4'-ethoxy-2,3-difluoro-4-(2-fluoro-3-(4-propylcyclohexyl)propoxy)-1,1'-biphenyl (No. 166). In addition, a solvent for measurement was $CDCl_3$.

Chemical shift δ (ppm); 7.42 (dd, 2H), 7.07 (dt, 1H), 6.97 (dd, 2H), 6.80 (dt, 1H), 5.05-4.91 (m, 1H), 4.22-4.13 (m, 2H), 4.08 (q, 2H), 1.89-1.73 (m, 6H), 1.44 (t, 3H), 1.36-1.25 (m, 3H), 1.18-1.14 (m, 3H), 1.06-0.86 (m, 7H).

A transition temperature of compound (No. 166) obtained was as described below.

Transition temperature: C 108.3 N 132.3 I.

Physical Properties of Compound (No. 166)

Liquid crystal composition C including 85% of mother liquid crystals i and 15% of 4'-ethoxy-2,3-difluoro-4-(2-fluoro-3-(4-propylcyclohexyl)propoxy)-1,1'-biphenyl (No. 166) obtained according to Example 2 was prepared. Physical properties of liquid crystal composition C obtained were measured and extrapolated values of physical properties of compound (No. 166) were determined based on the calculation by extrapolating the measured values. The values were as described below.

Maximum temperature ($T_{NI}$)=133.6° C.; dielectric anisotropy (Δ∈)=−7.51; optical anisotropy (Δn)=0.173.

Example 3

Synthesis of 4-(3-(4-ethoxy-2,3-difluorophenoxy)-2,2-difluoropropyl)-4'-propyl-1,1'-bi(cyclohexane) (No. 78)

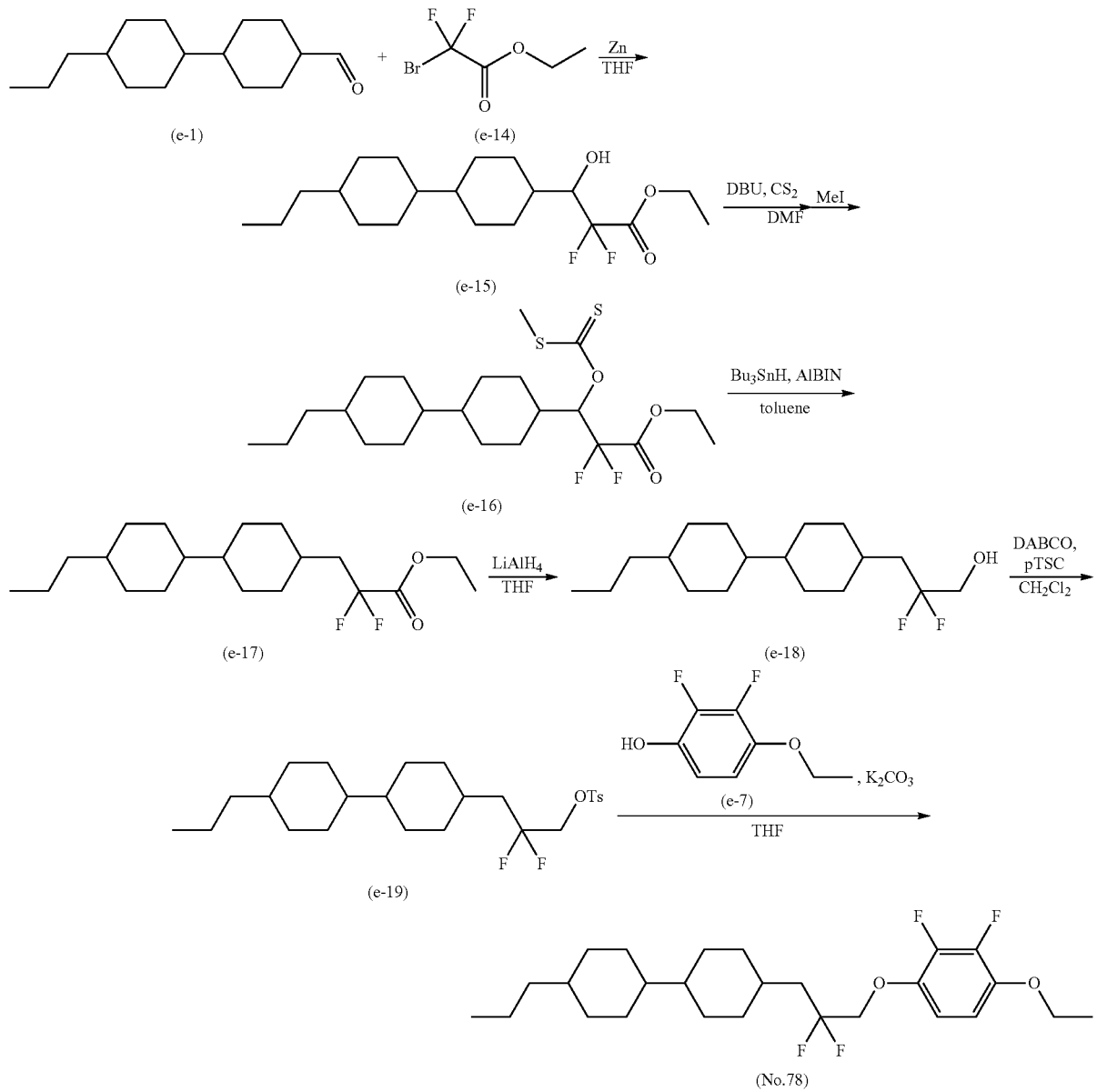

First Step

To a reaction vessel under a nitrogen atmosphere, 10.7 g of well-dried zinc, 25.0 g of ethyl bromodifluoroacetate (e-14) and 25 ml of THF were added, and the resultant mixture was cooled to 0° C. and stirred for 1 hour. The solution was slowly added dropwise in a temperature range of 20° C. to 25° C. to another reaction vessel under a nitrogen atmosphere in which 19.4 g of 4'-propyl-[1,1'-bi(cyclohexane)]-4-carboaldehyde (e-1) and 100 ml of THF were put, and the resultant mixture was further subjected to heating reflux for 4 hours. After cooling the resultant reaction mixture to 25° C., 300 ml of 1 N HCl aqueous solution and 300 ml of ethyl acetate were added to separate the mixture into an organic layer and an aqueous layer, and an extraction operation was performed. The resultant organic layer was isolated, and washed with water, a saturated aqueous solution of sodium hydrogencarbonate and water, and then the resultant solution was dried over anhydrous magnesium sulfate. Then, the solvent was distilled off under reduced pressure, the resultant residue was purified by a preparative isolation operation by means of column chromatography using a mixed solvent of toluene and ethyl acetate (toluene:ethyl acetate=9:1 in a volume ratio) as an eluent and silica gel as a filler, the resultant product was dried, and thus 16.2 g of ethyl 2,2-difluoro-3-hydroxy-3-(4'-propyl-[1,1'-bi(cyclohexane)]-4-yl)propanoate (e-15) was obtained. A yield based on compound (e-1) was 54.8%.

Second Step

To a reaction vessel under a nitrogen atmosphere, 16.2 g of ethyl 2,2-difluoro-3-hydroxy-3-(4'-propyl-[1,1'-bi(cyclohexane)]-4-yl)propanoate (e-15), 27.4 g of DBU, 27.2 ml of carbon disulfide and 100 ml of DMF were added, and the resultant mixture was stirred at 25° C. for 1.5 hours. Subsequently, 63.8 g of methyl iodide was added to a reaction mixture, and the resultant mixture was stirred at 25° C. for 1.5 hours. Then, 300 ml of water and 300 ml of ethyl acetate were added to separate the mixture into an organic layer and an aqueous layer, and an extraction operation was performed. The resultant organic layer was isolated, and washed with water, an aqueous solution of sodium thiosulfate, and water, and then the resultant solution was dried over anhydrous magnesium sulfate. The resultant solution was concentrated under reduced pressure, the resultant residue was purified by a preparative isolation operation by means of column chromatography using a mixed solvent of heptane and ethyl acetate (heptane:ethyl acetate=9:1 in a volume ratio) as an eluent and silica gel as a filler, the resultant product was dried, and thus 13.3 g of ethyl 2,2-difluoro-3-(((methylthio)carbonothioyl)oxy)-3-(4'-propyl-[1,1'-bi(cyclohexane)]-4-yl)propanoate (e-16) was obtained. A yield based on compound (e-15) was 66.5%.

Third Step

To a reaction vessel under a nitrogen atmosphere, 13.3 g of ethyl 2,2-difluoro-3-(((methylthio)carbonothioyl)oxy)-3-(4'-propyl-[1,1'-bi(cyclohexane)]-4-yl)propanoate (e-16), 25.6 g of tributyltin hydride, 1.0 g of AIBN and 100 ml of toluene were added, and the resultant mixture was subjected to heating reflux for 1 hour. After cooling the resultant reaction mixture to 25° C., 200 ml of water and 200 ml of toluene were added to separate the mixture into an organic layer and an aqueous layer, and an extraction operation was performed. The resultant organic layer was isolated, and washed with water, and then the resultant solution was dried over anhydrous magnesium sulfate. The resultant solution was concentrated under reduced pressure, the resultant residue was purified by a preparative isolation operation by means of column chromatography using a mixed solvent of heptane and ethyl acetate (heptane:ethyl acetate=20:1 in a volume ratio) as an eluent and silica gel as a filler, the resultant product was dried, and thus 11.9 g of ethyl 2,2-difluoro-3-(4'-propyl-[1,1'-bi(cyclohexane)]-4-yl) propanoate (e-17) was obtained.

Fourth Step

To a reaction vessel under a nitrogen atmosphere, 2.0 g of lithium aluminum hydride and 100 ml of THF were added, and the resultant mixture was cooled to −10° C. Thereto, 11.9 g of ethyl 2,2-difluoro-3-(4'-propyl-[1,1'-bi(cyclohexane)]-4-yl) propanoate (e-17) dissolved in 100 ml of THF was added dropwise in a temperature range of −10° C. to 0° C. Then, the resultant mixture was heated to 25° C., and stirred for 1 hour. Subsequently, 200 ml of 1 N HCl aqueous solution and 400 ml of ethyl acetate were added to separate the mixture into an organic layer and an aqueous layer, and an extraction operation was performed. The resultant organic layer was isolated, and washed with water, and then the resultant solution was dried over anhydrous magnesium sulfate. The resultant solution was concentrated under reduced pressure, the resultant residue was purified by a preparative isolation operation by means of column chromatography using a mixed solvent of toluene and ethyl acetate (toluene:ethyl acetate=5:1 in a volume ratio) as an eluent and silica gel as a filler, the resultant product was dried, and thus 4.0 g of 2,2-difluoro-3-(4'-propyl-[1,1'-bi(cyclohexane)]-4-yl) propan-1-ol (e-18) was obtained. A yield based on compound (e-16) was 45.1%.

Fifth Step

To a reaction vessel under a nitrogen atmosphere, 4.0 g of 2,2-difluoro-3-(4'-propyl-[1,1'-bi(cyclohexane)]-4-yl) propan-1-ol (e-18), 5.9 g of DABCO and 40 ml of dichloromethane were added, and the resultant mixture was cooled to 10° C. or lower. Thereto, 2.8 g of pTSC was added, and the resultant mixture was heated to 25° C. and stirred for 15 hours. Subsequently, 200 ml of water and 200 ml of toluene were added to separate the mixture into an organic layer and an aqueous layer, and an extraction operation was performed. The resultant organic layer was isolated, and washed with water, and then the resultant solution was dried over anhydrous magnesium sulfate. The resultant solution was concentrated under reduced pressure, the resultant residue was purified by a preparative isolation operation by means of column chromatography using a mixed solvent of heptane and ethyl acetate (heptane:ethyl acetate=10:1 in a volume ratio) as an eluent and silica gel as a filler, the resultant product was dried, and thus 4.3 g of 2,2-difluoro-3-(4'-propyl-[1,1'-bi(cyclohexane)]-4-yl) propyl 4-methylbenzenesulfonate (e-19) was obtained. A yield based on compound (e-18) was 70.3%.

Sixth Step

To a reaction vessel under a nitrogen atmosphere, 2.8 g of potassium carbonate, 1.8 g of 4-ethoxy-2,3-difluorophenol (e-7) and 60 ml of DMF were added, and the resultant mixture was heated to 60° C. and stirred for 1 hour. Thereto, 4.3 g of 2,2-difluoro-3-(4'-propyl-[1,1'-bi(cyclohexane)]-4-yl)propyl 4-methylbenzenesulfonate (e-19) dissolved in 40 ml of DMF was added dropwise, and the resultant mixture was heated to 100° C. and stirred for 40 hours. The mixture was then cooled to 25° C., 200 ml of water and 200 ml of toluene were added to separate the mixture into an organic layer and an aqueous layer, and an extraction operation was performed. The resultant organic layer was isolated, and washed with water, and then the resultant solution was dried over anhydrous magnesium sulfate. The resultant solution was concentrated under reduced pressure, the resultant residue was purified by a preparative isolation operation by means of column chromatography using a mixed solvent of heptane and ethyl acetate (heptane:ethyl acetate=10:1 in a volume ratio) as an eluent and silica gel as a filler. Furthermore, the resultant mixture was purified by recrystallization from heptane, and the resultant product was dried, and thus 1.5 g of 4-(3-(4-ethoxy-2,3-difluorophenoxy)-2,2-difluoropropyl)-4'-propyl-1,1'-bi(cyclohexane) (No. 78) was obtained. A yield based on compound (e-19) was 36.3%.

A chemical shift δ (ppm) according to $^1$H-NMR analysis was as described below, and the compound obtained could be identified to be 4-(3-(4-ethoxy-2,3-difluorophenoxy)-2,2-difluoropropyl)-4'-propyl-1,1'-bi(cyclohexane) (No. 78). In addition, a solvent for measurement was $CDCl_3$.

Chemical shift δ (ppm); 6.70-6.61 (m, 2H), 4.13-4.05 (m, 4H), 1.94-1.88 (m, 4H), 1.75-1.67 (m, 6H), 1.44-1.42 (t, 3H), 1.33-1.26 (m, 2H), 1.14-1.12 (m, 4H), 1.06-0.91 (m, 8H), 0.88-0.80 (m, 5H).

A transition temperature of compound (No. 78) obtained was as described below.

Transition temperature: C 92.3 ($S_A$ 72.1 N 83.6) I.

Physical Properties of Compound (No. 78)

Liquid crystal composition C including 85% of mother liquid crystals i and 15% of 4-(3-(4-ethoxy-2,3-difluorophenoxy)-2,2-difluoropropyl)-4'-propyl-1,1'-bi(cyclohexane) (No. 78) obtained according to Example 3 was prepared. Physical properties of composition C obtained were measured and extrapolated values of physical properties of compound (No. 78) were determined based on the calculation by extrapolating the measured values. The values were as described below.

Maximum temperature ($T_{NI}$)=65.9° C.; dielectric anisotropy ($\Delta\varepsilon$)=−5.16; refractive index anisotropy ($\Delta n$)=0.084.

Example 4

Synthesis of 4-(3-(4-ethoxy-2,3-difluorophenoxy)-1-fluoropropyl)-4'-propyl-1,1'-bi(cyclohexane) (No. 100)

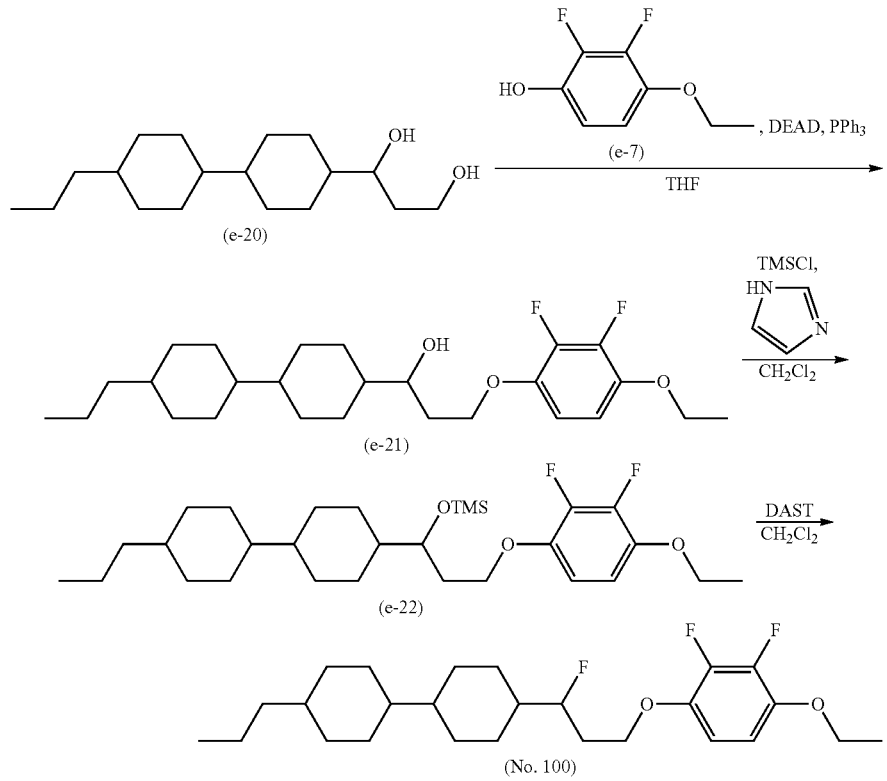

First Step

To a reaction vessel under a nitrogen atmosphere, 3.5 g of 1-(4'-propyl-[1,1'-bi(cyclohexane)]-4-yl)propane-1,3-diol (e-20), 2.3 g of 4-ethoxy-2,3-difluorophenol (e-7), 3.4 g of triphenyl phosphine and 70 ml of THF were added, and the resultant mixture was cooled to −10° C. Thereto, 6.0 ml of toluene solution of 2.2 M DEAD was added dropwise in a temperature range of −10° C. to 0° C. Then, the resultant mixture was heated to 25° C. and stirred for 1 hour, 200 ml of water and 200 ml of ethyl acetate were added to separate the mixture into an organic layer and an aqueous layer, and an extraction operation was performed. The resultant organic layer was isolated, and washed with water, and then the resultant solution was dried over anhydrous magnesium sulfate. The resultant solution was concentrated under reduced pressure, the resultant residue was purified by a preparative isolation operation by means of column chromatography using a mixed solvent of toluene and ethyl acetate (toluene:ethyl acetate=10:1 in a volume ratio) as an eluent and silica gel as a filler. Furthermore, the resultant mixture was purified by recrystallization from a mixed solvent of heptane and ethyl acetate (heptane:ethyl acetate=1:1 in a volume ratio), and the resultant product was dried, and thus 4.1 g of 3-(4-ethoxy-2,3-difluorophenoxy)-1-(4'-propyl-[',1'-bi(cyclohexane)]-4-yl)propan-1-ol (e-21) was obtained. A yield based on compound (e-20) was 75.2%.

Second Step

To a reaction vessel under a nitrogen atmosphere, 4.1 g of 3-(4-ethoxy-2,3-difluorophenoxy)-1-(4'-propyl-[1,1'-bi(cyclohexane)]-4-yl)propan-1-ol (e-21), 1.6 g of imidazole and 160 ml of dichloromethane were added, and the resultant mixture was cooled to 0° C. Thereto, 1.4 ml of TMSC1 was added dropwise in a temperature range of 0° C. to 10° C. Then, the resultant mixture was heated to 25° C., and stirred for 2 hours. Then, 300 ml of water and 300 ml of toluene were added to separate the mixture into an organic layer and an aqueous layer, and an extraction operation was performed. The resultant organic layer was isolated, and washed with water, and then the resultant solution was dried over anhydrous magnesium sulfate. The resultant solution was concentrated under reduced pressure, the resultant residue was purified by a preparative isolation operation by means of column chromatography using a mixed solvent of heptane and toluene (heptane:toluene=1:1 in a volume ratio) as an eluent and silica gel as a filler, the resultant product was dried, and thus 4.6 g of (3-(4-ethoxy-2,3-difluorophenoxy)-1-(4'-propyl-[1,1'-bi(cyclohexane)]-4-yl)propoxy)trimethylsilane (e-22) was obtained. A yield based on compound (e-21) was 95.4%.

Third Step

To a reaction vessel under a nitrogen atmosphere, 4.6 g of (3-(4-ethoxy-2,3-difluorophenoxy)-1-(4'-propyl-[1,1'-bi(cyclohexane)]-4-yl)propoxy)trimethylsilane (e-22) and 100 ml of dichloromethane were added, and the resultant mixture was cooled to −70° C. Thereto, 1.3 ml of DAST was added dropwise in a temperature range of −74° C. to −65° C. Then, the resultant mixture was heated to 25° C. and stirred for 15 hours. Subsequently, 200 ml of water and 200 ml of dichloromethane were added to separate the mixture into an organic layer and an aqueous layer, and an extraction operation was performed. The resultant organic layer was isolated, and washed with water, and then the resultant solution was dried over anhydrous magnesium sulfate. The resultant solution was concentrated under reduced pressure, the resultant residue was purified by a preparative isolation operation by means of column chromatography using a mixed solvent of heptane and toluene (heptane:toluene=3:1 in a volume ratio) as an eluent and silica gel as a filler. Furthermore, the resultant mixture was purified by recrystallization from heptane, and the resultant product was dried, and thus 1.1 g of 4-(3-(4-ethoxy-2,3-difluorophenoxy)-1-fluoropropyl)-4'-propyl-1,1'-bi(cyclohexane) (No. 100) was obtained. A yield based on compound (e-22) was 28.4%.

A chemical shift δ(ppm) according to $^1$H-NMR analysis was as described below, and the compound obtained could be identified to be 4-(3-(4-ethoxy-2,3-difluorophenoxy)-1-fluoropropyl)-4'-propyl-1,1'-bi(cyclohexane) (No. 100). In addition, a solvent for measurement was $CDCl_3$.

Chemical shift δ (ppm); 6.66-6.61 (m, 2H), 4.55-4.42 (m, 1H), 4.13-4.11 (dd, 2H), 4.06 (q, 2H), 2.15-1.98 (m, 2H), 1.95-1.91 (m, 1H), 1.80-1.69 (m, 10H), 1.53-1.44 (m, 7H), 1.42 (t, 3H), 1.34-1.25 (m, 2H), 1.15-0.93 (m, 10H), 0.88-0.80 (m, 5H).

A transition temperature of compound obtained (No. 100) was as described below.

Transition temperature: C 75.8 N 135.0 I.

Physical Properties of Compound (No. 100)

Liquid crystal composition D including 85% of mother liquid crystals i and 15% of 4-(3-(4-ethoxy-2,3-difluorophenoxy)-1-fluoropropyl)-4'-propyl-1,1'-bi(cyclohexane) (No. 100) was prepared. Physical properties of composition D obtained were measured and extrapolated values of physical properties of compound (No. 100) were determined based on the calculation by extrapolating the measured values. The values were as described below.

Maximum temperature $(T_{NI})$=125.3° C.; dielectric anisotropy $(\Delta\epsilon)$=−5.53; refractive index anisotropy $(\Delta n)$=0.100.

Example 5

Synthesis of 4-(2,2-difluoro-3-(4-propylphenyl)propoxy)-4'-ethoxy-2,3-difluoro-1,1'-biphenyl (No. 178)

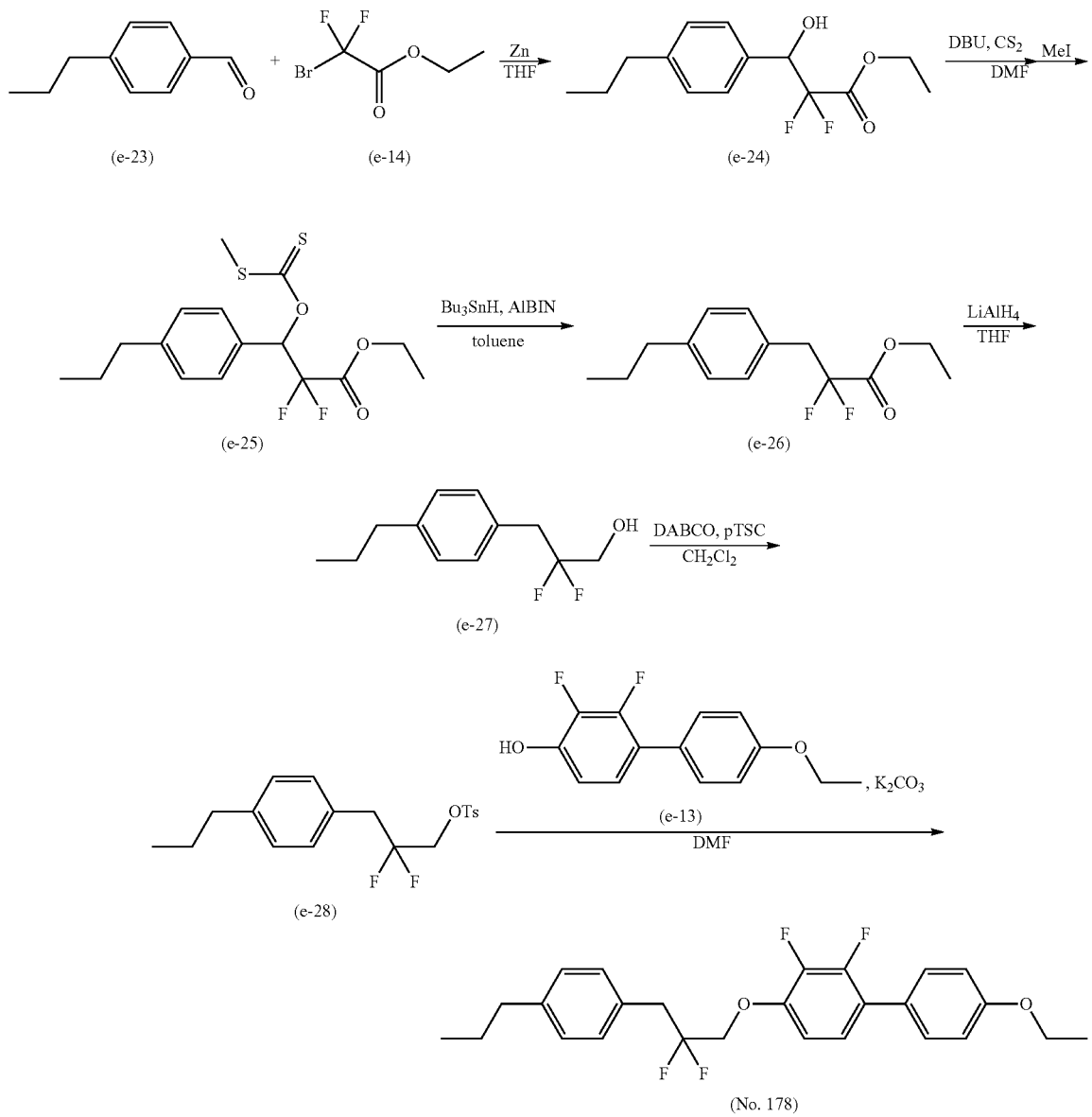

First Step

To a reaction vessel under a nitrogen atmosphere, 4.4 g of well-dried zinc, 10.3 g of ethyl bromodifluoroacetate (e-14) and 25 ml of THF were added, and the resultant mixture was cooled to 0° C. and stirred for 1 hour. The solution was slowly added dropwise in a temperature range of 20° C. to 25° C. to another reaction vessel under a nitrogen atmosphere in which 5.0 g of 4-propylbenzaldehyde (e-23) and 50 ml of THF were put, and the resultant mixture was further subjected to heating reflux for 4 hours. After cooling the resultant reaction mixture to 25° C., 200 ml of 1 N HCl aqueous solution and 200 ml of ethyl acetate were added to separate the mixture into an organic layer and an aqueous layer, and an extraction operation was performed. The resultant organic layer was isolated, and washed with water, a saturated aqueous solution of sodium hydrogencarbonate and water, and then the resultant solution was dried over anhydrous magnesium sulfate. Then, the solvent was distilled off under reduced pressure, the resultant residue was purified by a preparative isolation operation by means of column chromatography using a mixed solvent of heptane and ethyl acetate (heptane:ethyl acetate=20:1 in a volume ratio) as an eluent and silica gel as a filler, the resultant product was dried, and thus 9.0 g of ethyl 2,2-difluoro-3-hydroxy-3-(4-propylphenyl)propanoate (e-24) was obtained. A yield based on compound (e-23) was 97.8%.

Second Step

To a reaction vessel under a nitrogen atmosphere, 9.0 g of ethyl 2,2-difluoro-3-hydroxy-3-(4-propylphenyl)propanoate (e-24), 20.1 g of DBU, 19.9 ml of carbon disulfide and 90 ml of DMF were added, and the resultant mixture was stirred at 25° C. for 1.5 hours. Subsequently, 46.8 g of methyl iodide was added to a reaction mixture, and the resultant mixture was stirred at 25° C. for 1.5 hours. Then, 200 ml of water and 200 ml of ethyl acetate were added to separate the mixture into an organic layer and an aqueous layer, and an extraction operation was performed. The resultant organic layer was isolated, and washed with water, an aqueous solution of sodium thiosulfate, and water, and then the resultant solution was dried over anhydrous magnesium sulfate. The resultant solution was concentrated under reduced pressure, the resultant residue was purified by a preparative isolation operation by means of column chromatography using a mixed solvent of heptane and ethyl acetate (heptane:ethyl acetate=20:1 in a volume ratio) as an eluent and silica gel as a filler, the resultant product was dried, and thus 5.8 g of ethyl 2,2-difluoro-3-(((methylthio)carbonothioyl)oxy)-3-(4-propylphenyl) propanoate (e-25) was obtained. A yield based on compound (e-24) was 53.8%.

Third Step

To a reaction vessel under a nitrogen atmosphere, 5.8 g of ethyl 2,2-difluoro-3-(((methylthio)carbonothioyl)oxy)-3-(4-propylphenyl) propanoate (e-25), 15.5 g of tributyltin hydride, 0.5 g of AIBN and 50 ml of toluene were added, and the resultant mixture was subjected to heating reflux for 1 hour. After cooling the resultant reaction mixture to 25° C., 100 ml of water and 100 ml of toluene were added to separate the mixture into an organic layer and an aqueous layer, and an extraction operation was performed. The resultant organic layer was isolated, and washed with water, and then the resultant solution was dried over anhydrous magnesium sulfate. The resultant solution was concentrated under reduced pressure, the resultant residue was purified by a preparative isolation operation by means of column chromatography using a mixed solvent of heptane and ethyl acetate (heptane:ethyl acetate=10:1 in a volume ratio) as an eluent and silica gel as a filler, the resultant product was dried, and thus 3.9 g of ethyl 2,2-difluoro-3-(4-propylphenyl)propanoate (e-26) was obtained. A yield based on compound (e-25) was 94.9%.

Fourth Step

To a reaction vessel under a nitrogen atmosphere, 0.8 g of lithium aluminum hydride and 50 ml of THF were added, and the resultant mixture was cooled to −10° C. Thereto, 3.9 g of 2,2-difluoro-3-(4-propylphenyl)propanoate (e-26) dissolved in 10 ml of THF was added dropwise in a temperature range of −10° C. to 0° C. Then, the resultant mixture was heated to 25° C. and stirred for 1 hour. Subsequently, 100 ml of 1 N HCl aqueous solution and 200 ml of ethyl acetate were added to separate the mixture into an organic layer and an aqueous layer, and an extraction operation was performed. The resultant organic layer was isolated, and washed with water, and then the resultant solution was dried over anhydrous magnesium sulfate. The resultant solution was concentrated under reduced pressure, the resultant residue was purified by a preparative isolation operation by means of column chromatography using a mixed solvent of toluene and ethyl acetate (toluene:ethyl acetate=5:1 in a volume ratio) as an eluent and silica gel as a filler, the resultant product was dried, and thus 1.6 g of 2,2-difluoro-3-(4-propylphenyl)propan-1-ol (e-27) was obtained. A yield based on compound (e-26) was 50.4%.

Fifth Step

To a reaction vessel under a nitrogen atmosphere, 1.6 g of 2,2-difluoro-3-(4-propylphenyl)propan-1-ol (e-27), 1.5 g of DABCO and 30 ml of dichloromethane were added, and the resultant mixture was cooled to 10° C. or lower. Thereto, 1.6 g of pTSC was added, and the resultant mixture was heated to 25° C. and stirred for 15 hours. Subsequently, 100 ml of water and 100 ml of toluene were added to separate the mixture into an organic layer and an aqueous layer, and an extraction operation was performed. The resultant organic layer was isolated, and washed with water, and then the resultant solution was dried over anhydrous magnesium sulfate. The resultant solution was concentrated under reduced pressure, the resultant residue was purified by a preparative isolation operation by means of column chromatography using toluene as an eluent and silica gel as a filler, the resultant product was dried, and thus 4.3 g of 2,2-difluoro-3-(4-propylphenyl)propyl 4-methylbenzenesulfonate (e-28) was obtained. A yield based on compound (e-27) was 75.2%.

Sixth Step

To a reaction vessel under a nitrogen atmosphere, 1.7 g of potassium carbonate, 1.6 g of 4'-ethoxy-2,3-difluoro-[1,1'-biphenyl]-4-ol (e-13) and 50 ml of DMF were added, and the resultant mixture was heated to 60° C. and stirred for 1 hour. Thereto, 4.3 g of 2,2-difluoro-3-(4-propylphenyl)propyl 4-methylbenzenesulfonate (e-28) dissolved in 20 ml of DMF was added dropwise, and the resultant mixture was heated to 100° C. and stirred for 40 hours. The resultant mixture was cooled to 25° C., 200 ml of water and 200 ml of toluene were added to separate the mixture into an organic layer and an aqueous layer, and an extraction operation was performed. The resultant organic layer was isolated, and washed with water, and then the resultant solution was dried over anhydrous magnesium sulfate. The resultant solution was concentrated under reduced pressure, the resultant residue was purified by a preparative isolation operation by means of column chromatography using a mixed solvent of heptane and ethyl acetate (heptane:ethyl acetate=20:1 in a volume ratio) as an eluent and silica gel as a filler. Furthermore, the resultant mixture was purified by recrystallization from heptane, and the resultant product was dried, and thus 1.4 g of 4-(2,2-difluoro-3-(4-propylphenyl)propoxy)-4'-ethoxy-2,3-difluoro-1,1'-biphenyl (No. 277) was obtained. A yield based on compound (e-28) was 52.9%.

A chemical shift δ (ppm) according to ¹H-NMR analysis was as described below, and the compound obtained could be identified to be 4-(2,2-difluoro-3-(4-propylphenyl)propoxy)-4'-ethoxy-2,3-difluoro-1,1'-biphenyl (No. 178). In addition, a solvent for measurement was CDCl$_3$.

Chemical shift δ (ppm); 7.44-7.41 (m, 2H), 7.23-7.22 (m, 2H), 7.14-7.12 (m, 2H), 7.08-7.04 (m, 1H), 6.98-6.95 (m, 2H), 6.75-6.72 (m, 1H), 4.11-4.06 (m, 4H), 3.38 (t, 2H), 2.56 (t, 2H), 1.63 (dt, 2H), 1.44 (t, 3H), 0.93 (t, 3H).

A transition temperature of compound (No. 178) obtained was as described below.

Transition temperature: C 100.4 I.

Physical Properties of Compound (No. 178)

Liquid crystal composition E including 85% of mother liquid crystals i and 15% of 4-(3-(4-ethoxy-2,3-difluorophenoxy)-2,2-difluoropropyl)-4'-propyl-1,1'-bi(cyclohexane) (No. 178) obtained according to Example 5 was prepared. Physical properties of liquid crystal composition E obtained were measured and extrapolated values of physical properties of compound (No. 178) were determined based on the calculation by extrapolating the measured values. The values were as described below.

Maximum temperature ($T_{NI}$)=3.9° C.; dielectric anisotropy (Δ∈)=−3.01; refractive index anisotropy (Δn)=0.140.

Compounds No. 1 to No. 374 as described below can be prepared in a manner similar to the synthetic methods described in Examples 1 to 5. Attached data were measured in accordance with the techniques described above. As for a transition temperature, the attached data were described using measured values of the compounds per se. As for a maximum temperature ($T_{NI}$), dielectric anisotropy (Δ∈) and optical anisotropy (Δn), the attached data were described using values of physical properties converted, according to the extrapolation method described above, from measured values of a sample in which a compound was mixed with the mother liquid crystals (i).

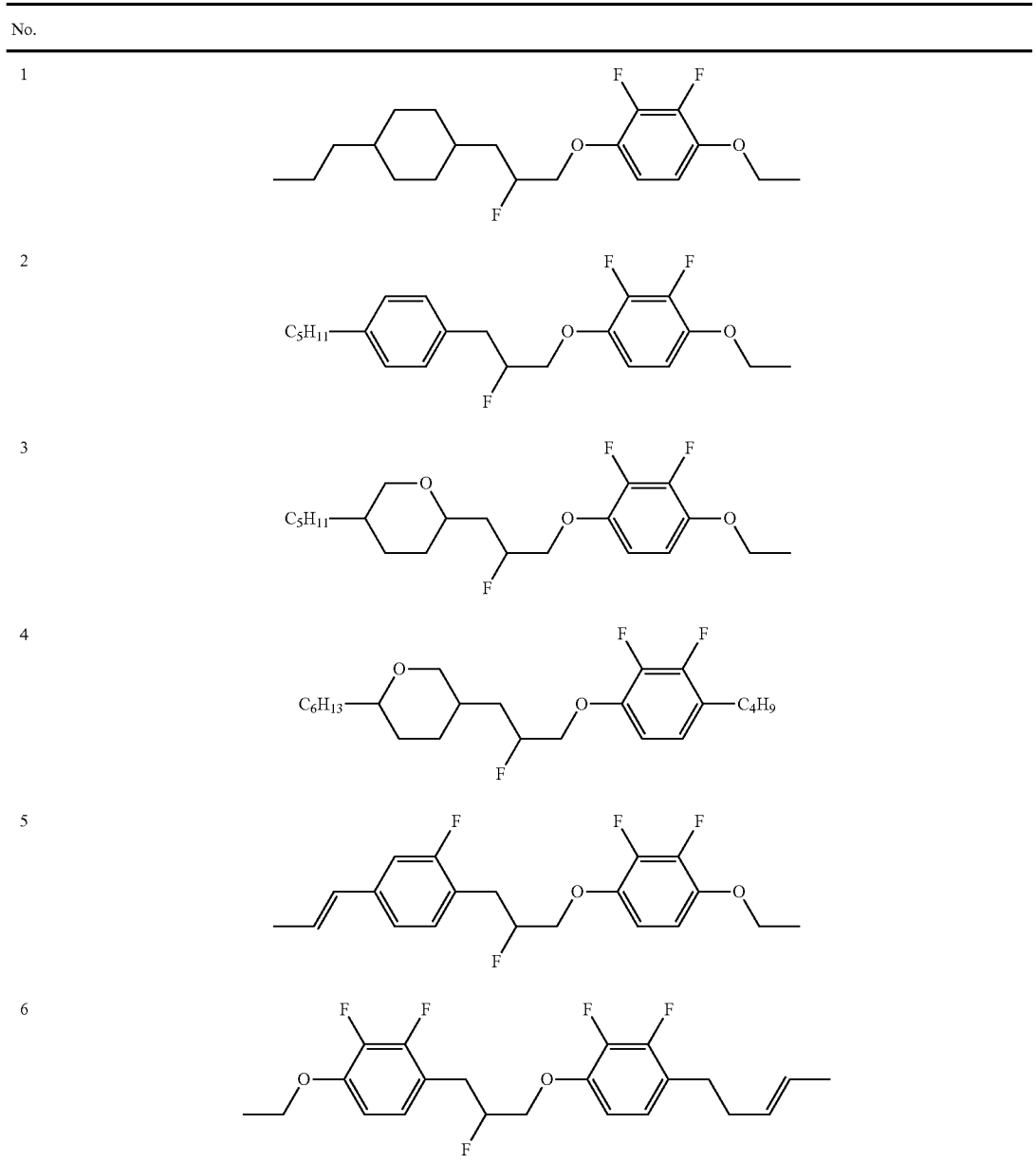

| No. | |
|---|---|
| 7 | 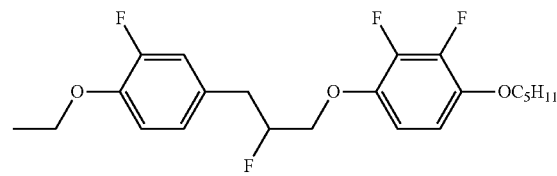 |
| 8 | 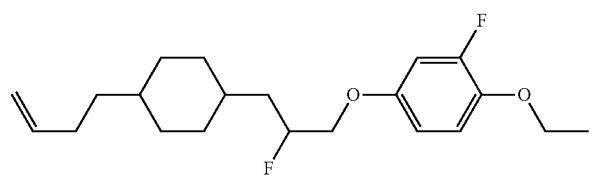 |
| 9 | 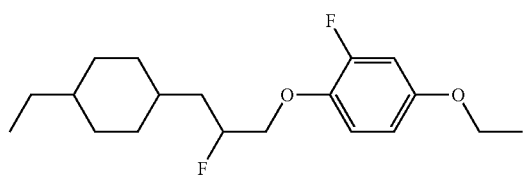 [SMILES: CCOc1ccc(OCC(F)CC2CCC(CC)CC2)c(F)c1] |
| 10 | 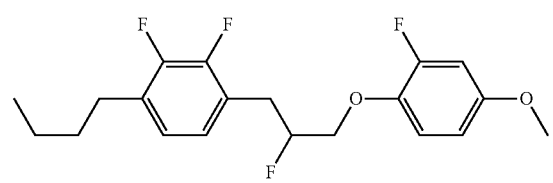 [SMILES: CCCCc1ccc(CC(F)COc2ccc(OC)cc2F)c(F)c1F] |
| 11 | 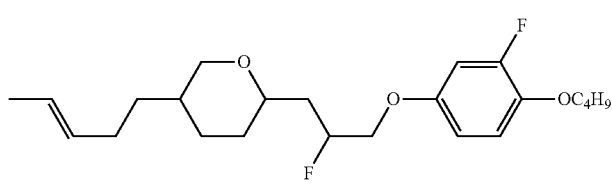 |
| 12 | 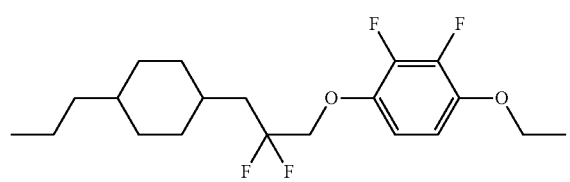 |
| 13 | 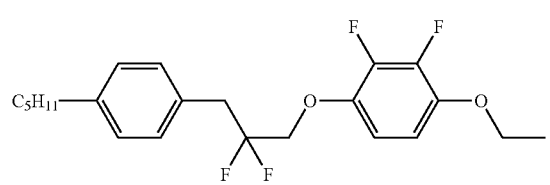 |
| 14 | 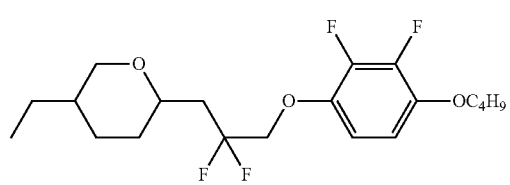 |

| No. |
|---|
| 15 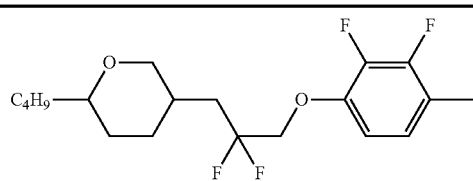 |
| 16 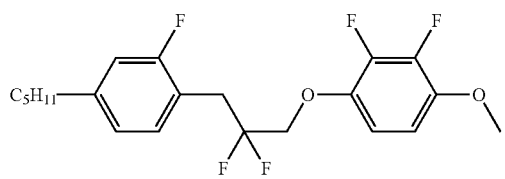 |
| 17 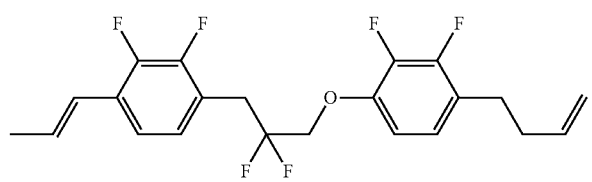 [SMILES: C=CCCc1ccc(OCC(F)(F)Cc2ccc(/C=C/C)c(F)c2F)c(F)c1F] |
| 18 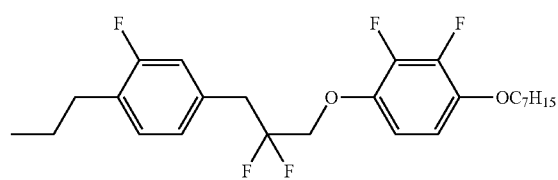 |
| 19 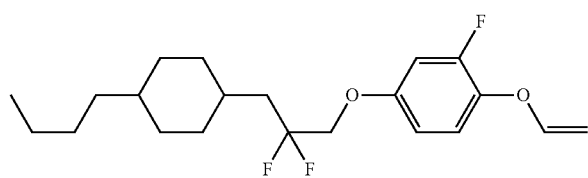 |
| 20 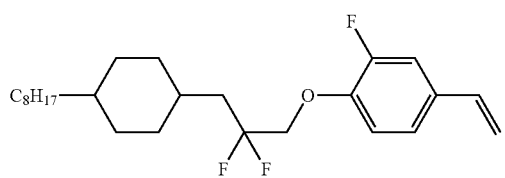 |
| 21 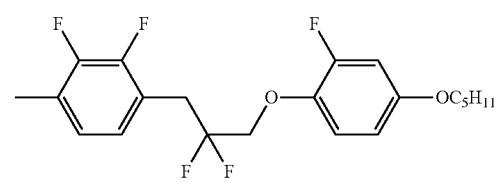 |
| 22 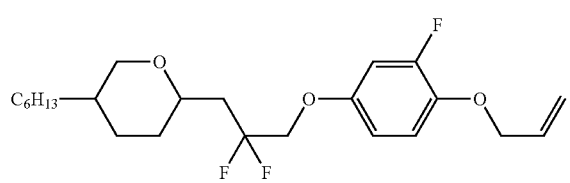 |
| 23 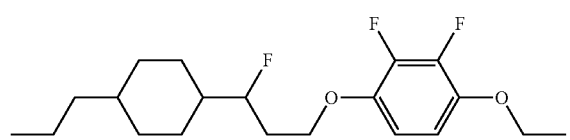 |

-continued
| No. |
|---|
24
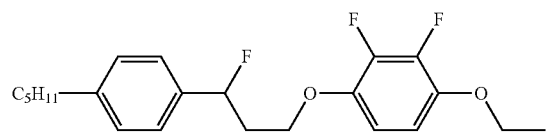
25
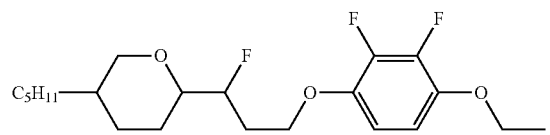
26
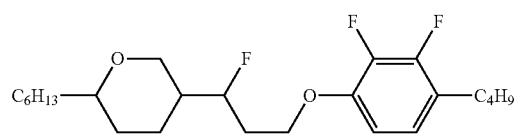
27
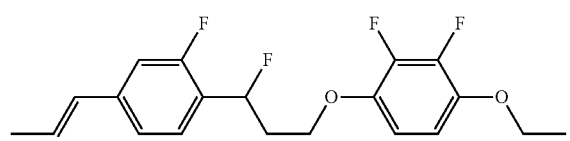
28
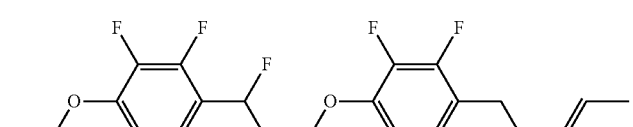
29
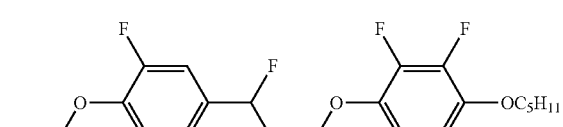
30
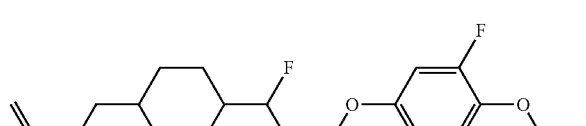
31
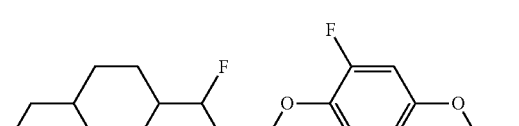
32
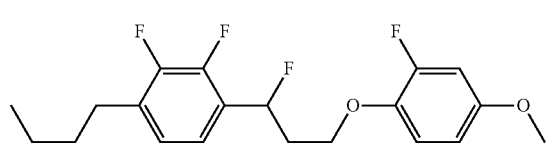 [SMILES: CCCCc1ccc(C(F)CCOc2ccc(OC)cc2F)c(F)c1F]
33
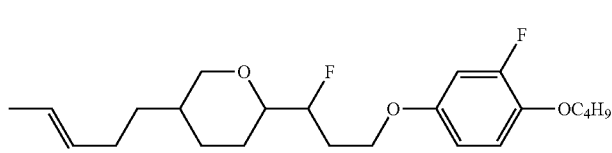
34
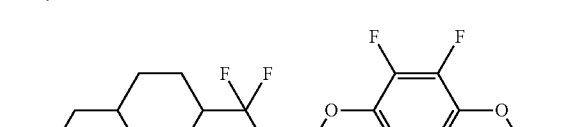

| No. | |
|---|---|
| 35 | 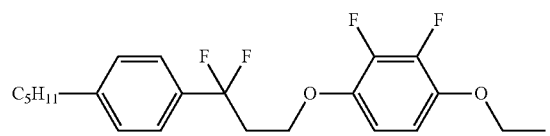 |
| 36 | 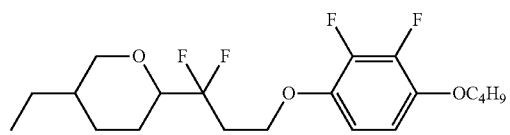 |
| 37 | 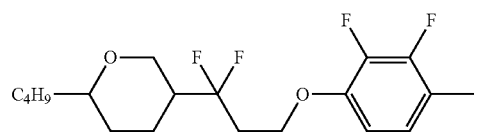 |
| 38 | 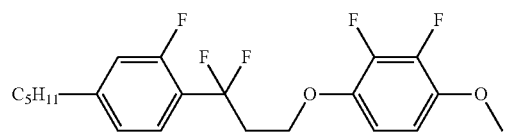 |
| 39 | 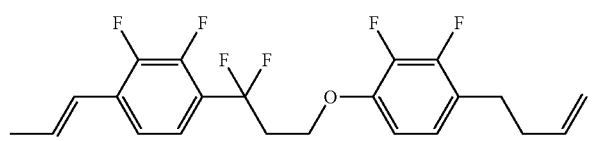 [SMILES: C=CCCc1ccc(OCCC(F)(F)c2ccc(/C=C/C)c(F)c2F)c(F)c1F] |
| 40 | 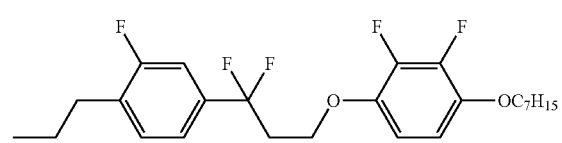 |
| 41 | 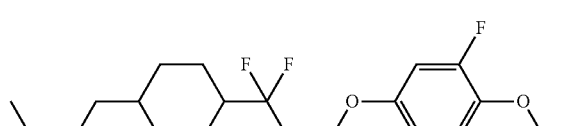 |
| 42 | 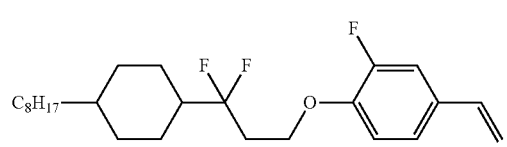 |
| 43 | 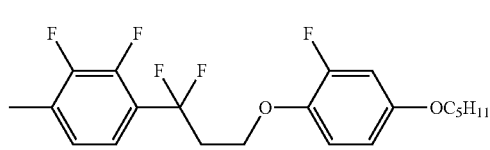 |
| 44 | 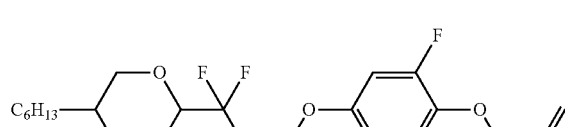 |
| 45 | 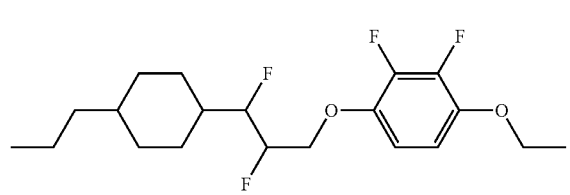 |

| No. | |
|---|---|
| 46 | 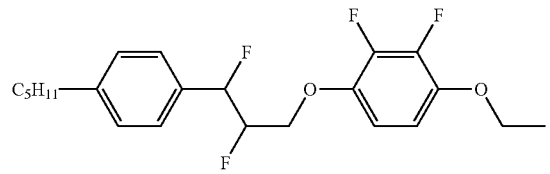 |
| 47 | 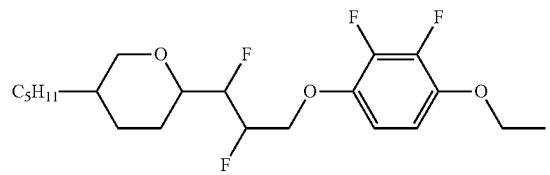 |
| 48 | 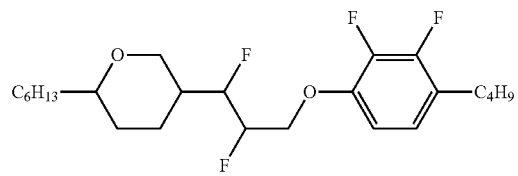 |
| 49 | 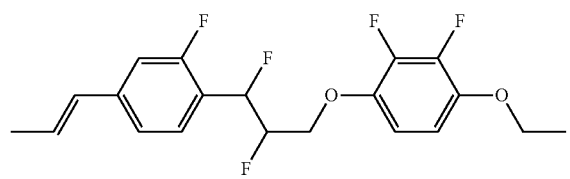 [SMILES: C/C=C/c1ccc(C(F)C(F)COc2ccc(OCC)c(F)c2F)c(F)c1] |
| 50 | 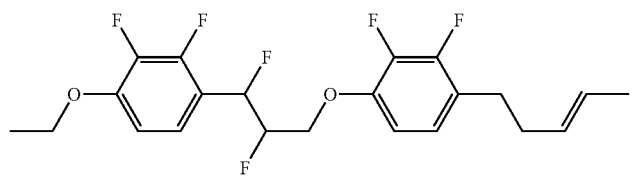 |
| 51 | 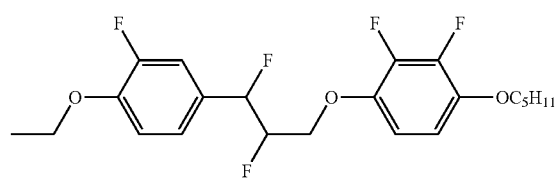 |
| 52 | 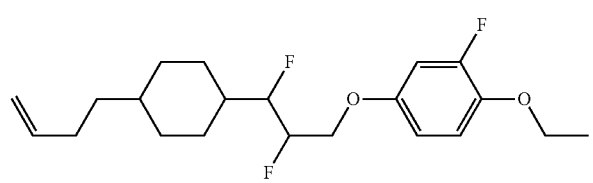 [SMILES: C=CCCC1CCC(C(F)C(F)COc2ccc(OCC)c(F)c2)CC1] |
| 53 | 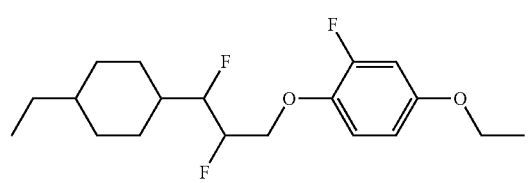 |

-continued
| No. | |
|---|---|
| 54 | 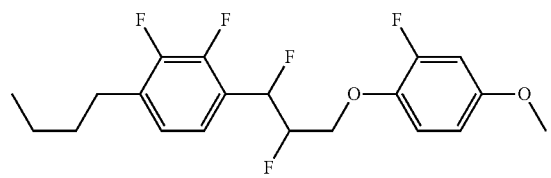 [SMILES: CCCCc1ccc(C(F)C(F)COc2ccc(OC)cc2F)c(F)c1F] |
| 55 | 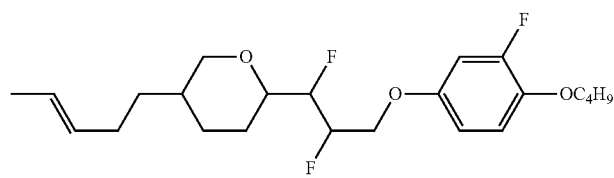 |
| 56 | 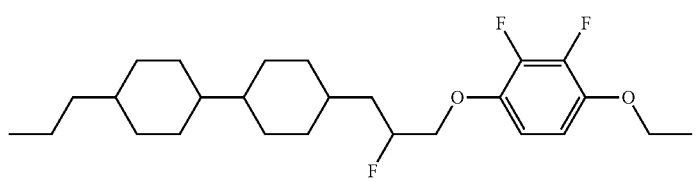
C 66.9 S$_B$ 86.0 N 136.5 I
T$_{NI}$; 127.3, Δ ε; −9.46, Δ n; 0.100 |
| 57 | 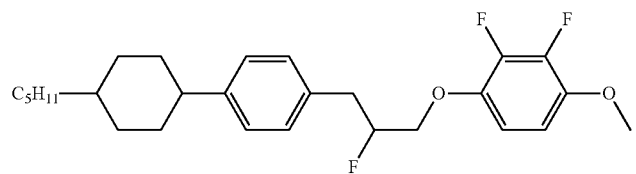 |
| 58 | 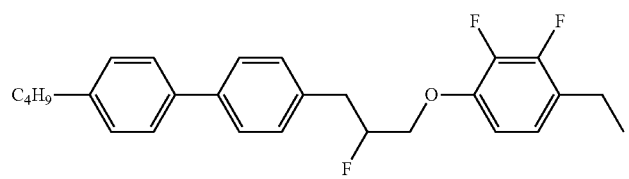 |
| 59 | 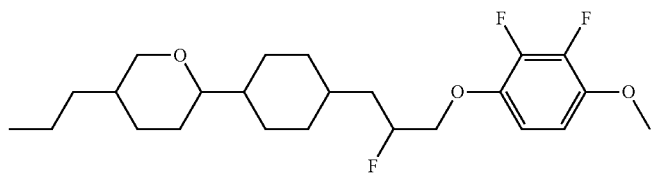 [SMILES: CCCC1CCC(C2CCC(CC(F)COc3ccc(OC)c(F)c3F)CC2)OC1] |
| 60 | 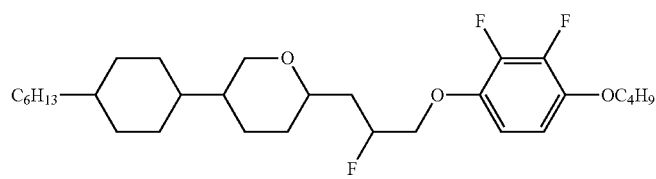 |
| 61 | 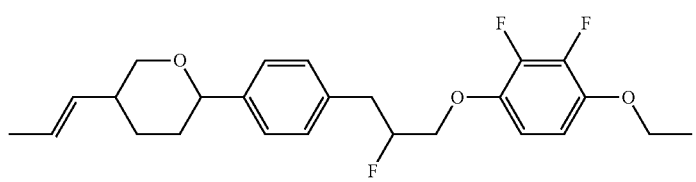 [SMILES: C/C=C/C1CCC(c2ccc(CC(F)COc3ccc(OCC)c(F)c3F)cc2)OC1] |

| No. | |
|---|---|
| 62 | 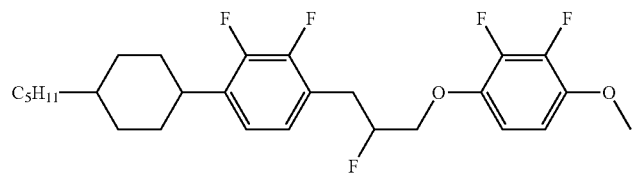 |
| 63 | 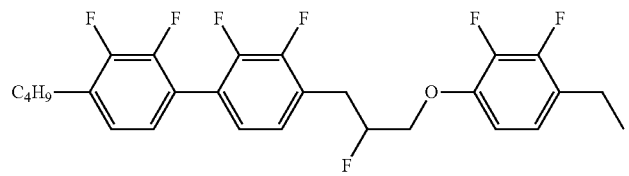 |
| 64 | 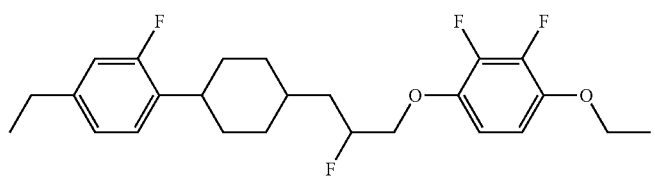 [SMILES: CCOc1ccc(OCC(F)CC2CCC(c3ccc(CC)cc3F)CC2)c(F)c1F] |
| 65 | 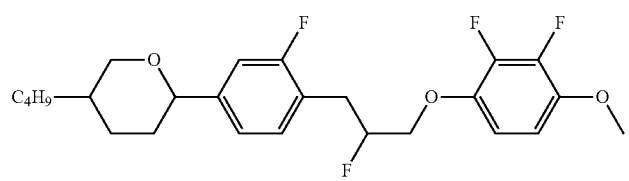 |
| 66 | 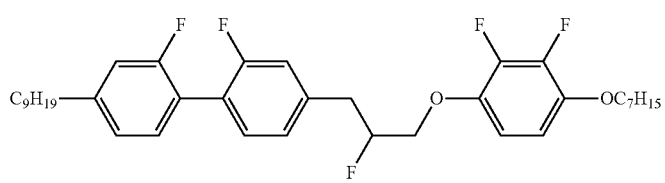 |
| 67 | 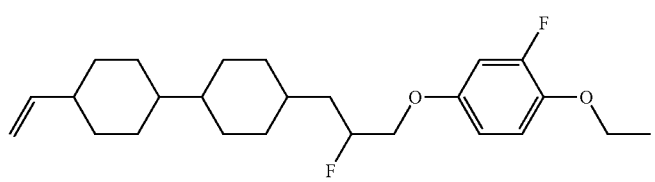 [SMILES: C=CC1CCC(C2CCC(CC(F)COc3ccc(OCC)c(F)c3)CC2)CC1] |
| 68 | 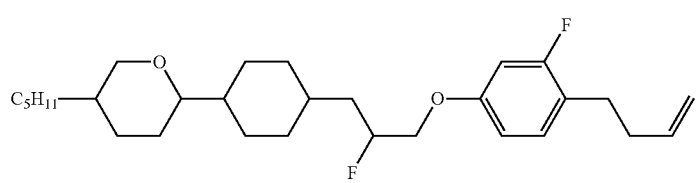 |
| 69 | 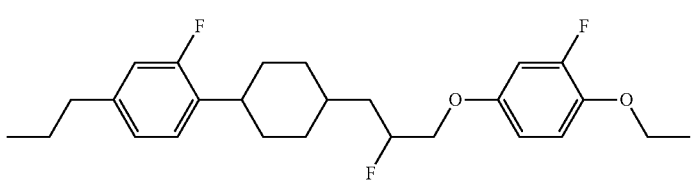 [SMILES: CCCc1ccc(C2CCC(CC(F)COc3ccc(OCC)c(F)c3)CC2)c(F)c1] |

-continued
| No. | |
|---|---|
| 70 | 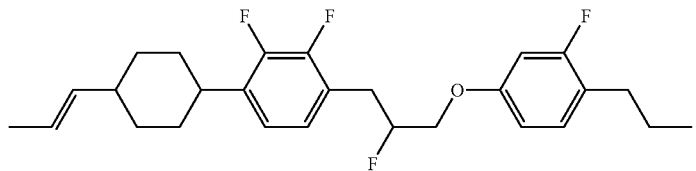 |
| 71 | 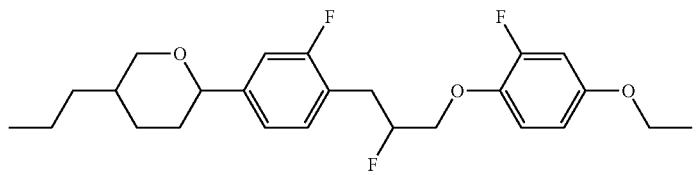 |
| 72 | 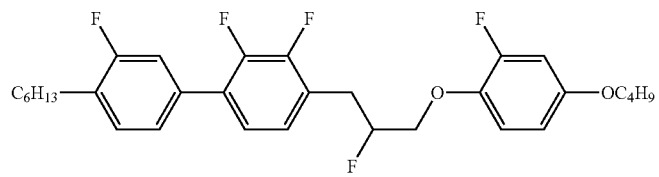 |
| 73 | 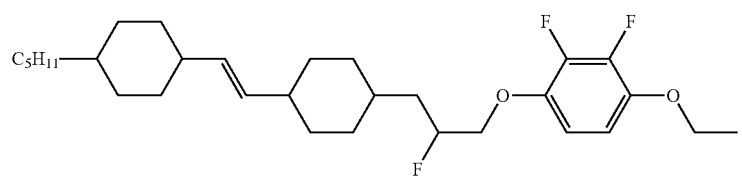 |
| 74 | 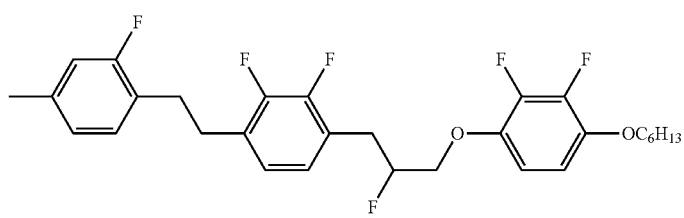 |
| 75 | 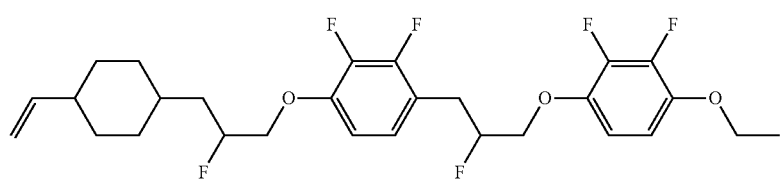 |
| 76 | 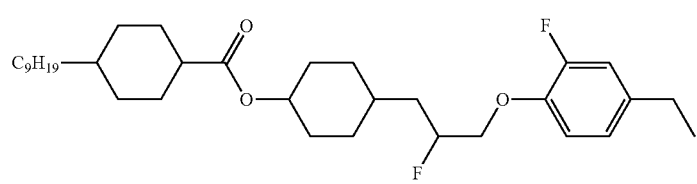 |
| 77 | 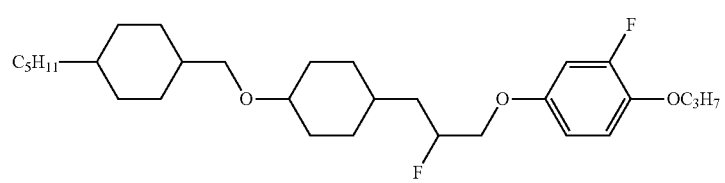 |

| No. | |
|---|---|
| 78 | 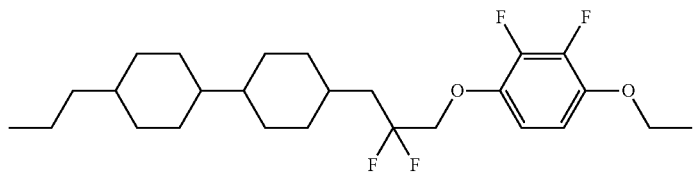
C 92.3 (S$_A$ 72.1 N 83.6) I
T$_{NI}$; 65.9, Δ ε; −5.16, Δ n; 0.084 |
| 79 | 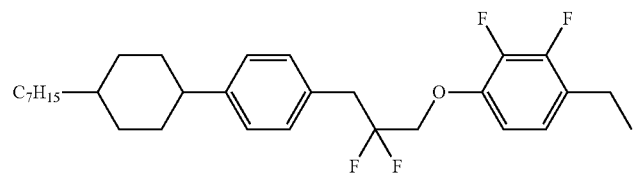 |
| 80 | 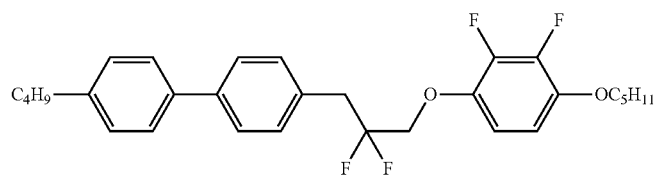 |
| 81 | 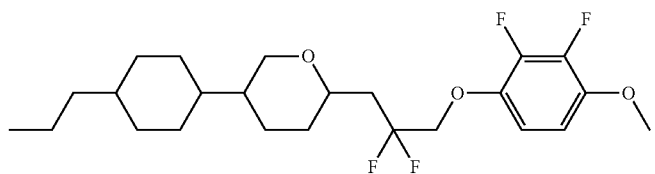 [SMILES: CCCC1CCC(C2CCC(CC(F)(F)COc3ccc(OC)c(F)c3F)OC2)CC1] |
| 82 | 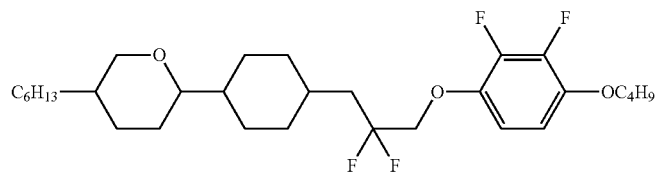 |
| 83 | 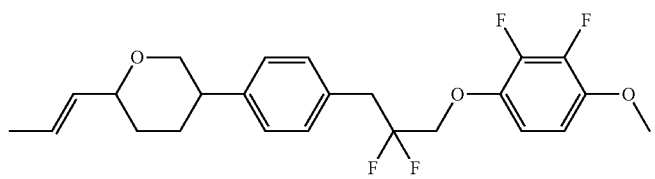 [SMILES: C/C=C/C1CCC(c2ccc(CC(F)(F)COc3ccc(OC)c(F)c3F)cc2)CO1] |
| 84 | 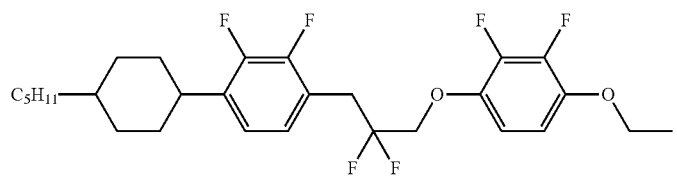 |
| 85 | 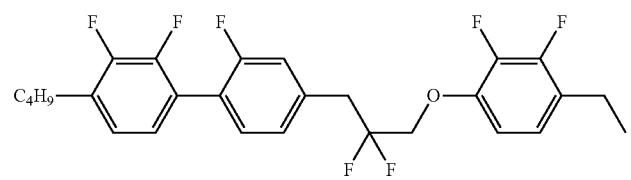 |

-continued
| No. | |
|---|---|
| 86 | 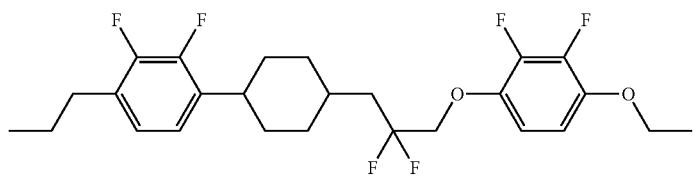 |
| 87 | 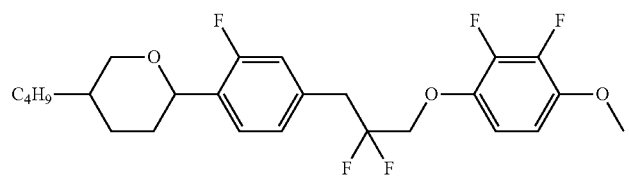 |
| 88 | 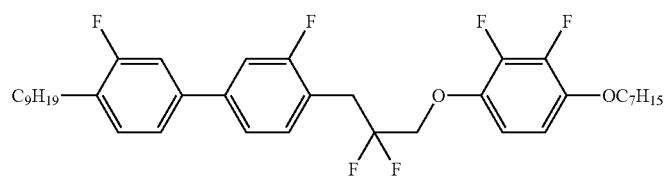 |
| 89 | 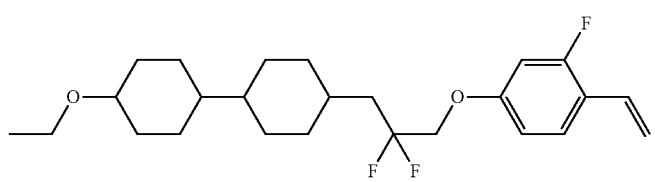 [SMILES: C=Cc1ccc(OCC(F)(F)CC2CCC(C3CCC(OCC)CC3)CC2)cc1F] |
| 90 | 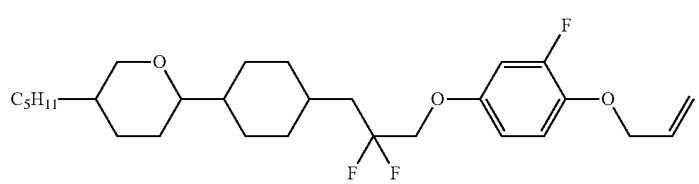 |
| 91 | 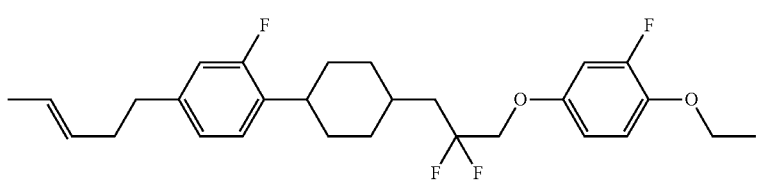 [SMILES: C/C=C/CCc1ccc(C2CCC(CC(F)(F)COc3ccc(OCC)c(F)c3)CC2)c(F)c1] |
| 92 | 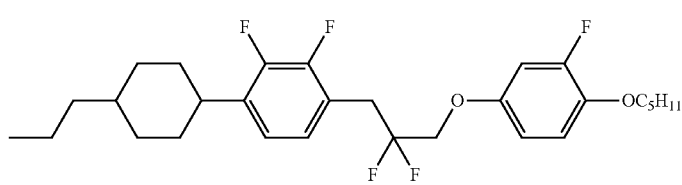 |
| 93 | 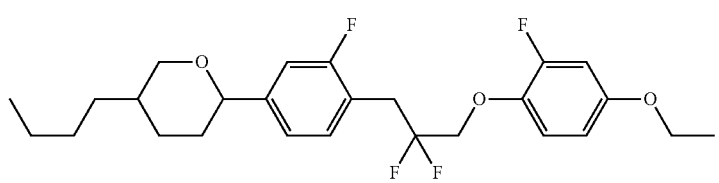 [SMILES: CCCCC1CCC(c2ccc(CC(F)(F)COc3ccc(OCC)cc3F)c(F)c2)OC1] |

-continued
| No. | |
|---|---|
| 94 | 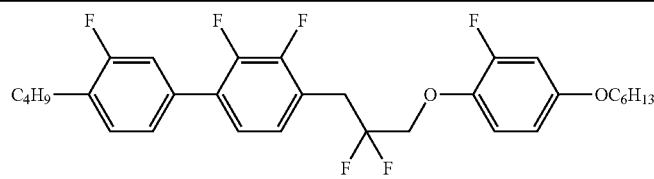 |
| 95 | 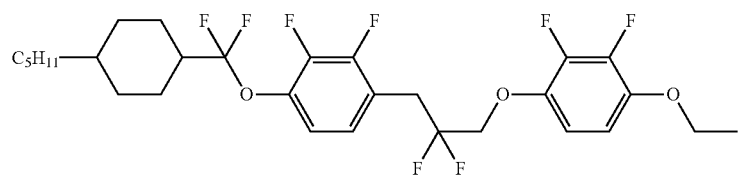 |
| 96 | 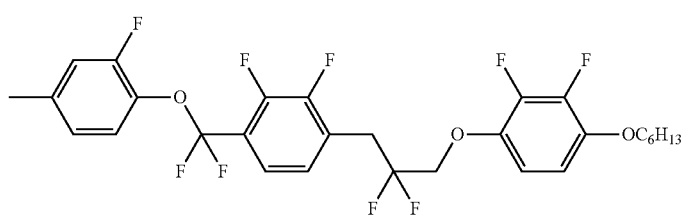 |
| 97 | 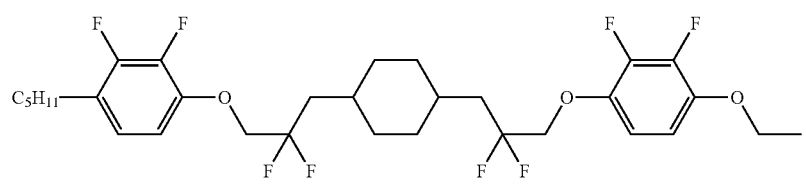 |
| 98 | 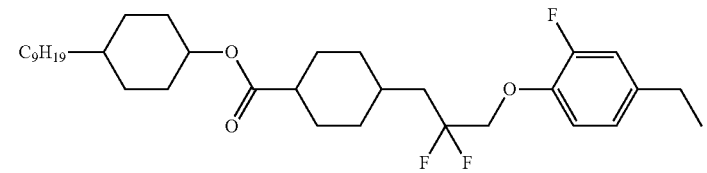 |
| 99 | 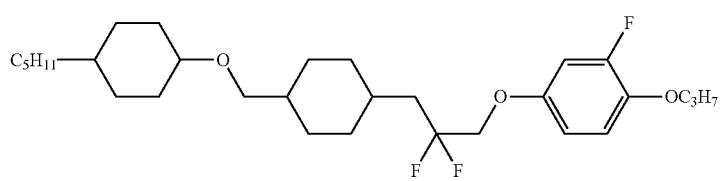 |
| 100 | 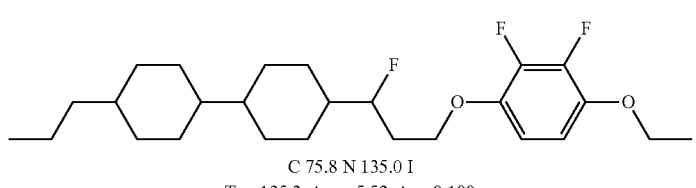<br>C 75.8 N 135.0 I<br>$T_{NI}$; 125.3, Δ ε; −5.53, Δ n; 0.100 |
| 101 | 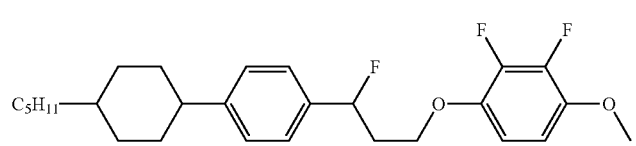 |
| 102 | 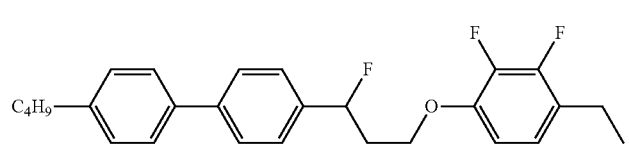 |

-continued
| No. | |
|---|---|
| 103 | 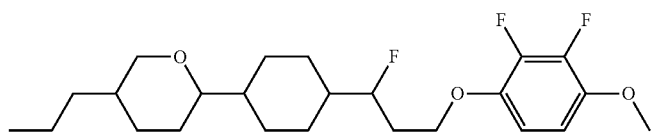 [SMILES: CCCC1CCC(C2CCC(C(F)CCOc3ccc(OC)c(F)c3F)CC2)OC1] |
| 104 | 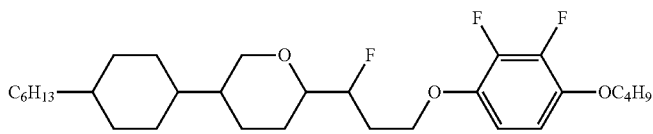 |
| 105 | 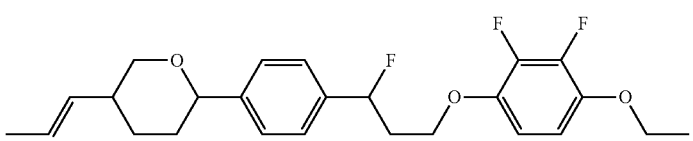 [SMILES: C/C=C/C1CCC(c2ccc(C(F)CCOc3ccc(OCC)c(F)c3F)cc2)OC1] |
| 106 | 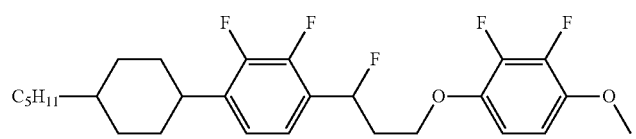 |
| 107 | 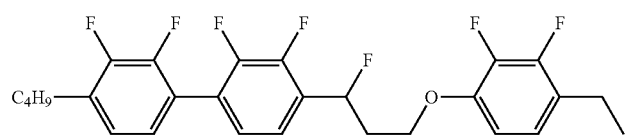 |
| 108 | 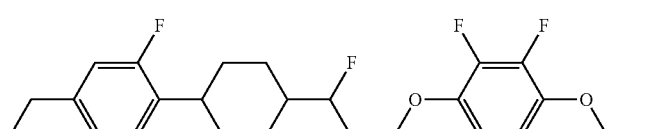 |
| 109 | 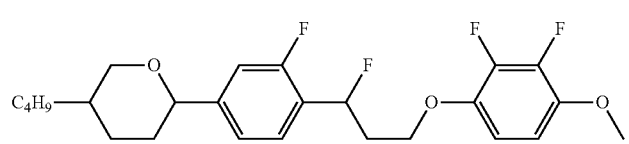 |
| 110 | 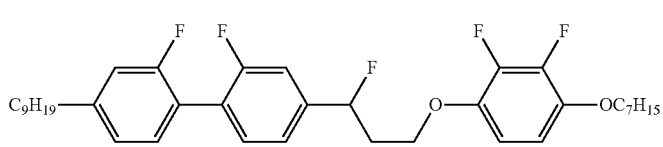 |
| 111 | 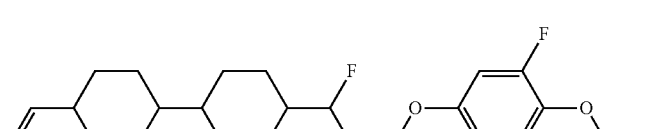 |
| 112 | 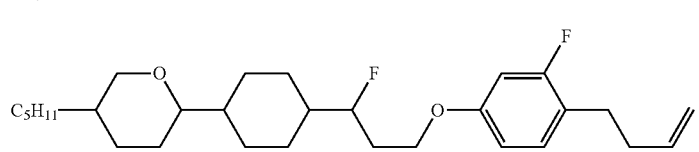 |
| 113 | 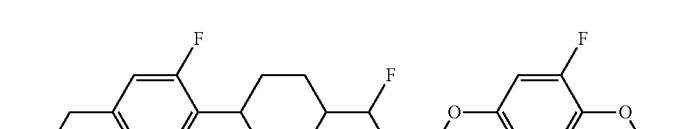 |

| No. |  |
|---|---|
| 114 |  |
| 115 | 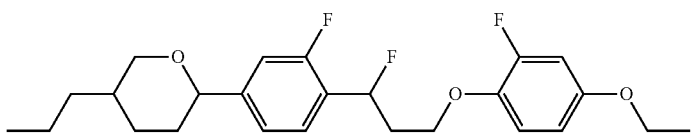 |
| 116 | 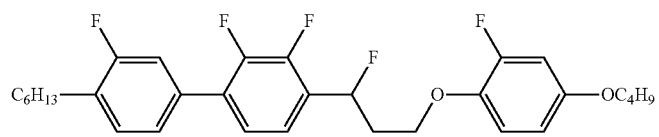 |
| 117 | 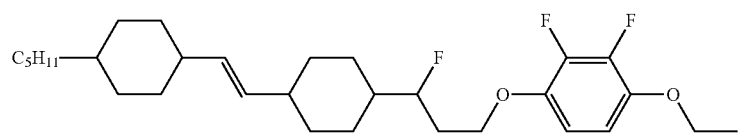 |
| 118 | 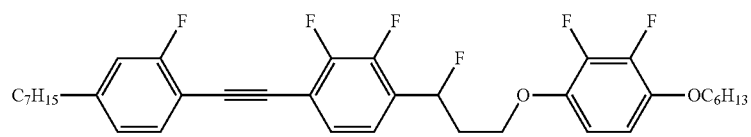 |
| 119 | 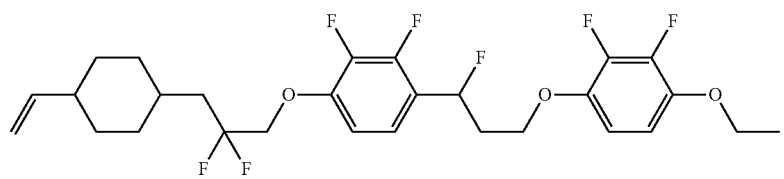 [SMILES: C=CC1CCC(CC(F)(F)COc2ccc(C(F)CCOc3ccc(OCC)c(F)c3F)c(F)c2F)CC1] |
| 120 | 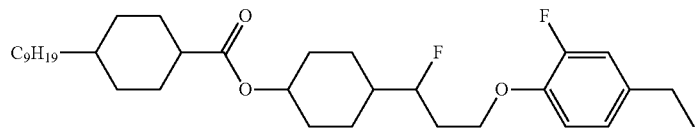 |
| 121 | 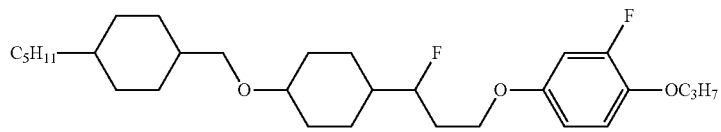 |
| 122 | 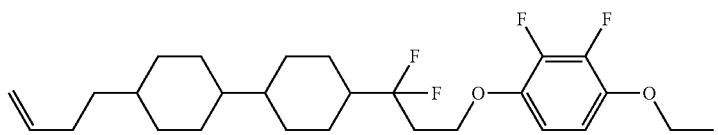 [SMILES: C=CCCC1CCC(C2CCC(C(F)(F)CCOc3ccc(OCC)c(F)c3F)CC2)CC1] |
| 123 | 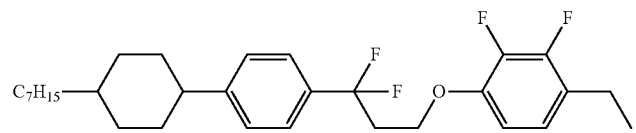 |
| 124 | 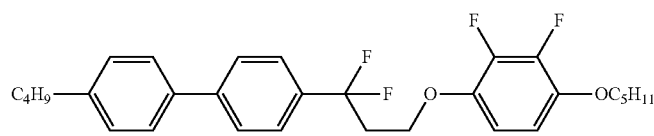 |

-continued
| No. |  |
|---|---|
| 125 | 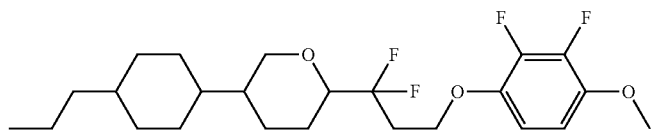 |
| 126 | 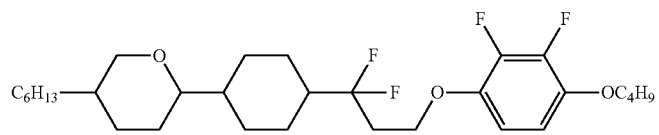 |
| 127 | 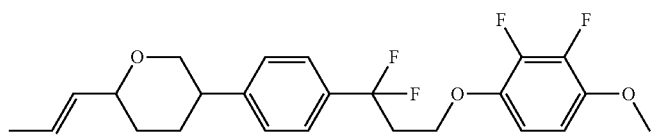 [SMILES: C/C=C/C1CCC(c2ccc(C(F)(F)CCOc3ccc(OC)c(F)c3F)cc2)CO1] |
| 128 | 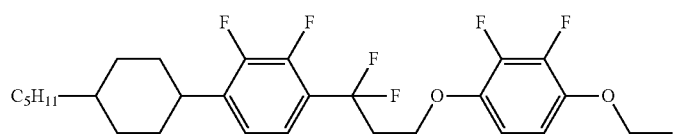 |
| 129 | 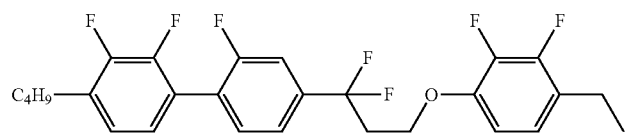 |
| 130 | 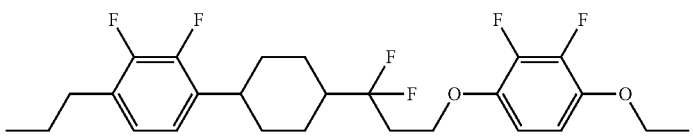 [SMILES: CCCc1ccc(C2CCC(C(F)(F)CCOc3ccc(OCC)c(F)c3F)CC2)c(F)c1F] |
| 131 | 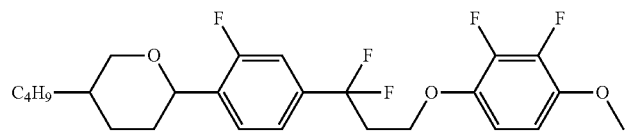 |
| 132 | 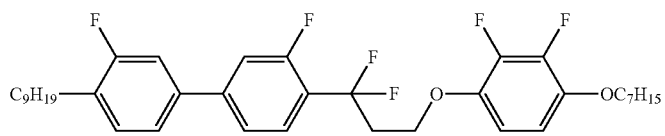 |
| 133 |  |
| 134 | 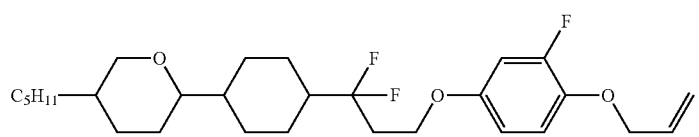 |
| 135 | 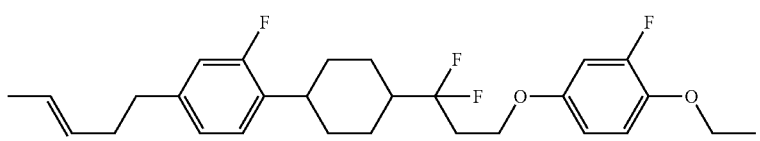 [SMILES: C/C=C/CCc1ccc(C2CCC(C(F)(F)CCOc3ccc(OCC)c(F)c3)CC2)c(F)c1] |

-continued
| No. | |
|---|---|
| 136 | 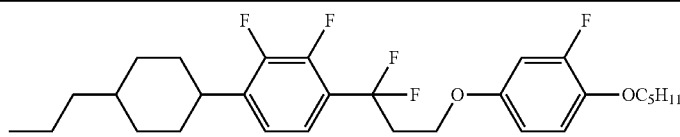 |
| 137 | 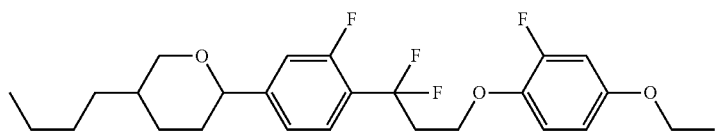 |
| 138 | 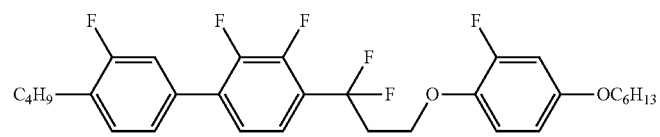 |
| 139 | 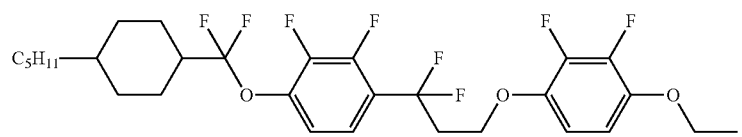 |
| 140 | 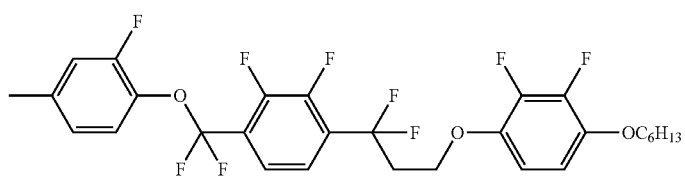 |
| 141 | 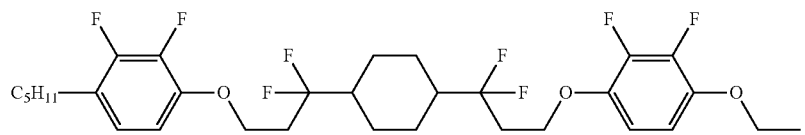 |
| 142 | 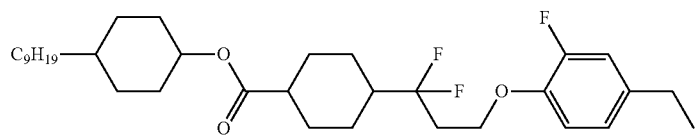 |
| 143 | 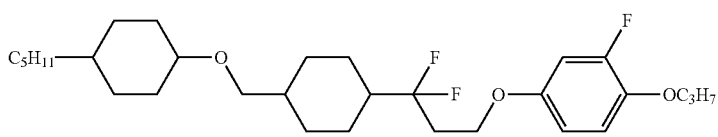 |
| 144 | 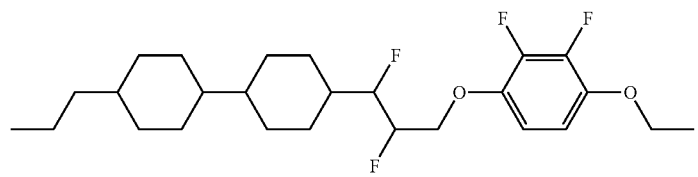 |
| 145 | 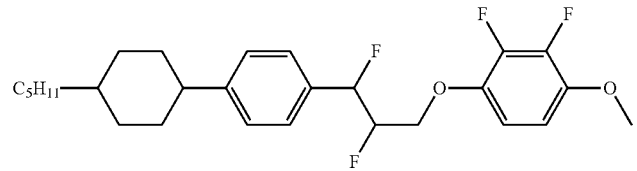 |

-continued
| No. | |
|---|---|
| 146 | 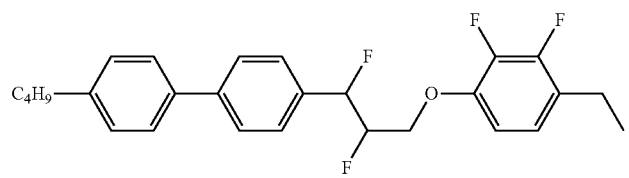 |
| 147 | 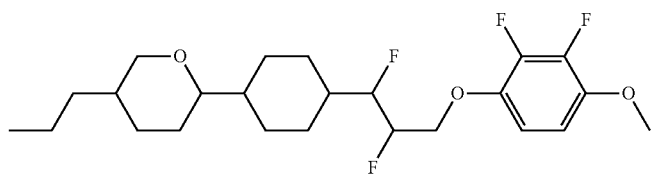 |
| 148 | 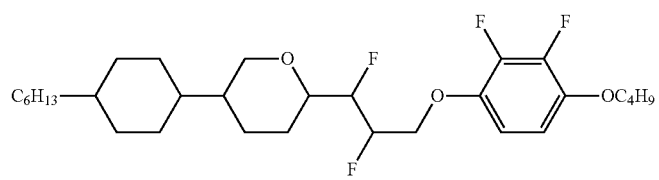 |
| 149 | 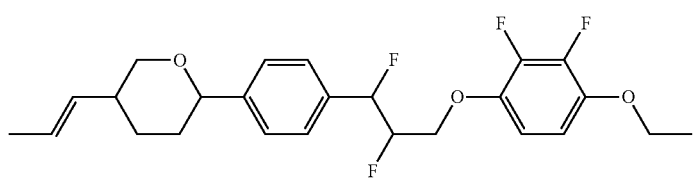 [SMILES: C/C=C/C1CCC(c2ccc(C(F)C(F)COc3ccc(OCC)c(F)c3F)cc2)OC1] |
| 150 | 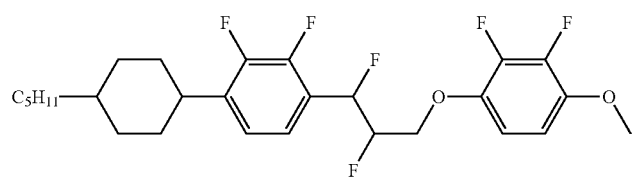 |
| 151 | 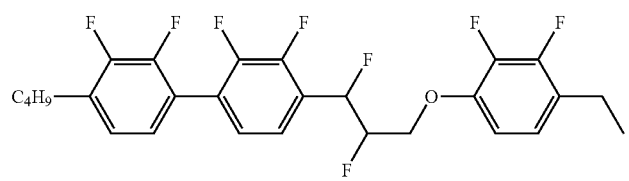 |
| 152 | 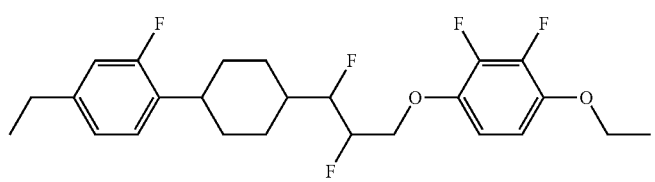 [SMILES: CCOc1ccc(OCC(F)C(F)C2CCC(c3ccc(CC)cc3F)CC2)c(F)c1F] |
| 153 | 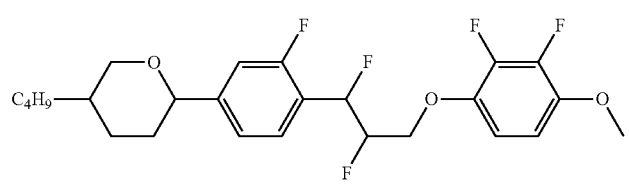 |

-continued
| No. | |
|---|---|
| 154 | 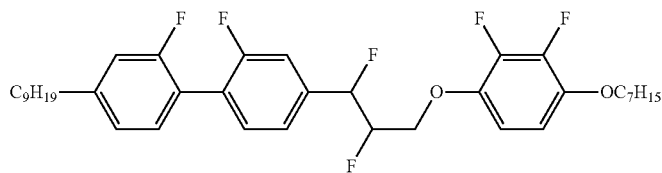 |
| 155 | 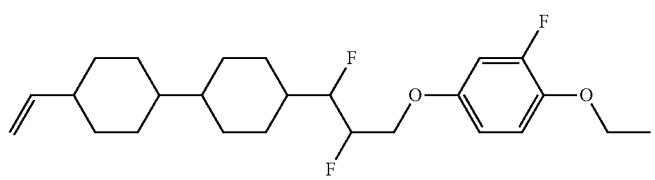 |
| 156 | 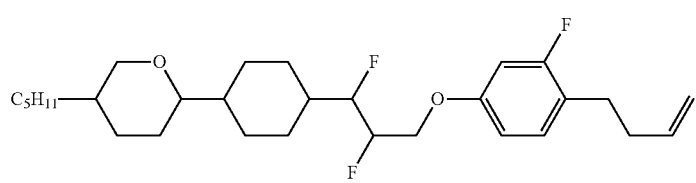 |
| 157 | 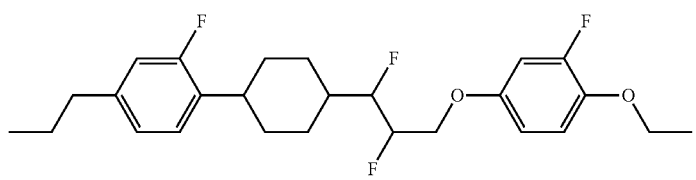 |
| 158 | 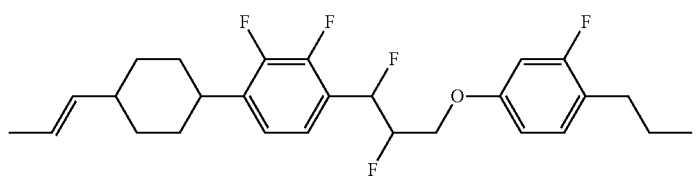 [SMILES: C/C=C/C1CCC(c2ccc(C(F)C(F)COc3ccc(CCC)c(F)c3)c(F)c2F)CC1] |
| 159 | 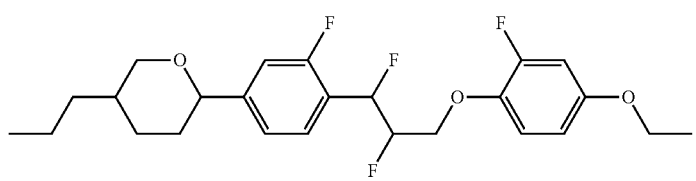 [SMILES: CCCC1CCC(c2ccc(C(F)C(F)COc3ccc(OCC)cc3F)c(F)c2)OC1] |
| 160 | 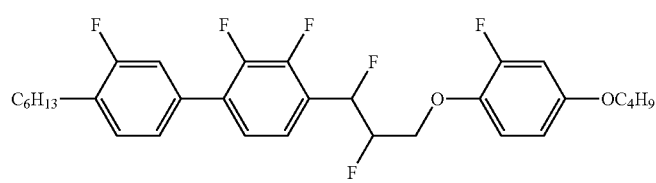 |
| 161 | 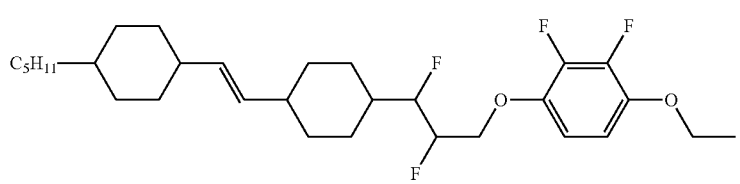 |

| No. | |
|---|---|
| 162 | 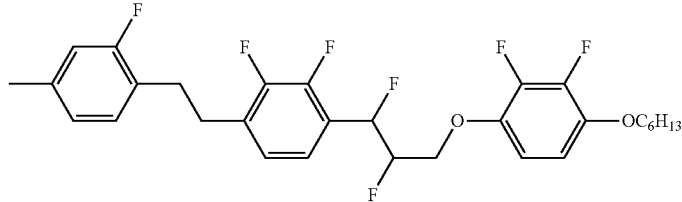 |
| 163 | 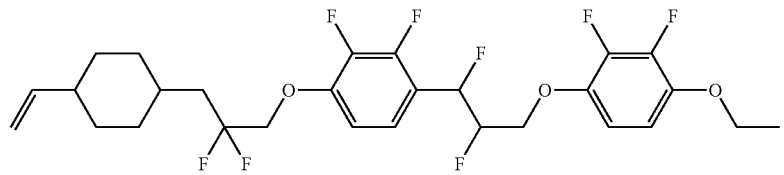 [SMILES: C=CC1CCC(CC(F)(F)COc2ccc(C(F)C(F)COc3ccc(OCC)c(F)c3F)c(F)c2F)CC1] |
| 164 | 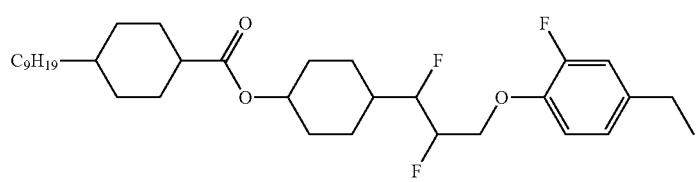 |
| 165 | 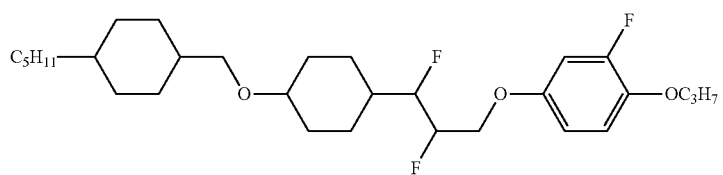 |
| 166 | 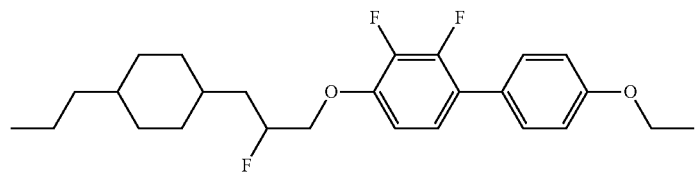<br>C 108.3 N 132.3 I<br>$T_{NI}$; 133.6, $\Delta\epsilon$; −7.51, $\Delta$ n; 0.173 |
| 167 | 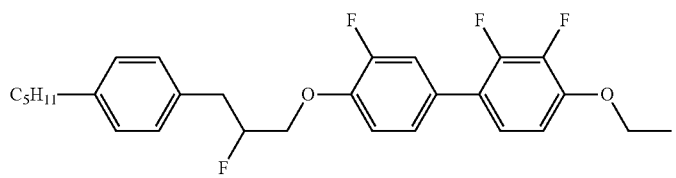 |
| 168 | 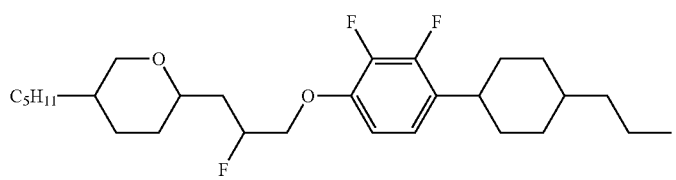 |
| 169 | 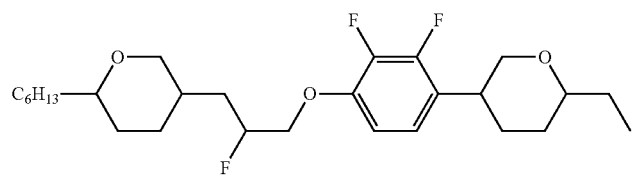 |

| No. | |
|---|---|
| 170 | 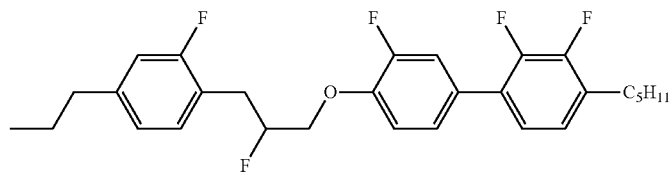 |
| 171 | 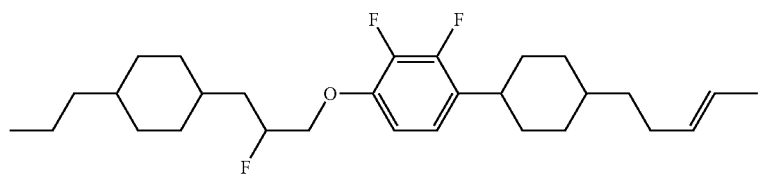 |
| 172 | 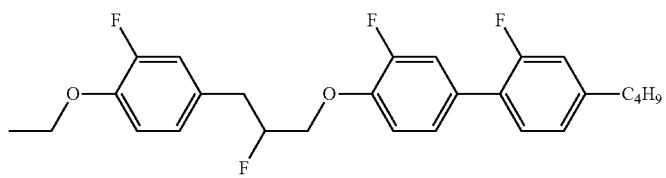 |
| 173 | 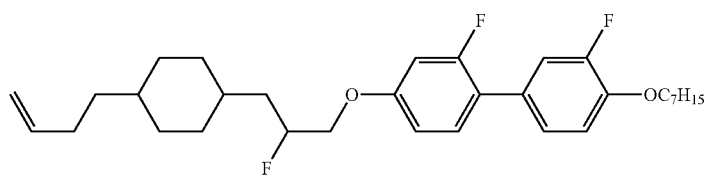 |
| 174 | 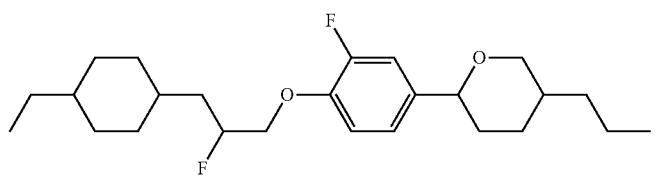 [SMILES: CCCC1CCC(c2ccc(OCC(F)CC3CCC(CC)CC3)c(F)c2)OC1] |
| 175 | 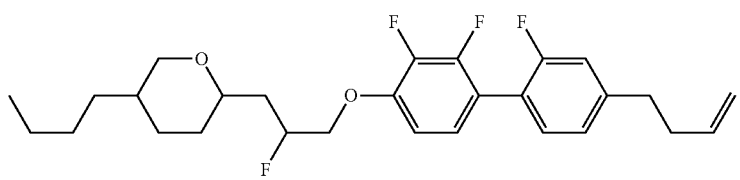 [SMILES: C=CCCc1ccc(-c2ccc(OCC(F)CC3CCC(CCCC)CO3)c(F)c2F)c(F)c1] |
| 176 | 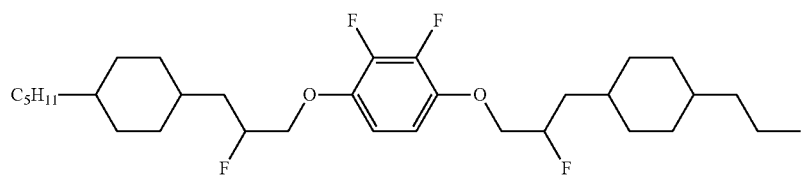 |
| 177 | 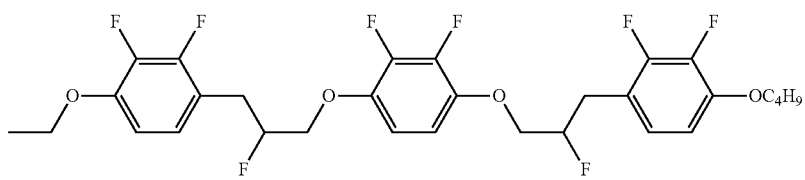 |

-continued
| No. | |
|---|---|
| 178 | 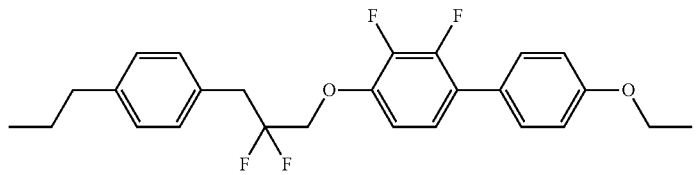<br>C 100.4 I<br>T_NI; 3.9, Δ ε; −3.01, Δ n; 0.140 |
| 179 | 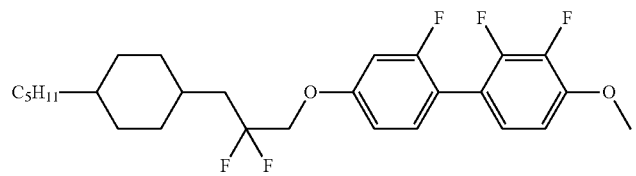 |
| 180 | 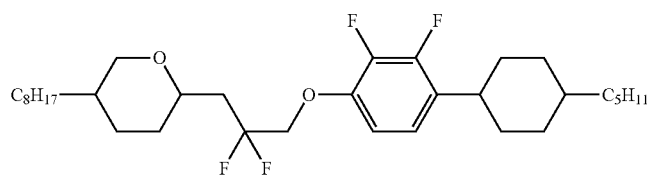 |
| 181 | 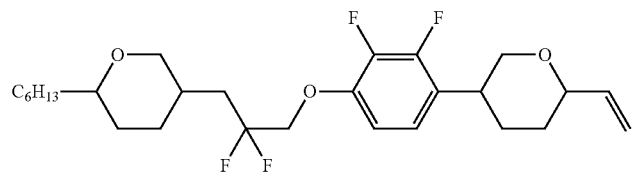 |
| 182 | 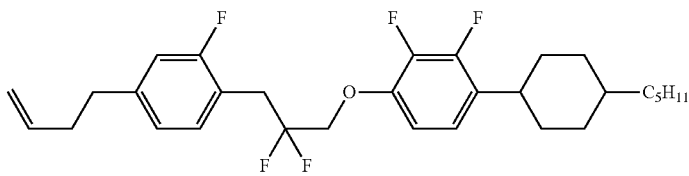 |
| 183 | 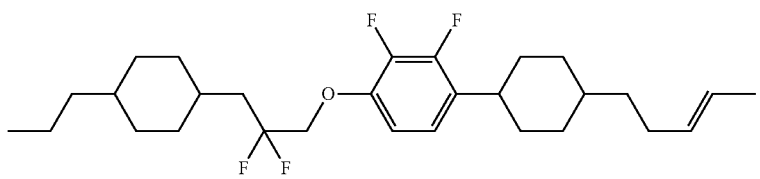 [SMILES: C/C=C/CCC1CCC(c2ccc(OCC(F)(F)CC3CCC(CCC)CC3)c(F)c2F)CC1] |
| 184 | 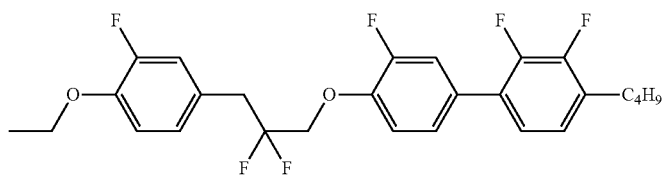 |
| 185 | 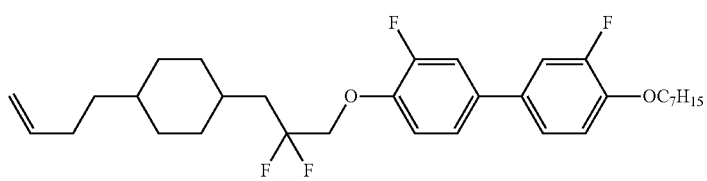 |

US 8,846,164 B2
-continued
| No. | |
|---|---|
| 186 | 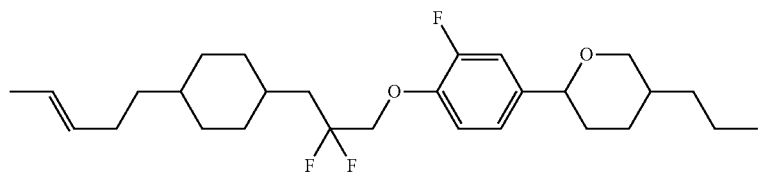 [SMILES: C/C=C/CCC1CCC(CC(F)(F)COc2ccc(C3CCC(CCC)CO3)cc2F)CC1] |
| 187 | 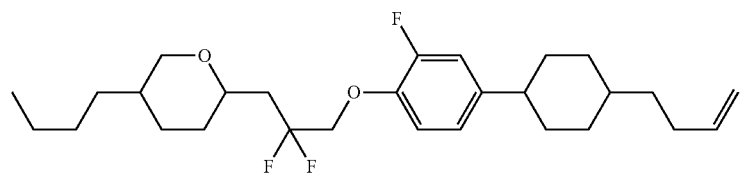 |
| 188 | 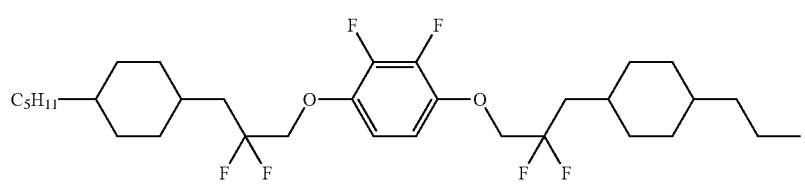 |
| 189 | 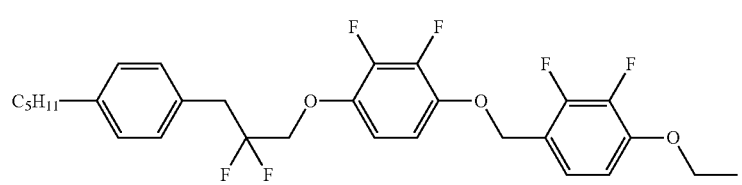 |
| 190 | 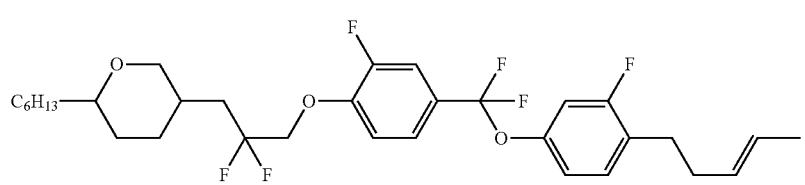 |
| 191 | 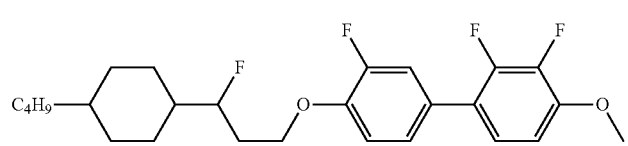 |
| 192 | 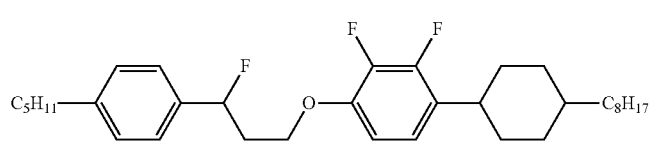 |
| 193 | 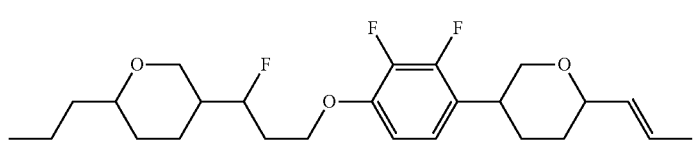 [SMILES: C/C=C/C1CCC(c2ccc(OCCC(F)C3CCC(CCC)OC3)c(F)c2F)CO1] |
| 194 | 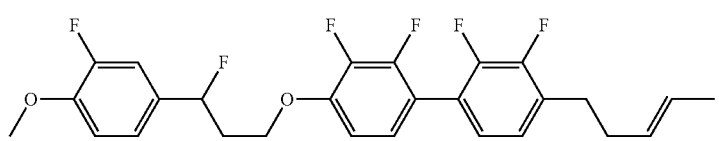 [SMILES: C/C=C/CCc1ccc(-c2ccc(OCCC(F)c3ccc(OC)c(F)c3)c(F)c2F)c(F)c1F] |
| 195 | 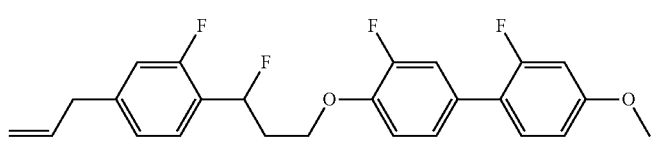 [SMILES: C=CCc1ccc(C(F)CCOc2ccc(-c3ccc(OC)cc3F)cc2F)c(F)c1] |

-continued
| No. | |
|---|---|
| 196 | 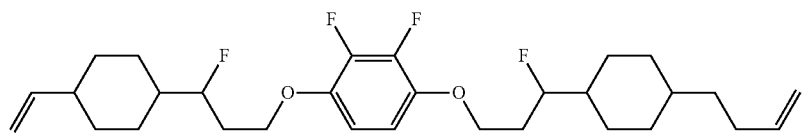 |
| 197 | 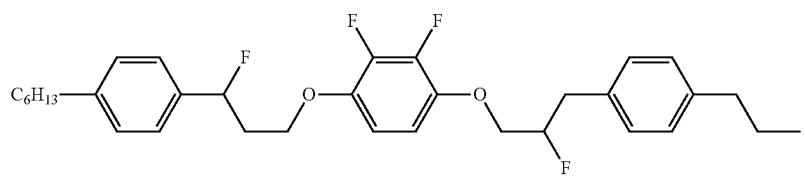 |
| 198 | 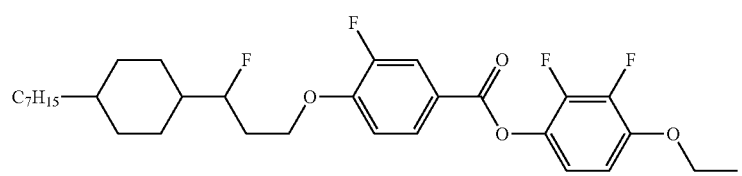 |
| 199 | 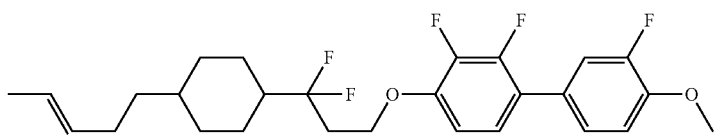 |
| 200 | 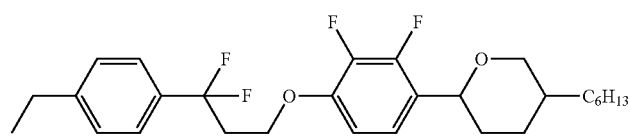 |
| 201 | 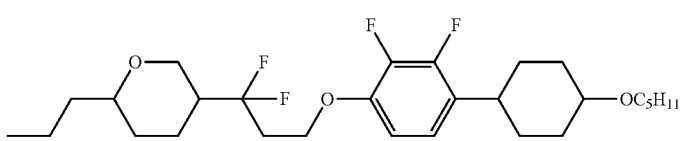 |
| 202 | 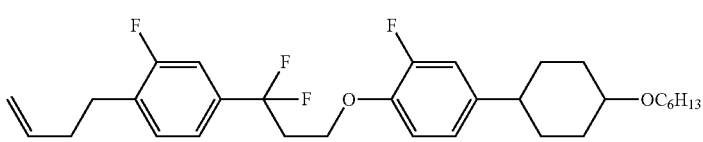 |
| 203 | 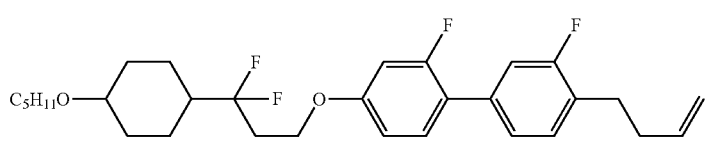 |
| 204 | 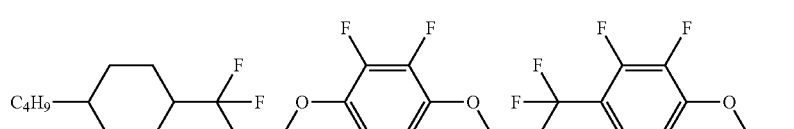 |
| 205 | 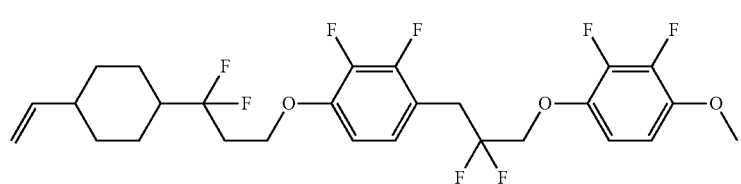 [SMILES: C=CC1CCC(C(F)(F)CCOc2ccc(CC(F)(F)COc3ccc(OC)c(F)c3F)c(F)c2F)CC1] |

-continued
| No. |  |
|---|---|
| 206 | 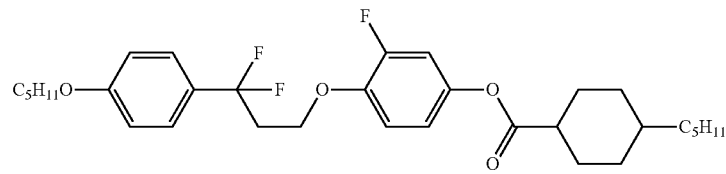 |
| 207 | 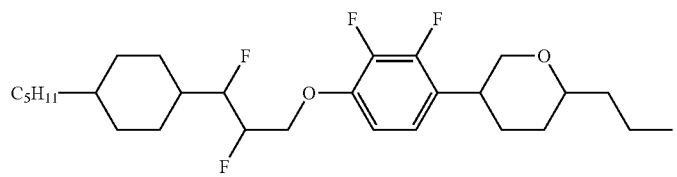 |
| 208 | 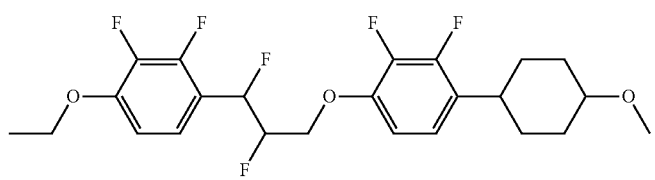 [SMILES: CCOc1ccc(C(F)C(F)COc2ccc(C3CCC(OC)CC3)c(F)c2F)c(F)c1F] |
| 209 | 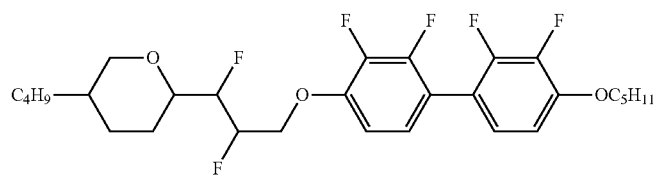 |
| 210 | 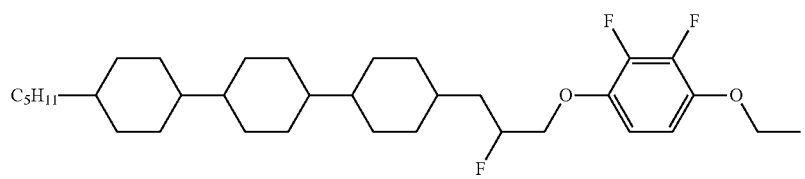 |
| 211 | 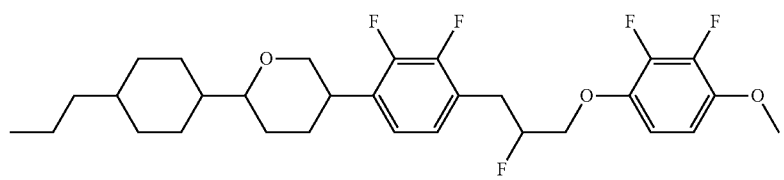 [SMILES: CCCC1CCC(C2CCC(c3ccc(CC(F)COc4ccc(OC)c(F)c4F)c(F)c3F)CO2)CC1] |
| 212 | 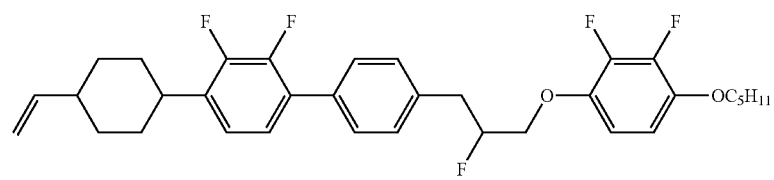 |
| 213 | 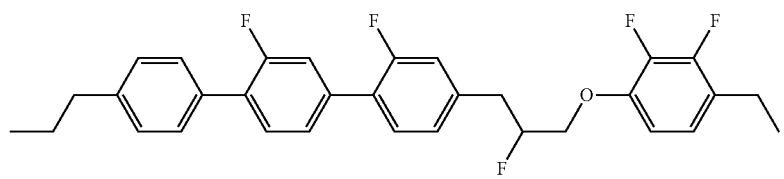 |

US 8,846,164 B2
139                                                                140
-continued
| No. |
|---|
| 214 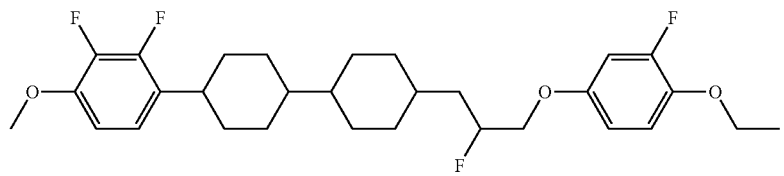 [SMILES: CCOc1ccc(OCC(F)CC2CCC(C3CCC(c4ccc(OC)c(F)c4F)CC3)CC2)cc1F] |
| 215 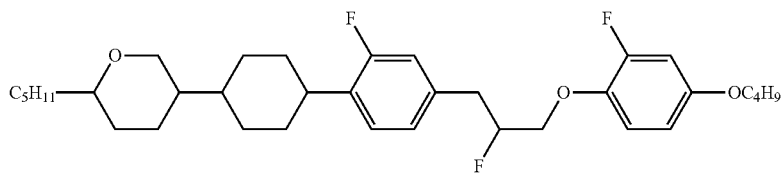 |
| 216 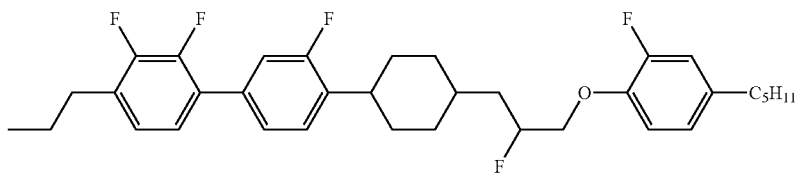 |
| 217 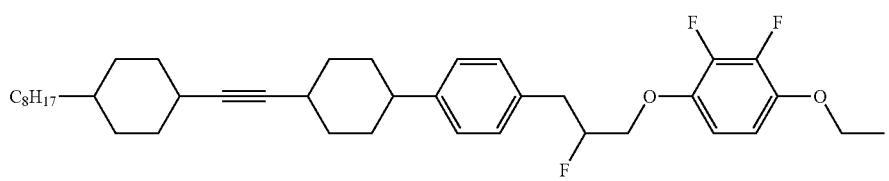 |
| 218 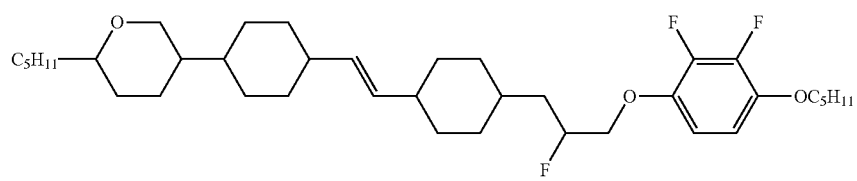 |
| 219 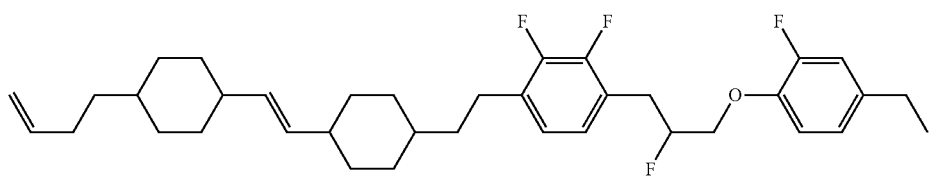 |
| 220 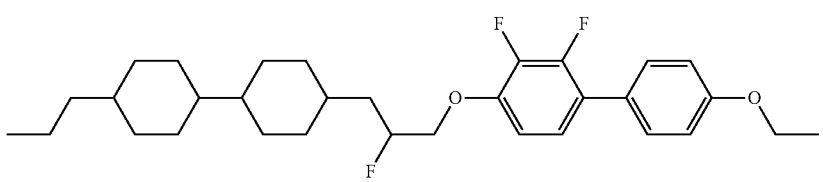 |
| 221 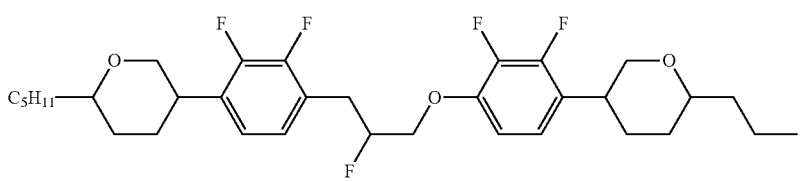 |

US 8,846,164 B2
141                                142
-continued
| No. |
|---|
| 222 | 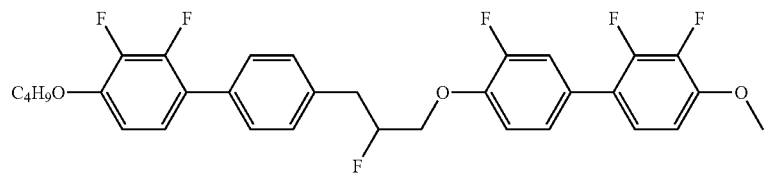 |
| 223 | 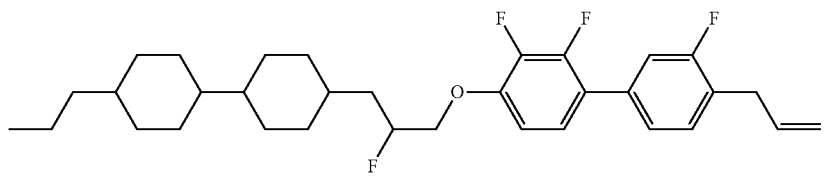 [SMILES: C=CCc1ccc(-c2ccc(OCC(F)CC3CCC(C4CCC(CCC)CC4)CC3)c(F)c2F)cc1F] |
| 224 | 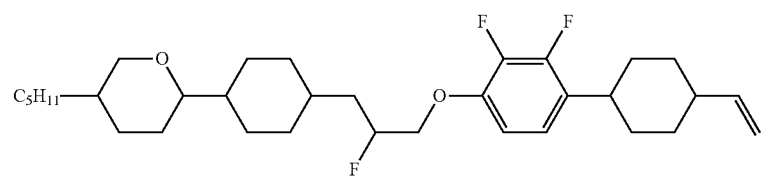 |
| 225 | 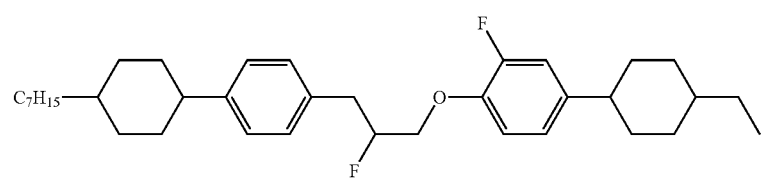 |
| 226 | 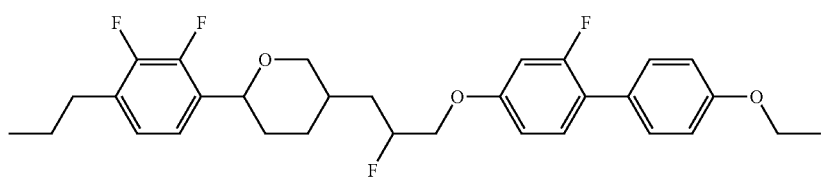 [SMILES: CCCc1ccc(C2CCC(CC(F)COc3ccc(-c4ccc(OCC)cc4)c(F)c3)CO2)c(F)c1F] |
| 227 | 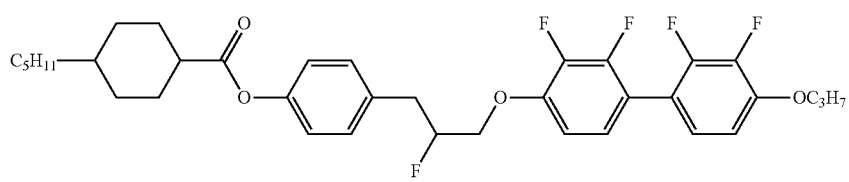 |
| 228 | 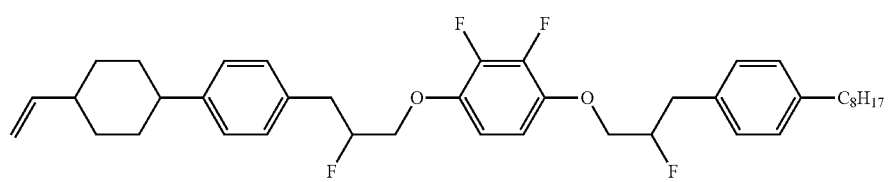 |
| 229 | 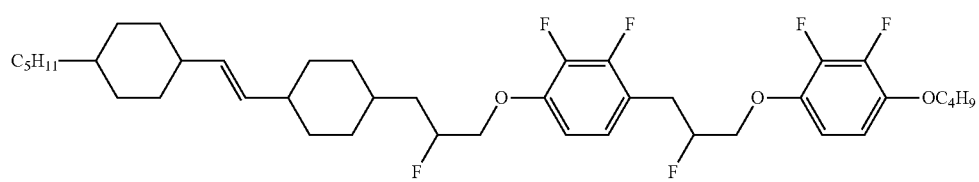 |

-continued
| No. | |
|---|---|
| 230 | 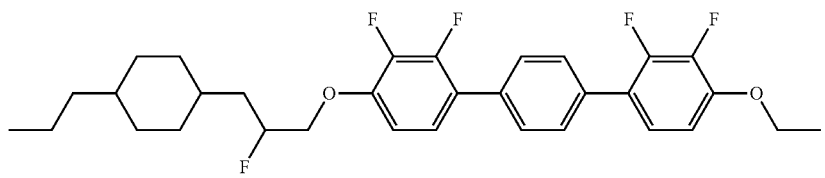 [SMILES: CCCC1CCC(CC(F)COc2ccc(-c3ccc(-c4ccc(OCC)c(F)c4F)cc3)c(F)c2F)CC1] |
| 231 | 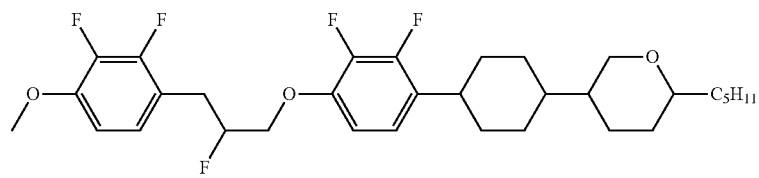 |
| 232 | 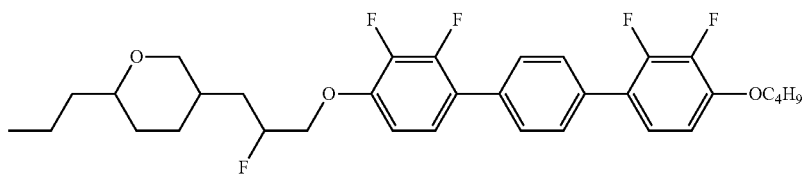 |
| 233 | 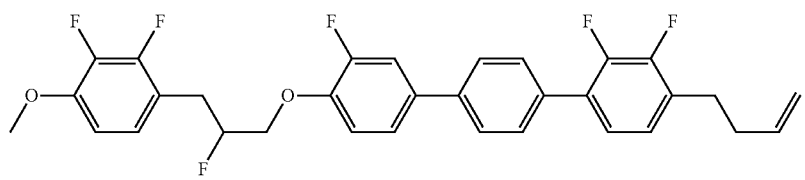 [SMILES: C=CCCc1ccc(-c2ccc(-c3ccc(OCC(F)Cc4ccc(OC)c(F)c4F)c(F)c3)cc2)c(F)c1F] |
| 234 | 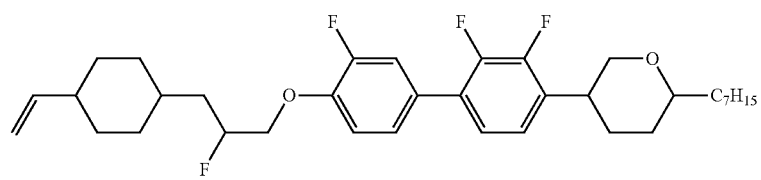 |
| 235 | 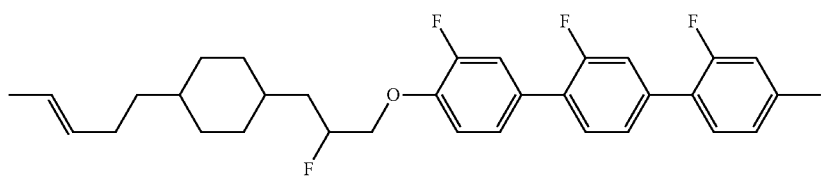 [SMILES: C/C=C/CCC1CCC(CC(F)COc2ccc(-c3ccc(-c4ccc(C)cc4F)cc3F)cc2F)CC1] |
| 236 | 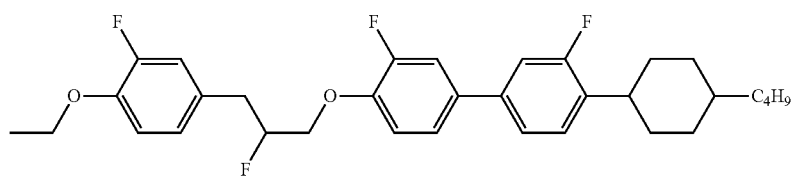 |
| 237 | 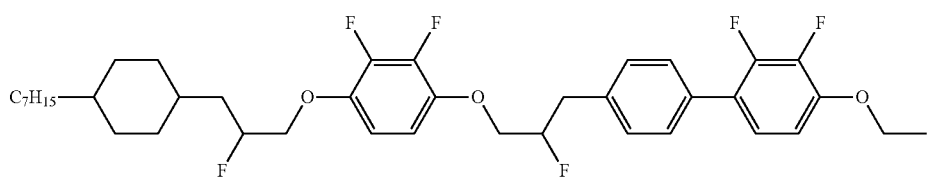 |

-continued
| No. | |
|---|---|
| 238 | 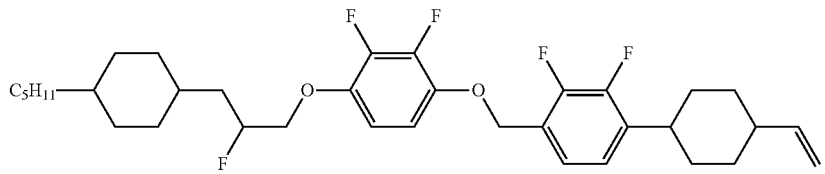 |
| 239 | 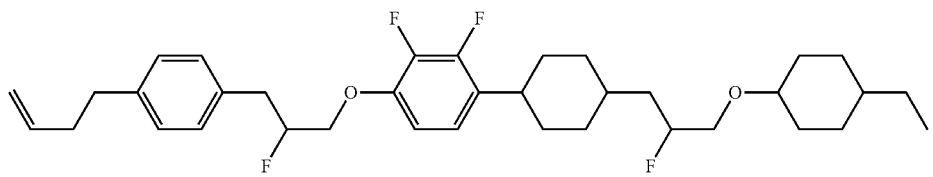 |
| 240 | 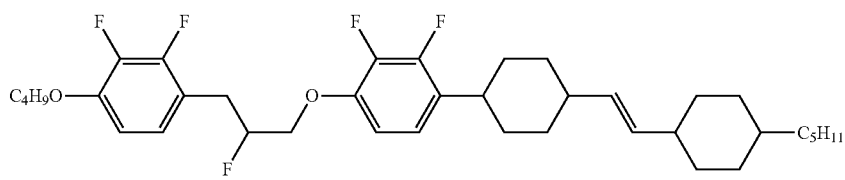 |
| 241 | 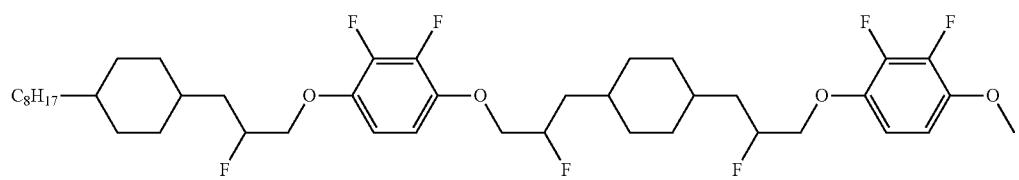 |
| 242 | 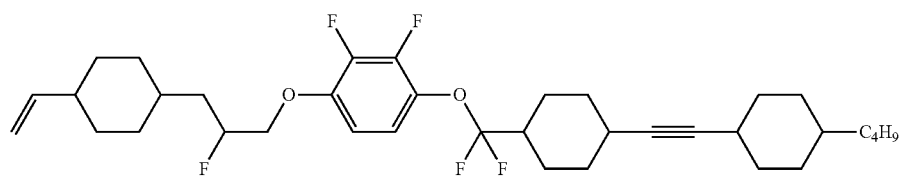 |
| 243 | 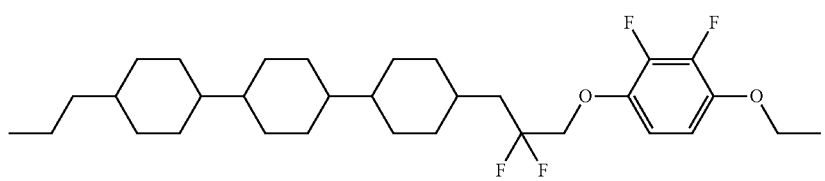 [SMILES: CCCC1CCC(C2CCC(C3CCC(CC(F)(F)COc4ccc(OCC)c(F)c4F)CC3)CC2)CC1] |
| 244 | 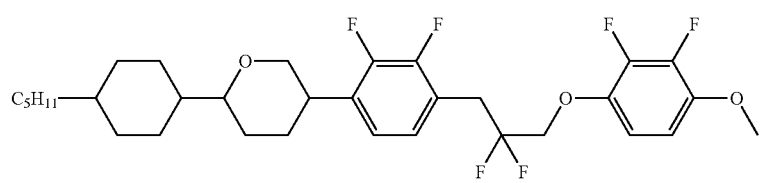 |
| 245 | 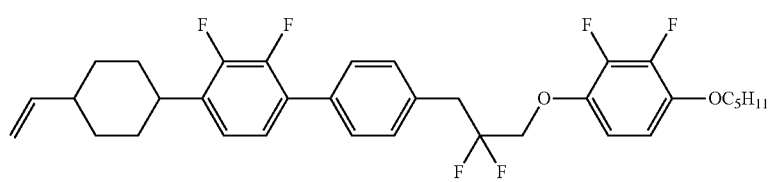 |

| No. | |
|---|---|
| 246 | 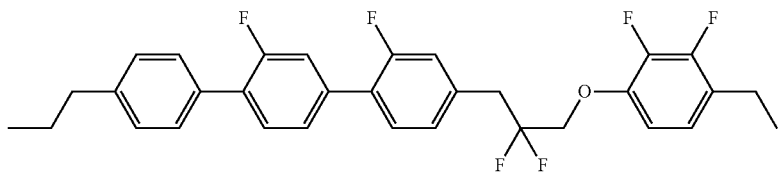 |
| 247 | 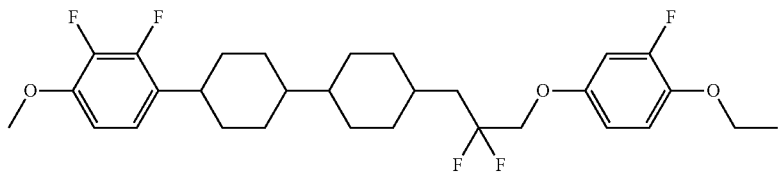 [SMILES: CCOc1ccc(OCC(F)(F)CC2CCC(C3CCC(c4ccc(OC)c(F)c4F)CC3)CC2)cc1F] |
| 248 | 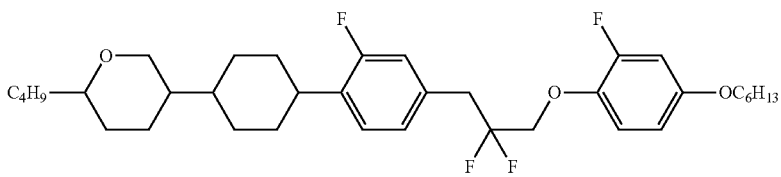 |
| 249 | 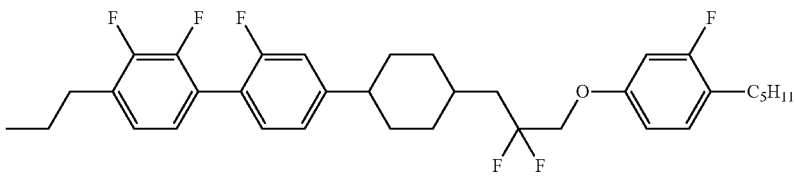 |
| 250 | 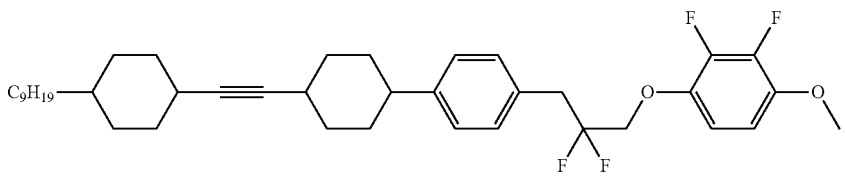 |
| 251 | 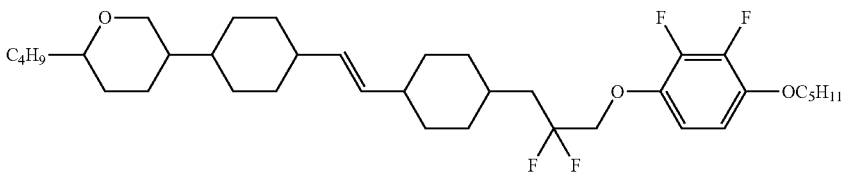 |
| 252 | 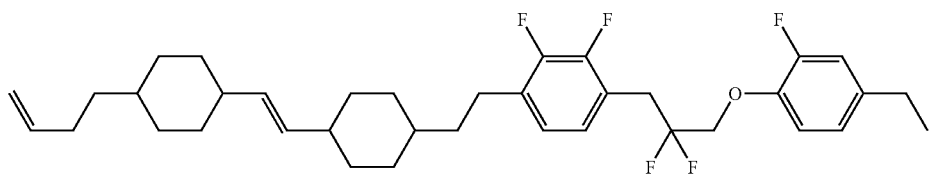 [SMILES: C=CCCC1CCC(/C=C/C2CCC(CCc3ccc(CC(F)(F)COc4ccc(CC)cc4F)c(F)c3F)CC2)CC1] |
| 253 | 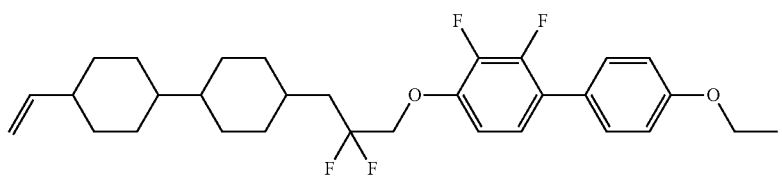 [SMILES: C=CC1CCC(C2CCC(CC(F)(F)COc3ccc(-c4ccc(OCC)cc4)c(F)c3F)CC2)CC1] |

-continued
| No. | |
|---|---|
| 254 | 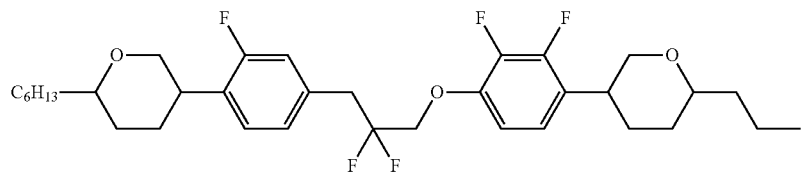 |
| 255 | 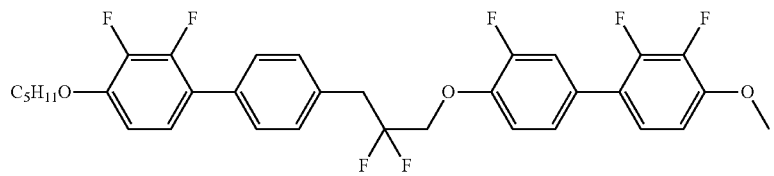 |
| 256 | 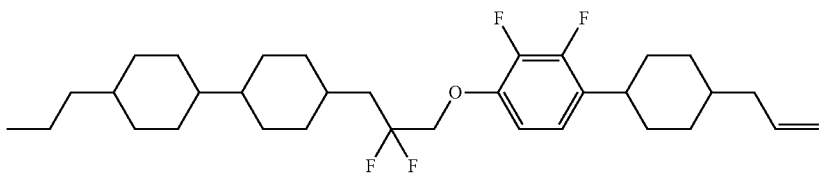 [SMILES: C=CCC1CCC(c2ccc(OCC(F)(F)CC3CCC(C4CCC(CCC)CC4)CC3)c(F)c2F)CC1] |
| 257 | 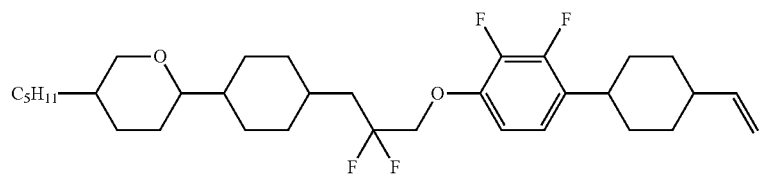 |
| 258 | 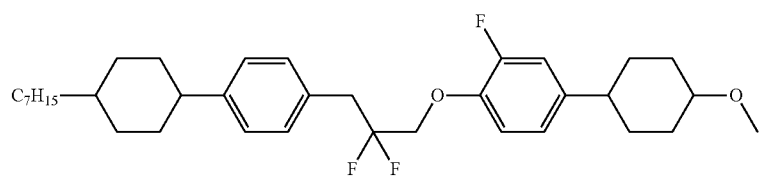 |
| 259 | 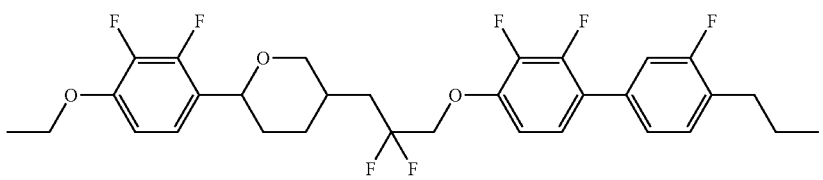 [SMILES: CCCc1ccc(-c2ccc(OCC(F)(F)CC3CCC(c4ccc(OCC)c(F)c4F)OC3)c(F)c2F)cc1F] |
| 260 | 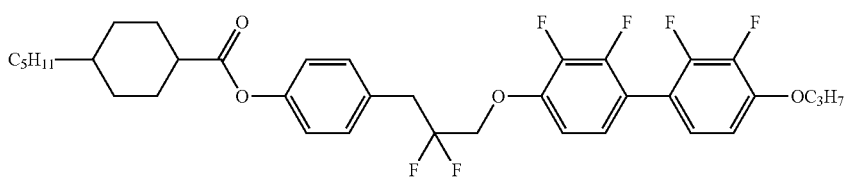 |
| 261 | 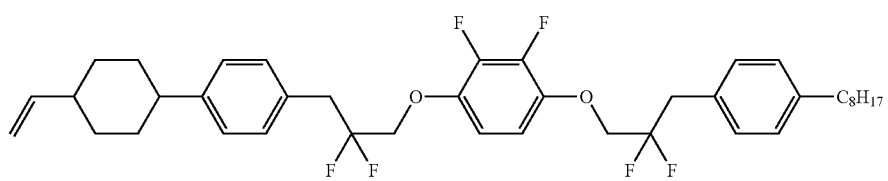 |

US 8,846,164 B2
151                                                      152
-continued
| No. |
|---|
262
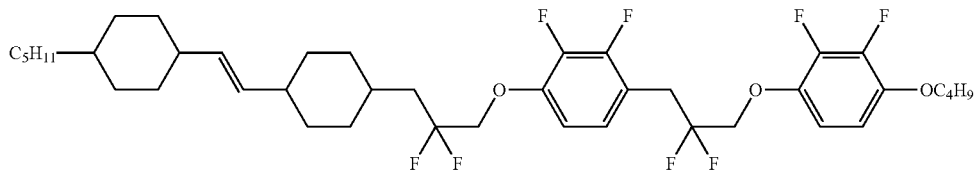
263
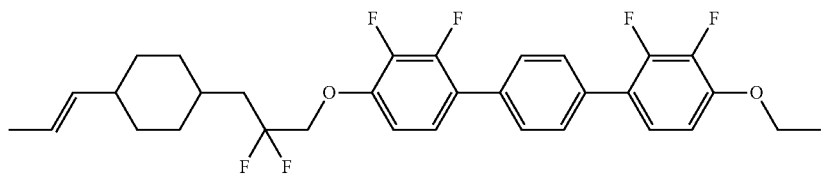
264
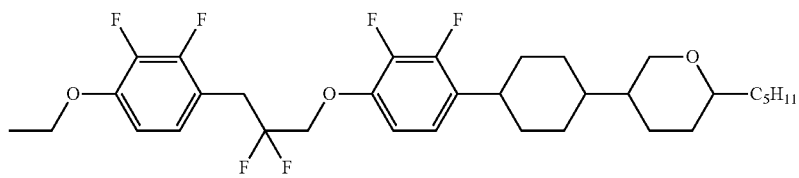
265
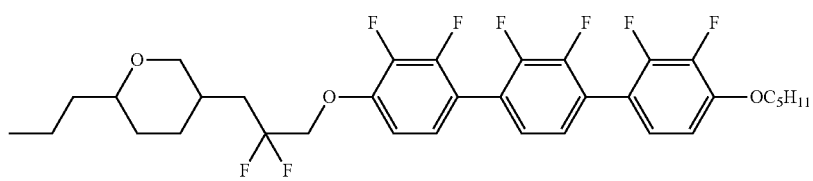
266
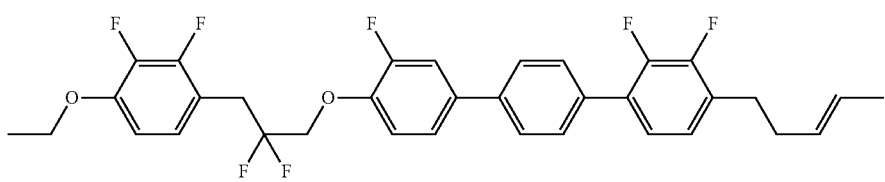 [SMILES: C/C=C/CCc1ccc(-c2ccc(-c3ccc(OCC(F)(F)Cc4ccc(OCC)c(F)c4F)c(F)c3)cc2)c(F)c1F]
267
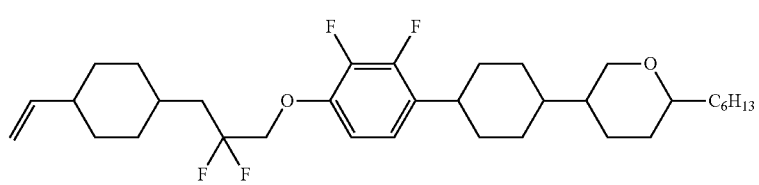
268
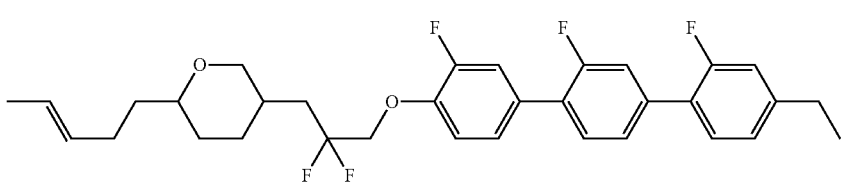 [SMILES: C/C=C/CCC1CCC(CC(F)(F)COc2ccc(-c3ccc(-c4ccc(CC)cc4F)cc3F)cc2F)CO1]
269
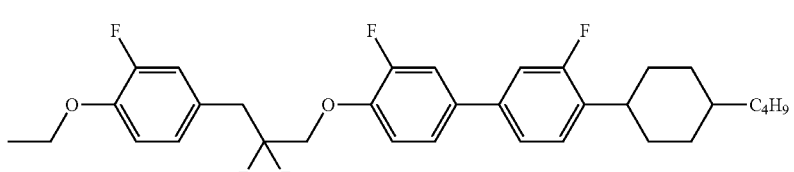

-continued
| No. |
|---|
| 270 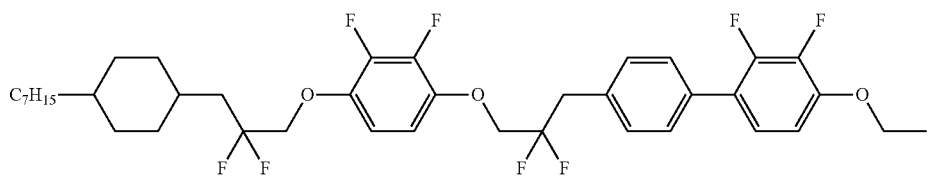 |
| 271 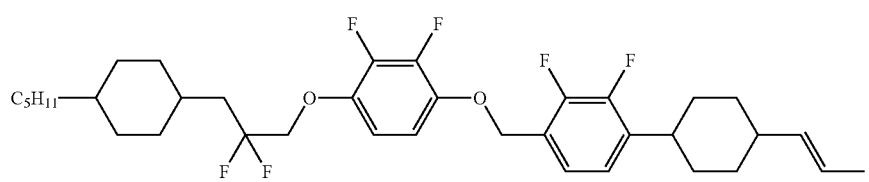 |
| 272 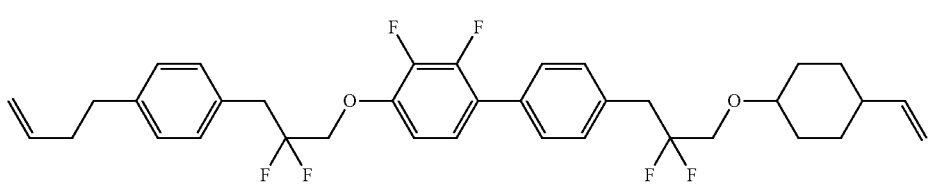 [SMILES: C=CCCc1ccc(CC(F)(F)COc2ccc(-c3ccc(CC(F)(F)COC4CCC(C=C)CC4)cc3)c(F)c2F)cc1] |
| 273 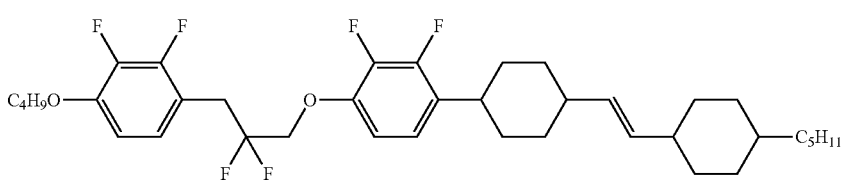 |
| 274 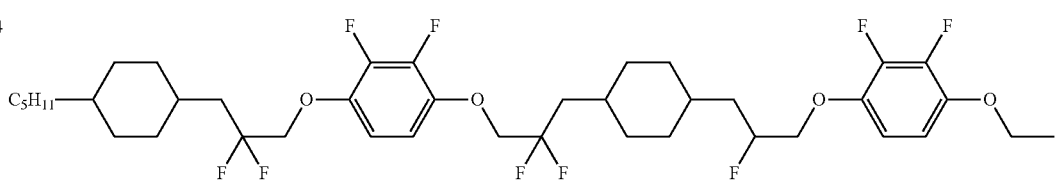 |
| 275 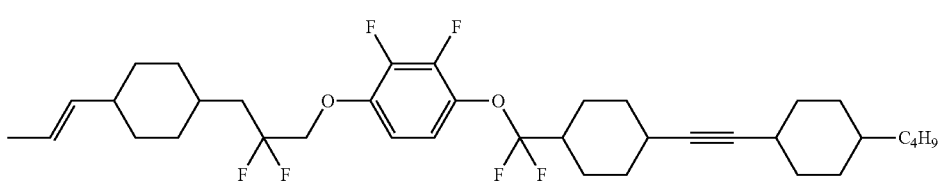 |
| 276 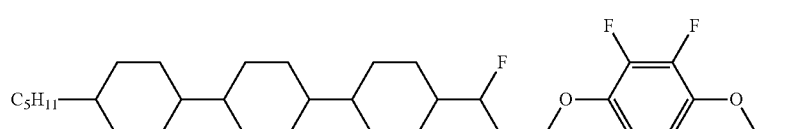 |
| 277 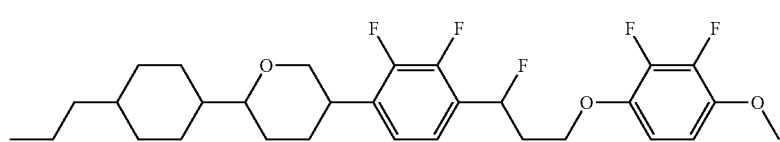 [SMILES: CCCC1CCC(C2CCC(c3ccc(C(F)CCOc4ccc(OC)c(F)c4F)c(F)c3F)CO2)CC1] |
| 278 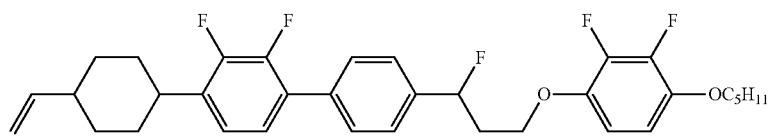 |

-continued
| No. | |
|---|---|
| 279 | 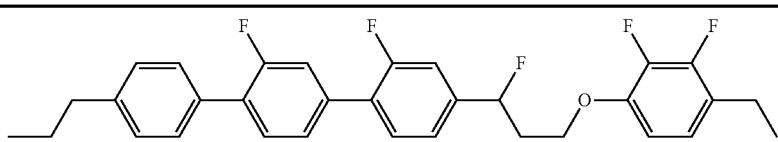 |
| 280 | 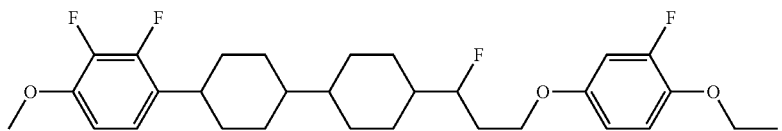 [SMILES: CCOc1ccc(OCCC(F)C2CCC(C3CCC(c4ccc(OC)c(F)c4F)CC3)CC2)cc1F] |
| 281 | 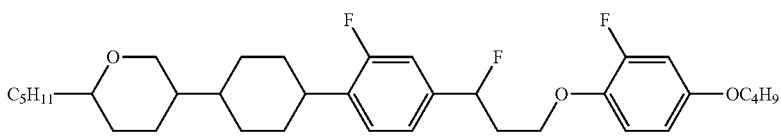 |
| 282 | 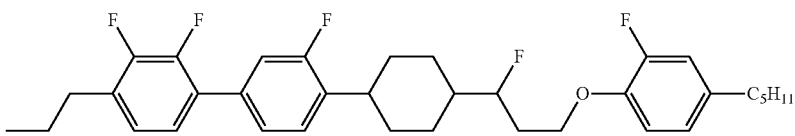 |
| 283 | 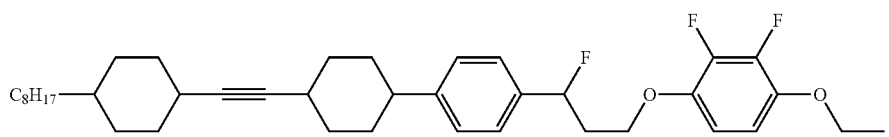 |
| 284 | 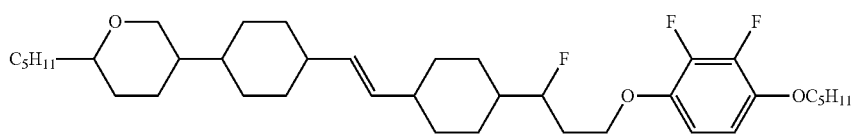 |
| 285 | 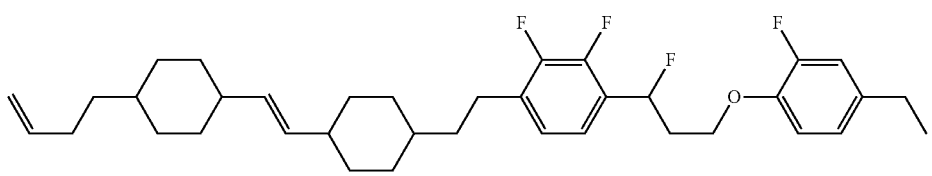 |
| 286 | 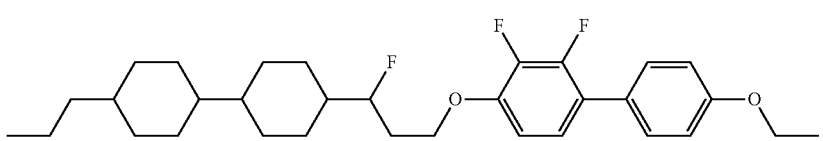 [SMILES: CCCC1CCC(C2CCC(C(F)CCOc3ccc(-c4ccc(OCC)cc4)c(F)c3F)CC2)CC1] |
| 287 | 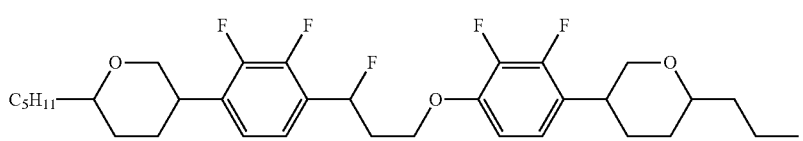 |
| 288 | 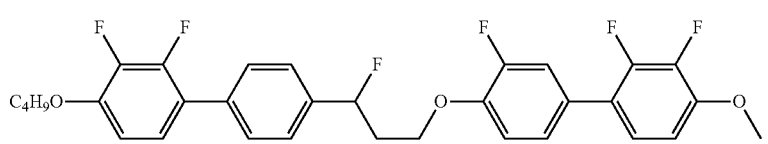 |
| 289 | 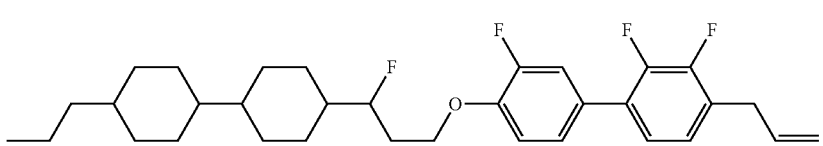 [SMILES: C=CCc1ccc(-c2ccc(OCCC(F)C3CCC(C4CCC(CCC)CC4)CC3)c(F)c2)c(F)c1F] |

-continued
| No. | |
|---|---|
| 290 | 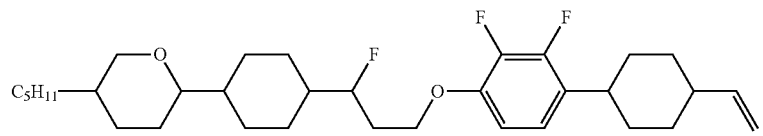 |
| 291 | 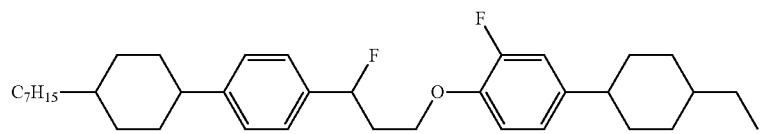 |
| 292 | 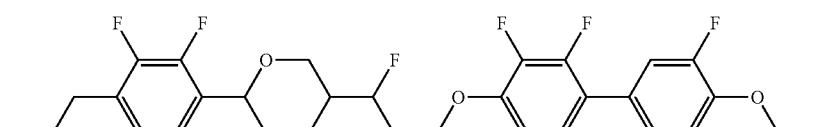 |
| 293 | 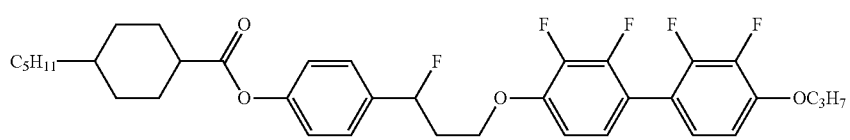 |
| 294 | 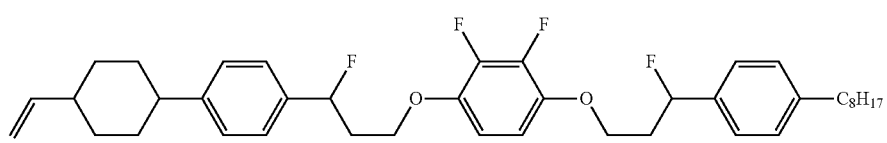 |
| 295 | 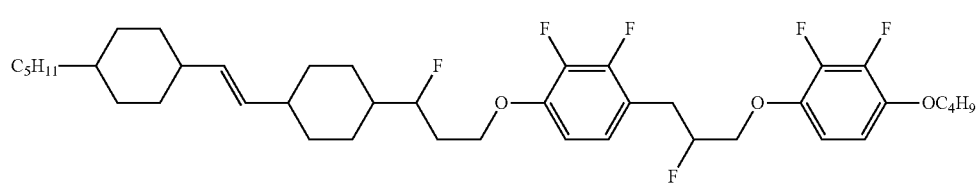 |
| 296 |  |
| 297 | 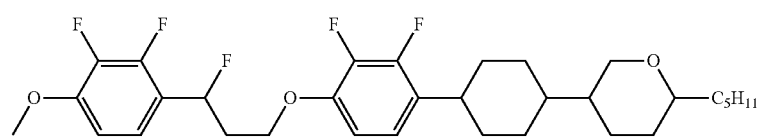 |
| 298 |  |
| 299 | 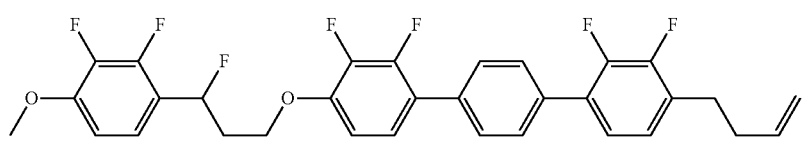 [SMILES: C=CCCc1ccc(-c2ccc(-c3ccc(OCCC(F)c4ccc(OC)c(F)c4F)c(F)c3F)cc2)c(F)c1F] |
| 300 | 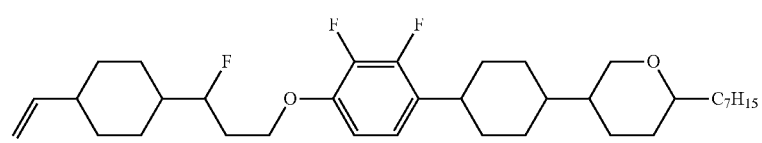 |

| No. | |
|---|---|
| 301 | 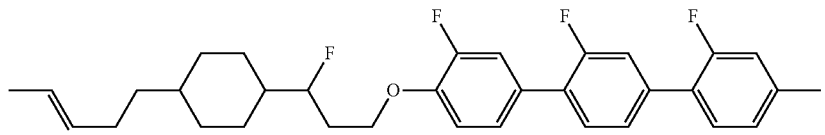 [SMILES: C/C=C/CCC1CCC(C(F)CCOc2ccc(-c3ccc(-c4ccc(C)cc4F)cc3F)cc2F)CC1] |
| 302 | 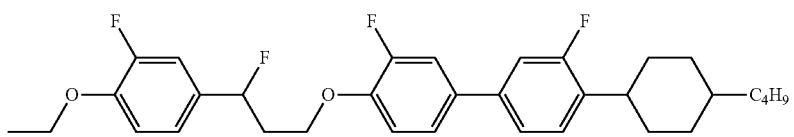 |
| 303 | 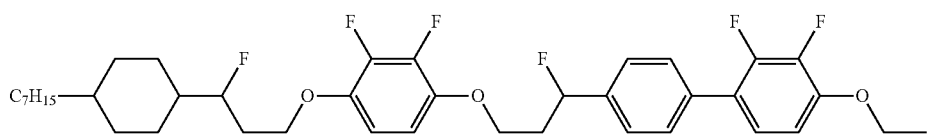 |
| 304 | 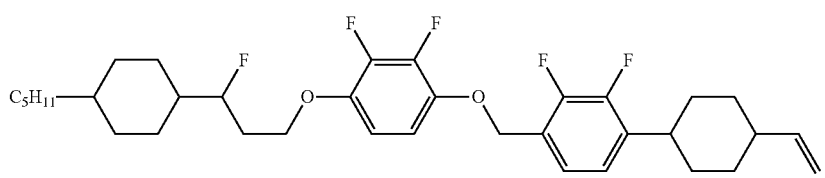 |
| 305 | 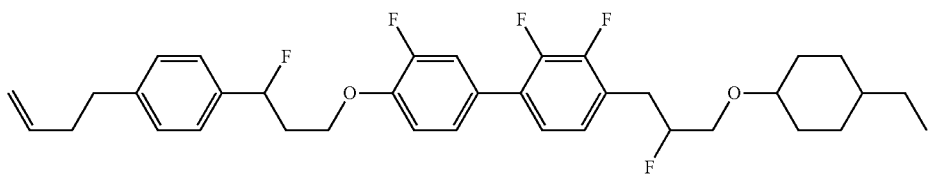 [SMILES: C=CCCc1ccc(C(F)CCOc2ccc(-c3ccc(CC(F)COC4CCC(CC)CC4)c(F)c3F)cc2F)cc1] |
| 306 | 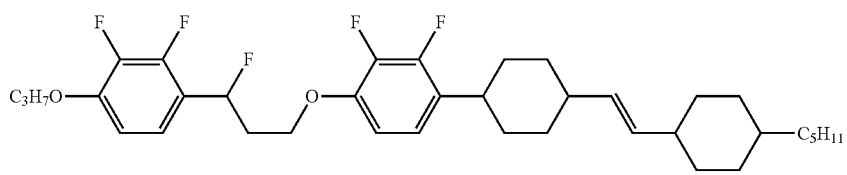 |
| 307 | 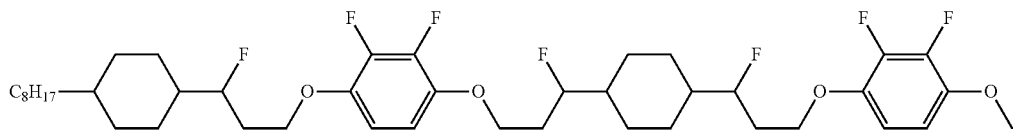 |
| 308 | 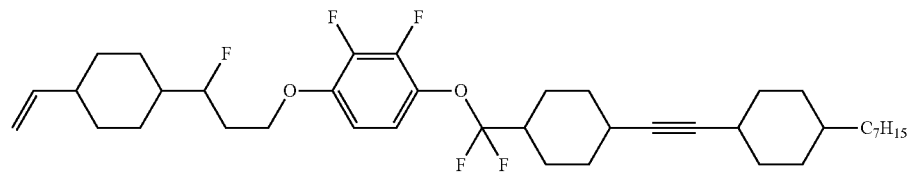 |
| 309 | 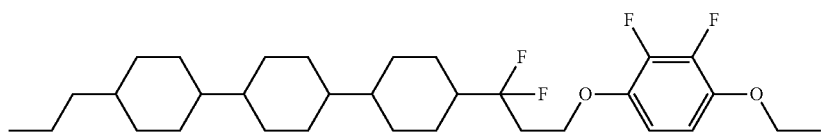 [SMILES: CCCC1CCC(C2CCC(C3CCC(C(F)(F)CCOc4ccc(OCC)c(F)c4F)CC3)CC2)CC1] |
| 310 | 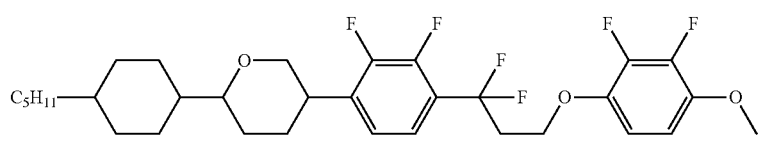 |

-continued
| No. | |
|---|---|
| 311 | 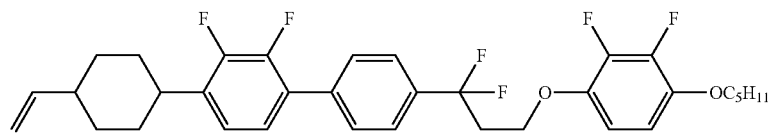 |
| 312 | 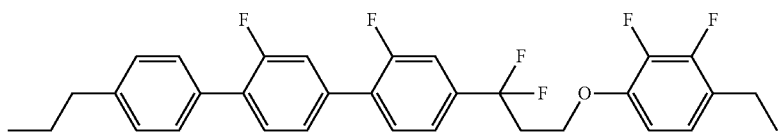 |
| 313 | 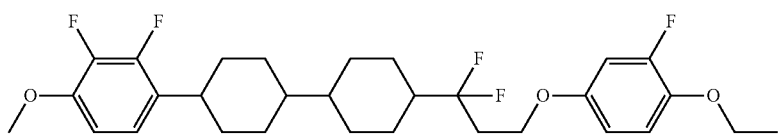 |
| 314 | 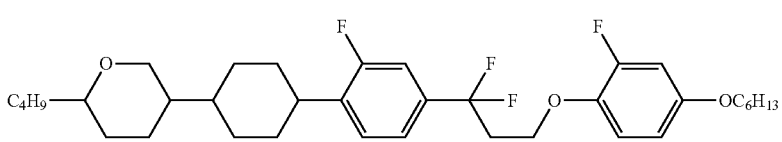 |
| 315 | 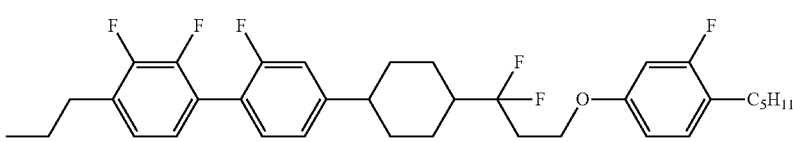 |
| 316 | 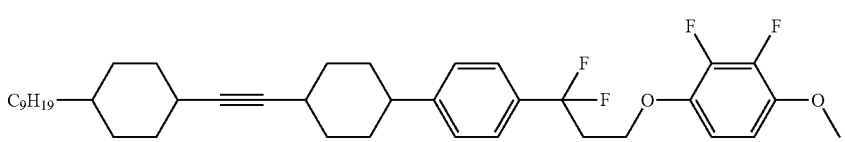 |
| 317 | 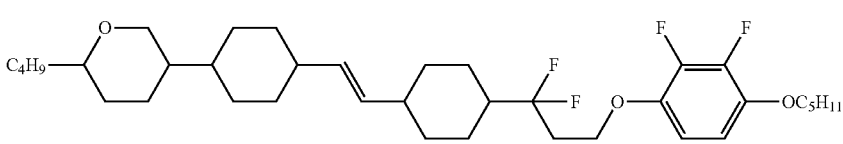 |
| 318 | 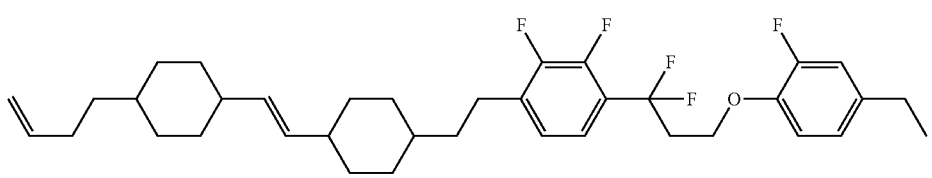 |
| 319 | 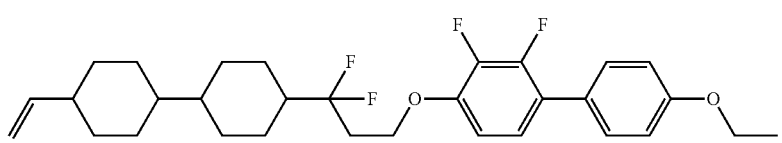 [SMILES: C=CC1CCC(C2CCC(C(F)(F)CCOc3ccc(-c4ccc(OCC)cc4)c(F)c3F)CC2)CC1] |
| 320 | 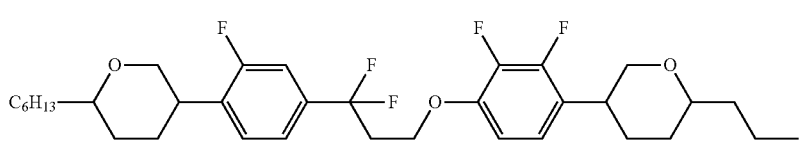 |
| 321 | 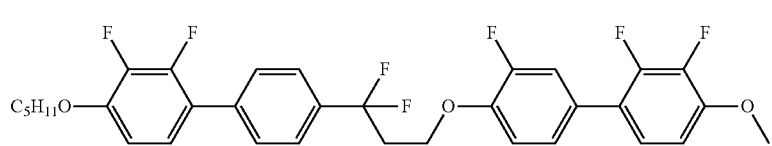 |

-continued
| No. | |
|---|---|
| 322 | 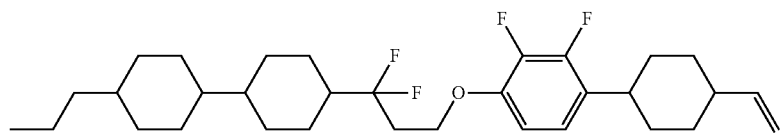 |
| 323 | 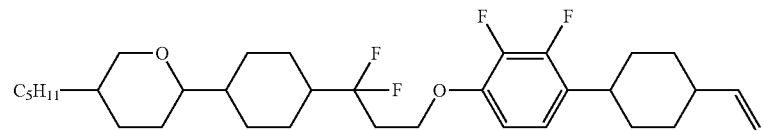 |
| 324 | 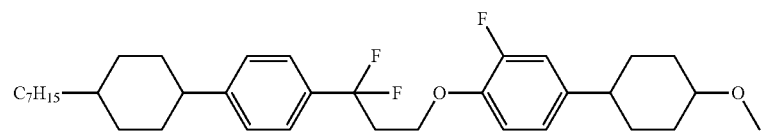 |
| 325 | 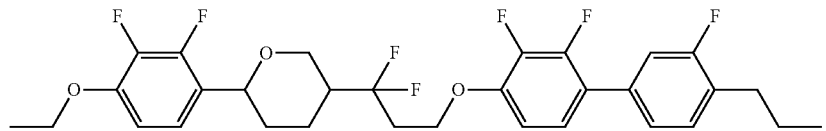 [SMILES: CCCc1ccc(-c2ccc(OCCC(F)(F)C3CCC(c4ccc(OCC)c(F)c4F)OC3)c(F)c2F)cc1F] |
| 326 | 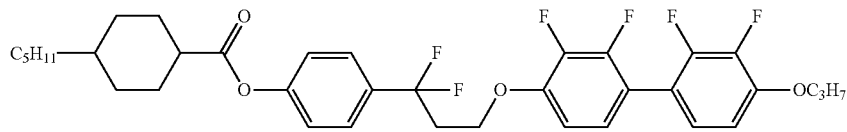 |
| 327 | 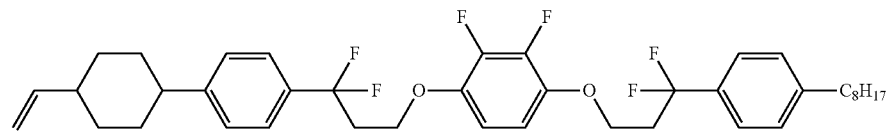 |
| 328 | 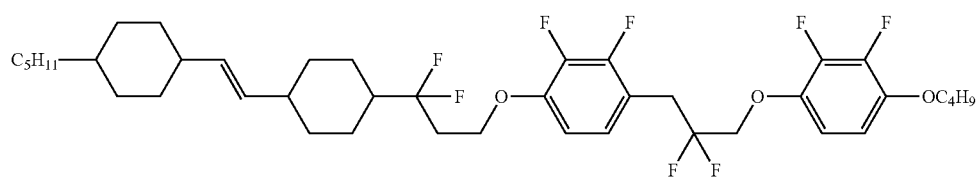 |
| 329 | 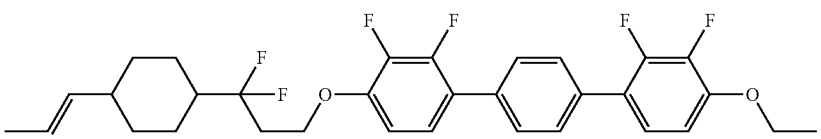 |
| 330 | 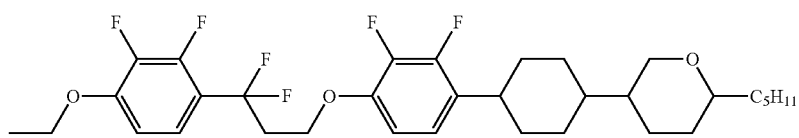 |
| 331 | 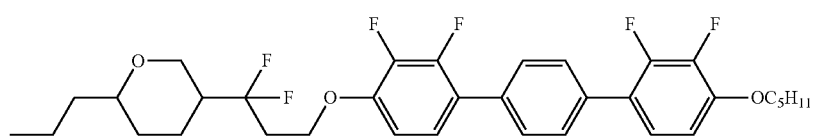 |
| 332 | 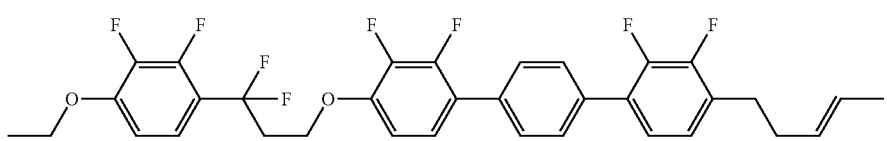 [SMILES: C/C=C/CCc1ccc(-c2ccc(-c3ccc(OCCC(F)(F)c4ccc(OCC)c(F)c4F)c(F)c3F)cc2)c(F)c1F] |

| No. | |
|---|---|
| 333 | 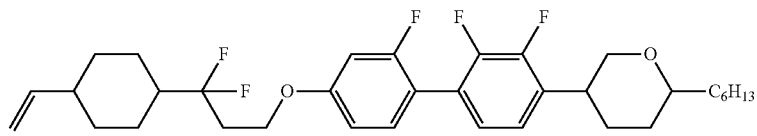 |
| 334 | 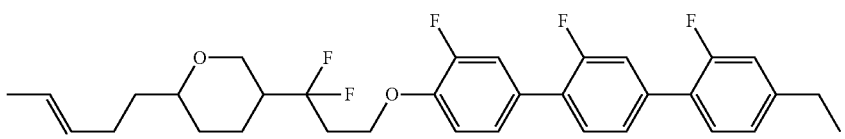 [SMILES: C/C=C/CCC1CCC(C(F)(F)CCOc2ccc(-c3ccc(-c4ccc(CC)cc4F)cc3F)cc2F)CO1] |
| 335 | 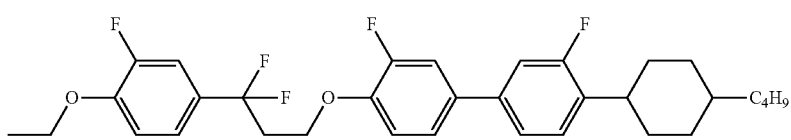 |
| 336 | 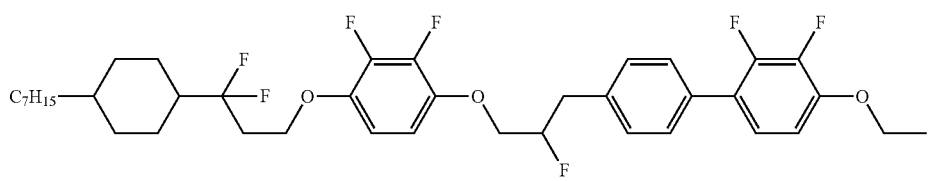 |
| 337 | 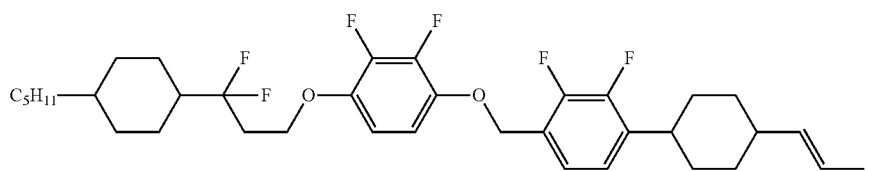 |
| 338 | 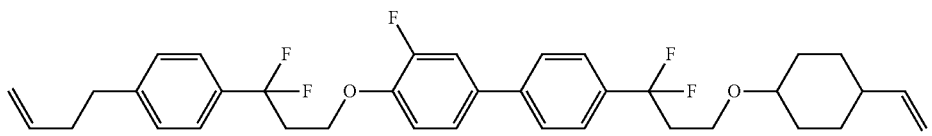 [SMILES: C=CCCc1ccc(C(F)(F)CCOc2ccc(-c3ccc(C(F)(F)CCOC4CCC(C=C)CC4)cc3)cc2F)cc1] |
| 339 | 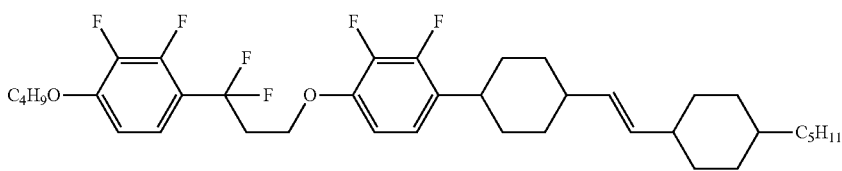 |
| 340 | 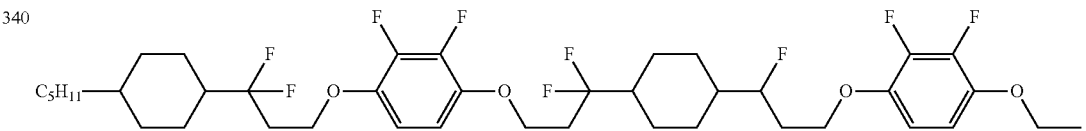 |
| 341 | 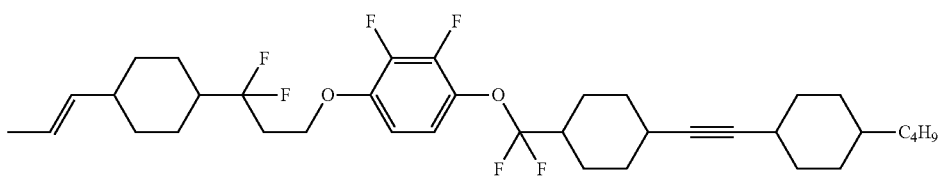 |

US 8,846,164 B2
167                                                                168
-continued
| No. | |
|---|---|
| 342 | 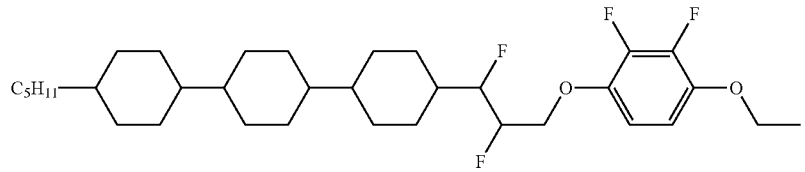 |
| 343 | 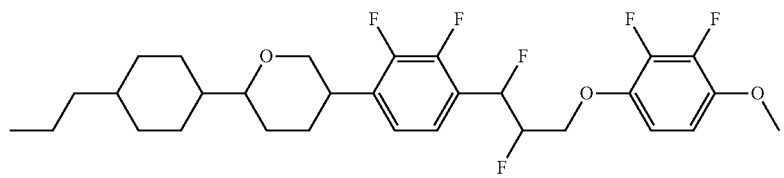 [SMILES: CCCC1CCC(C2CCC(c3ccc(C(F)C(F)COc4ccc(OC)c(F)c4F)c(F)c3F)CO2)CC1] |
| 344 | 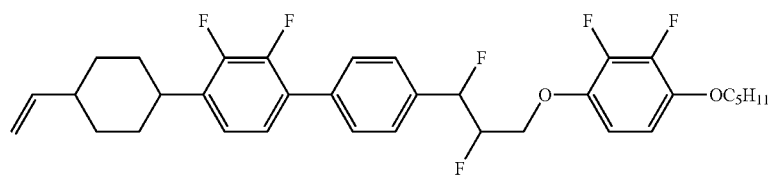 |
| 345 | 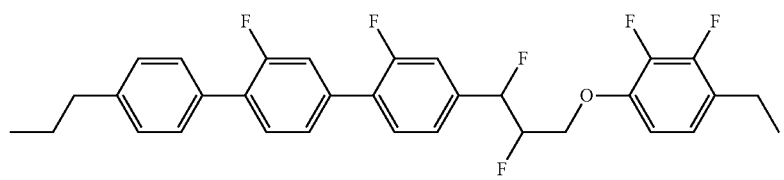 [SMILES: CCCc1ccc(-c2ccc(-c3ccc(C(F)C(F)COc4ccc(CC)c(F)c4F)cc3F)cc2F)cc1] |
| 346 | 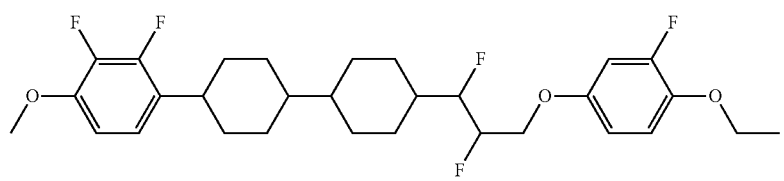 [SMILES: CCOc1ccc(OCC(F)C(F)C2CCC(C3CCC(c4ccc(OC)c(F)c4F)CC3)CC2)cc1F] |
| 347 | 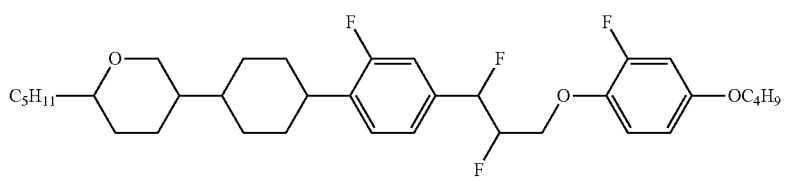 |
| 348 | 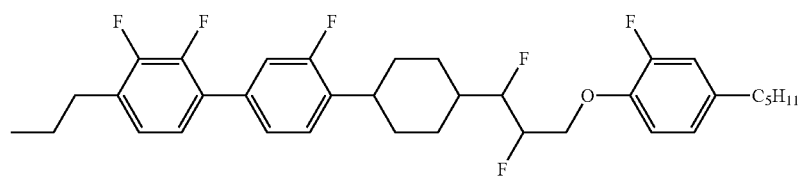 |
| 349 | 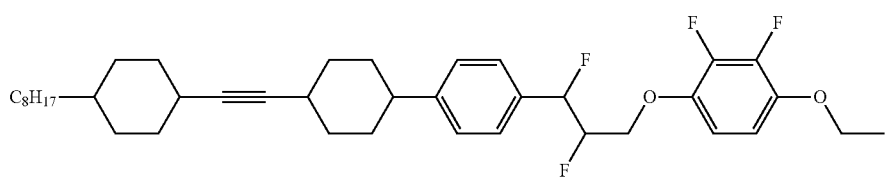 |

-continued
| No. | |
|---|---|
| 350 | 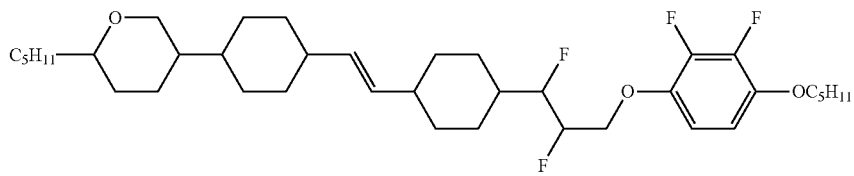 |
| 351 | 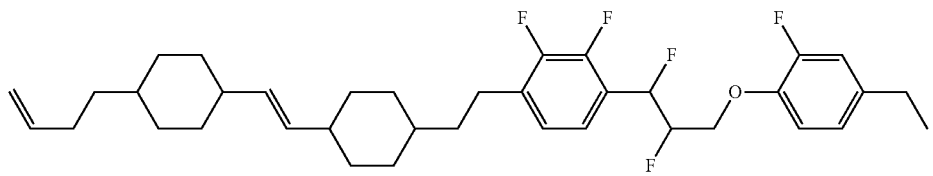 [SMILES: C=CCCC1CCC(/C=C/C2CCC(CCc3ccc(C(F)C(F)COc4ccc(CC)cc4F)c(F)c3F)CC2)CC1] |
| 352 | 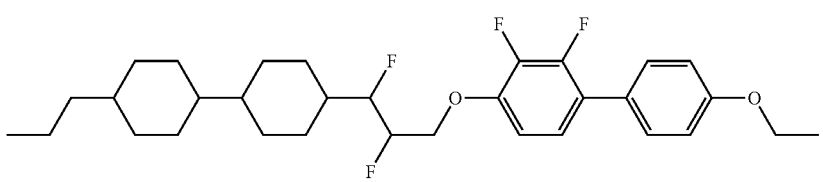 |
| 353 | 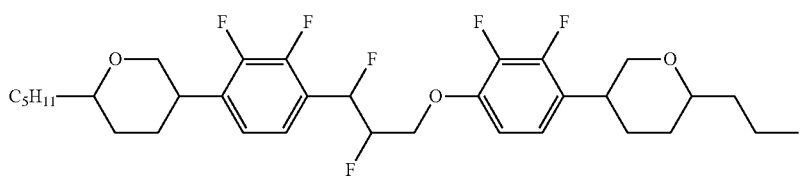 |
| 354 | 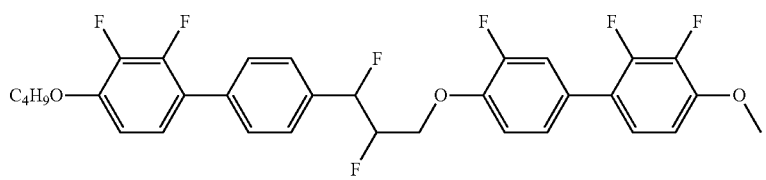 |
| 355 | 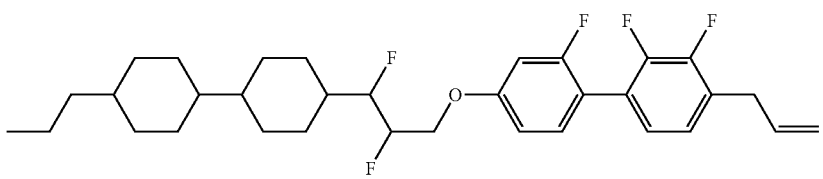 [SMILES: C=CCc1ccc(-c2ccc(OCC(F)C(F)C3CCC(C4CCC(CCC)CC4)CC3)cc2F)c(F)c1F] |
| 356 | 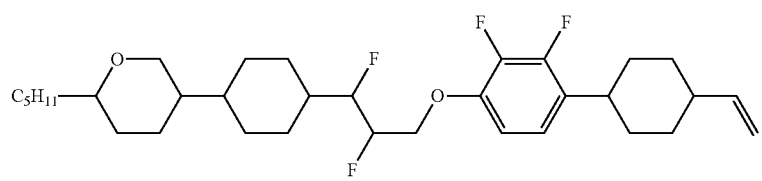 |
| 357 | 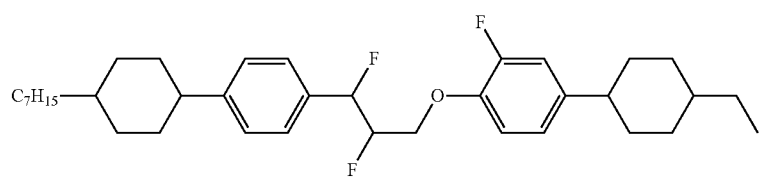 |

-continued
| No. | |
|---|---|
| 358 | 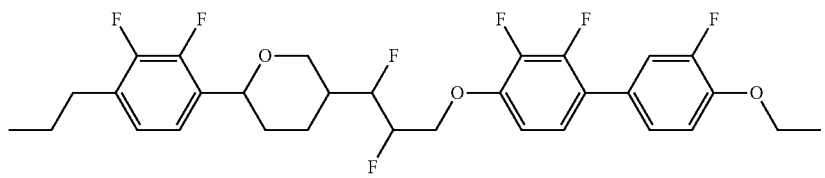 [SMILES: CCCc1ccc(C2CCC(C(F)C(F)COc3ccc(-c4ccc(OCC)c(F)c4)c(F)c3F)CO2)c(F)c1F] |
| 359 | 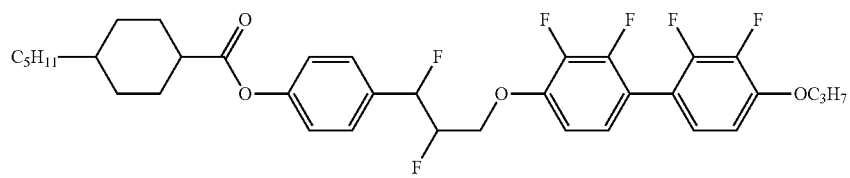 |
| 360 | 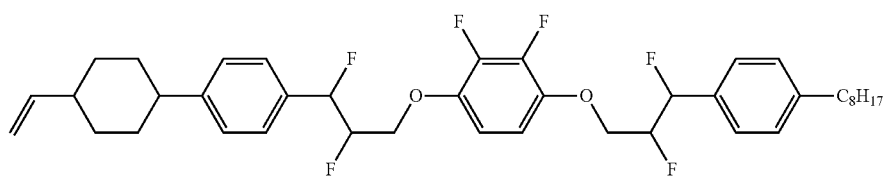 |
| 361 | 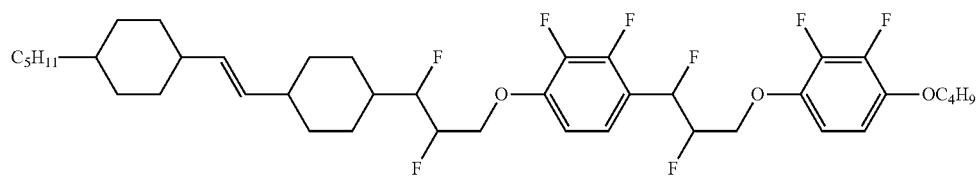 |
| 362 | 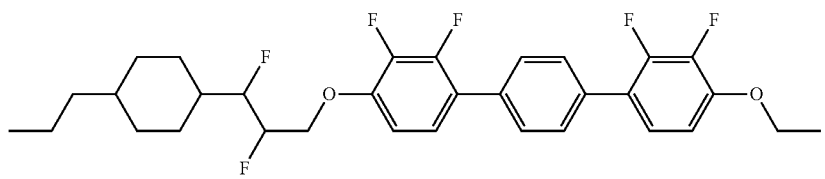 |
| 363 | 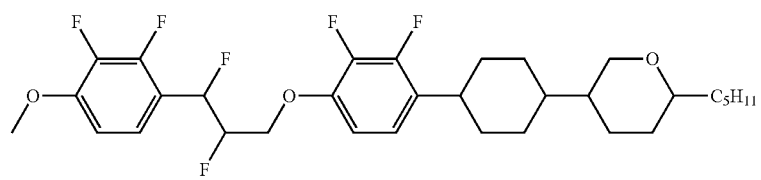 |
| 364 | 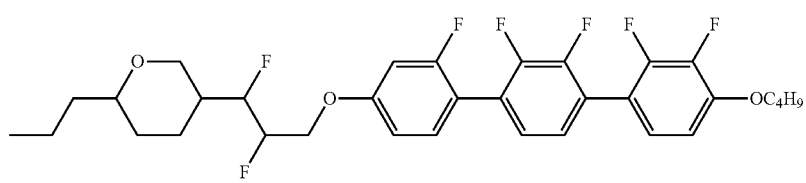 |
| 365 | 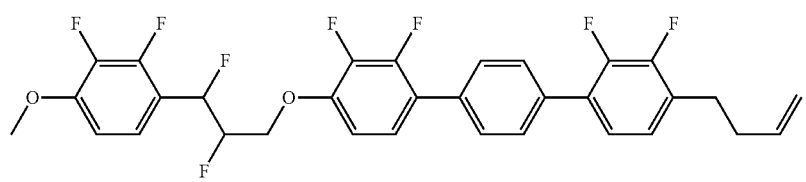 |

-continued
| No. | |
|---|---|
| 366 | 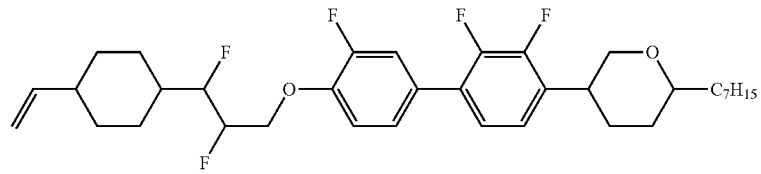 |
| 367 | 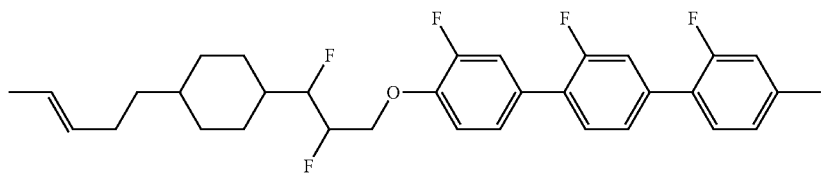 [SMILES: C/C=C/CCC1CCC(C(F)C(F)COc2ccc(-c3ccc(-c4ccc(C)cc4F)cc3F)cc2F)CC1] |
| 368 | 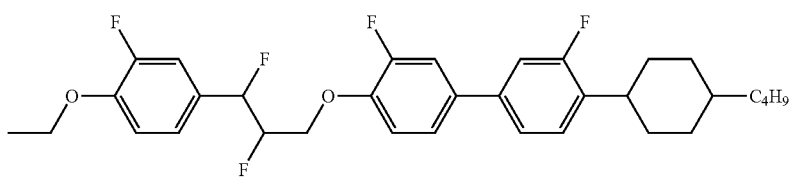 |
| 369 | 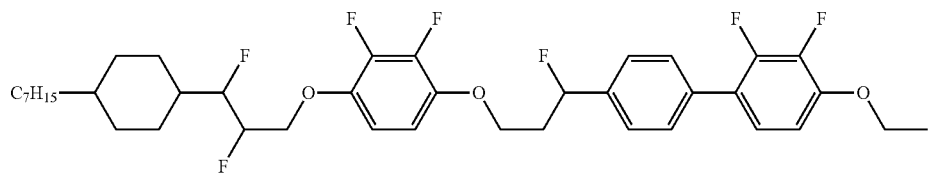 |
| 370 | 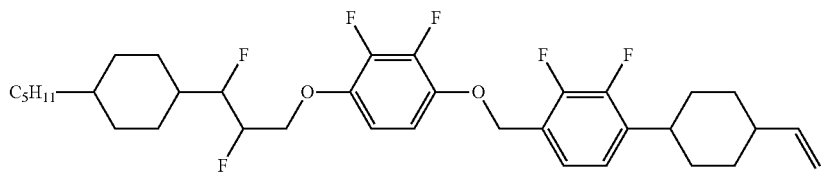 |
| 371 | 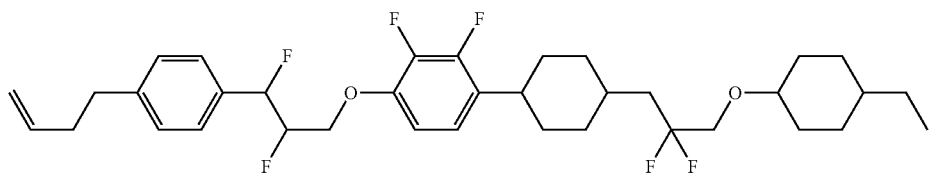 [SMILES: C=CCCc1ccc(C(F)C(F)COc2ccc(C3CCC(CC(F)(F)COC4CCC(CC)CC4)CC3)c(F)c2F)cc1] |
| 372 | 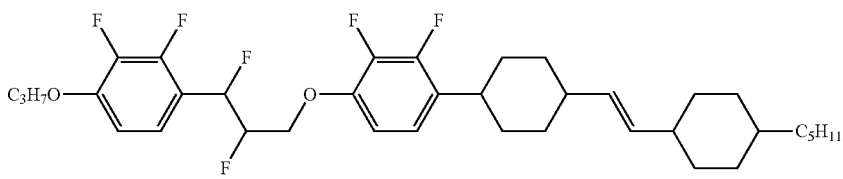 |
| 373 | 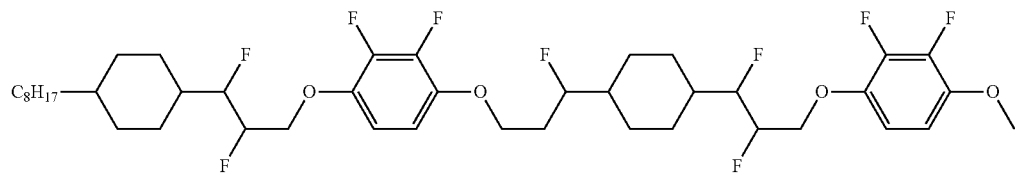 |

| No. | |
|---|---|
| 374 | 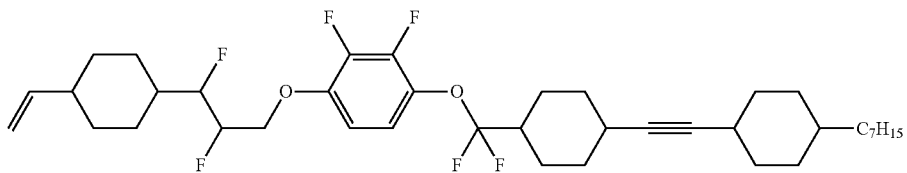 |

Comparative Example 1

As Comparative Example, 4-(3-(4-ethoxy-2,3-difluorophenoxy)-3,3-difluoropropyl)-4'-propyl-1,1'-bi(cyclohexane) (F) was prepared.

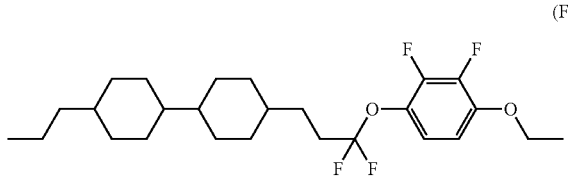

(F)

A chemical shift δ(ppm) according to $^1$H-NMR analysis was as described below, and the compound obtained could be identified to be 4-(3-(4-ethoxy-2,3-difluorophenoxy)-3,3-difluoropropyl)-4'-propyl-1,1'-bi(cyclohexane) (F). In addition, a solvent for measurement was CDCl$_3$.

Chemical shift δ (ppm); 6.97-6.94 (m, 1H), 6.67-6.63 (m, 1H), 4.10 (q, 2H), 2.20-2.12 (m, 2H), 1.80-1.68 (m, 8H), 1.55-1.50 (m, 3H), 1.45 (t, 3H), 1.34-1.12 (m, 5H), 1.12-0.82 (m, 13H).

A transition temperature of compound (F) was as described below.

Transition temperature: C 46.0 C 51.8 S$_A$ 98.9 N 163.0 I.

Liquid crystal composition ii including 85% of mother liquid crystals i and 15% of 4-(3-(4-ethoxy-2,3-difluorophenoxy)-3,3-difluoropropyl)-4'-propyl-1,1'-bi(cyclohexane) (F) as synthesized was prepared. Physical properties of composition ii obtained were measured and extrapolated values of physical properties of compound (F) were determined based on the calculation by extrapolating the measured values. The values were as described below.

Maximum temperature (T$_{NI}$)=141.3° C.; dielectric anisotropy (Δ∈)=−3.37; optical anisotropy (Δn)=0.100.

Comparison of comparative compound (F) with compound (No. 56) (maximum temperature (T$_{NI}$)=127.3° C.; dielectric anisotropy (Δ∈)=−9.46; optical anisotropy (Δn)=0.100) obtained according to Example 1 shows that compound (No. 56) has a larger negative dielectric anisotropy (Δ∈).

Comparative Example 2

As Comparative Example, 4-(4-(4-ethoxy-2,3-difluorophenoxy)butane-2-yl)-4'-propyl-1,1'-bi(cyclohexane) (G) was prepared.

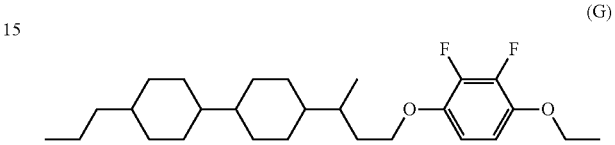

(G)

A chemical shift δ (ppm) according to $^1$H-NMR analysis was as described below, and the compound obtained could be identified to be 4-(4-(4-ethoxy-2,3-difluorophenoxy)butane-2-yl)-4'-propyl-1,1'-bi(cyclohexane) (G). In addition, a solvent for measurement was CDCl$_3$.

Chemical shift δ (ppm); 6.64-6.59 (m, 2H), 4.08-3.94 (m, 4H), 1.88 (m, 1H), 1.75-1.66 (m, 8H), 1.42 (t, 3H), 1.32-1.26 (m, 4H), 1.17-0.74 (m, 20H).

A transition temperature of compound (G) was as described below.

Transition temperature: C 73.5 N 93.3 I.

Liquid crystal composition iii including 85% of mother liquid crystals i and 15% of 4-(4-(4-ethoxy-2,3-difluorophenoxy)butane-2-yl)-4'-propyl-1,1'-bi(cyclohexane) (G) as synthesized was prepared. Physical properties of composition iii obtained were measured and extrapolated values of physical properties of compound (G) were determined based on the calculation by extrapolating the measured values. The values were as described below.

Maximum temperature (T$_{NI}$)=84.6° C.; dielectric anisotropy (Δ∈)=−6.48; optical anisotropy (Δn)=0.096.

Comparison of comparative compound (G) with compound (No. 166) (maximum temperature (T$_{NI}$)=133.6° C.; dielectric anisotropy (Δ∈)=−7.51; optical anisotropy (Δn)=0.173) obtained according to Example 2 shows that compound (No. 166) has a higher maximum temperature (T$_{NI}$) a negatively larger dielectric anisotropy (Δ∈), and a larger optical anisotropy (Δn).

Examples of Liquid Crystal Compositions

Hereinafter, liquid crystal compositions obtained according to the invention will be explained in greater detail by way of Examples. In addition, the liquid crystal compounds used in Examples are described using symbols based on definitions in Table below. In the Table, a configuration of 1,4-cyclohexylene is trans. Unless otherwise noted, a ratio (percentage) of each of compounds is expressed in terms of weight percent (% by weight) based on the total weight of the composition. Characteristics of the composition obtained are described in the last part of each Example.

The number described in a portion of a liquid crystal compound used in each Example corresponds to the number of formula representing a liquid crystal compound to be contained in the liquid crystal composition of the invention described above. When only a symbol "-" is described without description of the number of formula, the compound represents any other compound.

A method for description of compounds using symbols is described below.

TABLE

| Method for Description of Compounds using Symbols |
|---|
| $R—(A_1)—Z_1—\ldots—Z_n—(A_n)—R'$ |

| 1) Left-terminal Group R— | Symbol |
|---|---|
| $C_nH_{2n+1}—$ | n— |
| $C_nH_{2n+1}O—$ | nO— |
| $C_mH_{2m+1}OC_nH_{2n}—$ | mOn— |
| $CH_2=CH—$ | V— |
| $C_nH_{2n+1}—CH=CH—$ | nV— |
| $CH_2=CH—C_nH_{2n}—$ | Vn— |
| $C_mH_{2m+1}—CH=CH—C_nH_{2n}—$ | mVn— |
| $CF_2=CH—$ | VFF— |
| $CF_2=CH—C_nH_{2n}—$ | VFFn— |

| 2) Right-terminal Group | —R' Symbol |
|---|---|
| $—C_nH_{2n+1}$ | —n |
| $—OC_nH_{2n+1}$ | —On |
| $—CH=CH_2$ | —V |
| $—CH=CH—C_nH_{2n+1}$ | —Vn |
| $—C_nH_{2n}—CH=CH_2$ | —nV |
| $—CH=CF_2$ | —VFF |
| $—COOCH_3$ | —EMe |
| —CN | —C |
| —F | —F |
| —Cl | —CL |
| $—OCF_3$ | —OCF3 |

| 3) Bonding Group $—Z_n—$ | Symbol |
|---|---|
| $—C_nH_{2n}—$ | n |
| —COO— | E |
| —OCO— | e |
| —CH=CH— | V |
| $—CH_2O—$ | 1O |
| —CHF— | (1F) |
| $—CF_2O—$ | X |
| —C≡C— | T |

| 4) Ring Structure $—A_n—$ | Symbol |
|---|---|
|  | H |
|  | Ch |
|  | ch |
| 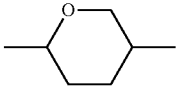 | Dh |
| 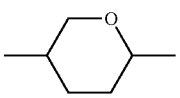 | dh |
| 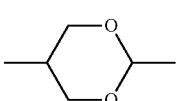 | G |
| 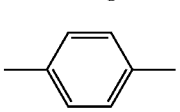 | B |

TABLE-continued
| Method for Description of Compounds using Symbols<br>R—(A$_1$)—Z$_1$—...—Z$_n$—(A$_n$)—R' | |
|---|---|
| 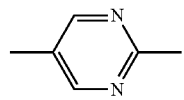 | Py |
| 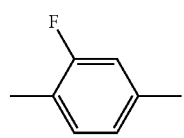 | B(2F) |
| 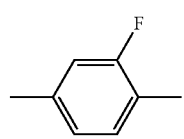 | B(F) |
| 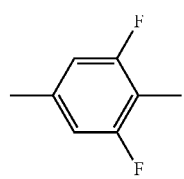 | B(F,F) |
| 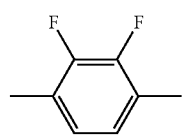 | B(2F,3F) |
| 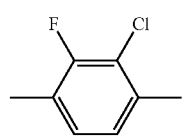 | B(2F,3CL) |
| 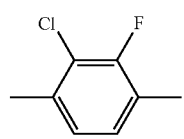 | B(2CL,3F) |
| Example of Description |
|---|
Example 1 3-HH1(1F)10B(2F,3F)-O2
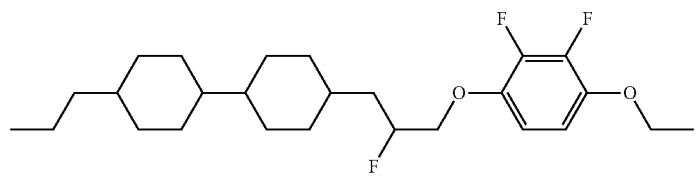
Example 2 3-H1(1F)10B(2F,3F)B-O2
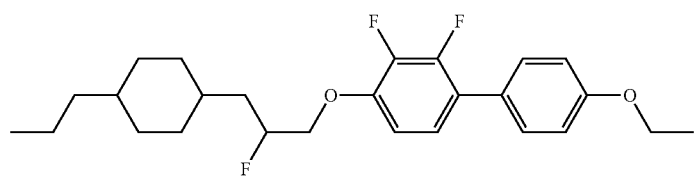 [SMILES: CCCC1CCC(CC(F)COc2ccc(-c3ccc(OCC)cc3)c(F)c2F)CC1]

TABLE-continued

Method for Description of Compounds using Symbols
R—(A₁)—Z₁—...—Zₙ—(Aₙ)—R'

Example 3 3HHB-3

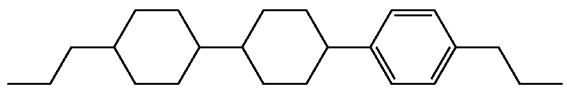 [SMILES: CCCc1ccc(C2CCC(C3CCC(CCC)CC3)CC2)cc1]

Example 4 3-HH-V

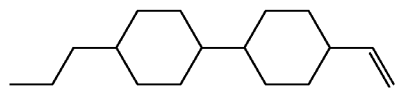

Characteristics were measured according to the methods described below. Most of the methods are applied as described in EIAJ ED-2521A of the Standard of Electronic Industries Association of Japan, or as modified thereon.

(1) Maximum Temperature of a Nematic Phase (NI; ° C.)

A sample was placed on a hot plate of a melting point apparatus equipped with a polarizing microscope and was heated at a rate of 1° C. per minute. Temperature when part of the sample began to change from a nematic phase to an isotropic liquid was measured. Hereinafter, a higher limit of the temperature range of a nematic phase may be abbreviated as "maximum temperature."

(2) Minimum Temperature of the Nematic Phase (Tc; ° C.)

A sample having the nematic phase was kept in freezers at temperatures of 0° C., −10° C., −20° C., −30° C. and −40° C. for 10 days, and then liquid crystal phases were observed. For example, when the sample maintained the nematic phase at −20° C. and changed to crystals or a smectic phase at −30° C., Tc was expressed as Tc≤−20° C. Hereinafter, a lower limit of the temperature range of the nematic phase may be abbreviated as "minimum temperature."

(3) Optical Anisotropy (Δn; Measured at 25° C.)

Measurement was carried out by means of Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of optical anisotropy was calculated from an equation: $\Delta n = n\parallel - n\perp$ (4) Viscosity (Bulk Viscosity; η; Measured at 20° C.; mPa·s)

A cone-plate (E-type) viscometer was used for measurement.

(5) Dielectric Anisotropy (Δ∈; Measured at 25° C.)

An ethanol (20 mL) solution of octadecyl triethoxysilane (0.16 mL) was applied to a well-washed glass substrate. After rotating the glass substrate with a spinner, the glass substrate was heated at 150° C. for 1 hour. A VA device in which a distance (cell gap) was 20 micrometers was assembled from two glass substrates.

A polyimide alignment film was prepared on the glass substrate in a similar manner. After rubbing treatment was applied to the alignment film formed on the glass substrate obtained, a TN device in which a distance between the two glass substrates was 9 micrometers and a twist angle was 80 degrees was assembled.

A sample (liquid crystal composition, or mixture of a liquid crystal compound and mother liquid crystals) was put in the VA device obtained, a voltage of 0.5 V (1 kHz, sine waves) was applied to the sample, and then a dielectric constant (∈∥) in the major axis direction of liquid crystal molecules was measured.

Moreover, a sample (liquid crystal composition, or mixture of a liquid crystal compound and mother liquid crystals) was put in the TN device obtained, a voltage of 0.5 V (1 kHz, sine waves) was applied to the sample, and then a dielectric constant (∈⊥) in the minor axis direction of the liquid crystal molecules was measured.

A value of dielectric anisotropy was calculated from an equation: Δ∈=∈∥−∈⊥.

A composition in which the value is negative has a negative dielectric anisotropy.

(6) Voltage Holding Ratio (VHR; Measured at 25° C. and 100° C.; %):

A TN device was prepared by putting a sample in a cell having a polyimide alignment film in which a distance (cell gap) between two glass substrates was 6 micrometers. The TN device was charged at 25° C. by applying pulse voltage (60 microseconds at 5 V). A waveform of the voltage applied to the TN device was observed with a cathode ray oscilloscope and an area between a voltage curve and a horizontal axis in a unit cycle (16.7 milliseconds) was determined. After the TN device was removed, an area was determined from a waveform of applied voltage in a similar manner. A value (%) of voltage holding ratio was calculated from an equation: (voltage holding ratio)={(value of area with a TN device)/(value of area without a TN device)}×100.

The thus obtained voltage holding ratio was described as "VHR-1." Next, the TN device was heated at 100° C. for 250 hours. After the TN device was returned to 25° C., a voltage holding ratio was measured in a manner similar to the method described above. The voltage holding ratio obtained after the heating test was conducted was described as "VHR-2." In addition, the heating test was conducted as an acceleration test and applied as a test corresponding to a long-time durability test for the TN device.

Example 6

| | | |
|---|---|---|
| 3-HH1(1F)1OB(2F,3F)-O2 | (No. 56) | 4% |
| 3-H1(1F)1OB(2F,3F)B-O2 | (No. 166) | 4% |
| 3-HH-O1 | (12-1) | 8% |
| 5-HH-O1 | (12-1) | 4% |

-continued

| | | |
|---|---|---|
| 3-HH-4 | (12-1) | 5% |
| 3-HB(2F,3F)-O2 | (6-1) | 16% |
| 5-HB(2F,3F)-O2 | (6-1) | 21% |
| 3-HHB(2F,3F)-1 | (7-1) | 7% |
| 3-HHB(2F,3F)-O2 | (7-1) | 14% |
| 5-HHB(2F,3F)-O2 | (7-1) | 17% |

NI=62.9° C.; Δn=0.080; η=26.5 mPa·s; Δ∈=−4.5.

Example 7

| | | |
|---|---|---|
| 3-HH(1F)2OB(2F,3F)-O2 | (No. 100) | 3% |
| 3-HH1(CF2)1OB(2F,3F)-O2 | (No. 78) | 3% |
| 3-HB-O1 | (12-5) | 15% |
| 3-HH-4 | (12-1) | 5% |
| 3-HB(2F,3F)-O2 | (6-1) | 12% |
| 5-HB(2F,3F)-O2 | (6-1) | 12% |
| 2-HHB(2F,3F)-1 | (7-1) | 12% |
| 3-HHB(2F,3F)-1 | (7-1) | 12% |
| 3-HHB(2F,3F)-O2 | (7-1) | 7% |
| 5-HHB(2F,3F)-O2 | (7-1) | 13% |
| 3-HHB-1 | (13-1) | 6% |

NI=82.7° C.; Δn=0.089; η=36.5 mPa·s; Δ∈=−3.4.

Example 8

| | | |
|---|---|---|
| 3-HH1(CF2)1OB(2F,3F)-O2 | (No. 78) | 6% |
| 3-B1(CF2)1OB(2F,3F)B-O2 | (No. 178) | 2% |
| 3-HH-4 | (12-1) | 6% |
| 3-H2B(2F,3F)-O2 | (6-4) | 22% |
| 5-H2B(2F,3F)-O2 | (6-4) | 22% |
| 2-HHB(2F,3CL)-O2 | (7-12) | 2% |
| 3-HHB(2F,3CL)-O2 | (7-12) | 3% |
| 4-HHB(2F,3CL)-O2 | (7-12) | 2% |
| 5-HHB(2F,3CL)-O2 | (7-12) | 2% |
| 3-HBB(2F,3F)-O2 | (7-7) | 9% |
| 5-HBB(2F,3F)-O2 | (7-7) | 9% |
| V-HHB-1 | (13-1) | 6% |
| 3-HHB-3 | (13-1) | 6% |
| 3-HHEBH-5 | (14-6) | 3% |

NI=78.9° C.; Δn=0.100; η=33.5 mPa·s; Δ∈=−4.4.

Example 9

| | | |
|---|---|---|
| 3-HH1(1F)1OB(2F,3F)-O2 | (No. 56) | 4% |
| 3-H1(1F)1OB(2F,3F)B-O2 | (No. 166) | 3% |
| 3-HB-O1 | (12-5) | 15% |
| 3-HH-4 | (12-1) | 4% |
| 3-HB(2F,3F)-O2 | (6-1) | 12% |
| 5-HB(2F,3F)-O2 | (6-1) | 12% |
| 2-HHB(2F,3F)-1 | (7-1) | 12% |
| 3-HHB(2F,3F)-1 | (7-1) | 12% |
| 3-HHB(2F,3F)-O2 | (7-1) | 10% |
| 5-HHB(2F,3F)-O2 | (7-1) | 10% |
| 6-HEB(2F,3F)-O2 | (6-6) | 6% |

NI=80.6° C.; Δn=0.089; η=37.0 mPa·s; Δ∈=−4.0.

A helical pitch was 60.5 micrometers when 0.25 part by weight of optically active compound (Op-5) was added to 100 parts by weight of the composition described above.

Example 10

| | | |
|---|---|---|
| 3-HH1(1F)1OB(2F,3F)-O2 | (No. 56) | 5% |
| 3-H1(1F)1OB(2F,3F)B-O2 | (No. 166) | 3% |
| 2-HH-5 | (12-1) | 3% |
| 3-HH-4 | (12-1) | 15% |
| 3-HH-5 | (12-1) | 4% |
| 3-HB-O2 | (12-5) | 12% |
| 3-H2B(2F,3F)-O2 | (6-4) | 15% |
| 5-H2B(2F,3F)-O2 | (6-4) | 15% |
| 3-HHB(2F,3CL)-O2 | (7-12) | 5% |
| 2-HBB(2F,3F)-O2 | (7-7) | 3% |
| 3-HBB(2F,3F)-O2 | (7-7) | 9% |
| 5-HBB(2F,3F)-O2 | (7-7) | 5% |
| 3-HHB-1 | (13-1) | 3% |
| 3-HHB-O1 | (13-1) | 3% |

NI=73.9° C.; Δn=0.092; η=22.6 mPa·s; Δ∈=−4.5.

Example 11

| | | |
|---|---|---|
| 3-HH1(1F)1OB(2F,3F)-O2 | (No. 56) | 4% |
| 3-H1(1F)1OB(2F,3F)B-O2 | (No. 166) | 3% |
| 3-HB-O1 | (12-5) | 12% |
| 3-HH-4 | (12-1) | 5% |
| 3-HB(2F,3F)-O2 | (6-1) | 12% |
| 5-HB(2F,3F)-O2 | (6-1) | 12% |
| 2-HHB(2F,3F)-1 | (7-1) | 12% |
| 3-HHB(2F,3F)-1 | (7-1) | 12% |
| 3-HHB(2F,3F)-O2 | (7-1) | 9% |
| 5-HHB(2F,3F)-O2 | (7-1) | 13% |
| 3-HHB-1 | (13-1) | 6% |

NI=89.0° C.; Δn=0.093; η=39.0 mPa·s; Δ∈=−3.8.

Example 12

| | | |
|---|---|---|
| 3-HH1(1F)1OB(2F,3F)-O2 | (No. 56) | 4% |
| 3-H1(1F)1OB(2F,3F)B-O2 | (No. 166) | 3% |
| 2-BEB(F)-C | (5-14) | 5% |
| 3-BEB(F)-C | (5-14) | 4% |
| 4-BEB(F)-C | (5-14) | 12% |
| 1V2-BEB(F,F)-C | (5-15) | 16% |
| 3-HB-O2 | (12-5) | 10% |
| 3-HH-4 | (12-1) | 3% |
| 3-HHB-F | (3-1) | 3% |
| 3-HHB-1 | (13-1) | 8% |
| 3-HHB-O1 | (13-1) | 4% |
| 3-HBEB-F | (3-37) | 4% |
| 3-HHEB-F | (3-10) | 3% |
| 5-HHEB-F | (3-10) | 4% |
| 3-H2BTB-2 | (13-17) | 4% |
| 3-H2BTB-3 | (13-17) | 4% |
| 3-H2BTB-4 | (13-17) | 4% |
| 3-HB(F)TB-2 | (13-18) | 5% |

NI=81.5° C.; Δn=0.141; Δ∈=27.2; η=39.3 mPa·s.

Example 13

| | | |
|---|---|---|
| 3-HH(1F)2OB(2F,3F)-O2 | (No. 100) | 3% |
| 3-B1(CF2)1OB(2F,3F)B-O2 | (No. 178) | 3% |

| | | |
|---|---|---|
| 1V2-BEB(F,F)-C | (5-15) | 6% |
| 3-HB-C | (5-1) | 18% |
| 2-BTB-1 | (12-10) | 10% |
| 5-HH-VFF | (—) | 30% |
| 3-HHB-1 | (13-1) | 4% |
| VFF-HHB-1 | (3-1) | 8% |
| VFF2-HHB-1 | (3-1) | 11% |
| 3-H2BTB-2 | (13-17) | 3% |
| 3-H2BTB-4 | (13-17) | 4% |

NI=75.0° C.; Δn=0.123; Δ∈=6.0; η=16.4 mPa·s.

Example 14

| | | |
|---|---|---|
| 3-HH1(1F)1OB(2F,3F)-O2 | (No. 56) | 4% |
| 3-H1(1F)1OB(2F,3F)B-O2 | (No. 166) | 3% |
| 2-HB-C | (5-1) | 5% |
| 3-HB-C | (5-1) | 12% |
| 3-HB-O2 | (12-5) | 12% |
| 2-BTB-1 | (12-10) | 3% |
| 3-HHB-F | (3-1) | 4% |
| 3-HHB-1 | (13-1) | 8% |
| 3-HHB-O1 | (13-1) | 5% |
| 3-HHB-3 | (13-1) | 12% |
| 3-HHEB-F | (3-10) | 2% |
| 5-HHEB-F | (3-10) | 4% |
| 2-HHB(F)-F | (3-2) | 7% |
| 3-HHB(F)-F | (3-2) | 7% |
| 5-HHB(F)-F | (3-2) | 7% |
| 3-HHB(F,F)-F | (3-3) | 5% |

NI=101.2° C.; Δn=0.102; Δ∈=3.7; η=22.0 mPa·s.

Example 15

| | | |
|---|---|---|
| 3-HH1(1F)1OB(2F,3F)-O2 | (No. 56) | 3% |
| 3-H1(1F)1OB(2F,3F)B-O2 | (No. 166) | 2% |
| 5-HB-CL | (2-1) | 16% |
| 3-HH-4 | (12-1) | 12% |
| 3-HH-5 | (12-1) | 4% |
| 3-HHB-F | (3-1) | 4% |
| 3-HHB-CL | (3-1) | 3% |
| 4-HHB-CL | (3-1) | 4% |
| 3-HHB(F)-F | (3-2) | 10% |
| 4-HHB(F)-F | (3-2) | 9% |
| 5-HHB(F)-F | (3-2) | 9% |
| 7-HHB(F)-F | (3-2) | 8% |
| 5-HBB(F)-F | (3-23) | 4% |
| 1O1-HBBH-5 | (14-1) | 3% |
| 5-HHBB(F,F)-F | (4-6) | 3% |
| 3-HH2BB(F,F)-F | (4-15) | 3% |
| 4-HH2BB(F,F)-F | (4-15) | 3% |

NI=112.1° C.; Δn=0.090; Δ∈=2.8; η=19.4 mPa·s.

Example 16

| | | |
|---|---|---|
| 3-HH1(1F)1OB(2F,3F)-O2 | (No. 56) | 3% |
| 3-H1(1F)1OB(2F,3F)B-O2 | (No. 166) | 3% |
| 5-HB-CL | (2-2) | 3% |
| 7-HB(F)-F | (2-3) | 7% |
| 3-HH-4 | (12-1) | 9% |
| 3-HH-EMe | (12-2) | 23% |
| 3-HHEB-F | (3-10) | 8% |
| 5-HHEB-F | (3-10) | 8% |
| 3-HHEB(F,F)-F | (3-12) | 10% |
| 4-HHEB(F,F)-F | (3-12) | 5% |
| 4-HGB(F,F)-F | (3-103) | 3% |
| 5-HGB(F,F)-F | (3-103) | 6% |
| 2-H2GB(F,F)-F | (3-106) | 4% |
| 3-H2GB(F,F)-F | (3-106) | 5% |
| 5-GHB(F,F)-F | (3-109) | 3% |

NI=84.5° C.; Δn=0.069; Δ∈=4.1; η=21.1 mPa·s.

INDUSTRIAL APPLICABILITY

A compound of the invention has general physical properties required for the compound, namely, stability to heat, light and so forth, a good compatibility with other compounds, a large negative dielectric anisotropy and a suitable optical anisotropy. A liquid crystal composition of the invention contains at least one of the compounds, and has a good compatibility from a low temperature region and a large negative dielectric anisotropy. A liquid crystal display device of the invention includes the composition and has a wide temperature range in which the device can be used, a short response time, a small electric power consumption, a large contrast ratio and a low driving voltage, and therefore the device can be widely utilized for a display of a watch, a calculator, a word processor and so forth.

What is claimed is:
1. A compound represented by formula (1):

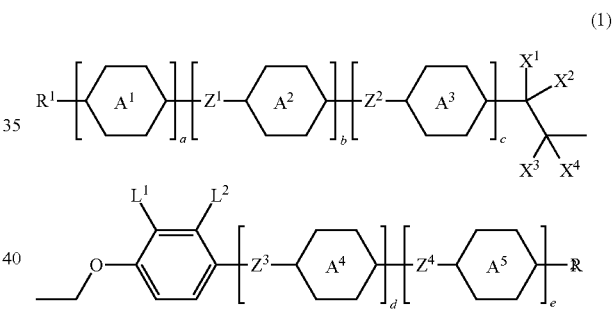

wherein, in formula (1), $R^1$ and $R^2$ are independently hydrogen, halogen or alkyl having 1 to 20 carbons, and in the alkyl, arbitrary —$CH_2$— may be replaced by —O— or —S— and arbitrary —$(CH_2)_2$— may be replaced by —CH=CH—, and in the groups, arbitrary hydrogen may be replaced by halogen; ring $A^1$, ring $A^2$, ring $A^3$, ring $A^4$ and ring $A^5$ are independently 1,4-cyclohexylene, tetrahydropyran-2,5-diyl, tetrahydropyran-3,6-diyl, 1,4-phenylene, or 1,4-phenylene in which arbitrary hydrogen is replaced by fluorine; $Z^1$, $Z^2$, $Z^3$ and $Z^4$ are independently a single bond, —$CH_2CH_2$—, —CH=CH—, —C≡C—, —COO—, —OCO—, —$CF_2O$—, —$OCF_2$—, —$CH_2O$—, —$OCH_2$—, —$C(FX^{11})C(X^{12}X^{13})CH_2O$—, —$OCH_2C(X^{12}X^{13})C(FX^{11})$—, —$CH_2C(X^{13}F)CH_2O$— and —$OCH_2C(X^{13}F)CH_2$—; a, b, c, d and e are independently 0 or 1, a sum of a, b and c is 1, 2 or 3, a sum of d and e is 0, 1 or 2, and a sum of a, b, c, d and e is 1, 2 or 3; $X^1$, $X^2$, $X^3$ and $X^4$ are independently hydrogen or fluorine, one or two of $X^1$, $X^2$, $X^3$ and $X^4$ is fluorine; $X^{11}$, $X^{12}$ and $X^{13}$ are independently hydrogen or fluorine, zero or one of $X^{11}$, $X^{12}$ and $X^{13}$ is fluorine; and $L^1$ and $L^2$ are independently hydrogen or fluorine, and at least one of $L^1$ and $L^2$ is fluorine.

2. The compound according to claim 1, wherein, in formula (1), all of $Z^1$, $Z^2$, $Z^3$ and $Z^4$ is a single bond.

3. The compound according to claim 1, represented by any one of formulas (1-1) to (1-4):

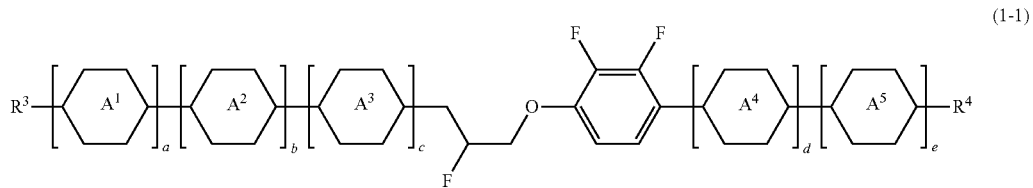
(1-1)

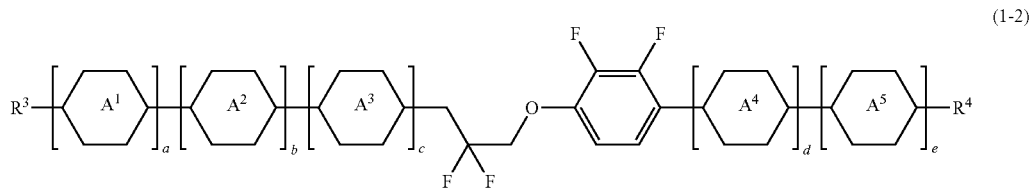
(1-2)

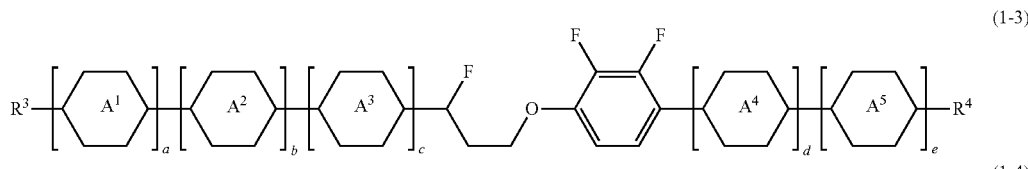
(1-3)

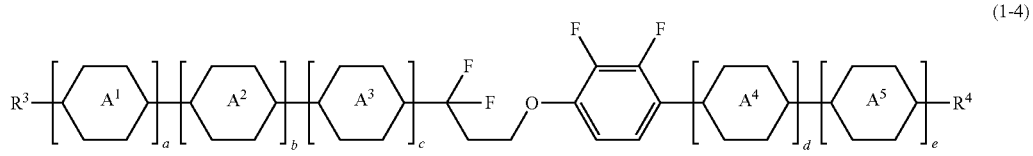
(1-4)

wherein, in formulas (1-1) to (1-4), $R^3$ and $R^4$ are independently hydrogen, halogen or alkyl having 1 to 15 carbons, and in the alkyl, arbitrary —CH$_2$— may be replaced by —O— or —S— and arbitrary —(CH$_2$)$_2$— may be replaced by —CH═CH—, and in the groups, arbitrary hydrogen may be replaced by halogen; ring $A^1$, ring $A^2$, ring $A^3$, ring $A^4$ and ring $A^5$ are independently 1,4-cyclohexylene, tetrahydropyran-2,5-diyl, tetrahydropyran-3,6-diyl, 1,4-phenylene, or 1,4-phenylene in which arbitrary hydrogen is replaced by fluorine; a, b, c, d and e are independently 0 or 1, a sum of a, b; and c is 1, 2 or 3, a sum of d; and e is 0, 1 or 2, and a sum of a, b, c, d; and e is 1, 2 or 3.

4. The compound according to claim 1, represented by any one of formulas (1-1-1) to (1-1-5), formulas (1-2-1) to (1-2-5), formulas (1-3-1) to (1-3-5) and formulas (1-4-1) to (1-4-5):

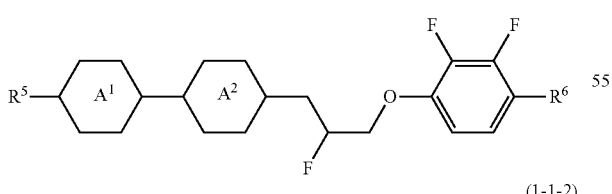
(1-1-1)

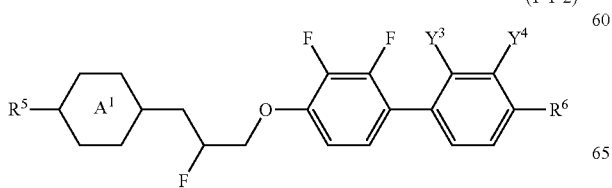
(1-1-2)

-continued

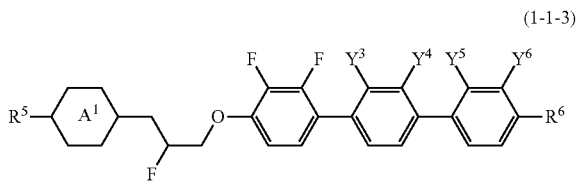
(1-1-3)

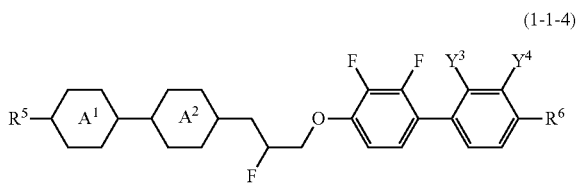
(1-1-4)

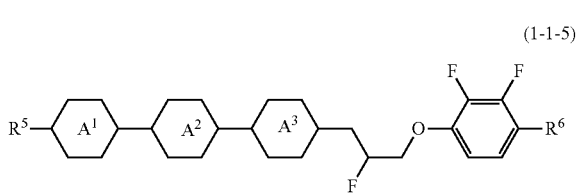
(1-1-5)

(1-2-1)

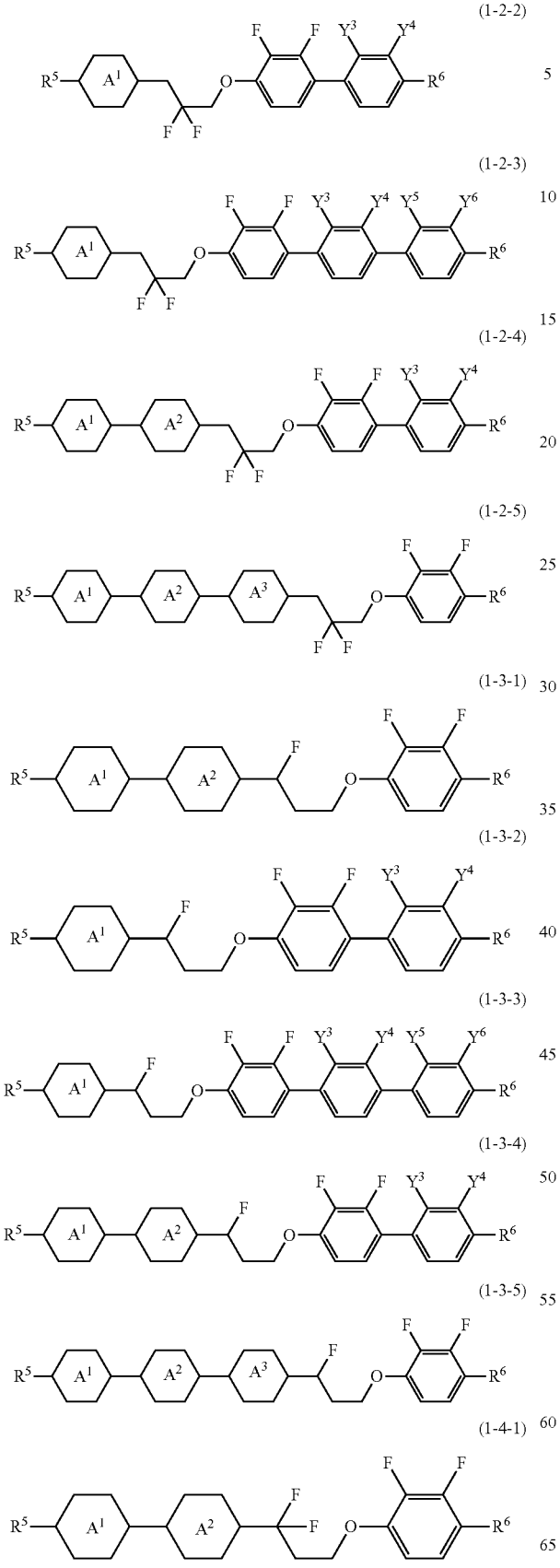

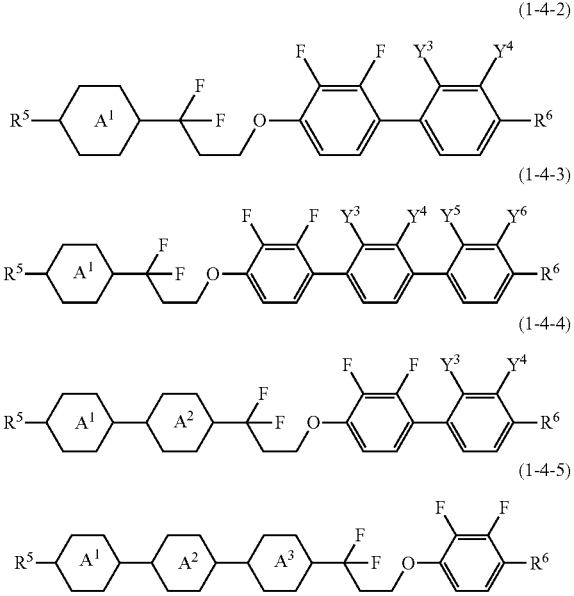

wherein, in formulas (1-1-1) to (1-1-5), formulas (1-2-1) to (1-2-5), formulas (1-3-1) to (1-3-5) and formulas (1-4-1) to (1-4-5), $R^5$ and $R^6$ are independently hydrogen, halogen or alkyl having 1 to 10 carbons, and in the alkyl, arbitrary —CH$_2$— may be replaced by —O— or —S— and arbitrary —(CH$_2$)$_2$— may be replaced by —CH=CH—, and in the groups, arbitrary hydrogen may be replaced by halogen; ring $A^1$, ring $A^2$ and ring $A^3$ are independently 1,4-cyclohexylene, tetrahydropyran-2,5-diyl, tetrahydropyran-3,6-diyl, 1,4-phenylene, or 1,4-phenylene in which arbitrary hydrogen is replaced by fluorine; and $Y^3$, $Y^4$, $Y^5$ and $Y^6$ are independently hydrogen or fluorine.

5. The compound according to claim 1, represented by any one of formulas (1-1-1-1) and (1-1-2-1):

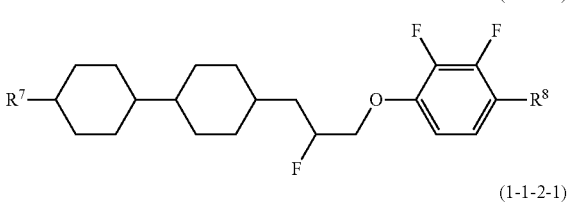

wherein, in formulas (1-1-1-1) and (1-1-2-1), $R^7$ is alkyl having 1 to 10 carbons and $R^8$ is alkoxy having 1 to 10 carbons.

6. A liquid crystal composition comprising two or more components, containing at least one compound according to claim 1, as one component.

7. The liquid crystal composition according to claim 6, containing at least one compound selected from the group of compounds represented by each of formulas (2), (3) and (4), as one component:

(2)

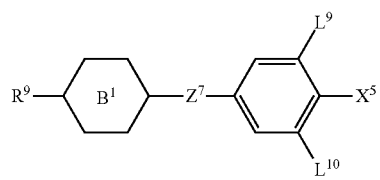

(3)

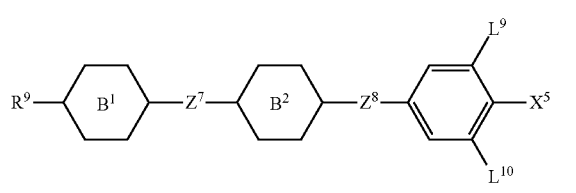

(4)

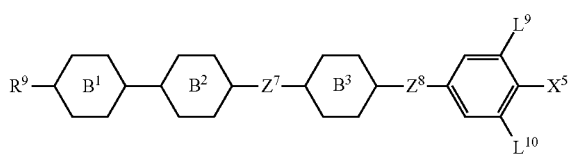

wherein, in formulas (2) to (4), $R^9$ is independently alkyl having 1 to 10 carbons or alkenyl having 2 to 10 carbons, and in the alkyl and the alkenyl, arbitrary hydrogen may be replaced by fluorine and arbitrary —CH$_2$— may be replaced by —O—; $X^5$ is fluorine, chlorine, —OCF$_3$, —OCHF$_2$, —CF$_3$, —CHF$_2$, —CH$_2$F, —CF=F$_2$, —OCF$_2$CHF$_2$ or —OCF$_2$CHFCF$_3$;

ring $B^1$, ring $B^2$ and ring $B^3$ are independently 1,4-cyclohexylene, 1,3-dioxane-2,5-diyl, pyrimidine-2,5-diyl, 1-pyran-2,5-diyl, 1,4-phenylene, 2-fluoro-1,4-phenylene, 3-fluoro-1,4-phenylene or 3,5-difluoro-1,4-phenylene;

$Z^7$ and $Z^8$ are independently —(CH$_2$)$_2$—, —(CH$_2$)$_4$—, —COO—, —CF$_2$O—, —OCF$_2$—, —CH=CH—, —C≡C—, —CH$_2$O— or a single bond; and $L^9$ and $L^{10}$ are independently hydrogen or fluorine.

8. The liquid crystal composition according to claim 6, containing at least one compound selected from the group of compounds represented by formula (5), as one component:

(5)

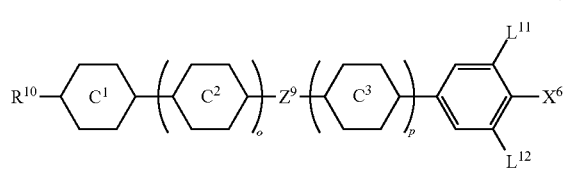

wherein, in formula (5), $R^{10}$ is alkyl having 1 to 10 carbons or alkenyl having 2 to 10 carbons, and in the alkyl and the alkenyl, arbitrary hydrogen may be replaced by fluorine and arbitrary —CH$_2$— may be replaced by —O—;

$X^6$ is —C≡N or —C≡C—C≡N;

ring $C^1$, ring $C^2$ and ring $C^3$ are independently 1,4-cyclohexylene, 1,4-phenylene in which arbitrary hydrogen may be replaced by fluorine, 1,3-dioxane-2,5-diyl, 1-pyran-2,5-diyl or pyrimidine-2,5-diyl;

$Z^9$ is —(CH$_2$)$_2$—, —COO—, —CF$_2$O—, —OCF$_2$—, —C≡C—, —CH$_2$O— or a single bond;

$L^{11}$ and $L^{12}$ are independently hydrogen or fluorine; and o is 0, 1 or 2, p is 0 or 1, and a sum of o and p is 0, 1, 2 or 3.

9. The liquid crystal composition according to claim 6, further containing at least one compound selected from the group of compounds represented by formulas (6), (7), (8), (9), (10) and (11):

(6)

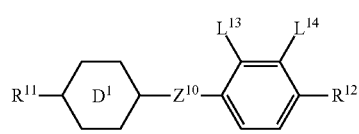

(7)

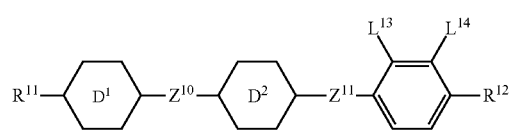

(8)

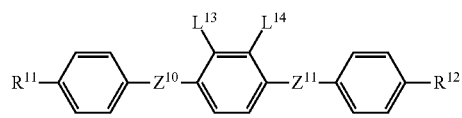

(9)

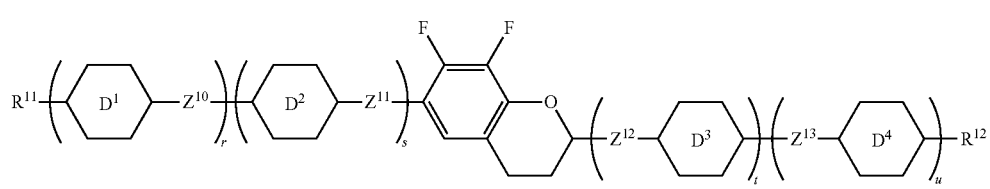

(10)

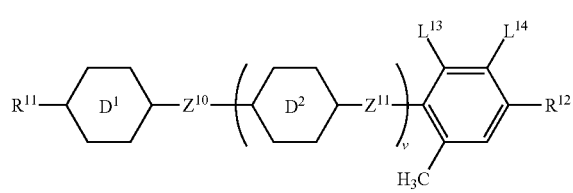

(11)

wherein, in formulas (6) to (11), $R^{11}$ and $R^{12}$ are independently alkyl having 1 to 10 carbons or alkenyl having 2 to 10 carbons, and in the alkyl and the alkenyl, arbitrary hydrogen may be replaced by fluorine and arbitrary —$CH_2$— may be replaced by —O—; ring $D^1$, ring $D^2$, ring $D^3$ and ring $D^4$ are independently 1,4-cyclohexylene, 1,4-cyclohexenylene, 1,4-phenylene in which arbitrary hydrogen may be replaced by fluorine, 6-pyran-2,5-diyl or decahydro-2,6-naphthalene; $Z^{10}$, $Z^{11}$, $Z^{12}$ and $Z^{13}$ are independently —$(CH_2)_2$—, —COO—, —$CH_2O$—, —$OCF_2$—, —$OCF_2(CH_2)_2$— or a single bond; $L^{13}$ and $L^{14}$ are independently fluorine or chlorine; and q, r, s, t, u and v are independently 0 or 1, and a sum of r, s, t and u is 1 or 2.

10. The liquid crystal composition according to claim 6, containing at least one compound selected from the group of compounds represented by formulas (12), (13) and (14), as one component:

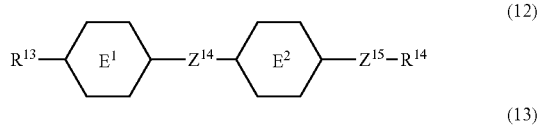
(12)

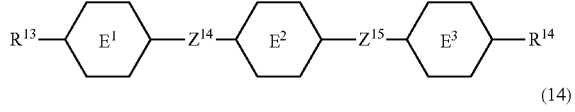
(13)

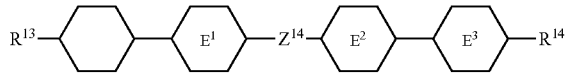
(14)

wherein, in formulas (12) to (14), $R^{13}$ and $R^{14}$ are independently alkyl having 1 to 10 carbons or alkenyl having 2 to 10 carbons, and in the alkyl and the alkenyl, arbitrary —$CH_2$— may be replaced by —O—;
ring $E^1$, ring $E^2$ and ring $E^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and
$Z^{14}$ and $Z^{15}$ are independently —C≡C—, —COO—, —$(CH_2)_2$—, —CH═CH— or a single bond.

11. The liquid crystal composition according to claim 9, further containing at least one compound selected from the group of compounds represented by formulas (12), (13) and (14):

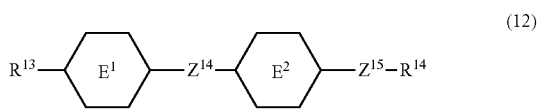
(12)

(13)

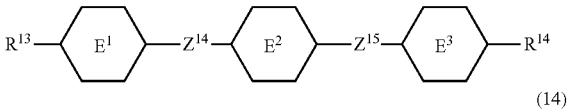
(14)

wherein, in formulas (12) to (14), $R^{13}$ and $R^{14}$ are independently alkyl having 1 to 10 carbons or alkenyl having 2 to 10 carbons, and in the alkyl and the alkenyl, arbitrary —$CH_2$— may be replaced by —O—;
ring $E^1$, ring $E^2$ and ring $E^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and
$Z^{14}$ and $Z^{15}$ are independently —C≡C—, —COO—, —$(CH_2)_2$—, —CH═CH— or a single bond.

12. The liquid crystal composition according to claim 6, further containing at least one optically active compound.

13. The liquid crystal composition according to claim 6, further containing at least one antioxidant and/or an ultraviolet absorber.

14. A liquid crystal display device, comprising the liquid crystal composition according to claim 6.

* * * * *